United States Patent
Bedi et al.

(10) Patent No.: US 8,993,524 B2
(45) Date of Patent: Mar. 31, 2015

(54) COMPOSITIONS AND METHODS FOR TARGETED IMMUNOMODULATORY ANTIBODIES AND FUSION PROTEINS

(75) Inventors: Atul Bedi, Timonium, MD (US); Rajani Ravi, Ruxton, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/582,717

(22) PCT Filed: Mar. 4, 2011

(86) PCT No.: PCT/US2011/027317
§ 371 (c)(1),
(2), (4) Date: Oct. 17, 2012

(87) PCT Pub. No.: WO2011/109789
PCT Pub. Date: Sep. 9, 2011

(65) Prior Publication Data
US 2013/0039911 A1    Feb. 14, 2013

Related U.S. Application Data

(60) Provisional application No. 61/435,671, filed on Jan. 24, 2011, provisional application No. 61/311,255, filed on Mar. 5, 2010.

(51) Int. Cl.
| | |
|---|---|
| A61K 38/00 | (2006.01) |
| A61K 38/10 | (2006.01) |
| A61K 39/00 | (2006.01) |
| A61K 39/385 | (2006.01) |
| C07K 16/00 | (2006.01) |
| C07K 1/00 | (2006.01) |
| C07K 14/495 | (2006.01) |
| C07K 14/705 | (2006.01) |
| C07K 14/71 | (2006.01) |
| C07K 16/28 | (2006.01) |

(52) U.S. Cl.
CPC ......... *C07K 14/495* (2013.01); *C07K 14/70532* (2013.01); *C07K 14/70575* (2013.01); *C07K 14/70578* (2013.01); *C07K 14/70596* (2013.01); *C07K 14/71* (2013.01); *C07K 16/28* (2013.01); *C07K 16/2812* (2013.01); *C07K 16/2815* (2013.01); *C07K 16/2851* (2013.01); *C07K 2319/00* (2013.01); *A61K 2039/505* (2013.01); *C07K 2317/73* (2013.01); *C07K 2317/76* (2013.01)
USPC ... 514/19.2; 514/21.2; 424/178.1; 424/185.1; 424/192.1; 424/194.1; 530/39.1; 530/391.7; 530/391.9; 530/350

(58) Field of Classification Search
None
See application file for complete search history.

(56) References Cited

U.S. PATENT DOCUMENTS

| | | | |
|---|---|---|---|
| 7,527,791 B2 * | 5/2009 | Adams et al. | 424/145.1 |
| 7,795,389 B2 * | 9/2010 | Sun et al. | 530/350 |
| 7,803,378 B2 | 9/2010 | Tranchand-Bunel | |
| 8,399,618 B2 * | 3/2013 | Lazar et al. | 530/350 |
| 8,815,247 B2 * | 8/2014 | Govindappa et al. | 424/179.1 |
| 2005/0054832 A1 | 3/2005 | Lazar | |
| 2006/0135459 A1 | 6/2006 | Epstein et al. | |
| 2006/0263368 A1 | 11/2006 | Rosenblum et al. | |
| 2007/0212337 A1 | 9/2007 | Bedi et al. | |
| 2008/0075717 A1 | 3/2008 | Tranchand-Bunel | |
| 2009/0226435 A1 | 9/2009 | Khare | |

OTHER PUBLICATIONS

Supplementary European Search Report regarding Application No. EP 11 75 1481.

* cited by examiner

*Primary Examiner* — Shulamith H Shafer
(74) *Attorney, Agent, or Firm* — DLA Piper LLP (US)

(57) ABSTRACT

The present invention is based on the seminal discovery that targeted immunomodulatory antibodies and fusion proteins can counter act or reverse immune tolerance of cancer cells. Cancer cells are able to escape elimination by chemotherapeutic agents or tumor-targeted antibodies via specific immunosuppressive mechanisms in the tumor microenvironment and such ability of cancer cells is recognized as immune tolerance. Such immune suppressive mechanisms include immunosuppressive cytokines (for example, Transforming growth factor beta (TGF-$\beta$) and regulatory T cells and/or immunosuppressive myeloid dendritic cells (DCs). By counteracting tumor-induced immune tolerance, the present invention provides effective compositions and methods for cancer treatment, optional in combination with another existing cancer treatment. The present invention provides strategies to counteract tumor-induced immune tolerance and enhance the antitumor efficacy of chemotherapy by activating and leveraging T cell-mediated adaptive antitumor immunity against resistant or disseminated cancer cells.

15 Claims, 75 Drawing Sheets

1. Amino acid sequences of transforming growth factor beta receptor type II (TGF-β-RII) or TGF-β-RIIB or a fragment thereof:

(i) Transforming growth factor beta receptor type II (TGF-β-RII) (SEQ ID NO: 79):

```
MGRGLLRGLW PLHIVLWTRI ASTIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPDL LLVIFQVTGI SLLPPLGVAI
SVIIIFYCYR VNRQQKLSST WETGKTRKLM EFSEHCAIIL EDDRSDISST CANNINHNTE
LLPIELDTLV GKGRFAEVYK AKLKQNTSEQ FETVAVKIFP YEEYASWKTE KDIFSDINLK
HENILQFLTA EERKTELGKQ YWLITAFHAK GNLQEYLTRH VISWEDLRKL GSSLARGIAH
LHSDHTPCGR PKMPIVHRDL KSSNILVKND LTCCLCDFGL SLRLDPTLSV DDLANSGQVG
TARYMAPEVL ESRMNLENVE SFKQTDVYSM ALVLWEMTSR CNAVGEVKDY EPPFGSKVRE
HPCVESMKDN VLRDRGRPEI PSFWLNHQGI QMVCETLTEC WDHDPEARLT AQCVAERFSE
LEHLDRLSGR SCSEEKIPED GSLNTTK
```

[Italic – Extracellular domain of Transforming growth factor beta Receptor II (TGFβ RII)]
[Underlined = TGFβ RII Extracellular domain (ECD) region that binds TGF-β)]

(ii) Transforming growth factor beta receptor type IIB (TGF-β-RIIB) (SEQ ID NO: 80):

```
MGRGLLRGLW PLHIVLWTRI ASTIPPHVQK SDVEMEAQKD EIICPSCNRT AHPLRHINND
MIVTDNNGAV KFPQLCKFCD VRFSTCDNQK SCMSNCSITS ICEKPQEVCV AVWRKNDENI
TLETVCHDPK LPYHDFILED AASPKCIMKE KKKPGETFFM CSCSSDECND NIIFSEEYNT
SNPDLLLVIF QVTGISLLPP LGVAISVIII FYCYRVNRQQ KLSSTWETGK TRKLMEFSEH
CAIILEDDRS DISSTCANNI NHNTELLPIE LDTLVGKGRF AEVYKAKLKQ NTSEQFETVA VKI FP
YEEYASWKTE KDIFSDINLK HENILQFLTA EERKTELGKQ YWLITAFHAK GNLQEYLTRH
VISWEDLRKL GSSLARGIAH LHSDHTPCGR PKMPIVHRDL KSSNILVKND LTCCLCDFGL
SLRLDPTLSV DDLANSGQVG TARYMAPEVL ESRMNLENVE SFKQTDVYSM ALVLWEMTSR
CNAVGEVKDY EPPFGSKVRE HPCVESMKDN VLRDRGRPEI PSFWLNHQGI QMVCETLTEC
WDHDPEARLT AQCVAERFSE LEHLDRLSGR SCSEEKIPED GSLNTTK
```

[Italic – Extracellular domain of Transforming growth factor beta Receptor IIB (TGFβ RIIB)]
[Underlined = TGFβ RIIB Extracellular domain (ECD) region that binds TGF-β)]

2. Truncated mutants of Transforming growth factor beta Receptor II (TGF-β-RII) or TGF-β-RIIB comprising the Extracellular domain (ECD) region that binds TGF-β

(i) TGF-β R-II (ΔC terminus): TGFβ RII lacking the last 38 amino acids from the C-terminus (SEQ ID NO: 81):

```
MGRGLLRGLW PLHIVLWTRI ASTIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPDL LLVIFQVTGI SLLPPLGVAI
SVIIIFYCYR VNRQQKLSST WETGKTRKLM EFSEHCAIIL EDDRSDISST CANNINHNTE
LLPIELDTLV GKGRFAEVYK AKLKQNTSEQ FETVAVKIFP YEEYASWKTE KDIFSDINLK
HENILQFLTA EERKTELGKQ YWLITAFHAK GNLQEYLTRH VISWEDLRKL GSSLARGIAH
LHSDHTPCGR PKMPIVHRDL KSSNILVKND LTCCLCDFGL SLRLDPTLSV DDLANSGQVG
TARYMAPEVL ESRMNLENVE SFKQTDVYSM ALVLWEMTSR CNAVGEVKDY EPPFGSKVRE
HPCVESMKDN VLRDRGRPEI PSFWLNHQGI QMVCETLTEC WDHDPEARL
```

Fig. 1A

TGF-β R-IIB (ΔC terminus): TGFβ RIIB lacking the last 38 aa from the C-terminus (SEQ ID NO: 82):

```
     MGRGLLRGLW PLHIVLWTRI ASTIPPHVQK SDVEMEAQKD EIICPSCNRT AHPLRHINND
MIVTDNNGAV KFPQLCKFCD VRFSTCDNQK SCMSNCSITS ICEKPQEVCV AVWRKNDENI
TLETVCHDPK LPYHDFILED AASPKCIMKE KKKPGETFFM CSCSSDECND NIIFSEEYNT
SNPDLLLVIF QVTGISLLPP LGVAISVIII FYCYRVNRQQ KLSSTWETGK TRKLMEFSEH
CAIILEDDRS DISSTCANNI NHNTELLPIE LDTLVGKGRF AEVYKAKLKQ NTSEQFETVA VKI FP
YEEYASWKTE KDIFSDINLK HENILQFLTA EERKTELGKQ YWLITAFHAK GNLQEYLTRH
VISWEDLRKL GSSLARGIAH LHSDHTPCGR PKMPIVHRDL KSSNILVKND LTCCLCDFGL
SLRLDPTLSV DDLANSGQVG TARYMAPEVL ESRMNLENVE SFKQTDVYSM ALVLWEMTSR
CNAVGEVKDY EPPFGSKVRE HPCVESMKDN VLRDRGRPEI PSFWLNHQGI QMVCETLTEC
WDHDPEARL
```

(ii) TGF-βR-II (Δcyt): TGFβRII lacking the kinase domain & juxtamembrane region (SEQ ID NO: 83):

```
MGRGLLRGLW PLHIVLWTRI ASTIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPDL LLVIFQVTGI SLLPPLGVAI
SVIIFYCYR VNRQQKLSS
```

TGF-βR-IIB (Δcyt): TGFβRIIB lacking the kinase domain & juxtamembrane region (SEQ ID NO: 84):

```
MGRGLLRGLW PLHIVLWTRI ASTIPPHVQK SDVEMEAQKD EIICPSCNRT AHPLRHINND
MIVTDNNGAV KFPQLCKFCD VRFSTCDNQK SCMSNCSITS ICEKPQEVCV AVWRKNDENI
TLETVCHDPK LPYHDFILED AASPKCIMKE KKKPGETFFM CSCSSDECND NIIFSEEYNT
SNPDLLLVIF QVTGISLLPP LGVAISVIII FYCYRVNRQQ KLSS
```

(iii) TGF-β R-II containing the N-terminus region including the extracellular domain (SEQ ID NO: 85):

```
MGRGLLRGLW PLHIVLWTRI ASTIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPDL LLVIFQ
```

TGF-β R-IIB containing the N-terminus region including the extracellular domain (SEQ ID NO: 86):

```
MGRGLLRGLW PLHIVLWTRI ASTIPPHVQK SDVEMEAQKD EIICPSCNRT AHPLRHINND
MIVTDNNGAV KFPQLCKFCD VRFSTCDNQK SCMSNCSITS ICEKPQEVCV AVWRKNDENI
TLETVCHDPK LPYHDFILED AASPKCIMKE KKKPGETFFM CSCSSDECND NIIFSEEYNT
SNPDLLLVIF Q
```

(iv) TGF-β R-II containing the extracellular domain that binds TGF-β (SEQ ID NO: 87):

```
TIPPHVQK SVNNDMIVTD NNGAVKFPQL CKFCDVRFST CDNQKSCMSN CSITSICEKP
QEVCVAVWRK NDENITLETV CHDPKLPYHD FILEDAASPK CIMKEKKKPG ETFFMCSCSS
DECNDNIIFS EEYNTSNPD
```

TGF-β R-IIB containing the extracellular domain that binds TGF-β (SEQ ID NO: 88):

```
TIPPHVQK SDVEMEAQKD EIICPSCNRT AHPLRHINND MIVTDNNGAV KFPQLCKFCD
VRFSTCDNQK SCMSNCSITS ICEKPQEVCV AVWRKNDENI TLETVCHDPK LPYHDFILED
AASPKCIMKE KKKPGETFFM CSCSSDECND NIIFSEEYNT SNPD
```

(v) TGF-β R-II containing the region of the extracellular domain that binds TGF-β (SEQ ID NO: 89):

```
PQL CKFCDVRFST CDNQKSCMSN CSITSICEKP QEVCVAVWRK NDENITLETV CHDPKLPYHD
FILEDAASPK CIMKEKKKPG ETFFMCSCSS DECNDNIIFS EEYNTSNPD
```

Fig. 1B

3. Kinase-deficient mutants, deletion mutants, or point mutants of Transforming growth factor beta Receptor II (TGFβ-RII) or TGFβ-RIIB or a fragment thereof which binds TGF-β

(i) Transforming growth factor beta Receptor II containing point mutations:

Amino acid sequence of TGF-β R-II (K277R) contains a point mutation in its ATP-binding site and is inactive as a kinase (SEQ ID NO: 90):

```
MGRGLLRGLW PLHIVLWTRI ASTIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPDL LLVIFQVTGI SLLPPLGVAI
SVIIIFYCYR VNRQQKLSST WETGKTRKLM EFSEHCAIIL EDDRSDISST CANNINHNTE
LLPIELDTLV GKGRFAEVYK AKLKQNTSEQ FETVAVRIFP YEEYASWKTE KDIFSDINLK
HENILQFLTA EERKTELGKQ YWLITAFHAK GNLQEYLTRH VISWEDLRKL GSSLARGIAH
LHSDHTPCGR PKMPIVHRDL KSSNILVKND LTCCLCDFGL SLRLDPTLSV DDLANSGQVG
TARYMAPEVL ESRMNLENVE SFKQTDVYSM ALVLWEMTSR CNAVGEVKDY EPPFGSKVRE
LEHLDRLSGR SCSEEKIPED GSLNTTK
```

(ii) Transforming growth factor beta Receptor II containing deletions in the amino acid sequence (deletion mutants): Transforming growth factor beta Receptor II (Δi)

TGF-β R-II (Δi2) contains a deletion of amino acids 498 to 508 and is inactive as a kinase (SEQ ID NO: 91):

```
MGRGLLRGLW PLHIVLWTRI ASTIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPDL LLVIFQVTGI SLLPPLGVAI
SVIIIFYCYR VNRQQKLSST WETGKTRKLM EFSEHCAIIL EDDRSDISST CANNINHNTE
LLPIELDTLV GKGRFAEVYK AKLKQNTSEQ FETVAVKIFP YEEYASWKTE KDIFSDINLK
HENILQFLTA EERKTELGKQ YWLITAFHAK GNLQEYLTRH VISWEDLRKL GSSLARGIAH
LHSDHTPCGR PKMPIVHRDL KSSNILVKND LTCCLCDFGL SLRLDPTLSV DDLANSGQVG
TARYMAPEVL ESRMNLENVE SFKQTDVYSM ALVLWEMTSR CNAVGEVKDY EPPFGSKVRE
HPCVESMKDA SGIQMVCETL TECWDHDPEA RLTAQCVAER FSELEHLDRL SGRSCSEEKI
PEDGSLNTTK
```

4. Amino acid sequences of transforming growth factor beta receptor type III (TGF-β-RIII) or or a fragment thereof.

5. Hybrid or fusion proteins containing amino acid sequences of transforming growth factor beta receptor type II (TGF-β-RII) and TGF-β-RIII.

6. Hybrid or fusion proteins containing amino acid sequences of transforming growth factor beta receptor type IIB (TGF-β-RIIB) and TGF-β-RIII.

Linker sequence used in fusion proteins (SEQ ID NO: 104):

GGGGSGGGGSGGGGS

Fig. 1C

Fusion proteins comprising Anti-HER2/neu antibody and Transforming growth factor-beta receptor II (TGFβ-RII) Extracellular domain (ECD).

Anti-HER2/neu heavy chain + TGFβ-RII ECD fusion amino acid sequence
(SEQ ID NO: 1):
<u>EVQLVESGGGLVQPGGSLRLSCAASGFNIKDTYIHWVRQAPGKGLEWVARIYPTNGYTRYADSVKG</u>
<u>RFTISADTSKNTAYLQMNSLRAEDTAVYYCSRWGDGFYAMDYWGQGTLVTVSS</u>ASTKGPSVFPLA
PSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK
*GGGGSGGGGSGGGGS* TIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPD

Anti-HER2/neu light chain amino acid sequence (SEQ ID NO: 70):
<u>DIQMTQSPSSLSASVGDRVTITCRASQDVNTAVAWYQQKPGKAPKLLIYSASFLYSGVPSRFSGSR</u>
<u>SGTDFTLTISSLQPEDFATYYCQQHYTTPPTFGQGTKVEIK</u>RTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC <u>Underlined</u>: Anti-HER2 antibody variable region
Plain: Anti-HER2 antibody constant region
*Italic: Linker*
Bold: TGFβRII ectodomain

Fig. 2

Fusion proteins comprising Anti-EGFR1 antibody and Transforming growth factor-beta receptor II (TGFβ-RII) Extracellular domain (ECD).

Anti-EGFR1 heavy chain + TGFβ-RII ECD fusion amino acid sequence
(SEQ ID NO: 2):
<u>QVQLKQSGPGLVQPSQSLSITCTVSGFSLTNYGVHWVRQSPGKGLEWLGVIWSGGNTDYNTPFTSR</u>
<u>LSINKDNSKSQVFFKMNSLQSNDTAIYYCARALTYYDYEFAYWGQGTLVTVSA</u>ASTKGPSVFPLAP
SSKSTSGGTAALGCLVKDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK
*GGGGSGGGGSGGGGS* TIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPD

Anti-EGFR1 light chain amino acid sequence (SEQ ID NO: 71):
<u>DILLTQSPVILSVSPGERVSFSCRASQSIGTNIHWYQQRTNGSPRLLIKYASESISGIPSRFSGSG</u>
<u>SGTDFTLSINSVESEDIADYYCQQNNNWPTTFGAGTKLELK</u>RTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC <u>Underlined</u>: Anti-EGFR antibody variable region
    Plain: Anti-EGFR antibody constant region
    *Italic*: Linker
    Bold: TGFβRII ectodomain

Fig. 3

Fusion proteins comprising Anti-CD20 antibody and Transforming growth factor-beta receptor II (TGFβ-RII) Extracellular domain (ECD).

Anti-CD20 heavy chain+ TGFβ-RII ECD fusion amino acid sequence
(SEQ ID NO: 3):
<u>QVQLQQPGAELVKPGASVKMSCKASGYTFTSYNMHWVKQTPGRGLEWIGAIYPGNGDTSYNQKFKG</u>
<u>KATLTADKSSSTAYMQLSSLTSEDSAVYYCARSTYYGGDWYFNVWGAGTTVTVSA</u>ASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKAEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS* TIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPD

Anti-CD20 light chain amino acid sequence (SEQ ID NO: 72):
<u>QIVLSQSPAILSASPGEKVTMTCRASSSVSYIHWFQQKPGSSPKPWIYATSNLASGVPVRFSGSGS</u>
<u>GTSYSLTISRVEAEDAATYYCQQWTSNPPTFGGGTKLEIKR</u>TVAAPSVFIFPPSDEQLKSGTASVV
CLLNNFYPREAKVQWKVDNALQSGNSQESVTEQDSKDSTYSLSSTLTLSKADYEKHKVYACEVTHQ
GLSSPVTKSFNRGEC <u>Underlined</u>: Anti-CD20 antibody variable region
    Plain: Anti-CD20 antibody constant region
    *Italic: Linker*
    Bold: TGFβRII ectodomain

Fig. 4

Fusion proteins comprising anti-VEGF antibody and Transforming growth factor-beta receptor II (TGFβ-RII) Extracellular domain (ECD).

Anti-VEGF heavy chain+ TGFβ-RII ECD fusion amino acid sequence
(SEQ ID NO: 4):
<u>EVQLVESGGGLVQPGGSLRLSCAASGYTFTNYGMNWVRQAPGKGLEWVGWINTYTGEPTYAADFKR</u>
<u>RFTFSLDTSKSTAYLQMNSLRAEDTAVYYCAKYPHYYGSSHWYFDVWGQGTLVTVSS</u>ASTKGPSVF
PLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPE
VTCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPGK
*GGGGSGGGGSGGGGS* TIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPD

Anti-VEGF Light chain sequence (SEQ ID NO: 73):
<u>DIQMTQSPSSLSASVGDRVTITCSASQDISNYLNWYQQKPGKAPKVLIYFTSSLHSGVPSRFSGSG</u>
<u>SGTDFTLTISSLQPEDFATYYCQQYSTVPWTFGQGTKVEIK</u>RTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC <u>Underlined</u>: Anti-VEGF antibody variable region
    Plain: Anti-VEGF antibody constant region
    *Italic*: Linker
    Bold: TGFβRII ectodomain

Fig. 5

Fusion proteins comprising anti-human CTLA-4 antibody and Transforming growth factor-beta receptor II (TGFβ-RII) Extracellular domain (ECD).

Anti-CTLA-4 heavy chain + TGFβ-RII Extracellular domain fusion amino acid sequence (SEQ ID NO: 5):

QVQLVESGGG VVQPGRSLRL SCAASGFTFS SYTMHWVRQA PGKGLEWVTF ISYDGNNKYY ADSVKGRFTI SRDNSKNTLY LQMNSLRAED TAIYYCARTG WLGPFDYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKRVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK *GGGGSGGGGSGGGGS* TIPPHVQK SVNNDMIVTD NNGAVKFPQL CKFCDVRFST CDNQKSCMSN CSITSICEKP QEVCVAVWRK NDENITLETV CHDPKLPYHD FILEDAASPK CIMKEKKKPG ETFFMCSCSS DECNDNIIFS EEYNTSNPD

Anti-CTLA-4 light chain (SEQ ID NO: 74):

EIVLTQSPGT LSLSPGERAT LSCRASQSVG SSYLAWYQQK PGQAPRLLIY GAFSRATGIP DRFSGSGSGT DFTLTISRLE PEDFAVYYCQ QYGSSPWTFG QGTKVEIKRT VAAPSVFIFP PSDEQLKSGT ASVVCLLNNF YPREAKVQWK VDNALQSGNS QESVTEQDSK DSTYSLSSTL TLSKADYEKH KVYACEVTHQ GLSSPVTKSF NRGEC

Underlined: Anti-CTLA-4 antibody heavy chain variable region

Plain: Anti-CTLA-4 antibody heavy chain constant region

*Italic: Linker*

Bold: TGFβRII ectodomain

Fig. 6

Fusion proteins comprising IL-2, Fc, and Transforming growth factor-beta receptor II (TGFβ-RII) Extracellular domain (ECD).

IL-2 + Fc + TGFβ-RII Extracellular domain (SEQ ID NO: 6):
<u>APTSSSTKKTQLQLEHLLLDLQMILNGINNYKNPKLTRMLTFKFYMPKKATELKHLQCLEEELKPL</u>
<u>EEVLNLAQSKNFHLRPRDLISNINVIVLELKGSETTFMCEYADETATIVEFLNRWITFCQSIISTL</u>
<u>T</u> *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS* TIPPHVQK SVNNDMIVTD
NNGAVKFPQL CKFCDVRFST CDNQKSCMSN CSITSICEKP QEVCVAVWRK NDENITLETV
CHDPKLPYHD FILEDAASPK CIMKEKKKPG ETFFMCSCSS DECNDNIIFSEEYNTSNPD

TGFβ-RII Extracellular domain + Fc + IL-2 (SEQ ID NO: 7):
TIPPHVQK SVNNDMIVTD NNGAVKFPQL CKFCDVRFST CDNQKSCMSN CSITSICEKP
QEVCVAVWRK NDENITLETV CHDPKLPYHD FILEDAASPK CIMKEKKKPG ETFFMCSCSS
DECNDNIIFS EEYNTSNPD *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
R<u>EE</u>MTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
<u>APTSSSTKKTQLQLEHLLLDLQMILNGINNYKNPKLTRMLTFKFYMPKKATELKHLQCLEEELKPL</u>
<u>EEVLNLAQSKNFHLRPRDLISNINVIVLELKGSETTFMCEYADETATIVEFLNRWITFCQSIISTL</u>
<u>T</u>

Bold: TGFβRII ectodomain
*Italic: Linker (Optional; other linker sequences)*
Plain: Fc
<u>Underlined: IL-2 fragment</u>
(Note: Can replace linker *GGGGSGGGGSGGGGS* SEQ ID NO: 104 with
*EPKSCDK* SEQ ID NO: 105)
(Note: Can replace underlined aa in Fc: <u>E</u> with D and <u>M</u> with L in Fc)

Fig. 7

Fusion proteins comprising anti-CD25 antibody and Transforming growth factor-beta receptor II (TGFβ-RII) Extracellular domain (ECD).

Anti-CD25 (Daclizumab) heavy chain and TGFβ-RII Extracellular domain
(SEQ ID NO: 8):

QVQLVQSGAE VKKPGSSVKV SCKASGYTFT SYRMHWVRQA PGQGLEWIGY INPSTGYTEY
NQKFKDKATI TADESTNTAY MELSSLRSED TAVYYCARGG GVFDYWGQGT LVTVSSASTK
GPSVFPLAPS SKSTSGGTAA LGCLVKDYFP EPVTVSWNSG ALTSGVHTFP AVLQSSGLYS
LSSVVTVPSS SLGTQTYICN VNHKPSNTKV DKKVEPKSCD KTHTCPPCPA PELLGGPSVF
LFPPKPKDTL MISRTPEVTC VVVDVSHEDP EVKFNWYVDG VEVHNAKTKP REEQYNSTYR
VVSVLTVLHQ DWLNGKEYKC KVSNKALPAP IEKTISKAKG QPREPQVYTL PPSRDELTKN
QVSLTCLVKG FYPSDIAVEW ESNGQPENNY KTTPPVLDSD GSFFLYSKLT VDKSRWQQGN
VFSCSVMHEA LHNHYTQKSL SLSPGK *GGGGSGGGGSGGGGS* TIPPHVQK SVNNDMIVTD
NNGAVKFPQL CKFCDVRFST CDNQKSCMSN CSITSICEKP QEVCVAVWRK NDENITLETV
CHDPKLPYHD FILEDAASPK CIMKEKKKPG ETFFMCSCSS DECNDNIIFS EEYNTSNPD

Anti-CD25 (Daclizumab) light chain (SEQ ID NO: 75):
DIQMTQSPST LSASVGDRVT ITCSASSSIS YMHWYQQKPG KAPKLLIYTT SNLASGVPAR
FSGSGSGTEF TLTISSLQPD DFATYYCHQR STYPLTFGQG TKVEVKRTVA APSVFIFPPS
DEQLKSGTAS VVCLLNNFYP REAKVQWKVD NALQSGNSQE SVTEQDSKDS TYSLSSTLTL
SKADYEKHKV YACEVTHQGL SSPVTKSFNR GEC Plain: Anti-CD25 antibody
  *Italic: Linker*
  Bold: TGFβRII ectodomain

Fig. 8A

Anti-CD25 (Basiliximab) heavy chain and TGFβ-RII Extracellular domain
(SEQ ID NO: 9):

QLQQSGTVLA RPGASVKMSC KASGYSFTRY WMHWIKQRPG QGLEWIGAIY PGNSDTSYNQ
KFEGKAKLTA VTSASTAYME LSSLTHEDSA VYYCSRDYGY YFDFWGQGTT LTVSSASTKG
PSVFPLAPSS KSTSGGTAAL GCLVKDYFPE PVTVSWNSGA LTSGVHTFPA VLQSSGLYSL
SSVVTVPSSS LGTQTYICNV NHKPSNTKVD KRVEPKSCDK THTCPPCPAP ELLGGPSVFL
FPPKPKDTLM ISRTPEVTCV VVDVSHEDPE VKFNWYVDGV EVHNAKTKPR EEQYNSTYRV
VSVLTVLHQD WLNGKEYKCK VSNKALPAPI EKTISKAKGQ PREPQVYTLP PSRDELTKNQ
VSLTCLVKGF YPSDIAVEWE SNGQPENNYK TTPPVLDSDG SFFLYSKLTV DKSRWQQGNV
FSCSVMHEAL HNHYTQKSLS LSPGK *GGGGSGGGGSGGGGS* **TIPPHVQK SVNNDMIVTD
NNGAVKFPQL CKFCDVRFST CDNQKSCMSN CSITSICEKP QEVCVAVWRK NDENITLETV
CHDPKLPYHD FILEDAASPK CIMKEKKKPG ETFFMCSCSS DECNDNIIFS EEYNTSNPD**

Anti-CD25 (Basiliximab) light chain (SEQ ID NO: 76):
QIVSTQSPAI MSASPGEKVT MTCSASSSRS YMQWYQQKPG TSPKRWIYDT SKLASGVPAR
FSGSGSGTSY SLTISSMEAE DAATYYCHQR SSYTFGGGTK LEIKRTVAAP SVFIFPPSDE
QLKSGTASVV CLLNNFYPRE AKVQWKVDNA LQSGNSQESV TEQDSKDSTY SLSSTLTLSK
ADYEKHKVYA CEVTHQGLSS PVTKSFNRGEC Plain: Anti-CD25 antibody
*Italic: Linker*
Bold: TGFβRII ectodomain

Fig. 8B

Fusion proteins comprising anti-CD4 antibody and Transforming growth factor-beta receptor II (TGFβ-RII) Extracellular domain (ECD).

Anti-CD4 heavy chain and TGFβ-RII Extracellular domain (SEQ ID NO: 10):
Heavy chain fusion protein:

QVQLQEAGPGLVKPSETLSLTCSVSGGSISGDYYWFWIRQSPGKGLEWIGYIYGSGGGTNYNPSLN
NRVSISIDTSKNLFSLKLRSVTAADTAVYYCASNILKYLHWLLYWGQGVLVTVSSASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS* **TIPPHVQKSVNNDMIVTDNNGAVKFPQLCKFCDVRF
STCDNQKSCMSNCSITSICEKPQEVCVAVWRKNDENITLETVCHDPKLPYHDFILEDAASPKCIMK
EKKKPGETFFMCSCSSDECNDNIIFSEEYNTSNPD**

Anti-CD4 light chain (SEQ ID NO: 77):

Light chain:

SYELSQPRSVSVSPGQTAGFTCGGDNVGRKSVQWYQQKPPQAPVLVIYADSERPSGIPARFSGSNS
GNTATLTISGVEAGDEADYYCQVWDSTADHWVFGGGTRLTVLGRTVAAPSVFIFPPSDEQLKSGTA
SVVCLLNNFYPREAKVQWKVDNALQSGNSQESVTEQDSKDSTYSLSSTLTLSKADYEKHKVYACEV
THQGLSSPVTKSFNRGEC

Plain: Anti-CD4 antibody (variable region – underlined)

*Italic: Linker*

Bold: TGFβRII ectodomain

Fig. 9

Fusion proteins comprising PD-1 Ectodomain, Fc, and Transforming growth factor-beta receptor II (TGFβ-RII) Extracellular domain (ectodomain).

PD-1 ectodomain + Fc + TGFβRII ectodomain (SEQ ID NO: 11):
PGWFLDSPDRPWNPPTFSPALLVVTEGDNATFTCSFSNTSESFVLNWYRMSPSNQTDKLAAFPEDR
SQPGQDCRFRVTQLPNGRDFHMSVVRARRNDSGTYLCGAISLAPKAQIKESLRAELRVTERRAEVP
TAHPSPSPRPAGQFQTLV *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
**TIPPHVQKSVNNDMIVTDNNGAVKFPQLCKFCDVRFSTCDNQKSCMSNCSITSICEKPQEVCVAVW
RKNDENITLETVCHDPKLPYHDFILEDAASPKCIMKEKKKPGETFFMCSCSSDECNDNIIFSEEYN
TSNPD**

TGFβRII ectodomain + Fc + PD-1 ectodomain (SEQ ID NO: 12):
**TIPPHVQKSVNNDMIVTDNNGAVKFPQLCKFCDVRFSTCDNQKSCMSNCSITSICEKPQEVCVAVW
RKNDENITLETVCHDPKLPYHDFILEDAASPKCIMKEKKKPGETFFMCSCSSDECNDNIIFSEEYN
TSNPD** *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
PGWFLDSPDRPWNPPTFSPALLVVTEGDNATFTCSFSNTSESFVLNWYRMSPSNQTDKLAAFPEDR
SQPGQDCRFRVTQLPNGRDFHMSVVRARRNDSGTYLCGAISLAPKAQIKESLRAELRVTERRAEVP
TAHPSPSPRPAGQFQTLV Underlined: PD-1 ectodomain
*Italic: Linkers*
Plain: IgG1 Fc
Bold: TGFβRII ectodomain
(Note: The first linker sequence *GGGGSGGGGSGGGGS* is optional and may be replaced with *EPKSCDK* SEQ ID NO: 105 or deleted)

Fig. 10

Fusion proteins comprising Transforming growth factor-beta receptor II (TGFβ-RII) ectodomain, Fc, and Receptor activator of nuclear factor–κB (RANK) Ectodomain:

TGFβRII ectodomain – Fc - RANK ectodomain (SEQ. ID. NO: 13):

TIPPHVQKSVNNDMIVTDNNGAVKFPQLCKFCDVRFSTCDNQKSCMSNCSITSICEKPQEVCVAVW
RKNDENITLETVCHDPKLPYHDFILEDAASPKCIMKEKKKPGETFFMCSCSSDECNDNIIFSEEYN
TSNPD*GGGGSGGGGSGGGGS*THTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK *GGGGSGGGGSGGGGS* <u>QI</u>
<u>APPCTSEKHY  EHLGRCCNKC  EPGKYMSSKC  TTTSDSVCLP  CGPDEYLDSW  NEEDKCLLHK</u>
<u>VCDTGKALVA  VVAGNSTTPR  RCACTAGYHW  SQDCECCRRN  TECAPGLGAQ  HPLQLNKDTV</u>
<u>CKPCLAGYFS  DAFSSTDKCR  PWTNCTFLGK  RVEHHGTEKS  DAVCSSSLPA  RKPPNEPHVY  LPG</u>

RANK ectodomain – Fc - TGFβRII ectodomain (SEQ. ID. NO: 14):

<u>QI  APPCTSEKHY  EHLGRCCNKC  EPGKYMSSKC  TTTSDSVCLP  CGPDEYLDSW  NEEDKCLLHK</u>
<u>VCDTGKALVA  VVAGNSTTPR  RCACTAGYHW  SQDCECCRRN  TECAPGLGAQ  HPLQLNKDTV</u>
<u>CKPCLAGYFS  DAFSSTDKCR  PWTNCTFLGK  RVEHHGTEKS  DAVCSSSLPA  RKPPNEPHVY  LPG</u>
*GGGGSGGGGSGGGGS*THTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGKGGGGSGGGGSGGGGSTIPPHVQKS
VNNDMIVTDNNGAVKFPQLCKFCDVRFSTCDNQKSCMSNCSITSICEKPQEVCVAVWRKNDENITL
ETVCHDPKLPYHDFILEDAASPKCIMKEKKKPGETFFMCSCSSDECNDNIIFSEEYNTSNPD

Bold: TGFβRII ectodomain
Plain: IgG1 Fc
*Italics: Linker*
<u>Underlined: RANK ectodomain</u>
(optional linker 1 may be deleted or replaced with another linker such as IEGRDMD (SEQ. ID. NO:106) or EPKSCDK (SEQ.ID. NO: 105))

Fig. 11

(i) Full-length PD-1 or fragment thereof (SEQ ID NO: 92):

```
1   MQIPQAPWPV VWAVLQLGWR PGWFLDSPDR PWNPPTFSPA LLVVTEGDNA TFTCSFSNTS
61  ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL
```

*Italic: PD-1 ectodomain*
*Underlined Italic: ligand-binding domain*

(ii) PD-1 extracellular domain (ectodomain) or fragment thereof
(SEQ ID NO: 93):

PGWFLDSPDR PWNPPTFSPA LLVVTEGDNA TFTCSFSNTS ESFVLNWYRM SPSNQTDKLA
AFPEDRSQPG QDCRFRVTQL PNGRDFHMSV VRARRNDSGT YLCGAISLAP KAQIKESLRA
ELRVTERRAE VPTAHPSPSP RPAGQFQTLV (iii) PD-1 extracellular domain (ectodomain) ligand-binding region
(SEQ ID NO: 94):

DSPDR PWNPPTFSPA LLVVTEGDNA TFTCSFSNTS ESFVLNWYRM SPSNQTDKLA
AFPEDRSQPG QDCRFRVTQL PNGRDFHMSV VRARRNDSGT YLCGAISLAP KAQIKESLRA
ELRVTERRAE VPTAHPSPSP RPAGQFQ (iv). Mutant of PD-1 or a fragment thereof which binds Programmed Death-1 ligand
[PD-L1 (B7-H1) or PD-L2 (B7-DC)]

Fig. 12

Fusion proteins comprising Anti-HER2/neu antibody and PD-1 Ectodomain.

Anti-HER2/neu heavy chain + PD-1 ectodomain fusion amino acid sequence
(SEQ ID NO: 15):
<u>EVQLVESGGGLVQPGGSLRLSCAASGFNIKDTYIHWVRQAPGKGLEWVARIYPTNGYTRYADSVKG
RFTISADTSKNTAYLQMNSLRAEDTAVYYCSRWGGDGFYAMDYWGQGTLVTVSS</u>ASTKGPSVFPLA
PSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK
*GGGGSGGGGSGGGGS* **PGWFLDSPDR PWNPPTFSPA LLVVTEGDNA TFTCSFSNTS
ESFVLNWYRM SPSNQTDKLA AFPEDRSQPG QDCRFRVTQL PNGRDFHMSV VRARRNDSGT
YLCGAISLAP KAQIKESLRA ELRVTERRAE VPTAHPSPSP RPAGQFQTLV**

Anti-HER2/neu light chain amino acid sequence (SEQ ID NO: 70):
<u>DIQMTQSPSSLSASVGDRVTITCRASQDVNTAVAWYQQKPGKAPKLLIYSASFLYSGVPSRFSGSR
SGTDFTLTISSLQPEDFATYYCQQHYTTPPTFGQGTKVEIK</u>RTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC <u>Underlined</u>: Anti-HER2/neu Variable region
    Plain: Anti-HER2/neu Constant region
    *Italic: Linker*
    Bold: PD-1 ectodomain

Fig. 13

Fusion proteins comprising Anti-EGFR1 antibody and PD-1 Ectodomain.

Anti-EGFR heavy chain + PD-1 ectodomain fusion amino acid sequence
(SEQ ID NO: 16):
<u>QVQLKQSGPGLVQPSQSLSITCTVSGFSLTNYGVHWVRQSPGKGLEWLGVIWSGGNTDYNTPFTSR</u>
<u>LSINKDNSKSQVFFKMNSLQSNDTAIYYCARALTYYDYEFAYWGQGTLVTVSA</u>ASTKGPSVFPLAP
SSKSTSGGTAALGCLVKDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK
*GGGGSGGGGSGGGGS* PGWFLDSPDR PWNPPTFSPA LLVVTEGDNA TFTCSFSNTS
ESFVLNWYRM SPSNQTDKLA AFPEDRSQPG QDCRFRVTQL PNGRDFHMSV VRARRNDSGT
YLCGAISLAP KAQIKESLRA ELRVTERRAE VPTAHPSPSP RPAGQFQTLV

Anti-EGFR light chain amino acid sequence (SEQ ID NO: 71):
<u>DILLTQSPVILSVSPGERVSFSCRASQSIGTNIHWYQQRTNGSPRLLIKYASESISGIPSRFSGSG</u>
<u>SGTDFTLSINSVESEDIADYYCQQNNNWPTTFGAGTKLELK</u>RTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC <u>Underlined</u>: Anti-EGFR Variable region
    Plain: Anti-EGFR Constant region
    *Italic*: *Linker*
    Bold: PD-1 ectodomain

Fig. 14

Fusion proteins comprising Anti-CD20 antibody and PD-1 Ectodomain.

Anti-CD20 heavy chain + PD-1 ectodomain fusion amino acid sequence
(SEQ ID NO: 17):
<u>QVQLQQPGAELVKPGASVKMSCKASGYTFTSYNMHWVKQTPGRGLEWIGAIYPGNGDTSYNQKFKG</u>
<u>KATLTADKSSSTAYMQLSSLTSEDSAVYYCARSTYYGGDWYFNVWGAGTTVTVSAA</u>STKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKAEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS* PGWFLDSPDR PWNPPTFSPA LLVVTEGDNA TFTCSFSNTS
ESFVLNWYRM SPSNQTDKLA AFPEDRSQPG QDCRFRVTQL PNGRDFHMSV VRARRNDSGT
YLCGAISLAP KAQIKESLRA ELRVTERRAE VPTAHPSPSP RPAGQFQTLV

Anti-CD20 light chain amino acid sequence (SEQ ID NO: 72):
<u>QIVLSQSPAILSASPGEKVTMTCRASSSVSYIHWFQQKPGSSPKPWIYATSNLASGVPVRFSGSGS</u>
<u>GTSYSLTISRVEAEDAATYYCQQWTSNPPTFGGGTKLEIK</u>RTVAAPSVFIFPPSDEQLKSGTASVV
CLLNNFYPREAKVQWKVDNALQSGNSQESVTEQDSKDSTYSLSSTLTLSKADYEKHKVYACEVTHQ
GLSSPVTKSFNRGEC > <u>Underlined</u>: Anti-CD20 Variable region
> Plain: Anti-CD20 Constant region
> *Italic: Linker*
> Bold: PD-1 ectodomain

Fig. 15

Fusion proteins comprising Anti-VEGF antibody and PD-1 Ectodomain.

Anti-VEGF heavy chain + PD-1 ectodomain fusion amino acid sequence
(SEQ ID NO: 18):

<u>EVQLVESGGGLVQPGGSLRLSCAASGYTFTNYGMNWVRQAPGKGLEWVGWINTYTGEPTYAADFKR</u>
<u>RFTFSLDTSKSTAYLQMNSLRAEDTAVYYCAKYPHYYGSSHWYFDVWGQGTLVTVSS</u>ASTKGPSVF
PLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPE
VTCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPGK
*GGGGSGGGGSGGGGS* PGWFLDSPDR PWNPPTFSPA LLVVTEGDNA TFTCSFSNTS
ESFVLNWYRM SPSNQTDKLA AFPEDRSQPG QDCRFRVTQL PNGRDFHMSV VRARRNDSGT
YLCGAISLAP KAQIKESLRA ELRVTERRAE VPTAHPSPSP RPAGQFQTLV

Anti-VEGF Light chain sequence (SEQ ID NO: 73):
<u>DIQMTQSPSSLSASVGDRVTITCSASQDISNYLNWYQQKPGKAPKVLIYFTSSLHSGVPSRFSGSG</u>
<u>SGTDFTLTISSLQPEDFATYYCQQYSTVPWTFGQGTKVEIK</u>RTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC <u>Underlined</u>: Anti-VEGF Variable region
Plain: Anti-VEGF Constant region
*Italic*: Linker
Bold: PD-1 ectodomain

Fig. 16

Fusion proteins comprising anti-human CTLA-4 antibody and PD-1 Ectodomain.

Anti-(human CTLA-4) (human γ1-chain)-PD-1 ectodomain fusion protein, disulfide with human κ-chain, dimer Anti-CTLA-4 heavy chain + PD-1 ectodomain fusion amino acid sequence
(SEQ ID NO: 19):

<u>QVQLVESGGG VVQPGRSLRL SCAASGFTFS SYTMHWVRQA PGKGLEWVTF ISYDGNNKYY</u>
<u>ADSVKGRFTI SRDNSKNTLY LQMNSLRAED TAIYYCARTG WLGPFDYWGQ GTLVTVSSAS</u>
TKGPSVFPLA PSSKSTSGGT AALGCLVKDY FPEPVTVSWN SGALTSGVHT FPAVLQSSGL
YSLSSVVTVP SSSLGTQTYI CNVNHKPSNT KVDKRVEPKS CDKTHTCPPC PAPELLGGPS
VFLFPPKPKD TLMISRTPEV TCVVVDVSHE DPEVKFNWYV DGVEVHNAKT KPREEQYNST
YRVVSVLTVL HQDWLNGKEY KCKVSNKALP APIEKTISKA KGQPREPQVY TLPPSRDELT
KNQVSLTCLV KGFYPSDIAV EWESNGQPEN NYKTTPPVLD SDGSFFLYSK LTVDKSRWQQ
GNVFSCSVMH EALHNHYTQKSLSLSPGK *GGGGSGGGGSGGGGS* PGWFLDSPDR
PWNPPTFSPA LLVVTEGDNA TFTCSFSNTS ESFVLNWYRM SPSNQTDKLA AFPEDRSQPG
QDCRFRVTQL PNGRDFHMSV VRARRNDSGT YLCGAISLAP KAQIKESLRA ELRVTERRAE
VPTAHPSPSP RPAGQFQTLV

Anti-CTLA-4 light chain (SEQ ID NO: 74):
<u>EIVLTQSPGT LSLSPGERAT LSCRASQSVG SSYLAWYQQK PGQAPRLLIY GAFSRATGIP</u>
<u>DRFSGSGSGT DFTLTISRLE PEDFAVYYCQ QYGSSPWTFG QGTKVEIKRT</u> VAAPSVFIFP
PSDEQLKSGT ASVVCLLNNF YPREAKVQWK VDNALQSGNS QESVTEQDSK DSTYSLSSTL
TLSKADYEKH KVYACEVTHQ GLSSPVTKSF NRGEC Underlined: Anti-CTLA-4 Variable region
    Plain: Anti-CTLA-4 Constant region
    *Italic: Linker*
    Bold: PD-1 ectodomain

Fig. 17

Fusion proteins comprising anti-CD25 antibody and PD-1 Ectodomain.

Anti-CD25 (Daclizumab) heavy chain and PD-1 ectodomain (SEQ ID NO: 20):
QVQLVQSGAE VKKPGSSVKV SCKASGYTFT SYRMHWVRQA PGQGLEWIGY INPSTGYTEY
NQKFKDKATI TADESTNTAY MELSSLRSED TAVYYCARGG GVFDYWGQGT LVTVSSASTK
GPSVFPLAPS SKSTSGGTAA LGCLVKDYFP EPVTVSWNSG ALTSGVHTFP AVLQSSGLYS
LSSVVTVPSS SLGTQTYICN VNHKPSNTKV DKKVEPKSCD KTHTCPPCPA PELLGGPSVF
LFPPKPKDTL MISRTPEVTC VVVDVSHEDP EVKFNWYVDG VEVHNAKTKP REEQYNSTYR
VVSVLTVLHQ DWLNGKEYKC KVSNKALPAP IEKTISKAKG QPREPQVYTL PPSRDELTKN
QVSLTCLVKG FYPSDIAVEW ESNGQPENNY KTTPPVLDSD GSFFLYSKLT VDKSRWQQGN
VFSCSVMHEA LHNHYTQKSL SLSPGK *GGGGSGGGGSGGGGS*
PGWFLDSPDRPWNPPTFSPALLVVTEGDNATFTCSFSNT
SESFVLNWYRMSPSNQTDKLAAFPEDRSQPGQDCRFRVTQLPNGRDFHMSVVRAR
RNDSGTYLCGAISLAPKAQIKESLRAELRVTERRAEVPTAHPSPSPRPAGQFQTLV

Anti-CD25 (Daclizumab) light chain (SEQ ID NO: 75):
DIQMTQSPST LSASVGDRVT ITCSASSSIS YMHWYQQKPG KAPKLLIYTT SNLASGVPAR
FSGSGSGTEF TLTISSLQPD DFATYYCHQR STYPLTFGQG TKVEVKRTVA APSVFIFPPS
DEQLKSGTAS VVCLLNNFYP REAKVQWKVD NALQSGNSQE SVTEQDSKDS TYSLSSTLTL
SKADYEKHKV YACEVTHQGL SSPVTKSFNR GEC Plain: Anti-CD25 antibody
*Italic: Linker*
Bold: PD-1 ectodomain

Fig. 18A

Anti-CD25 (Basiliximab) heavy chain and PD-1 ectodomain (SEQ ID NO: 21):
QLQQSGTVLA RPGASVKMSC KASGYSFTRY WMHWIKQRPG QGLEWIGAIY PGNSDTSYNQ
KFEGKAKLTA VTSASTAYME LSSLTHEDSA VYYCSRDYGY YFDFWGQGTT LTVSSASTKG
PSVFPLAPSS KSTSGGTAAL GCLVKDYFPE PVTVSWNSGA LTSGVHTFPA VLQSSGLYSL
SSVVTVPSSS LGTQTYICNV NHKPSNTKVD KRVEPKSCDK THTCPPCPAP ELLGGPSVFL
FPPKPKDTLM ISRTPEVTCV VVDVSHEDPE VKFNWYVDGV EVHNAKTKPR EEQYNSTYRV
VSVLTVLHQD WLNGKEYKCK VSNKALPAPI EKTISKAKGQ PREPQVYTLP PSRDELTKNQ
VSLTCLVKGF YPSDIAVEWE SNGQPENNYK TTPPVLDSDG SFFLYSKLTV DKSRWQQGNV
FSCSVMHEAL HNHYTQKSLS LSPGK *GGGGSGGGGSGGGGS*
PGWFLDSPDRPWNPPTFSPALLVVTEGDNATFTCSFSNT
SESFVLNWYRMSPSNQTDKLAAFPEDRSQPGQDCRFRVTQLPNGRDFHMSVVRAR
RNDSGTYLCGAISLAPKAQIKESLRAELRVTERRAEVPTAHPSPSRPAGQFQTLV

Anti-CD25 (Basiliximab) light chain (SEQ ID NO: 76):
QIVSTQSPAI MSASPGEKVT MTCSASSSRS YMQWYQQKPG TSPKRWIYDT SKLASGVPAR
FSGSGSGTSY SLTISSMEAE DAATYYCHQR SSYTFGGGTK LEIKRTVAAP SVFIFPPSDE
QLKSGTASVV CLLNNFYPRE AKVQWKVDNA LQSGNSQESV TEQDSKDSTY SLSSTLTLSK
ADYEKHKVYA CEVTHQGLSS PVTKSFNRGEC Plain: Anti-CD25 antibody
  *Italic: Linker*
  Bold: PD-1 ectodomain

Fig. 18B

Fusion proteins comprising IL-2, Fc, and PD-1 ectodomain.

IL-2 + Fc + PD-1 ectodomain (SEQ ID NO: 16):

<u>APTSSSTKKTQLQLEHLLLDLQMILNGINNYKNPKLTRMLTFKFYMPKKATELKHLQCLEEELKPL
EEVLNLAQSKNFHLRPRDLISNINVIVLELKGSETTFMCEYADETATIVEFLNRWITFCQSIISTL
T</u> *GGGGSGGGGSGGGGS*
THTCPPCPAPELLGGPSVFLFPPKPKDTLMISRTPEVTCVVVDVSH<u>E</u>DPEVKFNWYVDGVEVHNAK
TKPREEQYNSTYRVVSVLTVLHQDWLNGKEYKCKVSNKALPAPIEKTISKAKGQPREPQVYTLPPS
R<u>EEM</u>TKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
**PGWFLDSPDRPWNPPTFSPALLVVTEGDNATFTCSFSNTSESFVLNWYRMSPSNQTDKLAAFPEDR
SQPGQDCRFRVTQLPNGRDFHMSVVRARRNDSGTYLCGAISLAPKAQIKESLRAELRVTERRAEVP
TAHPSPSPRPAGQFQTLV**

PD-1 ectodomain + Fc + IL-2 (SEQ ID NO: 23):

**PGWFLDSPDRPWNPPTFSPALLVVTEGDNATFTCSFSNTSESFVLNWYRMSPSNQTDKLAAFPEDR
SQPGQDCRFRVTQLPNGRDFHMSVVRARRNDSGTYLCGAISLAPKAQIKESLRAELRVTERRAEVP
TAHPSPSPRPAGQFQTLV** *GGGGSGGGGSGGGGS*
THTCPPCPAPELLGGPSVFLFPPKPKDTLMISRTPEVTCVVVDVSH<u>E</u>DPEVKFNWYVDGVEVHNAK
TKPREEQYNSTYRVVSVLTVLHQDWLNGKEYKCKVSNKALPAPIEKTISKAKGQPREPQVYTLPPS
R<u>EEM</u>TKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
<u>APTSSSTKKTQLQLEHLLLDLQMILNGINNYKNPKLTRMLTFKFYMPKKATELKHLQCLEEELKPL
EEVLNLAQSKNFHLRPRDLISNINVIVLELKGSETTFMCEYADETATIVEFLNRWITFCQSIISTL
T</u>

> <u>Underlined</u>: IL-2 fragment
> *Italic*: Linker
> Plain: Fc
> Bold: human PD-1 ectodomain
> (Note: Can replace optional linker 1 *GGGGSGGGGSGGGGS* SEQ ID NO: 104 with *EPKSCDK* SEQ ID NO: 105)
> (Note: Can replace underlined aa in Fc: <u>E</u> with D and <u>M</u> with L)

Fig. 19

Fusion proteins comprising anti-CD4 antibody and PD-1 Extracellular domain

Anti-CD4 heavy chain and PD-1 Extracellular domain (SEQ ID NO: 24):
Heavy chain fusion protein:

QVQLQEAGPGLVKPSETLSLTCSVSGGSISGDYYWFWIRQSPGKGLEWIGYIYGSGGGTNYNPSLN
NRVSISIDTSKNLFSLKLRSVTAADTAVYYCASNILKYLHWLLYWGQGVLVTVSSASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK

*GGGGSGGGGSGGGGS*

**PGWFLDSPDRPWNPPTFSPALLVVTEGDNATFTCSFSNTSESFVLNWYRMSPSNQTDKLAAFPEDR
SQPGQDCRFRVTQLPNGRDFHMSVVRARRNDSGTYLCGAISLAPKAQIKESLRAELRVTERRAEVP
TAHPSPSPRPAGQFQTLV**

Anti-CD4 light chain (SEQ ID NO: 77):

Light chain:

SYELSQPRSVSVSPGQTAGFTCGGDNVGRKSVQWYQQKPPQAPVLVIYADSERPSGIPARFSGSNS
GNTATLTISGVEAGDEADYYCQVWDSTADHWVFGGGTRLTVLGRTVAAPSVFIFPPSDEQLKSGTA
SVVCLLNNFYPREAKVQWKVDNALQSGNSQESVTEQDSKDSTYSLSSTLTLSKADYEKHKVYACEV
THQGLSSPVTKSFNRGEC

Plain: Anti-CD4 antibody (Variable region – underlined)

*Italic: Linker*

Bold: PD-1 ectodomain

Fig. 20

Fusion proteins comprising PD-1 Ectodomain, Fc, and Receptor activator of nuclear factor-κB (RANK) Extracellular domain (ectodomain):

RANK ectodomain – Fc – PD-1 ectodomain (SEQ. ID. NO: 25):

<u>QI APPCTSEKHY EHLGRCCNKC EPGKYMSSKC TTTSDSVCLP CGPDEYLDSW NEEDKCLLHK</u>
<u>VCDTGKALVA VVAGNSTTPR RCACTAGYHW SQDCECCRRN TECAPGLGAQ HPLQLNKDTV</u>
<u>CKPCLAGYFS DAFSSTDKCR PWTNCTFLGK RVEHHGTEKS DAVCSSSLPA RKPPNEPHVY LPG</u>
*GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
PGWFLDSPDRPWNPPTFSPALLVVTEGDNATFTCSFSNTSESFVLNWYRMSPSNQTDKLAAFPEDR
SQPGQDCRFRVTQLPNGRDFHMSVVRARRNDSGTYLCGAISLAPKAQIKESLRAELRVTERRAEVP
TAHPSPSRPAGQFQTLV

PD-1 ectodomain – Fc – RANK ectodomain (SEQ. ID. NO: 26):

PGWFLDSPDRPWNPPTFSPALLVVTEGDNATFTCSFSNTSESFVLNWYRMSPSNQTDKLAAFPEDR

SQPGQDCRFRVTQLPNGRDFHMSVVRARRNDSGTYLCGAISLAPKAQIKESLRAELRVTERRAEVP

TAHPSPSRPAGQFQTLV*GGGGSGGGGSGGGGS*

THTCPPCPAPELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFFLYSKLTVDKSRWQQG

NVFSCSVMHEALHNHYTQKSLSLSPGK *GGGGSGGGGSGGGGS* <u>QI APPCTSEKHY EHLGRCCNKC</u>

<u>EPGKYMSSKC TTTSDSVCLP CGPDEYLDSW NEEDKCLLHK VCDTGKALVA VVAGNSTTPR</u>

<u>RCACTAGYHW SQDCECCRRN TECAPGLGAQ HPLQLNKDTV CKPCLAGYFS DAFSSTDKCR</u>

<u>PWTNCTFLGK RVEHHGTEKS DAVCSSSLPA RKPPNEPHVY LPG</u>

Bold: PD-1 ectodomain
*Italics: Linker (optional: may delete linker 1 or replace with IEGRDMD or EPKSCDK)*
Plain: IgG1 Fc
<u>Underlined:    RANK ectodomain</u>

Fig. 21

Moieties that bind Receptor activator of nuclear factor-κB (RANK) ligand

(i)    Full-length RANK (TNFRSF11A) or fragment thereof (SEQ. ID. NO: 95):

```
  1   MAPRARRRRP  LFALLLLCAL  LARLQVALQI  APPCTSEKHY  EHLGRCCNKC  EPGKYMSSKC
 61   TTTSDSVCLP  CGPDEYLDSW  NEEDKCLLHK  VCDTGKALVA  VVAGNSTTPR  RCACTAGYHW
121   SQDCECCRRN  TECAPGLGAQ  HPLQLNKDTV  CKPCLAGYFS  DAFSSTDKCR  PWTNCTFLGK
181   RVEHHGTEKS  DAVCSSSLPA  RKPPNEPHVY  LPGLIILLLF  ASVALVAAII  FGVCYRKKGK
241   ALTANLWHWI  NEACGRLSGD  KESSGDSCVS  THTANFGQQG  ACEGVLLLTL  EEKTFPEDMC
301   YPDQGGVCQG  TCVGGGPYAQ  GEDARMLSLV  SKTEIEEDSF  RQMPTEDEYM  DRPSQPTDQL
361   LFLTEPGSKS  TPPFSEPLEV  GENDSLSQCF  TGTQSTVGSE  SCNCTEPLCR  TDWTPMSSEN
421   YLQKEVDSGH  CPHWAASPSP  NWADVCTGCR  NPPGEDCEPL  VGSPKRGPLP  QCAYGMGLPP
481   EEEASRTEAR  DQPEDGADGR  LPSSARAGAG  SGSSPGGQSP  ASGNVTGNSN  STFISSGQVM
541   NFKGDIIVVY  VSQTSQEGAA  AAAEPMGRPV  QEETLARRDS  FAGNGPRFPD  PCGGPEGLRE
601   PEKASRPVQE  QGGAKA
```

Bold: RANK extracellular domain (RANK ligand-binding domain)

(ii)    RANK extracellular domain (ectodomain) or fragment thereof (SEQ. ID. NO: 96):

QI APPCTSEKHY EHLGRCCNKC EPGKYMSSKC TTTSDSVCLP CGPDEYLDSW NEEDKCLLHK VCDTGKALVA VVAGNSTTPR RCACTAGYHW SQDCECCRRN TECAPGLGAQ HPLQLNKDTV CKPCLAGYFS DAFSSTDKCR PWTNCTFLGK RVEHHGTEKS DAVCSSSLPA RKPPNEPHVY LPG (iii)    Peptide sequences in RANKL binding domains of RANK or peptides containing key RANKL-binding residues of RANK (SEQ. ID. NO: 97):

```
  1   MAPRARRRRP  LFALLLLCAL  LARLQVALQI  APPCTSEKHY  EHLGRCCNKC  EPGKYMSSKC
 61   TTTSDSVCLP  CGPDEYLDSW  NEEDKCLLHK  VCDTGKALVA  VVAGNSTTPR  RCACTAGYHW
121   SQDCECCRRN  TECAPGLGAQ  HPLQLNKDTV  CKPCLAGYFS  DAFSSTDKCR  PWTNCTFLGK
181   RVEHHGTEKS  DAVCSSSLPA  RKPPNEPHVY  LPG
```

Bold: RANK extracellular domain (RANK ligand-binding domain)
        RANK peptide sequences (Underlined) and residues (Italics) involved in binding RANKL.

(iv).    Mutant of RANK or a fragment thereof which binds Receptor activator of nuclear factor-κB (RANK) ligand (RANKL)

(v)    Full-length Osteoprotegerin (OPG, TNFRSF11B) or fragment thereof (SEQ. ID. NO: 98):

```
  1   MNKLLCCALV  FLDISIKWTT  QETFPPKYLH  YDEETSHQLL  CDKCPPGTYL  KQHCTAKWKT
 61   VCAPCPDHYY  TDSWHTSDEC  LYCSPVCKEL  QYVKQECNRT  HNRVCECKEG  RYLEIEFCLK
121   HRSCPPGFGV  VQAGTPERNT  VCKRCPDGFF  SNETSSKAPC  RKHTNCSVFG  LLLTQKGNAT
181   HDNICSGNSE  STQKCGIDVT  LCEEAFFRFA  VPTKFTPNWL  SVLVDNLPGT  KVNAESVERI
241   KRQHSSQEQT  FQLLKLWKHQ  NKAQDIVKKI  IQDIDLCENS  VQRHIGHANL  TFEQLRSLME
301   SLPGKKVGAE  DIEKTIKACK  PSDQILKLLS  LWRIKNGDQD  TLKGLMHALK  HSKTYHFPKT
361   VTQSLKKTIR  FLHSFTMYKL  YQKLFLEMIG  NQVQSVKISC  L
```

Bold: RANK ligand-binding domain

Fig. 22

Fusion proteins comprising Anti-HER2/neu antibody and Receptor activator of nuclear factor–κB (RANK) Extracellular domain (ECD).

Anti-HER2/neu heavy chain+ RANK ECD fusion amino acid sequence (SEQ. ID. NO: 27):

<u>EVQLVESGGGLVQPGGSLRLSCAASGFNIKDTYIHWVRQAPGKGLEWVARIYPTNGYTRYADSVKGRFTISA</u>
<u>DTSKNTAYLQMNSLRAEDTAVYYCSRWGGDGFYAMDYWGQGTLVTVSS</u>ASTKGPSVFPLAPSSKSTSGGTAA
LGCLVKDYFPEPVTVSWNSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRWQQGNVFSCSVMH
EALHNHYTQKSLSLSPGK *GGGGSGGGGSGGGGS* QI APPCTSEKHY EHLGRCCNKC EPGKYMSSKC
TTTSDSVCLP CGPDEYLDSW NEEDKCLLHK VCDTGKALVA VVAGNSTTPR RCACTAGYHW
SQDCECCRRN TECAPGLGAQ HPLQLNKDTV CKPCLAGYFS DAFSSTDKCR PWTNCTFLGK
RVEHHGTEKS DAVCSSSLPA RKPPNEPHVY LPG

Anti-HER2/neu light chain amino acid sequence (SEQ. ID. NO: 70):

<u>DIQMTQSPSSLSASVGDRVTITCRASQDVNTAVAWYQQKPGKAPKLLIYSASFLYSGVPSRFSGSRSGTDFT</u>
<u>LTISSLQPEDFATYYCQQHYTTPPTFGQGTKVEIK</u>RTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGEC

<u>Underlined:</u> Anti-HER2 antibody variable region
Plain: Anti-HER2 antibody constant region
*Italics:* Linker
Bold: RANK ectodomain

Fig. 23

Fusion proteins comprising Anti-EGFR1 antibody and Receptor activator of nuclear factor-κB (RANK) Extracellular domain (ECD).

Anti-EGFR1 heavy chain + RANK ECD fusion amino acid sequence (SEQ. ID. NO: 28):

<u>QVQLKQSGPGLVQPSQSLSITCTVSGFSLTNYGVHWVRQSPGKGLEWLGVIWSGGNTDYNTPFTSRLSINKD</u>
<u>NSKSQVFFKMNSLQSNDTAIYYCARALTYYDYEFAYWGQGTLVTVSA</u>ASTKGPSVFPLAPSSKSTSGGTAAL
GCLVKDYFPEPVTVSWNSGALTSGVHTFPAVLQSSGLYSLSSVVTVPSSSLGTQTYICNVNHKPSNTKVDKR
VEPKSCDKTHTCPPCPAPELLGGPSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQQGNVFSCSVMHE
ALHNHYTQKSLSLSPGK *GGGGSGGGGSGGGGS* QI APPCTSEKHY EHLGRCCNKC EPGKYMSSKC
TTTSDSVCLP CGPDEYLDSW NEEDKCLLHK VCDTGKALVA VVAGNSTTPR RCACTAGYHW
SQDCECCRRN TECAPGLGAQ HPLQLNKDTV CKPCLAGYFS DAFSSTDKCR PWTNCTFLGK
RVEHHGTEKS DAVCSSSLPA RKPPNEPHVY LPG

Anti-EGFR1 light chain amino acid sequence (SEQ. ID. NO: 71):

<u>DILLTQSPVILSVSPGERVSFSCRASQSIGTNIHWYQQRTNGSPRLLIKYASESISGIPSRFSGSGSGTDFT</u>
<u>LSINSVESEDIADYYCQQNNNWPTTFGAGTKLELK</u>RTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGEC

<u>Underlined</u>: Anti-EGFR antibody variable region
Plain: Anti-EGFR antibody constant region
Italics: Linker
Bold: RANK ectodomain

Fig. 24

Fusion proteins comprising Anti-CD20 antibody and Receptor activator of nuclear factor–κB (RANK) Extracellular domain (ECD).

Anti-CD20 heavy chain+ RANK ECD fusion amino acid sequence (SEQ. ID. NO: 29):

<u>QVQLQQPGAELVKPGASVKMSCKASGYTFTSYNMHWVKQTPGRGLEWIGAIYPGNGDTSYNQKFKGKATLTA</u>
<u>DKSSSTAYMQLSSLTSEDSAVYYCARSTYYGGDWYFNVWGAGTTVTVSA</u>ASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVD
KKAEPKSCDKTHTCPPCPAPELLGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKSRWQQGNVFSCSVM
HEALHNHYTQKSLSLSPGK *GGGGSGGGGSGGGGS* QI APPCTSEKHY EHLGRCCNKC EPGKYMSSKC
TTTSDSVCLP CGPDEYLDSW NEEDKCLLHK VCDTGKALVA VVAGNSTTPR RCACTAGYHW
SQDCECCRRN TECAPGLGAQ HPLQLNKDTV CKPCLAGYFS DAFSSTDKCR PWTNCTFLGK
RVEHHGTEKS DAVCSSSLPA RKPPNEPHVY LPG

Anti-CD20 light chain amino acid sequence (SEQ. ID. NO: 72):

<u>QIVLSQSPAILSASPGEKVTMTCRASSSVSYIHWFQQKPGSSPKPWIYATSNLASGVPVRFSGSGSGTSYSL</u>
<u>TISRVEAEDAATYYCQQWTSNPPTFGGGTKLEIKR</u>TVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSFNRGEC

<u>Underlined</u>: Anti-CD20 antibody variable region
Plain: Anti-CD20 antibody constant region
*Italics*: Linker
Bold: RANK ectodomain

Fig. 25

Fusion proteins comprising anti-VEGF antibody and Receptor activator of nuclear factor–κB (RANK) Extracellular domain (ECD).

Anti-VEGF heavy chain+ RANK ECD fusion amino acid sequence (SEQ. ID. NO: 30):

<u>EVQLVESGGGLVQPGGSLRLSCAASGYTFTNYGMNWVRQAPGKGLEWVGWINTYTGEPTYAADF</u>
<u>KRRFTFSLDTSKSTAYLQMNSLRAEDTAVYYCAKYPHYYGSSHWYFDVWGQGTLVTVSS</u>ASTKG
PSVFPLAPSSKSTSGGTAALGCLVKDYFPEPVTVSWNSGALTSGVHTFPAVLQSSGLYSLSSVVTVP
SSSLGTQTYICNVNHKPSNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHYTQKSLSLSPGK
*GGGGSGGGGSGGGGS* QI APPCTSEKHY EHLGRCCNKC EPGKYMSSKC TTTSDSVCLP
CGPDEYLDSW NEEDKCLLHK VCDTGKALVA VVAGNSTTPR RCACTAGYHW SQDCECCRRN
TECAPGLGAQ HPLQLNKDTV CKPCLAGYFS DAFSSTDKCR PWTNCTFLGK RVEHHGTEKS
DAVCSSSLPA RKPPNEPHVY LPG

Anti-VEGF Light chain sequence (SEQ. ID. NO: 73):

<u>DIQMTQSPSSLSASVGDRVTITCSASQDISNYLNWYQQKPGKAPKVLIYFTSSLHSGVPSRFSGSGSG</u>
<u>TDFTLTISSLQPEDFATYYCQQYSTVPWTFGQGTKVEIK</u>RTVAAPSVFIFPPSDEQLKSGTASVVCLL
NNFYPREAKVQWKVDNALQSGNSQESVTEQDSKDSTYSLSSTLTLSKADYEKHKVYACEVTHQGL
SSPVTKSFNRGEC

<u>Underlined: Anti-VEGF antibody variable region</u>
Plain: Anti-VEGF antibody constant region
Italics: Linker
Bold: RANK ectodomain

Fig. 26

Fusion proteins comprising anti-human CTLA-4 antibody and Receptor activator of nuclear factor–κB (RANK) Extracellular domain (ECD).

Anti-CTLA-4 heavy chain + RANK ECD fusion sequence (SEQ. ID. NO: 31):

<u>QVQLVESGGG VVQPGRSLRL SCAASGFTFS SYTMHWVRQA PGKGLEWVTF ISYDGNNKYY</u>
<u>ADSVKGRFTI SRDNSKNTLY LQMNSLRAED TAIYYCARTG WLGPFDYWGQ GTLVTVSSAS</u>
TKGPSVFPLA PSSKSTSGGT AALGCLVKDY FPEPVTVSWN SGALTSGVHT FPAVLQSSGL
YSLSSVVTVP SSSLGTQTYI CNVNHKPSNT KVDKRVEPKS CDKTHTCPPC PAPELLGGPS
VFLFPPKPKD TLMISRTPEV TCVVVDVSHE DPEVKFNWYV DGVEVHNAKT KPREEQYNST
YRVVSVLTVL HQDWLNGKEY KCKVSNKALP APIEKTISKA KGQPREPQVY TLPPSRDELT
KNQVSLTCLV KGFYPSDIAV EWESNGQPEN NYKTTPPVLD SDGSFFLYSK LTVDKSRWQQ
GNVFSCSVMH EALHNHYTQK SLSLSPGK *GGGGSGGGGSGGGGS* QI APPCTSEKHY EHLGRCCNKC
EPGKYMSSKC TTTSDSVCLP CGPDEYLDSW NEEDKCLLHK VCDTGKALVA VVAGNSTTPR
RCACTAGYHW SQDCECCRRN TECAPGLGAQ HPLQLNKDTV CKPCLAGYFS DAFSSTDKCR
PWTNCTFLGK RVEHHGTEKS DAVCSSSLPA RKPPNEPHVY LPG

Anti-CTLA-4 light chain (SEQ. ID. NO: 74):

<u>EIVLTQSPGT LSLSPGERAT LSCRASQSVG SSYLAWYQQK PGQAPRLLIY GAFSRATGIP</u>
<u>DRFSGSGSGT DFTLTISRLE PEDFAVYYCQ QYGSSPWTFG QGTKVEIKRT</u> VAAPSVFIFP
PSDEQLKSGT ASVVCLLNNF YPREAKVQWK VDNALQSGNS QESVTEQDSK DSTYSLSSTL
TLSKADYEKH KVYACEVTHQ GLSSPVTKSF NRGEC

<u>Underlined: Anti-CTLA-4 antibody variable region</u>
Plain: Anti-CTLA-4 antibody constant region
*Italics: Linker*
Bold: RANK ectodomain

Fig. 27

Fusion proteins comprising anti-CD25 antibody and Receptor activator of nuclear factor-κB (RANK) Extracellular domain (ECD).

Anti-CD25 and RANK ectodomain - Heavy chain (SEQ. ID. NO: 32):

QVQLVQSGAE VKKPGSSVKV SCKASGYTFT SYRMHWVRQA PGQGLEWIGY INPSTGYTEY
NQKFKDKATI TADESTNTAY MELSSLRSED TAVYYCARGG GVFDYWGQGT LVTVSSASTK
GPSVFPLAPS SKSTSGGTAA LGCLVKDYFP EPVTVSWNSG ALTSGVHTFP AVLQSSGLYS
LSSVVTVPSS SLGTQTYICN VNHKPSNTKV DKKVEPKSCD KTHTCPPCPA PELLGGPSVF
LFPPKPKDTL MISRTPEVTC VVVDVSHEDP EVKFNWYVDG VEVHNAKTKP REEQYNSTYR
VVSVLTVLHQ DWLNGKEYKC KVSNKALPAP IEKTISKAKG QPREPQVYTL PPSRDELTKN
QVSLTCLVKG FYPSDIAVEW ESNGQPENNY KTTPPVLDSD GSFFLYSKLT VDKSRWQQGN
VFSCSVMHEA LHNHYTQKSL SLSPGK *GGGGSGGGGSGGGGS* QI APPCTSEKHY EHLGRCCNKC
EPGKYMSSKC TTTSDSVCLP CGPDEYLDSW NEEDKCLLHK VCDTGKALVA VVAGNSTTPR
RCACTAGYHW SQDCECCRRN TECAPGLGAQ HPLQLNKDTV CKPCLAGYFS DAFSSTDKCR
PWTNCTFLGK RVEHHGTEKS DAVCSSSLPA RKPPNEPHVY LPG

Anti-CD25 - Light chain (SEQ. ID. NO. 75):

DIQMTQSPST LSASVGDRVT ITCSASSSIS YMHWYQQKPG KAPKLLIYTT SNLASGVPAR
FSGSGSGTEF TLTISSLQPD DFATYYCHQR STYPLTFGQG TKVEVKRTVA APSVFIFPPS
DEQLKSGTAS VVCLLNNFYP REAKVQWKVD NALQSGNSQE SVTEQDSKDS TYSLSSTLTL
SKADYEKHKV YACEVTHQGL SSPVTKSFNR GEC

Plain: Anti-CD25 antibody

*Italics: Linker*

Bold: RANK ectodomain

Fig. 28A

Fusion proteins comprising anti-CD25 antibody and Receptor activator of nuclear factor–κB (RANK) Extracellular domain (ECD).

Anti-CD25 and RANK ectodomain - Heavy chain (SEQ. ID. NO: 33):

QLQQSGTVLA RPGASVKMSC KASGYSFTRY WMHWIKQRPG QGLEWIGAIY PGNSDTSYNQ
KFEGKAKLTA VTSASTAYME LSSLTHEDSA VYYCSRDYGY YFDFWGQGTT LTVSSASTKG
PSVFPLAPSS KSTSGGTAAL GCLVKDYFPE PVTVSWNSGA LTSGVHTFPA VLQSSGLYSL
SSVVTVPSSS LGTQTYICNV NHKPSNTKVD KRVEPKSCDK THTCPPCPAP ELLGGPSVFL
FPPKPKDTLM ISRTPEVTCV VVDVSHEDPE VKFNWYVDGV EVHNAKTKPR EEQYNSTYRV
VSVLTVLHQD WLNGKEYKCK VSNKALPAPI EKTISKAKGQ PREPQVYTLP PSRDELTKNQ
VSLTCLVKGF YPSDIAVEWE SNGQPENNYK TTPPVLDSDG SFFLYSKLTV DKSRWQQGNV
FSCSVMHEAL HNHYTQKSLS LSPGK *GGGGSGGGGSGGGGS* QI APPCTSEKHY EHLGRCCNKC
EPGKYMSSKC TTTSDSVCLP CGPDEYLDSW NEEDKCLLHK VCDTGKALVA VVAGNSTTPR
RCACTAGYHW SQDCECCRRN TECAPGLGAQ HPLQLNKDTV CKPCLAGYFS DAFSSTDKCR
PWTNCTFLGK RVEHHGTEKS DAVCSSSLPA RKPPNEPHVY LPG

Anti-CD25 – Light chain (SEQ. ID. NO: 76):

QIVSTQSPAI MSASPGEKVT MTCSASSSRS YMQWYQQKPG TSPKRWIYDT SKLASGVPAR
FSGSGSGTSY SLTISSMEAE DAATYYCHQR SSYTFGGGTK LEIKRTVAAP SVFIFPPSDE
QLKSGTASVV CLLNNFYPRE AKVQWKVDNA LQSGNSQESV TEQDSKDSTY SLSSTLTLSK
ADYEKHKVYA CEVTHQGLSS PVTKSFNRGEC

Plain: Anti-CD25 antibody
*Italics: Linker*
Bold: RANK ectodomain

Fig. 28B

Fusion proteins comprising IL-2, Fc, and Receptor activator of nuclear factor–κB (RANK) Extracellular domain (ECD).

IL2 – Fc – RANK ECD (SEQ. ID. NO: 34):

<u>APTSSSTKKTQLQLEHLLLDLQMILNGINNYKNPKLTRMLTFKFYMPKKATELKHLQCLEEELKPLEEVLNL</u>
<u>AQSKNFHLRPRDLISNINVIVLELKGSETTFMCEYADETATIVEFLNRWITFCQSIISTLT</u>*GGGGSGGGGSG*
*GGGS*THTCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVYTLPPSR<u>E</u>EMTKNQ
VSLTCLVKGFYPSDIAVEWESNGQPENNYKTTPPVLDSDGSFFLYSKLTVDKSRWQQGNVFSCSVMHEALHN
HYTQKSLSLSPGK *GGGGSGGGGSGGGGS* QI APPCTSEKHY EHLGRCCNKC EPGKYMSSKC
TTTSDSVCLP CGPDEYLDSW NEEDKCLLHK VCDTGKALVA VVAGNSTTPR RCACTAGYHW
SQDCECCRRN TECAPGLGAQ HPLQLNKDTV CKPCLAGYFS DAFSSTDKCR PWTNCTFLGK
RVEHHGTEKS DAVCSSSLPA RKPPNEPHVY LPG

RANK ECD – Fc – IL-2 (SEQ. ID. NO: 35):

QI APPCTSEKHY EHLGRCCNKC EPGKYMSSKC TTTSDSVCLP CGPDEYLDSW NEEDKCLLHK
VCDTGKALVA VVAGNSTTPR RCACTAGYHW SQDCECCRRN TECAPGLGAQ HPLQLNKDTV
CKPCLAGYFS DAFSSTDKCR PWTNCTFLGK RVEHHGTEKS DAVCSSSLPA RKPPNEPHVY LPG
*GGGGSGGGGSGGGGS*THTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTISKAKGQPREPQVYTL
PPSR<u>E</u>EMTKNQVSLTCLVKGFYPSDIAVEWESNGQPENNYKTTPPVLDSDGSFFLYSKLTVDKSRWQQGNVF
SCSVMHEALHNHYTQKSLSLSPGK*GGGGSGGGGSGGGGS*<u>APTSSSTKKTQLQLEHLLLDLQMILNGINNYKN</u>
<u>PKLTRMLTFKFYMPKKATELKHLQCLEEELKPLEEVLNLAQSKNFHLRPRDLISNINVIVLELKGSETTFMC</u>
<u>EYADETATIVEFLNRWITFCQSIISTLT</u>

Bold: RANK ectodomain
*Italics: Linker* (Optional; any linker sequence)
Plain: Fc
<u>Underlined: IL2 fragment that binds CD25 (IL-2Rα)</u>

(Can replace linker 1 with <u>EPKSCDK</u> or <u>IEGRDMD</u>)
(Can replace underlined aa in Fc: <u>E</u> with D and <u>M</u> with L)

Fig. 29

Fusion protein comprising anti-CD4 antibody and Receptor activator of nuclear factor-κB (RANK) Extracellular domain (ECD)

Anti-CD4 heavy chain and RANK Extracellular domain (SEQ ID NO: 36):
Heavy chain fusion protein:

QVQLQEAGPGLVKPSETLSLTCSVSGGSISGDYYWFWIRQSPGKGLEWIGYIYGSGGGTNYNPSLN

NRVSISIDTSKNLFSLKLRSVTAADTAVYYCASNILKYLHWLLYWGQGVLVTVSSASTKGPSVFPL

APSSKSTSGGTAALGCLVKDYFPEPVTVSWNSGALTSGVHTFPAVLQSSGLYSLSSVVTVPSSSLG

TQTYICNVNHKPSNTKVDKRVEPKSCDKTHTCPPCPAPELLGGPSVFLFPPKPKDTLMISRTPEVT

CVVVDVSHEDPEVKFNWYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGK

*GGGGSGGGGSGGGGS* QI APPCTSEKHY EHLGRCCNKC EPGKYMSSKC TTTSDSVCLP

CGPDEYLDSW NEEDKCLLHK VCDTGKALVA VVAGNSTTPR RCACTAGYHW SQDCECCRRN

TECAPGLGAQ HPLQLNKDTV CKPCLAGYFS DAFSSTDKCR PWTNCTFLGK RVEHHGTEKS

DAVCSSSLPA RKPPNEPHVY LPG

Anti-CD4 light chain (SEQ ID NO: 77):

Light chain:

SYELSQPRSVSVSPGQTAGFTCGGDNVGRKSVQWYQQKPPQAPVLVIYADSERPSGIPARFSGSNS

GNTATLTISGVEAGDEADYYCQVWDSTADHWVFGGGTRLTVLGRTVAAPSVFIFPPSDEQLKSGTA

SVVCLLNNFYPREAKVQWKVDNALQSGNSQESVTEQDSKDSTYSLSSTLTLSKADYEKHKVYACEV

THQGLSSPVTKSFNRGEC

Underlined: Anti-CD4 antibody variable region

Plain: Anti-CD4 antibody constant region

*Italic: Linker*

Bold: PD-1 ectodomain

Fig. 30

(i) Full-length human PD-1 ligand 1 (B7-H1; PDCD1L1; PDL1; CD274) protein or a fragment thereof (SEQ ID NO: 99):

MRIFAVFIFM TYWHLLNAFT VTVPKDLYVV EYGSNMTIEC KFPVEKQLDL AALIVYWEME
DKNIIQFVHG EEDLKVQHSS YRQRARLLKD QLSLGNAALQ ITDVKLQDAG VYRCMISYGG
ADYKRITVKV NAPYNKINQR ILVVDPVTSE HELTCQAEGY PKAEVIWTSS DHQVLSGKTT
TTNSKREEKL FNVTSTLRIN TTTNEIFYCT FRRLDPEENH TAELVIPELP LAHPPNERTH
LVILGAILLC LGVALTFIFR LRKGRMMDVK KCGIQDTNSK KQSDTHLEET (ii) PD-L1 extracellular binding domain (ectodomain) or fragment thereof (SEQ ID NO: 100):

AFT VTVPKDLYVV EYGSNMTIEC KFPVEKQLDL AALIVYWEME DKNIIQFVHG
EEDLKVQHSS YRQRARLLKD QLSLGNAALQ ITDVKLQDAG VYRCMISYGG ADYKRITVKV
NAPYNKINQR ILVVDPVTSE HELTCQAEGY PKAEVIWTSS DHQVLSGKTT TTNSKREEKL
FNVTSTLRIN TTTNEIFYCT FRRLDPEENH TAELVI (iii) Human PD-1 ligand 2 [PD-L2 (B7-DC)] or a fragment thereof.

(iv) Mutant of Programmed Death-1 ligand [PD-L1 (B7-H1) or PD-L2 (B7-DC)] or a fragment thereof which binds Programmed Death-1 (PD-1).

Sequence used in fusion proteins (SEQ ID NO: 101):

RIFAVFIFM TYWHLLNAFT VTVPKDLYVV EYGSNMTIEC KFPVEKQLDL AALIVYWEME
DKNIIQFVHG EEDLKVQHSS YRQRARLLKD QLSLGNAALQ ITDVKLQDAG VYRCMISYGG
ADYKRITVKV NAPYNKINQR ILVVDPVTSE HELTCQAEGY PKAEVIWTSS DHQVLSGKTT
TTNSKREEKL FNVTSTLRIN TTTNEIFYCT FRRLDPEENH TAELVIPELP LAHPPNERTH
LVILGAILLC LGVALTFIFR LRKGRMMDVK KCGIQDTNSK KQSDTHLEET

Bold: PD-L1 extracellular domain (ectodomain)
<u>Underlined Bold</u>: <u>Ligand Binding domain</u>

Fig. 31

Fusion proteins comprising anti-tumor necrosis factor (TNFα) antibody and PD-1 ligand 1 or PD-1 ligand 2

Anti-TNFα heavy chain + PD-L1 (SEQ ID NO: 37):

<u>EVQLVESGGGLVQPGRSLRLSCAASGFTFDDYAMHWVRQAPGKGLEWVSAITWNSGHIDYADSVEG</u>
<u>RFTISRDNAKNSLYLQMNSLRAEDTAVYYCALVSYLSTASSLDYWGQGTLVTVSSA</u>STKGPSVFPL
APSSKSTSGGTAALGCLVKDYFPEPVTVSWNSGALTSGVHTFPAVLQSSGLYSLSSVVTVPSSSLG
TQTYICNVNHKPSNTKVD<u>KKAE</u>PKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS*
RIFAVFIFMTYWHLLNAFTVTVPKDLYVVEYGSNMTIECKFPVEKQLDLAALIVYWEMEDKNIIQF
VHGEEDLKVQHSSYRQRARLLKDQLSLGNAALQITDVKLQDAGVYRCMISYGGADYKRITVKVNAP
YNKINQRILVVDPVTSEHELTCQAEGYPKAEVIWTSSDHQVLSGKTTTTNSKREEKLFNVTSTLRI
NTTTNEIFYCTFRRLDPEENHTAELVIPELPLAHPPNERTHLVILGAILLCLGVALTFIFRLRKGR
MMDVKKCGIQDTNSKKQSDTHLEET

Anti-TNFα light chain (SEQ ID NO: 78):

<u>DIQMTQSPSSLSASVGDRVTITCRASQGIRNYLAWYQQLPGKAPKLLIYAASTLQSGVPSRFSGSG</u>
<u>SGTDFTLTISSLQPEDVATYYCQRYNRAPYTFGQGTKVEIKR</u>TVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC

<u>Underlined</u>: anti-TNFα antibody variable region
    Plain: anti-TNFα antibody constant region
    *Italic: Linker*
    Bold: human PD-1 ligand 1 (PD-L1)
    (Note: Fc region KKAE SEQ ID NO: 106 can be replaced with KRVE SEQ ID NO: 107 or KKVE SEQ ID NO: 108)

Fig. 32

Fusion proteins comprising TNFR2 Extracellular ligand binding domain, Fc, and PD-1 ligand: (TNFR2 ECD + IgG Cγ1 + PD-L1)

TNFR2 ECD + IgG Cγ1 + PD-L1 (SEQ ID NO: 38):

<u>LPAQVAFTPYAPEPGSTCRLREYYDQTAQMCCSKCSPGQHAKVFCTKTSDTVCDSCEDSTYTQLWN
WVPECLSCGSRCSSDQVETQACTREQNRICTCRPGWYCALSKQEGCRLCAPLRKCRPGFGVARPGT
ETSDVVCKPCAPGTFSNTTSSTDICRPHQICNVVAIPGNASMDAVCTSTSPTRSMAPGAVHLPQPV
STRSQHTQPTPEPSTAPSTSFLLPMGPSPPAEGSTGD</u> *EPKSCDK*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
**RIFAVFIFMTYWHLLNAFTVTVPKDLYVVEYGSNMTIECKFPVEKQLDLAALIVYWEMEDKNIIQF
VHGEEDLKVQHSSYRQRARLLKDQLSLGNAALQITDVKLQDAGVYRCMISYGGADYKRITVKVNAP
YNKINQRILVVDPVTSEHELTCQAEGYPKAEVIWTSSDHQVLSGKTTTTNSKREEKLFNVTSTLRI
NTTTNEIFYCTFRRLDPEENHTAELVIPELPLAHPPNERTHLVILGAILLCLGVALTFIFRLRKGR
MMDVKKCGIQDTNSKKQSDTHLEET**

Fusion proteins comprising PD-1 ligand, Fc, and TNFR2 Extracellular ligand binding domain: (PD-L1 + IgG Cγ1 + TNFR2 ECD)

PD-L1 + IgG Cγ1 + TNFR2 ECD (SEQ ID NO: 39):

**MRIFAVFIFMTYWHLLNAFTVTVPKDLYVVEYGSNMTIECKFPVEKQLDLAALIVYWEMEDKNIIQ
FVHGEEDLKVQHSSYRQRARLLKDQLSLGNAALQITDVKLQDAGVYRCMISYGGADYKRITVKVNA
PYNKINQRILVVDPVTSEHELTCQAEGYPKAEVIWTSSDHQVLSGKTTTTNSKREEKLFNVTSTLR
INTTTNEIFYCTFRRLDPEENHTAELVIPELPLAHPPNERTHLVILGAILLCLGVALTFIFR
LRKGRMMDVKKCGIQDTNSKKQSDTHLEET** *GGGGSGGGGSGGGGS EPKSCDK*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
<u>LPAQVAFTPYAPEPGSTCRLREYYDQTAQMCCSKCSPGQHAKVFCTKTSDTVCDSCEDSTYTQLWN
WVPECLSCGSRCSSDQVETQACTREQNRICTCRPGWYCALSKQEGCRLCAPLRKCRPGFGVARPGT
ETSDVVCKPCAPGTFSNTTSSTDICRPHQICNVVAIPGNASMDAVCTSTSPTRSMAPGAVHLPQPV
STRSQHTQPTPEPSTAPSTSFLLPMGPSPPAEGSTGD</u>

> <u>Underlined</u>: TNFR2 ligand-binding domain
> Plain: human IgG1 heavy chain constant region (IgG Cγ1 domain = H, CH2, CH3)
> *Italic: Linker (Linker 1 is optional and may be replaced with another linker such as EPKSCDK or GGGGSGGGGSGGGGS)*
> Bold: human PD-1 ligand 1 or extracellular binding domain of PD-L1

Fig. 33

Fusion proteins comprising anti-CD20 antibody and PD-1 ligand 1 (PD-L1).

Anti-CD20 heavy chain + PD-L1 sequence (SEQ ID NO: 40):
<u>QVQLQQPGAELVKPGASVKMSCKASGYTFTSYNMHWVKQTPGRGLEWIGAIYPGNGDTSYNQKFKG</u>
<u>KATLTADKSSSTAYMQLSSLTSEDSAVYYCARSTYYGGDWYFNVWGAGTTVTVSAA</u>STKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKAEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS*
RIFAVFIFMTYWHLLNAFTVTVPKDLYVVEYGSNMTIECKFPVEKQLDLAALIVYWEMEDKNIIQF
VHGEEDLKVQHSSYRQRARLLKDQLSLGNAALQITDVKLQDAGVYRCMISYGGADYKRITVKVNAP
YNKINQRILVVDPVTSEHELTCQAEGYPKAEVIWTSSDHQVLSGKTTTTNSKREEKLFNVTSTLRI
NTTTNEIFYCTFRRLDPEENHTAELVIPELPLAHPPNERTHLVILGAILLCLGVALTFIFRLRKGR
MMDVKKCGIQDTNSKKQSDTHLEET

Anti-CD20 light chain sequence (SEQ ID NO: 72):
<u>QIVLSQSPAILSASPGEKVTMTCRASSSVSYIHWFQQKPGSSPKPWIYATSNLASGVPVRFSGSGS</u>
<u>GTSYSLTISRVEAEDAATYYCQQWTSNPPTFGGGTKLEIK</u>RTVAAPSVFIFPPSDEQLKSGTASVV
CLLNNFYPREAKVQWKVDNALQSGNSQESVTEQDSKDSTYSLSSTLTLSKADYEKHKVYACEVTHQ
GLSSPVTKSFNRGEC <u>Underlined</u>: anti-CD20 antibody variable region
Plain: anti-CD20 antibody constant region
*Italic*: Linker
Bold: human PD-1 ligand 1 or extracellular binding domain of PD-L1

Fig. 34

Fusion proteins comprising anti-CD25 antibody and PD-1 ligand 1 (PD-L1).

Anti-CD25 (Daclizumab) heavy chain and PD-L1 (SEQ ID NO: 41):

QVQLVQSGAE VKKPGSSVKV SCKASGYTFT SYRMHWVRQA PGQGLEWIGY INPSTGYTEY
NQKFKDKATI TADESTNTAY MELSSLRSED TAVYYCARGG GVFDYWGQGT LVTVSSASTK
GPSVFPLAPS SKSTSGGTAA LGCLVKDYFP EPVTVSWNSG ALTSGVHTFP AVLQSSGLYS
LSSVVTVPSS SLGTQTYICN VNHKPSNTKV DKKVEPKSCD KTHTCPPCPA PELLGGPSVF
LFPPKPKDTL MISRTPEVTC VVVDVSHEDP EVKFNWYVDG VEVHNAKTKP REEQYNSTYR
VVSVLTVLHQ DWLNGKEYKC KVSNKALPAP IEKTISKAKG QPREPQVYTL PPSRDELTKN
QVSLTCLVKG FYPSDIAVEW ESNGQPENNY KTTPPVLDSD GSFFLYSKLT VDKSRWQQGN
VFSCSVMHEA LHNHYTQKSL SLSPGK *GGGGSGGGGSGGGGS*
<u>RIFAVFIFMTYWHLLNAFTVTVPKDLYVVEYGSNMTIECK</u>
<u>FPVEKQLDLAALIVYWEMEDKNIIQFVHGEEDLKVQHSSYRQRARLLKDQLSLGNA</u>
<u>ALQITDVKLQDAGVYRCMISYGGADYKRITVKVNAPYNKINQRILVVDPVTSEHEL</u>
<u>TCQAEGYPKAEVIWTSSDHQVLSGKTTTTNSKREEKLFNVTSTLRINTTTNEIFYC</u>
TFRRLDPEENHTAELVIPELPLAHPPNERTHLVILGAILLCLGVALTFIFRLRKGR
MMDVKKCGIQDTNSKKQSDTHLEET

Anti-CD25 (Daclizumab) light chain (SEQ ID NO: 75):

DIQMTQSPST LSASVGDRVT ITCSASSSIS YMHWYQQKPG KAPKLLIYTT SNLASGVPAR
FSGSGSGTEF TLTISSLQPD DFATYYCHQR STYPLTFGQG TKVEVKRTVA APSVFIFPPS
DEQLKSGTAS VVCLLNNFYP REAKVQWKVD NALQSGNSQE SVTEQDSKDS TYSLSSTLTL
SKADYEKHKV YACEVTHQGL SSPVTKSFNR GEC

Plain: anti-CD25 antibody
   *Italic: Linker (optional and may be replaced)*
   Bold: human PD-1 ligand 1 or extracellular binding domain of PD-L1 (underlined)

Fig. 35A

Anti-CD25 (Basiliximab) heavy chain and PD-1 ectodomain (SEQ ID NO: 42)
QLQQSGTVLA RPGASVKMSC KASGYSFTRY WMHWIKQRPG QGLEWIGAIY PGNSDTSYNQ
KFEGKAKLTA VTSASTAYME LSSLTHEDSA VYYCSRDYGY YFDFWGQGTT LTVSSASTKG
PSVFPLAPSS KSTSGGTAAL GCLVKDYFPE PVTVSWNSGA LTSGVHTFPA VLQSSGLYSL
SSVVTVPSSS LGTQTYICNV NHKPSNTKVD KRVEPKSCDK THTCPPCPAP ELLGGPSVFL
FPPKPKDTLM ISRTPEVTCV VVDVSHEDPE VKFNWYVDGV EVHNAKTKPR EEQYNSTYRV
VSVLTVLHQD WLNGKEYKCK VSNKALPAPI EKTISKAKGQ PREPQVYTLP PSRDELTKNQ
VSLTCLVKGF YPSDIAVEWE SNGQPENNYK TTPPVLDSDG SFFLYSKLTV DKSRWQQGNV
FSCSVMHEAL HNHYTQKSLS LSPGK *GGGGSGGGGSGGGGS*
RIFAVFIFMTYWHLLNAFTVTVPKDLYVVEYGSNMTIECK
FPVEKQLDLAALIVYWEMEDKNIIQFVHGEEDLKVQHSSYRQRARLLKDQLSLGNA
ALQITDVKLQDAGVYRCMISYGGADYKRITVKVNAPYNKINQRILVVDPVTSEHEL
TCQAEGYPKAEVIWTSSDHQVLSGKTTTTNSKREEKLFNVTSTLRINTTTNEIFYC
TFRRLDPEENHTAELVIPELPLAHPPNERTHLVILGAILLCLGVALTFIFRLRKGR
MMDVKKCGIQDTNSKKQSDTHLEET Anti-CD25 (Basiliximab) light chain (SEQ ID NO: 76):
QIVSTQSPAI MSASPGEKVT MTCSASSSRS YMQWYQQKPG TSPKRWIYDT SKLASGVPAR
FSGSGSGTSY SLTISSMEAE DAATYYCHQR SSYTFGGGTK LEIKRTVAAP SVFIFPPSDE
QLKSGTASVV CLLNNFYPRE AKVQWKVDNA LQSGNSQESV TEQDSKDSTY SLSSTLTLSK
ADYEKHKVYA CEVTHQGLSS PVTKSFNRGE Plain: anti-CD25 antibody
*Italic: Linker*
Bold: human PD-1 ligand 1 or extracellular binding domain of PD-L1 (underlined)

Fig. 35B

Fusion proteins comprising IL-2, Fc, and PD-1 ligand 1 (PD-L1)

Fusion protein: hPD-1 ligand 1 + Fc + IL-2 (SEQ ID NO: 43):

MRIFAVFIFMTYWHLLNA<u>FTVTVPKDLYVVEYGSNMTIECKFPVEKQLDLAALIVYWEMEDKNIIQFVHGEE</u>
<u>DLKVQHSSYRQRARLLKDQLSLGNAALQITDVKLQDAGVYRCMISYGGADYKRITVKV</u>
<u>NAPYNKINQRILVVDPVTSEHELTCQAEGYPKAEVIWTSSDHQVLSGKTTTTNSKREEKLFNVTSTLRINTT</u>
<u>TNEIFYCTFRRLDPEENHTAELVIPELPLAHPPNERTHLVILGAILLCLGVALTFIFR</u>
<u>LRKGRMMDVKKCGIQDTNSKKQSDTHLEET</u> *GGGGSGGGGSGGGGS*
THTCPPCPAPELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSR<u>E</u>EMTKNQVSLT
CLVKGFYPSDIAVEWESNGQPENNYKTTPPVLDSDGSFFLYSKLTVDKSRWQQGNVFSCSVMHEALHNHYTQ
KSLSLSPGK *GGGGSGGGGSGGGGS*
<u>APTSSSTKKTQLQLEHLLLDLQMILNGINNYKNPKLTRMLTFKFYMPKKATELKHLQCLEEELKPLEEVLNL</u>
<u>AQSKNFHLRPRDLISNINVIVLELKGSETTFMCEYADETATIVEFLNRWITFCQSIISTLT</u>

Fusion protein: IL-2 + Fc + PD-1 ligand 1 (SEQ ID NO: 44):

<u>APTSSSTKKTQLQLEHLLLDLQMILNGINNYKNPKLTRMLTFKFYMPKKATELKHLQCLEEELKPLEEVLNL</u>
<u>AQSKNFHLRPRDLISNINVIVLELKGSETTFMCEYADETATIVEFLNRWITFCQSIISTLT</u>
*GGGGSGGGGSGGGGS*
THTCPPCPAPELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSR<u>E</u>EMTKNQVSLT
CLVKGFYPSDIAVEWESNGQPENNYKTTPPVLDSDGSFFLYSKLTVDKSRWQQGNVFSCSVMHEALHNHYTQ
KSLSLSPGK *GGGGSGGGGSGGGGS*
<u>RIFAVFIFMTYWHLLNAFTVTVPKDLYVVEYGSNMTIECKFPVEKQLDLAALIVYWEMEDKNIIQFVHGEED</u>
<u>LKVQHSSYRQRARLLKDQLSLGNAALQITDVKLQDAGVYRCMISYGGADYKRITVKVNAPYNKINQRILVVD</u>
<u>PVTSEHELTCQAEGYPKAEVIWTSSDHQVLSGKTTTTNSKREEKLFNVTSTLRINTTTNEIFYCTFRRLDPE</u>
<u>ENHTAELVIPELPLAHPPNERTHLVILGAILLCLGVALTFIFRLRKGRMMDVKKCGIQDTNSKKQSDTHLEE</u>
<u>T</u>

<u>Underlined</u>: IL-2 fragment
*Italic: Linker (optional)*
Plain: Fc
Bold: human PD-1 ligand 1 or extracellular binding domain of PD-1L (underlined)
(Note: Can replace linker 1 *GGGGSGGGGSGGGGS* SEQ ID NO: 104 with
*EPKSCDK* SEQ ID NO: 105)
(Note: Can replace underlined aa in Fc: <u>E</u> with D and <u>M</u> with L)

Fig. 36

Fusion protein comprising anti-CD4 antibody and PD-1 ligand 1 (PD-L1)

Anti-CD4 heavy chain and PD-1 ligand 1 (SEQ ID NO: 45)
Heavy chain fusion protein:

<u>QVQLQEAGPGLVKPSETLSLTCSVSGGSISGDYYWFWIRQSPGKGLEWIGYIYGSGGGTNYNPSLN</u>
<u>NRVSISIDTSKNLFSLKLRSVTAADTAVYYCASNILKYLHWLLYWGQGVLVTVSS</u>ASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS*
RIFAVFIFMTYWHLLNAFTVTVPKDLYVVEYGSNMTIECKFPVEKQLDLAALIVYWEMEDKNIIQF
VHGEEDLKVQHSSYRQRARLLKDQLSLGNAALQITDVKLQDAGVYRCMISYGGADYKRITVKVNAP
YNKINQRILVVDPVTSEHELTCQAEGYPKAEVIWTSSDHQVLSGKTTTTNSKREEKLFNVTSTLRI
NTTTNEIFYCTFRRLDPEENHTAELVIPELPLAHPPNERTHLVILGAILLCLGVALTFIFRLRKGR
MMDVKKCGIQDTNSKKQSDTHLEET

Anti-CD4 light chain (SEQ ID NO: 77)
Light chain:

<u>SYELSQPRSVSVSPGQTAGFTCGGDNVGRKSVQWYQQKPPQAPVLVIYADSERPSGIPARFSGSNS</u>
<u>GNTATLTISGVEAGDEADYYCQVWDSTADHWVFGGGTRLTVL</u>GRTVAAPSVFIFPPSDEQLKSGTA
SVVCLLNNFYPREAKVQWKVDNALQSGNSQESVTEQDSKDSTYSLSSTLTLSKADYEKHKVYACEV
THQGLSSPVTKSFNRGEC

<u>Underlined: Anti-CD4 antibody variable region</u>
Plain: Anti-CD4 antibody constant region
*Italic: Linker*
Bold: human PD-1 ligand 1 or extracellular binding domain of PD-1L (underlined)

Fig. 37

Fusion proteins comprising the extracellular domain of CTLA-4, Immunoglobulin Fc (IgG Cγ1), and a sequence from PD-1 ligand (PD-L1)

Oncostatin M signal peptide + CTLA-4 ECD + IgG Cγ1 + PD-L1 (SEQ ID NO: 46):

*MGVLLTQRTLLSLVLALLFPSMASM*<u>AMHVAQPAVVLASSRGIASFVCEYASPGKATEVRVTVLRQA</u>
<u>DSQVTEVCAATYMMGNELTFLDDSICTGTSSGNQVNLTIQGLRAMDTGLYICKVELMYPPPYYLGI</u>
<u>GNGTQIYVIDPEPCPDSD</u> *QEPKSCDKTHTCPPC*PAPELLGGPSVFLFPPKPKDTLM
ISRTPEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSLSLSPGK
*GGGGSGGGGSGGGGS*
RIFAVFIFMTYWHLLNAFTVTVPKDLYVVEYGSNMTIECKFPVEKQLDLAALIVYWEMEDKNIIQF
VHGEEDLKVQHSSYRQRARLLKDQLSLGNAALQITDVKLQDAGVYRCMISYGGADYKRITVKVNAP
YNKINQRILVVDPVTSEHELTCQAEGYPKAEVIWTSSDHQVLSGKTTTTNSKREEKLFNVTSTLRI
NTTTNEIFYCTFRRLDPEENHTAELVIPELPLAHPPNERTHLVILGAILLCLGVALTFIFRLRKGR
MMDVKKCGIQDTNSKKQSDTHLEET

Fusion proteins comprising the extracellular domain of PD-1 ligand (PD-L1), Immunoglobulin Fc (IgG Cγ1), and a sequence from the extracellular domain of CTLA-4.

PD-L1 + IgG Cγ1 + CTLA-4 ECD (SEQ ID NO: 47):

MRIFAVFIFMTYWHLLNAFTVTVPKDLYVVEYGSNMTIECKFPVEKQLDLAALIVYWEMEDKNIIQ
FVHGEEDLKVQHSSYRQRARLLKDQLSLGNAALQITDVKLQDAGVYRCMISYGGADYKRITVKVNA
PYNKINQRILVVDPVTSEHELTCQAEGYPKAEVIWTSSDHQVLSGKTTTTNSKREEKLFNVTSTLR
INTTTNEIFYCTFRRLDPEENHTAELVIPELPLAHPPNERTHLVILGAILLCLGVALTFIFR
LRKGRMMDVKKCGIQDTNSKKQSDTHLEET *GGGGSGGGGSGGGGS*
*QEPKSCDKTHTCPPC*PAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSKLTV
DKSRWQQGNVFSCSVMHEALHNHYTQKSLSLSPGK *GGGGSGGGGSGGGGS*
<u>AMHVAQPAVVLASSRGIASFVCEYASPGKATEVRVTVLRQADSQVTEVCAATYMMGNELTFLDDSI</u>
<u>CTGTSSGNQVNLTIQGLRAMDTGLYICKVELMYPPPYYLGIGNGTQIYVIDPEPCPDSD</u>

<u>*Underlined Italic*</u>: *Oncostatin M Signal Peptide (-25 to -1)*
Underlined: CTLA-4 extracellular domain (1-125)
Plain: human IgG1 heavy chain constant region (IgG Cγ1 domain = H, CH2, CH3)
*Italic: Linker (optional)*
Bold: human PD-1 ligand 1 (PD-1L) or extracellular binding domain of PD-1L (underlined)
(Note: Optional C to S conversion in IgG sequence (bold underlined))
(Note: The linker *QEPKSCDK* SEQ ID NO: 110 can be replaced with *EPKSCDK* SEQ ID NO: 105 or another linker sequence)

Fig. 38

Fusion proteins comprising a sequence of transforming growth factor-β (TGF-β), Immunoglobulin Fc (IgG Cβ1), and a sequence of PD-1 ligand (PD-L1)

TGFβ-1 + Fc + PD-L1 (SEQ ID NO: 48):
ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
RIFAVFIFMTYWHLLNAFTVTVPKDLYVVEYGSNMTIECKFPVEKQLDLAALIVYWEMEDKNIIQF
VHGEEDLKVQHSSYRQRARLLKDQLSLGNAALQITDVKLQDAGVYRCMISYGGADYKRITVKVNAP
YNKINQRILVVDPVTSEHELTCQAEGYPKAEVIWTSSDHQVLSGKTTTTNSKREEKLFNVTSTLRI
NTTTNEIFYCTFRRLDPEENHTAELVIPELPLAHPPNERTHLVILGAILLCLGVALTFIFRLRKGR
MMDVKKCGIQDTNSKKQSDTHLEET

Fusion protein comprising a sequence of PD-1 ligand (PD-L1), Immunoglobulin Fc (IgG Cγ1), and a sequence of Transforming growth factor beta (TGF- β)

PD-L1 + Fc + TGFβ-1 (SEQ ID NO: 49):
MRIFAVFIFMTYWHLLNAFTVTVPKDLYVVEYGSNMTIECKFPVEKQLDLAALIVYWEMEDKNIIQ
FVHGEEDLKVQHSSYRQRARLLKDQLSLGNAALQITDVKLQDAGVYRCMISYGGADYKRITVKVNA
PYNKINQRILVVDPVTSEHELTCQAEGYPKAEVIWTSSDHQVLSGKTTTTNSKREEKLFNVTSTLR
INTTTNEIFYCTFRRLDPEENHTAELVIPELPLAHPPNERTHLVILGAILLCLGVALTFIFRLRKG
RMMDVKKCGIQDTNSKKQSDTHLEET *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS

> Underlined: TGFβ-1
> *Italic: Linker (optional)*
> Plain: Fc
> Bold: human PD-1 ligand 1 or extracellular binding domain of PD-1L (underlined)
> (Note: Can replace linker *GGGGSGGGGSGGGGS* SEQ ID NO: 104 with
> *EPKSCDK* SEQ ID NO: 105)
> (Note: Can replace underlined aa in Fc: E with D and M with L)

Fig. 39

(i) Transforming growth factor-beta (TGF-β1, TGF-β2, or TGF-β3 or a fragment thereof:

TGF-β1 full sequence (SEQ ID NO: 102):

```
1    MPPSGLRLLP  LLLPLLRLLV  LTPGRPAAGL  STCKTIDMEL  VKRKRIEAIR  GQILSKLRLS
61   SPPSQGEVPP  VPLPEAVLAL  YNSTRDRVAG  ESAEPEPEPE  ADYYAKEVTR  VLMVENTNKI
121  YEKVKKSPHS  IYMLFNTSEL  REAVPEPVLL  SRAELRLLRL  KLKAEQHVEL  YQKYSNDSWR
181  YLSNRLLAPS  DTPEWLSFDV  TGVVRQWLSH  GGEVEGFRLS  AHCSCDSKDN  TLQVDINGFS
241  SSRRGDLATI  HGMNRPFLLL  MATPLERAQH  LHSSRQRRAL  DTNYCFSSTE  KNCCVRQLYI
301  DFRKDLGWKW  IHEPKGYHAN  FCLGPCPYIW  SLDTQYSKVL  ALYNQHNPGA  SAAPCCVPQA
361  LEPLPIVYYV  GRKPKVEQLS  NMIVRSCKCS
```

Underlined: Mature (active) TGF-β1 sequence (Ala 279 – Ser 390; 112 aa).

(ii) Mature (active) TGF-β1 sequence (Ala 279 – Ser 390; 112 aa)
(SEQ ID NO: 103):
AL DTNYCFSSTE KNCCVRQLYI DFRKDLGWKW IHEPKGYHAN FCLGPCPYIW
SLDTQYSKVL ALYNQHNPGA SAAPCCVPQA LEPLPIVYYV GRKPKVEQLS NMIVRSCKCS

Fig. 40

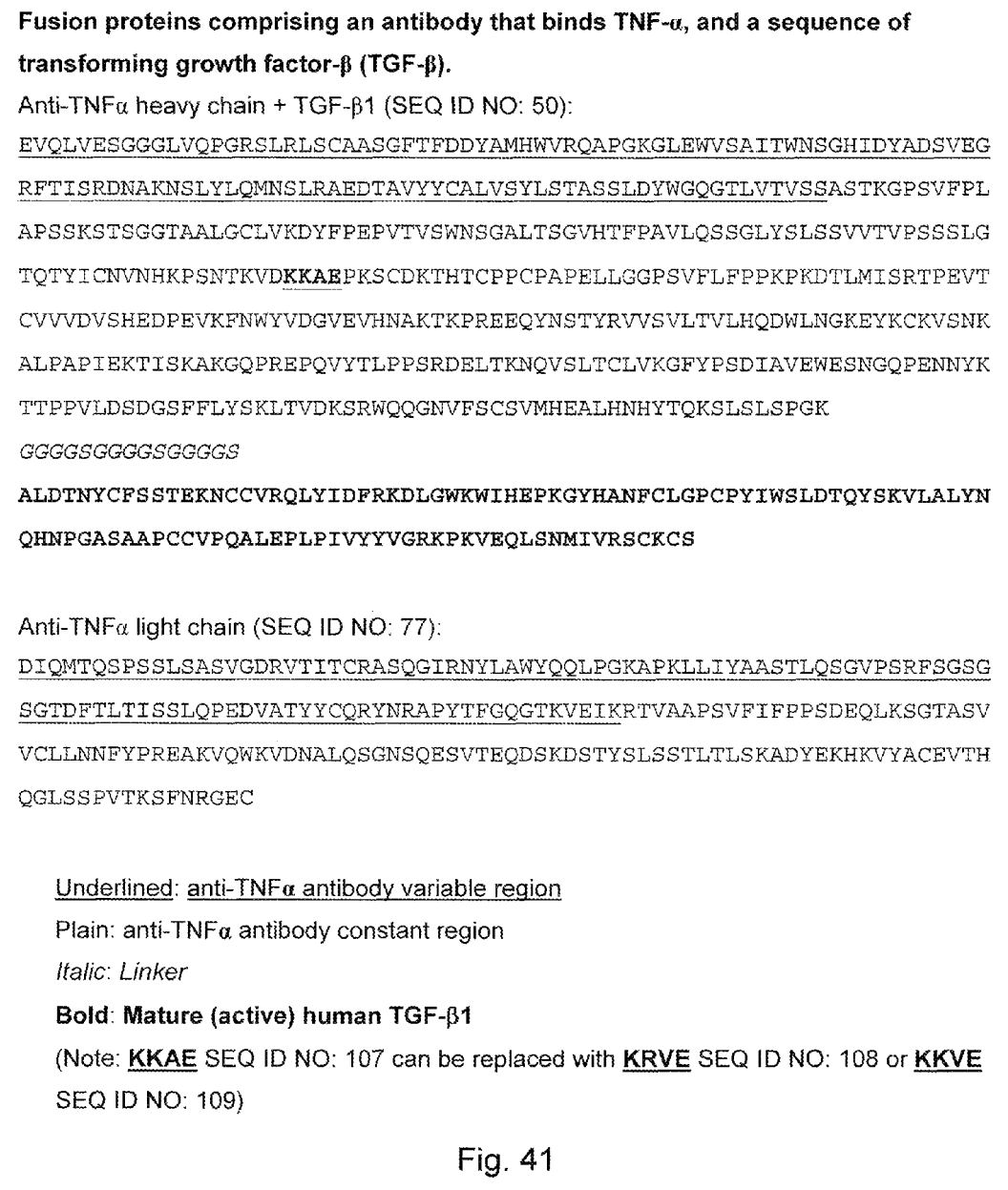

Fusion proteins comprising an antibody that binds TNF-α, and a sequence of transforming growth factor-β (TGF-β).

Anti-TNFα heavy chain + TGF-β1 (SEQ ID NO:

Fusion proteins comprising TNFR2 Extracellular ligand binding domain, Fc, and a sequence from transforming growth factor-β (TGF-β)

TNFR2 ECD + IgG Cγ1 + TGF-β1 (SEQ ID NO: 51):

<u>LPAQVAFTPYAPEPGSTCRLREYYDQTAQMCCSKCSPGQHAKVFCTKTSDTVCDSCEDSTYTQLWN
WVPECLSCGSRCSSDQVETQACTREQNRICTCRPGWYCALSKQEGCRLCAPLRKCRPGFGVARPGT
ETSDVVCKPCAPGTFSNTTSSTDICRPHQICNVVAIPGNASMDAVCTSTSPTRSMAPGAVHLPQPV
STRSQHTQPTPEPSTAPSTSFLLPMGPSPPAEGSTGD</u> *EPKSCDK*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
R<u>EE</u>MTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
**ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS**

Fusion proteins comprising a sequence from transforming growth factor-β (TGF-β), Fc, and TNFR2 Extracellular ligand binding domain:

TGF-β1 + IgG Cγ1 + TNFR2 ECD (SEQ ID NO: 52):

**ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS** *GGGGSGGGGSGGGGS*
THTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKT
ISKAKGQPREPQVYTLPPSR<u>EE</u>MTKNQVSLTCLVKGFYPSDIAVEWESNGQPENNYKTTPPVLDSD
GSFFLYSKLTVDKSRWQQGNVFSCSVMHEALHNHYTQKSLSLSPGK *GGGGSGGGGSGGGGS*
<u>LPAQVAFTPYAPEPGSTCRLREYYDQTAQMCCSKCSPGQHAKVFCTKTSDTVCDSCEDSTYTQLWN
WVPECLSCGSRCSSDQVETQACTREQNRICTCRPGWYCALSKQEGCRLCAPLRKCRPGFGVARPGT
ETSDVVCKPCAPGTFSNTTSSTDICRPHQICNVVAIPGNASMDAVCTSTSPTRSMAPGAVHLPQPV
STRSQHTQPTPEPSTAPSTSFLLPMGPSPPAEGSTGD</u>

Underlined: TNFR2 ligand-binding domain

Plain: human IgG1 heavy chain constant region (IgG Cγ1 domain = H, CH2, CH3)

*Italic: Linker*

Bold: Mature (active) human TGF-β1

(Note: Can replace linker 1 with *GGGGSGGGGSGGGGS* SEQ ID NO: 104 or *EPKSCDK* SEQ ID NO: 105)

(Note: Can replace underlined aa in Fc: <u>E</u> with D and <u>M</u> with L)

Fig. 42

Fusion proteins comprising anti-CD20 antibody and a sequence from transforming growth factor-β (TGF-β)

Anti-CD20 heavy chain + mature TGFβ1 sequence (SEQ ID NO: 53):

QVQLQQPGAELVKPGASVKMSCKASGYTFTSYNMHWVKQTPGRGLEWIGAIYPGNGDTSYNQKFKG
KATLTADKSSSTAYMQLSSLTSEDSAVYYCARSTYYGGDWYFNVWGAGTTVTVSAASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKAEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS*
ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS

Anti-CD20 light chain sequence (SEQ ID NO: 72):

QIVLSQSPAILSASPGEKVTMTCRASSSVSYIHWFQQKPGSSPKPWIYATSNLASGVPVRFSGSGS
GTSYSLTISRVEAEDAATYYCQQWTSNPPTFGGGTKLEIKRTVAAPSVFIFPPSDEQLKSGTASVV
CLLNNFYPREAKVQWKVDNALQSGNSQESVTEQDSKDSTYSLSSTLTLSKADYEKHKVYACEVTHQ
GLSSPVTKSFNRGEC

Underlined: anti-CD20 antibody variable region

Plain: anti-CD20 antibody constant region

*Italic: Linker*

Bold: Mature (active) human TGF-β1

Fig. 43

Fusion proteins comprising anti-CD25 antibody and a sequence from transforming growth factor-β (TGF-β).

Anti-CD25 (Daclizumab) heavy chain and TGF-β1 (SEQ ID NO: 54):
QVQLVQSGAE VKKPGSSVKV SCKASGYTFT SYRMHWVRQA PGQGLEWIGY INPSTGYTEY
NQKFKDKATI TADESTNTAY MELSSLRSED TAVYYCARGG GVFDYWGQGT LVTVSSASTK
GPSVFPLAPS SKSTSGGTAA LGCLVKDYFP EPVTVSWNSG ALTSGVHTFP AVLQSSGLYS
LSSVVTVPSS SLGTQTYICN VNHKPSNTKV DKKVEPKSCD KTHTCPPCPA PELLGGPSVF
LFPPKPKDTL MISRTPEVTC VVVDVSHEDP EVKFNWYVDG VEVHNAKTKP REEQYNSTYR
VVSVLTVLHQ DWLNGKEYKC KVSNKALPAP IEKTISKAKG QPREPQVYTL PPSRDELTKN
QVSLTCLVKG FYPSDIAVEW ESNGQPENNY KTTPPVLDSD GSFFLYSKLT VDKSRWQQGN
VFSCSVMHEA LHNHYTQKSL SLSPGK *GGGGSGGGGSGGGGS* **ALDTNYCFSSTEKNCCVRQLY
IDFRKDLGWKWIHEPKGYHANFCLGPCPYIWSLDTQYSKVLALYNQHNPGASAAPCCVPQALEPLP
IVYYVGRKPKVEQLSNMIVRSCKCS**

Anti-CD25 (Daclizumab) light chain (SEQ ID NO: 75):

DIQMTQSPST LSASVGDRVT ITCSASSSIS YMHWYQQKPG KAPKLLIYTT SNLASGVPAR
FSGSGSGTEF TLTISSLQPD DFATYYCHQR STYPLTFGQG TKVEVKRTVA APSVFIFPPS
DEQLKSGTAS VVCLLNNFYP REAKVQWKVD NALQSGNSQE SVTEQDSKDS TYSLSSTLTL
SKADYEKHKV YACEVTHQGL SSPVTKSFNR GEC

Plain: anti-CD25 antibody

*Italic: Linker*

Bold: Mature (active) human TGF-β1

Fig. 44A

Anti-CD25 (Basiliximab) heavy chain and TGF-β1 (SEQ ID NO: 55):

QLQQSGTVLA RPGASVKMSC KASGYSFTRY WMHWIKQRPG QGLEWIGAIY PGNSDTSYNQ
KFEGKAKLTA VTSASTAYME LSSLTHEDSA VYYCSRDYGY YFDFWGQGTT LTVSSASTKG
PSVFPLAPSS KSTSGGTAAL GCLVKDYFPE PVTVSWNSGA LTSGVHTFPA VLQSSGLYSL
SSVVTVPSSS LGTQTYICNV NHKPSNTKVD KRVEPKSCDK THTCPPCPAP ELLGGPSVFL
FPPKPKDTLM ISRTPEVTCV VVDVSHEDPE VKFNWYVDGV EVHNAKTKPR EEQYNSTYRV
VSVLTVLHQD WLNGKEYKCK VSNKALPAPI EKTISKAKGQ PREPQVYTLP PSRDELTKNQ
VSLTCLVKGF YPSDIAVEWE SNGQPENNYK TTPPVLDSDG SFFLYSKLTV DKSRWQQGNV
FSCSVMHEAL HNHYTQKSLS LSPGK *GGGGSGGGGSGGGGS*
ALDTNYCFSSTEKNCCVRQLYIDFRKDLGWKWIHEPKGYHAN
FCLGPCPYIWSLDTQYSKVLALYNQHNPGASAAPCCVPQALEPLPIVYYVGRKPKVEQ
LSNMIVRSCKCS

Anti-CD25 (Basiliximab) light chain (SEQ ID NO: 76):
QIVSTQSPAI MSASPGEKVT MTCSASSSRS YMQWYQQKPG TSPKRWIYDT SKLASGVPAR
FSGSGSGTSY SLTISSMEAE DAATYYCHQR SSYTFGGGTK LEIKRTVAAP SVFIFPPSDE
QLKSGTASVV CLLNNFYPRE AKVQWKVDNA LQSGNSQESV TEQDSKDSTY SLSSTLTLSK
ADYEKHKVYA CEVTHQGLSS PVTKSFNRGEC Plain: anti-CD25 antibody
*Italic: Linker*
Bold: Mature (active) human TGF-β1

Fig. 44B

Fusion proteins comprising IL-2, Fc, and a sequence from transforming growth factor-β (TGF-β).

TGF-β1 + Fc + IL-2 (SEQ ID NO: 56):
**ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS** *GGGGSGGGGSGGGGS*
THTCPPCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFFLYSKLTVDKSRWQQG NVFSCSVMHEALHNHYTQKSLSLSPGK *GGGGSGGGGSGGGGS* APTSSSTKKTQLQLEHLLLDLQMILNGINNYKNPKLTRMLTFKFYMPKKATELKHLQCLEEELKPL EEVLNLAQSKNFHLRPRDLISNINVIVLELKGSETTFMCEYADETATIVEFLNRWITFCQSIISTL T

IL-2 + Fc + TGF-β1 (SEQ ID NO: 57):

APTSSSTKKTQLQLEHLLLDLQMILNGINNYKNPKLTRMLTFKFYMPKKATELKHLQCLEEELKPL EEVLNLAQSKNFHLRPRDLISNINVIVLELKGSETTFMCEYADETATIVEFLNRWITFCQSIISTL T *GGGGSGGGGSGGGGS* THTCPPCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFFLYSKLTVDKSRWQQG NVFSCSVMHEALHNHYTQKSLSLSPGK *GGGGSGGGGSGGGGS* ALDTNYCFSSTEKNCCVRQLYIDFRKDLGWKWIHEPKGYHANFCLGPCPYIWSLDTQYSKVLALYN QHNPGASAAPCCVPQALEPLPIVYYVGRKPKVEQLSNMIVRSCKCS

Underlined: IL-2 fragment
*Italic: Linker (optional)*
Plain: Fc
Bold: Mature (active) human TGF-β1
(Note: Can replace linker 1 *GGGGSGGGGSGGGGS* SEQ ID NO: 104 with *EPKSCDK* SEQ ID NO: 105)
(Note: Can replace underlined aa in Fc: E with D and M with L)

Fig. 45

Fusion protein comprising anti-CD4 antibody and a sequence from transforming growth factor-β (TGF-β).

Anti-CD4 heavy chain and TGF-β1 (SEQ ID NO: 58)
Heavy chain fusion protein:

<u>QVQLQEAGPGLVKPSETLSLTCSVSGGSISGDYYWFWIRQSPGKGLEWIGYIYGSGGGTNYNPSLN</u>
<u>NRVSISIDTSKNLFSLKLRSVTAADTAVYYCASNILKYLHWLLYWGQGVLVTVSS</u>ASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS*
ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS

Anti-CD4 light chain (SEQ ID NO: 77)
Light chain:

<u>SYELSQPRSVSVSPGQTAGFTCGGDNVGRKSVQWYQQKPPQAPVLVIYADSERPSGIPARFSGSNS</u>
<u>GNTATLTISGVEAGDEADYYCQVWDSTADHWVFGGGTRLTVL</u>GRTVAAPSVFIFPPSDEQLKSGTA
SVVCLLNNFYPREAKVQWKVDNALQSGNSQESVTEQDSKDSTYSLSSTLTLSKADYEKHKVYACEV
THQGLSSPVTKSFNRGEC

<u>Underlined: Anti-CD4 antibody variable region</u>
Plain: Anti-CD4 antibody constant region
*Italic: Linker*
Bold: Mature (active) human TGF-β1

Fig. 46

Fusion proteins comprising the extracellular domain of CTLA-4, Immunoglobulin Fc (IgG Cγ1), and a sequence from a sequence from transforming growth factor-β (TGF-β)

Oncostatin M signal peptide + CTLA-4 ECD + IgG Cγ1 + TGF-β1 (SEQ ID NO: 59):

*MGVLLTQRTLLSLVLALLFPSMAS*MAMHVAQPAVVLASSRGIASFVCEYASPGKATEVRVTVLRQA
DSQVTEVCAATYMMGNELTFLDDSICTGTSSGNQVNLTIQGLRAMDTGLYICKVELMYPPPYYLGI
GNGTQIYVIDPEPCPDSD*QEPKSCDK* THTCPPCPAPELLGGPSVFLFPPKPKDTLM
ISRTPEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSLSLSPGK
*GGGGSGGGGSGGGGS*
**ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS**

Fusion proteins comprising a sequence from transforming growth factor-β (TGF-β), Immunoglobulin Fc (IgG Cγ1), and a sequence from the extracellular domain of CTLA-4

TGF-β1 + IgG Cγ1 + CTLA-4 ECD (SEQ ID NO: 60):

**ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS** *EPKSCDK*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
<u>AMHVAQPAVVLASSRGIASFVCEYASPGKATEVRVTVLRQADSQVTEVCAATYMMGNELTFLDDSI
CTGTSSGNQVNLTIQGLRAMDTGLYICKVELMYPPPYYLGIGNGTQIYVIDPEPCPDSD</u>

<u>*Underlined Italic*</u>: <u>*Oncostatin M Signal Peptide (-25 to -1)*</u>
<u>Underlined</u>: <u>CTLA-4 extracellular domain (1-125)</u>
Plain: human IgG1 heavy chain constant region (IgG Cγ1 domain = H, CH2, CH3)
*Italic: Linker (optional)*
Bold: Mature (active) human TGF-β1
(Note: Optional C to S conversion in IgG sequence (bold underlined))
(Note: The linker *QEPKSCDK* SEQ ID NO: 110 can be replaced with *EPKSCDK* SEQ ID NO: 105 or another linker sequence)

Fig. 47

Fusion proteins comprising an antibody that binds TNF-α, and a RANKL-binding sequence of receptor activator of nuclear factor-kB (RANK)

Anti-TNFα heavy chain + RANK ectodomain (SEQ ID NO: 61):
<u>EVQLVESGGGLVQPGRSLRLSCAASGFTFDDYAMHWVRQAPGKGLEWVSAITWNSGHIDYADSVEG</u>
<u>RFTISRDNAKNSLYLQMNSLRAEDTAVYYCALVSYLSTASSLDYWGQGTLVTVSS</u>ASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKAEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS* QI APPCTSEKHY EHLGRCCNKC EPGKYMSSKC TTTSDSVCLP
CGPDEYLDSW NEEDKCLLHK VCDTGKALVA VVAGNSTTPR RCACTAGYHW SQDCECCRRN
TECAPGLGAQ HPLQLNKDTV CKPCLAGYFS DAFSSTDKCR PWTNCTFLGK RVEHHGTEKS
DAVCSSSLPA RKPPNEPHVY LPG

Anti-TNFα light chain (SEQ ID NO: 78):
<u>DIQMTQSPSSLSASVGDRVTITCRASQGIRNYLAWYQQLPGKAPKLLIYAASTLQSGVPSRFSGSG</u>
<u>SGTDFTLTISSLQPEDVATYYCQRYNRAPYTFGQGTKVEIK</u>RTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC > Underlined: anti-TNFα antibody variable region
> Plain: anti-TNFα antibody constant region
> *Italic: Linker*
> Bold: RANK ectodomain
> (Note: KKAE SEQ ID NO: 107 can be replaced with KRVE SEQ ID NO: 108 or KKVE SEQ ID NO: 109)

Fig. 48

Fusion proteins comprising TNFR2 Extracellular ligand binding domain, Fc, and a RANKL-binding sequence of receptor activator of nuclear factor-kB (RANK)
TNFR2 ECD + IgG Cγ1 + RANK ectodomain (SEQ ID NO: 62):

<u>LPAQVAFTPYAPEPGSTCRLREYYDQTAQMCCSKCSPGQHAKVFCTKTSDTVCDSCEDSTYTQLWN
WVPECLSCGSRCSSDQVETQACTREQNRICTCRPGWYCALSKQEGCRLCAPLRKCRPGFGVARPGT
ETSDVVCKPCAPGTFSNTTSSTDICRPHQICNVVAIPGNASMDAVCTSTSPTRSMAPGAVHLPQPV
STRSQHTQPTPEPSTAPSTSFLLPMGPSPPAEGSTGD</u> *EPKSCDK*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
R<u>E</u>E<u>M</u>TKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS* **QI APPCTSEKHY
EHLGRCCNKC EPGKYMSSKC TTTSDSVCLP CGPDEYLDSW NEEDKCLLHK VCDTGKALVA
VVAGNSTTPR RCACTAGYHW SQDCECCRRN TECAPGLGAQ HPLQLNKDTV CKPCLAGYFS
DAFSSTDKCR PWTNCTFLGK RVEHHGTEKS DAVCSSSLPA RKPPNEPHVY LPG**

**Fusion proteins comprising a RANKL-binding sequence of receptor activator of
nuclear factor-kB (RANK), Fc, and TNFR2 Extracellular ligand binding domain:**
RANK ectodomain + IgG Cγ1 + TNFR2 ECD (SEQ ID NO: 63):

**QI APPCTSEKHY EHLGRCCNKC EPGKYMSSKC TTTSDSVCLP CGPDEYLDSW
NEEDKCLLHK VCDTGKALVA VVAGNSTTPR RCACTAGYHW SQDCECCRRN TECAPGLGAQ
HPLQLNKDTV CKPCLAGYFS DAFSSTDKCR PWTNCTFLGK RVEHHGTEKS DAVCSSSLPA
RKPPNEPHVY LPG**
*GGGGSGGGGSGGGGS* THTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKT
ISKAKGQPREPQVYTLPPSR<u>E</u>E<u>M</u>TKNQVSLTCLVKGFYPSDIAVEWESNGQPENNYKTTPPVLDSD
GSFFLYSKLTVDKSRWQQGNVFSCSVMHEALHNHYTQKSLSLSPGK *GGGGSGGGGSGGGGS*
<u>LPAQVAFTPYAPEPGSTCRLREYYDQTAQMCCSKCSPGQHAKVFCTKTSDTVCDSCEDSTYTQLWN
WVPECLSCGSRCSSDQVETQACTREQNRICTCRPGWYCALSKQEGCRLCAPLRKCRPGFGVARPGT
ETSDVVCKPCAPGTFSNTTSSTDICRPHQICNVVAIPGNASMDAVCTSTSPTRSMAPGAVHLPQPV
STRSQHTQPTPEPSTAPSTSFLLPMGPSPPAEGSTGD</u>

Underlined: TNFR2 ligand-binding domain

Plain: human IgG1 heavy chain constant region (IgG Cγ1 domain = H, CH2, CH3)

*Italic: Linker*

Bold: RANK ectodomain

(Note: Can replace linker 1 with *GGGGSGGGGSGGGGS* SEQ ID NO: 104 or
*EPKSCDK* SEQ ID NO: 105)
(Note: Can replace underlined aa in Fc: <u>E</u> with D and <u>M</u> with L)

Fig. 49

Fusion proteins comprising the extracellular domain of CTLA-4, Immunoglobulin Fc (IgG Cγ1), and a RANKL-binding sequence of receptor activator of nuclear factor-kB (RANK)

Oncostatin M signal peptide + CTLA-4 ECD + IgG Cγ1 + RANK ectodomain (SEQ ID NO: 64):

*MGVLLTQRTLLSLVLALLFPSMASM*AMHVAQPAVVLASSRGIASFVCEYASPGKATEVRVTVLRQA
DSQVTEVCAATYMMGNELTFLDDSICTGTSSGNQVNLTIQGLRAMDTGLYICKVELMYPPPYYLGI
GNGTQIYVIDPEPCPDSD*QEPKSCDK* THTCPPCPAPELLGGPSVFLFPPKPKDTLM
ISRTPEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSLSLSPGK
*GGGGSGGGGSGGGGS* **QI APPCTSEKHY EHLGRCCNKC EPGKYMSSKC TTTSDSVCLP
CGPDEYLDSW NEEDKCLLHK VCDTGKALVA VVAGNSTTPR RCACTAGYHW SQDCECCRRN
TECAPGLGAQ HPLQLNKDTV CKPCLAGYFS DAFSSTDKCR PWTNCTFLGK RVEHHGTEKS
DAVCSSSLPA RKPPNEPHVY LPG**

Fusion proteins comprising a RANKL-binding sequence of receptor activator of nuclear factor-kB (RANK), Immunoglobulin Fc (IgG Cγ1), and a sequence from the extracellular domain of CTLA-4

RANK ectodomain + IgG Cγ1 + CTLA-4 ECD (SEQ ID NO: 65):

**QI APPCTSEKHY EHLGRCCNKC EPGKYMSSKC TTTSDSVCLP CGPDEYLDSW
NEEDKCLLHK VCDTGKALVA VVAGNSTTPR RCACTAGYHW SQDCECCRRN TECAPGLGAQ
HPLQLNKDTV CKPCLAGYFS DAFSSTDKCR PWTNCTFLGK RVEHHGTEKS DAVCSSSLPA
RKPPNEPHVY LPG** *EPKSCDK*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
AMHVAQPAVVLASSRGIASFVCEYASPGKATEVRVTVLRQADSQVTEVCAATYMMGNELTFLDDSI
CTGTSSGNQVNLTIQGLRAMDTGLYICKVELMYPPPYYLGIGNGTQIYVIDPEPCPDSD

> *Underlined Italic*: Oncostatin M Signal Peptide (-25 to -1)
> Underlined: CTLA-4 extracellular domain (1-125)
> Plain: human IgG1 heavy chain constant region (IgG Cγ1 domain = H, CH2, CH3)
> *Italic: Linker (optional)*
> Bold: RANK ectodomain
> (Note: Optional C to S conversion in IgG sequence (bold underlined))
> (Note: The linker *QEPKSCDK* SEQ ID NO: 110 can be replaced with *EPKSCDK* SEQ ID NO: 105 or another linker sequence)

Fig. 50

Fusion proteins comprising a RANKL-binding sequence of receptor activator of nuclear factor-kB (RANK), Fc, and a sequence from transforming growth factor-β (TGF-β).

TGF-β1 + Fc + RANK ectodomain (SEQ ID NO: 66):

<u>ALDTNYCFSSTEKNCCVRQLYIDFRKDLGWKWIHEPKGYHANFCLGPCPYIWSLDTQYSKVLALYN</u>

<u>QHNPGASAAPCCVPQALEPLPIVYYVGRKPKVEQLSNMIVRSCKCS</u> *GGGGSGGGGSGGGGS*

THTCPPCPAPELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAKGQPREPQVYTLPPS

RE<u>E</u>MTKNQVSLTCLVKGFYPSDIAVEWESNGQPENNYKTTPPVLDSDGSFFLYSKLTVDKSRWQQG

NVFSCSVMHEALHNHYTQKSLSLSPGK *GGGGSGGGGSGGGGS* QI APPCTSEKHY

EHLGRCCNKC EPGKYMSSKC TTTSDSVCLP CGPDEYLDSW NEEDKCLLHK VCDTGKALVA

VVAGNSTTPR RCACTAGYHW SQDCECCRRN TECAPGLGAQ HPLQLNKDTV CKPCLAGYFS

DAFSSTDKCR PWTNCTFLGK RVEHHGTEKS DAVCSSSLPA RKPPNEPHVY LPG

RANK ectodomain + Fc + TGF-β1 (SEQ ID NO: 67):

QI APPCTSEKHY EHLGRCCNKC EPGKYMSSKC TTTSDSVCLP CGPDEYLDSW
NEEDKCLLHK VCDTGKALVA VVAGNSTTPR RCACTAGYHW SQDCECCRRN TECAPGLGAQ
HPLQLNKDTV CKPCLAGYFS DAFSSTDKCR PWTNCTFLGK RVEHHGTEKS DAVCSSSLPA
RKPPNEPHVY LPG *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
RE<u>E</u>MTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
<u>ALDTNYCFSSTEKNCCVRQLYIDFRKDLGWKWIHEPKGYHANFCLGPCPYIWSLDTQYSKVLALYN</u>
<u>QHNPGASAAPCCVPQALEPLPIVYYVGRKPKVEQLSNMIVRSCKCS</u>

> Underlined: Mature (active) human TGF-β1
> *Italic: Linker (optional)*
> Plain: Fc
> Bold: RANK ectodomain
> (Note: Can replace linker 1 *GGGGSGGGGSGGGGS* SEQ ID NO: 104 with
> *EPKSCDK* SEQ ID NO: 105)
> (Note: Can replace underlined aa in Fc: <u>E</u> with D and <u>M</u> with L)

Fig. 51

Fusion proteins comprising a RANKL-binding sequence of receptor activator of nuclear factor-kB (RANK), Fc, and a sequence from PD-1 ligand 1

PD-1L1 + Fc + RANK ectodomain (SEQ ID NO: 68):
RIFAVFIFMTYWHLLNAFTVTVPKDLYVVEYGSNMTIECKFPVEKQLDLAALIVYWEMEDKNIIQFVHGEED
LKVQHSSYRQRARLLKDQLSLGNAALQITDVKLQDAGVYRCMISYGGADYKRITVKVNAPYNKINQRILVVD
PVTSEHELTCQAEGYPKAEVIWTSSDHQVLSGKTTTTNSKREEKLFNVTSTLRINTTTNEIFYCTFRRLDPE
ENHTAELVIPELPLAHPPNERTHLVILGAILLCLGVALTFIFRLRKGRMMDVKKCGIQDTNSKKQSDTHLEE
T *GGGGSGGGGSGGGGS*
THTCPPCPAPELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQQGNVFSCSVMHEALHNHYTQ
KSLSLSPGK *GGGGSGGGGSGGGGS* <u>QI APPCTSEKHY EHLGRCCNKC EPGKYMSSKC TTTSDSVCLP
CGPDEYLDSW NEEDKCLLHK VCDTGKALVA VVAGNSTTPR RCACTAGYHW SQDCECCRRN
TECAPGLGAQ HPLQLNKDTV CKPCLAGYFS DAFSSTDKCR PWTNCTFLGK RVEHHGTEKS
DAVCSSSLPA RKPPNEPHVY LPG</u>

RANK ectodomain + Fc + PD-1L1 (SEQ ID NO: 69):
<u>QI APPCTSEKHY EHLGRCCNKC EPGKYMSSKC TTTSDSVCLP CGPDEYLDSW NEEDKCLLHK
VCDTGKALVA VVAGNSTTPR RCACTAGYHW SQDCECCRRN TECAPGLGAQ HPLQLNKDTV
CKPCLAGYFS DAFSSTDKCR PWTNCTFLGK RVEHHGTEKS DAVCSSSLPA RKPPNEPHVY LPG</u>
*GGGGSGGGGSGGGGS*
THTCPPCPAPELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQQGNVFSCSVMHEALHNHYTQ
KSLSLSPGK *GGGGSGGGGSGGGGS*
RIFAVFIFMTYWHLLNAFTVTVPKDLYVVEYGSNMTIECKFPVEKQLDLAALIVYWEMEDKNIIQFVHGEED
LKVQHSSYRQRARLLKDQLSLGNAALQITDVKLQDAGVYRCMISYGGADYKRITVKVNAPYNKINQRILVVD
PVTSEHELTCQAEGYPKAEVIWTSSDHQVLSGKTTTTNSKREEKLFNVTSTLRINTTTNEIFYCTFRRLDPE
ENHTAELVIPELPLAHPPNERTHLVILGAILLCLGVALTFIFRLRKGRMMDVKKCGIQDTNSKKQSDTHLEE
T <u>Bold: PD-1L1 (May use PD-1L1 extracellular domain – underlined)</u>
*Italic: Linker (optional)*
Plain: Fc
Underlined: RANK ectodomain
(Note: Can replace linker 1 *GGGGSGGGGSGGGGS* SEQ ID NO: 104 with
*EPKSCDK* SEQ ID NO: 105)
(Note: Can replace underlined aa in Fc: E with D and M with L)

Fig. 52

A
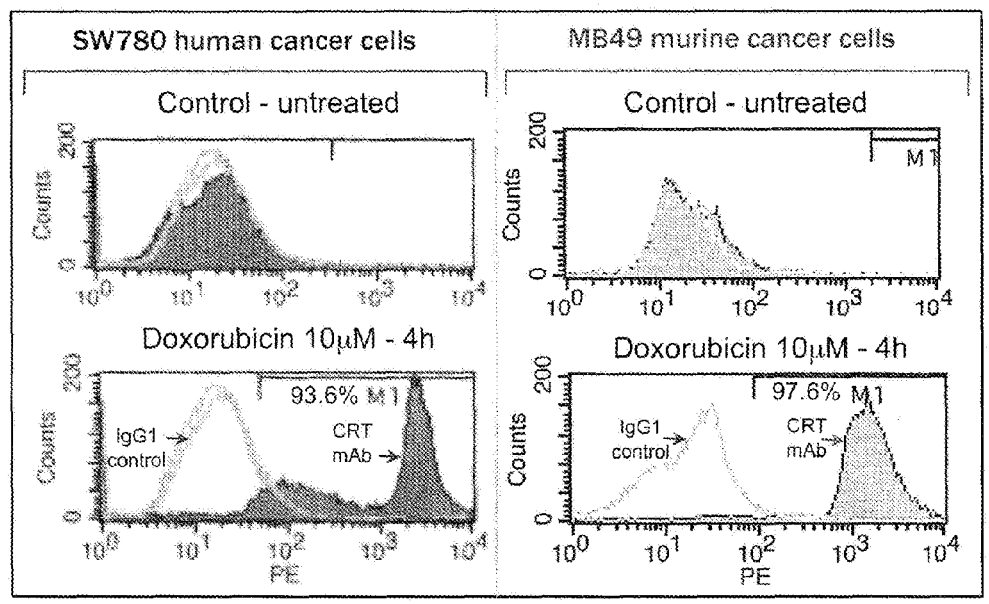
B
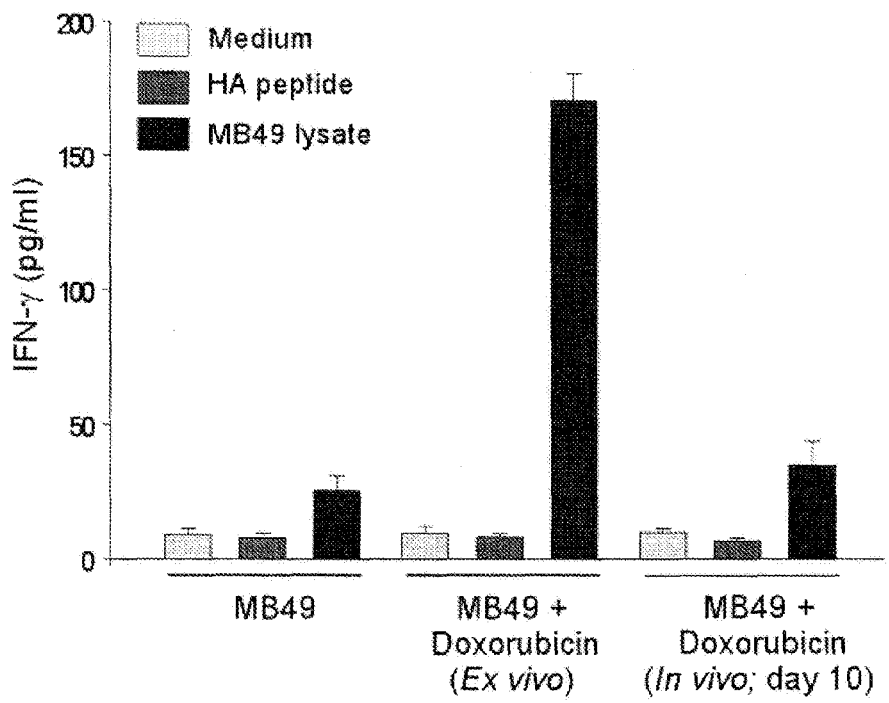
Fig. 53 A & B

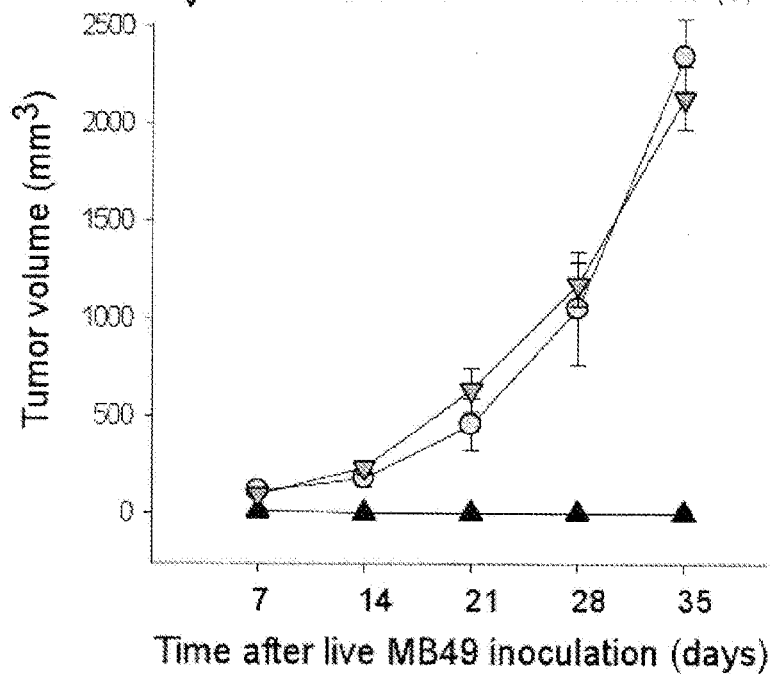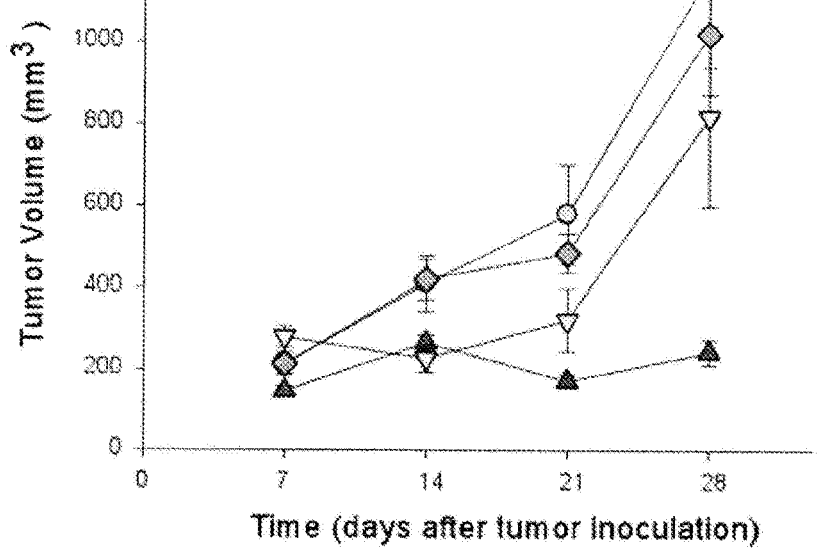
Fig. 53 C & D

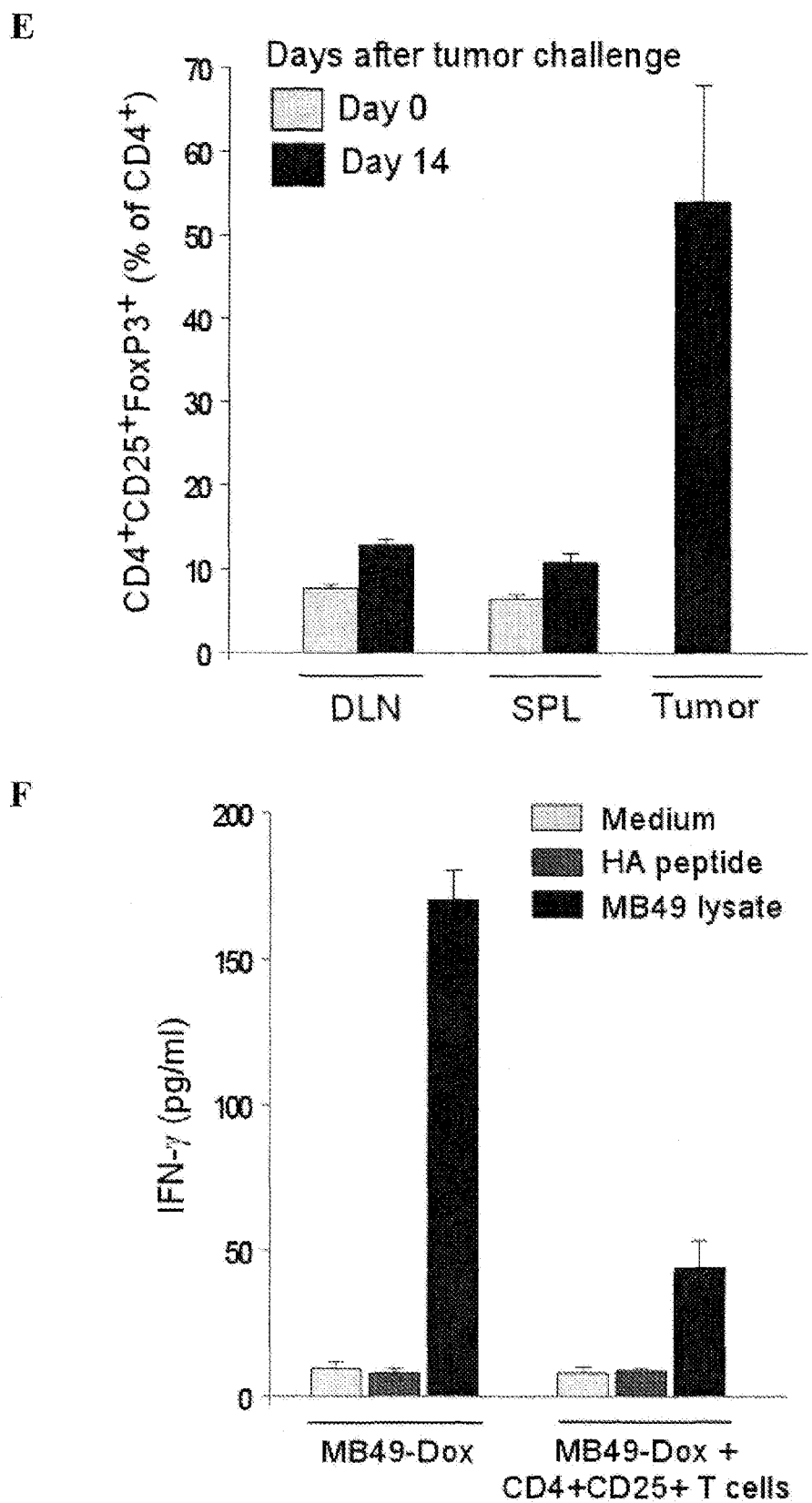
Fig. 53 E & F

A
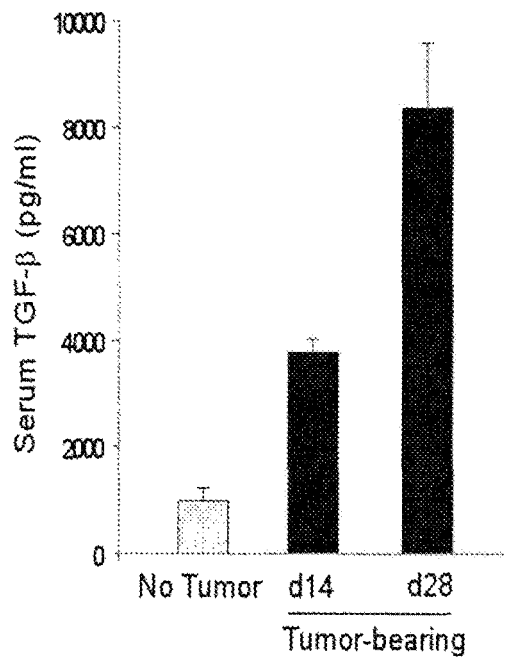
B
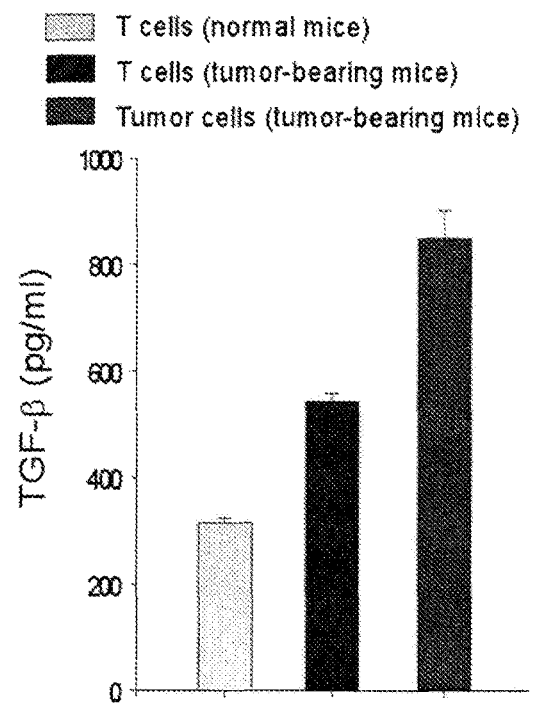
Fig. 54 A & B

C
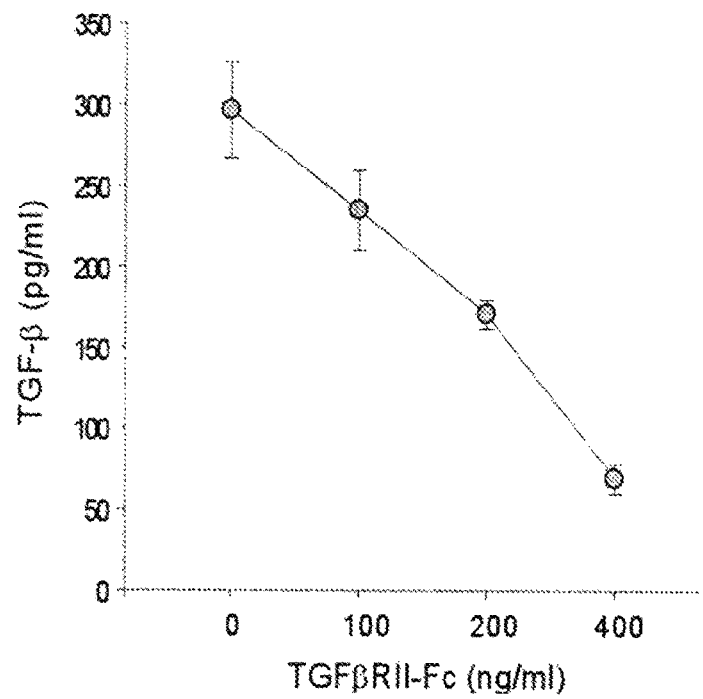
D
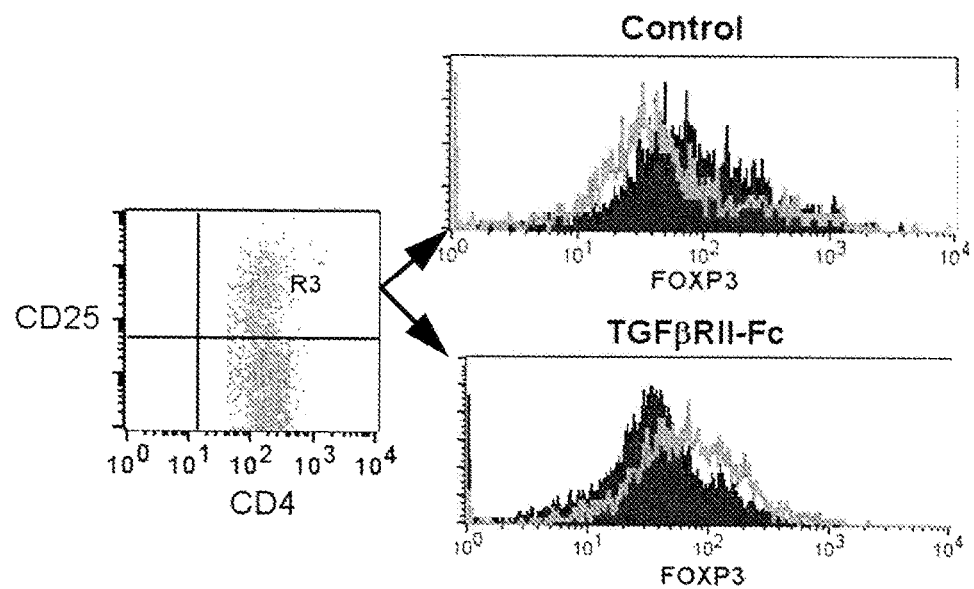
Fig. 54 C & D

E
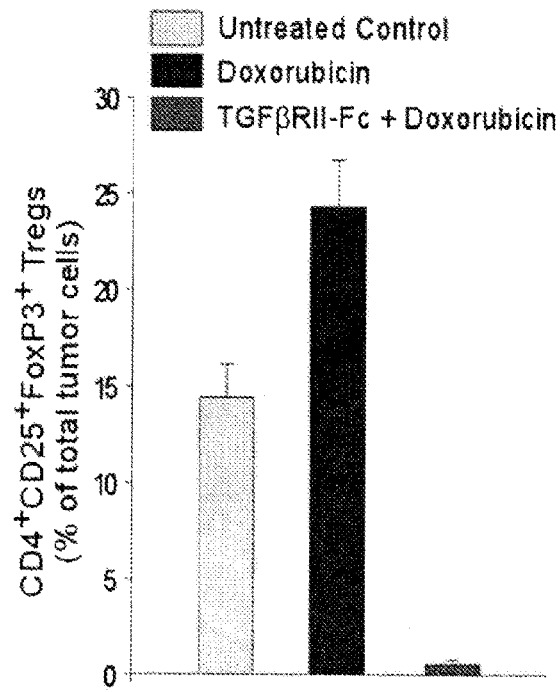
F
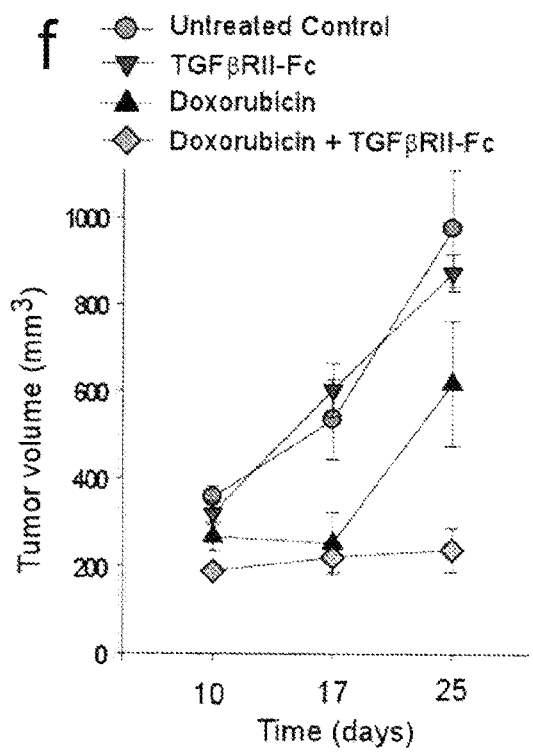
Fig. 54 E & F

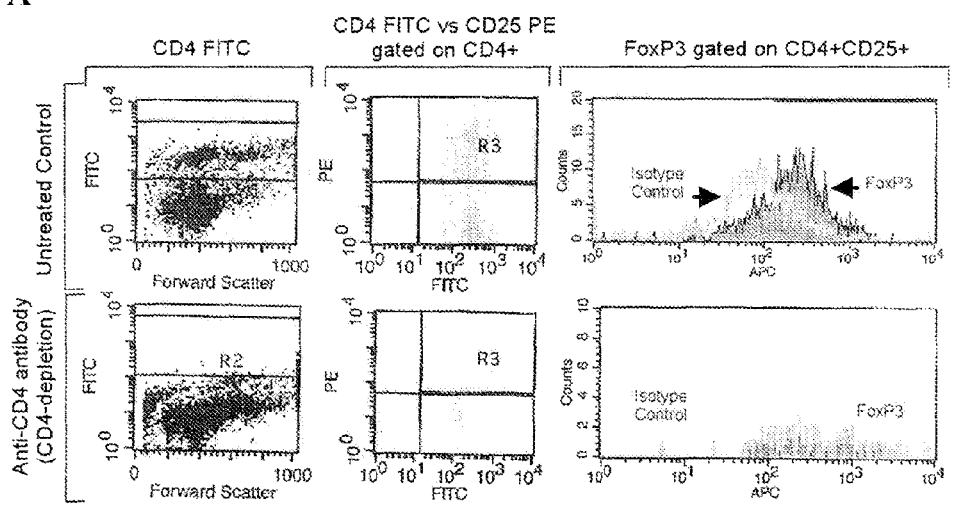
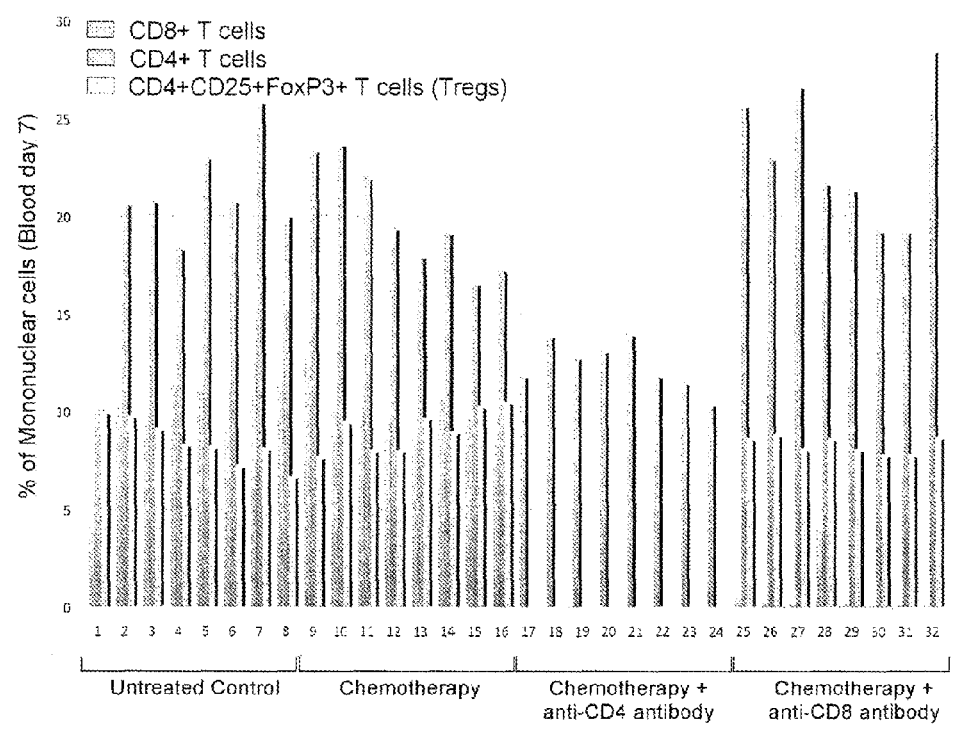
Fig. 55 A & B

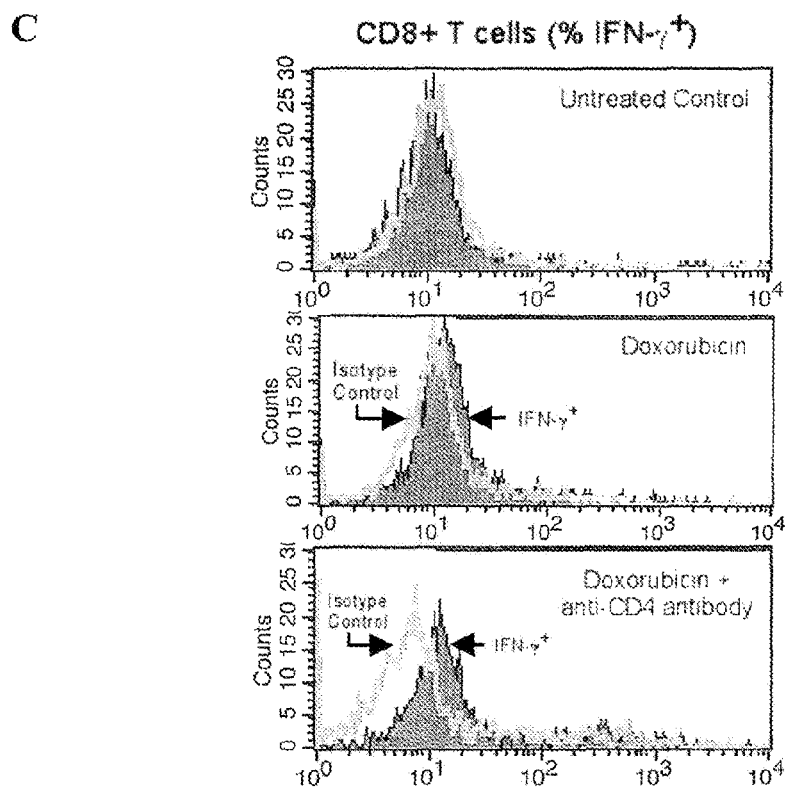
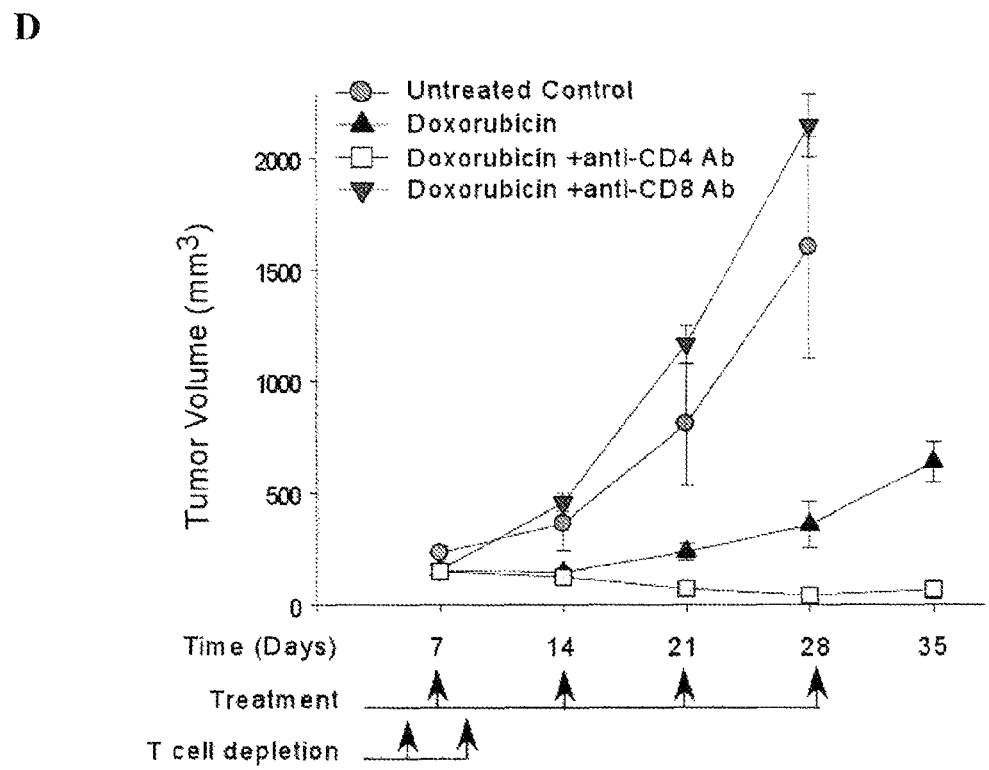
Fig. 55 C & D

A
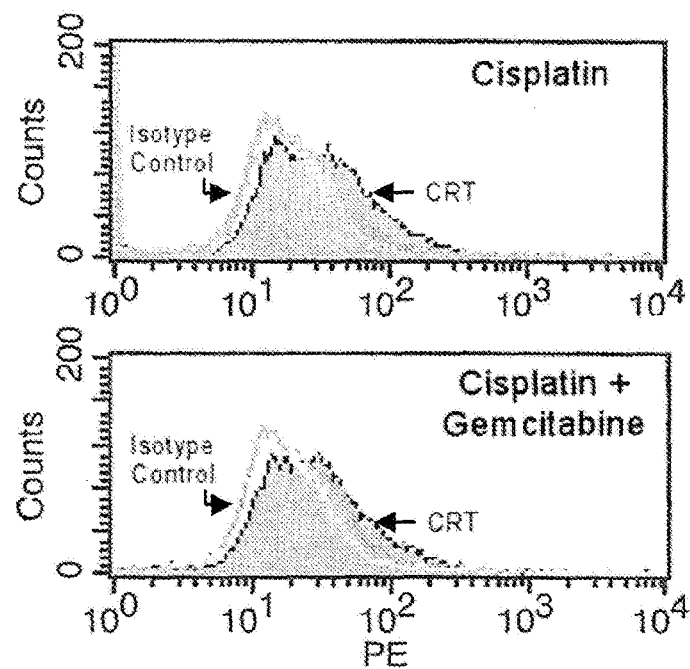
B
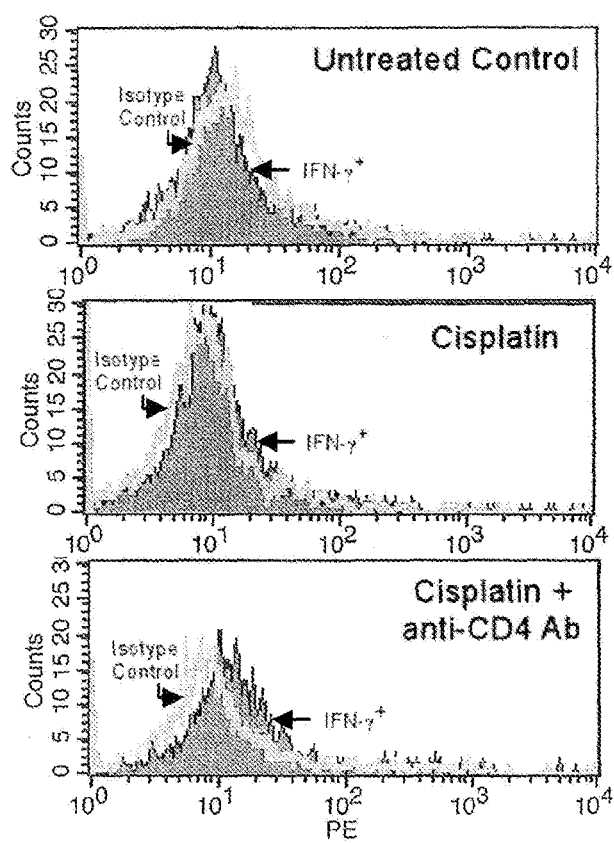
Fig. 56 A & B

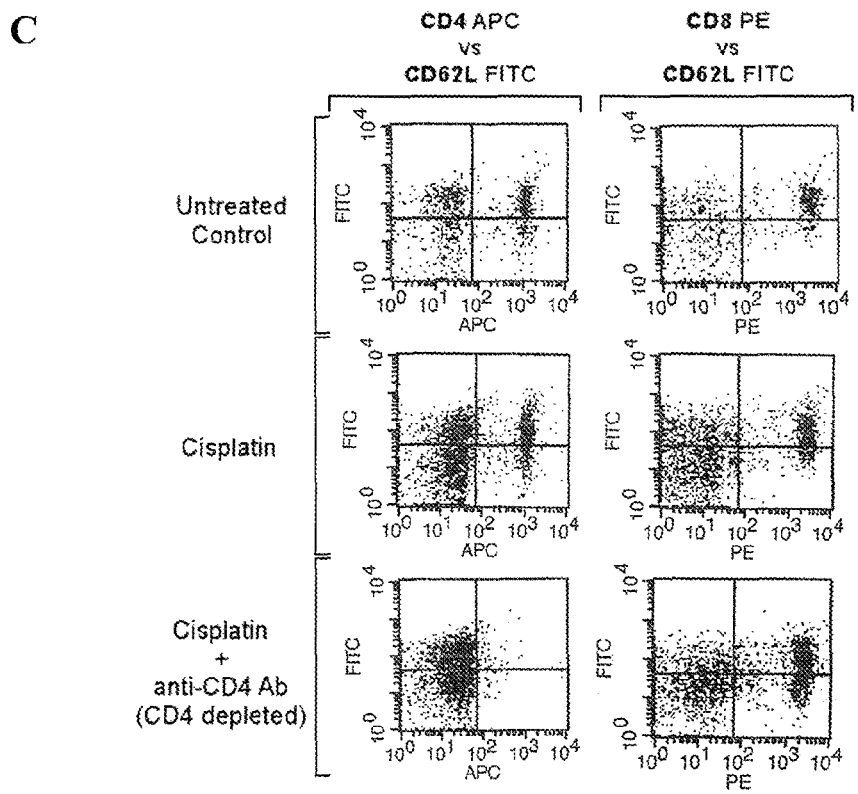
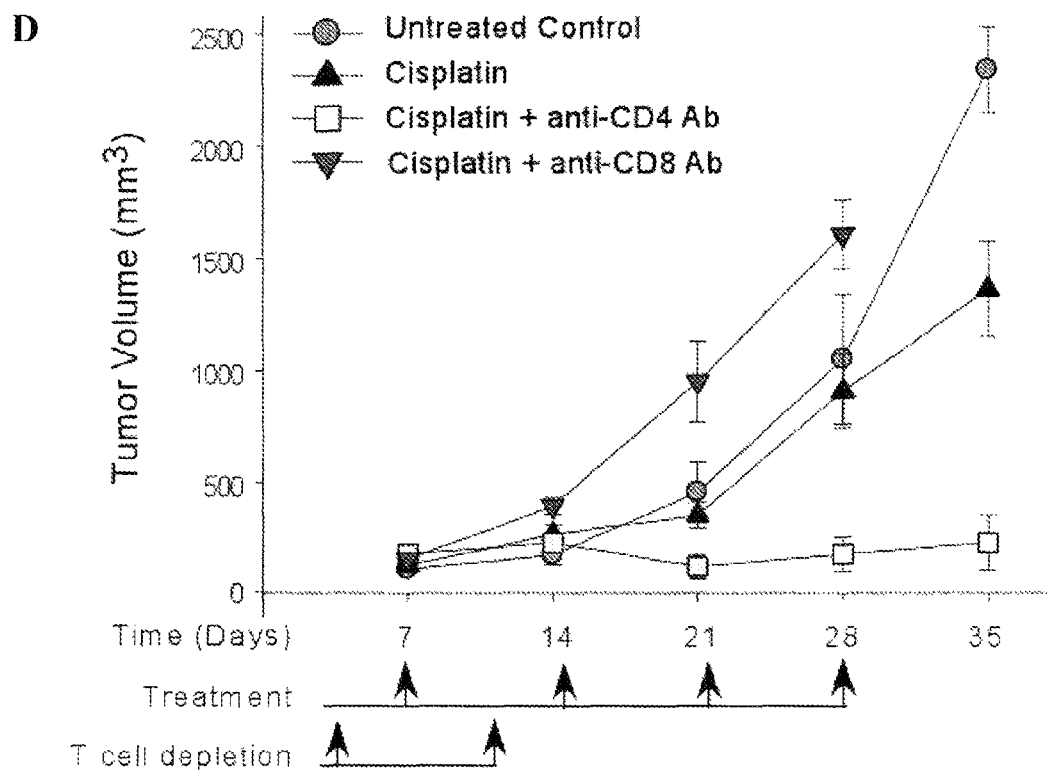
Fig. 56 C & D

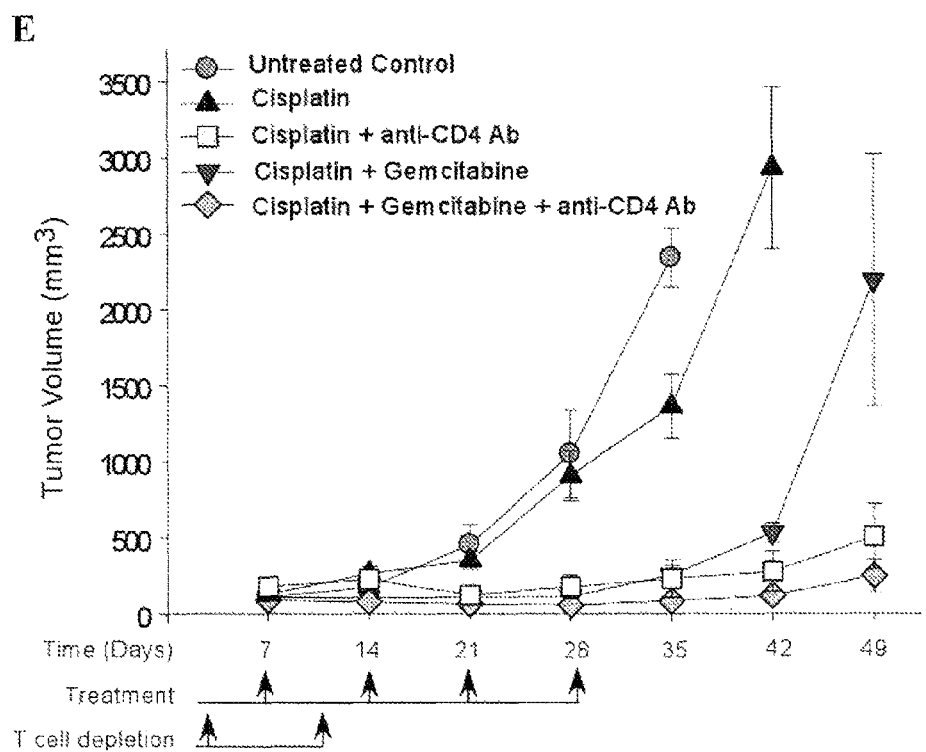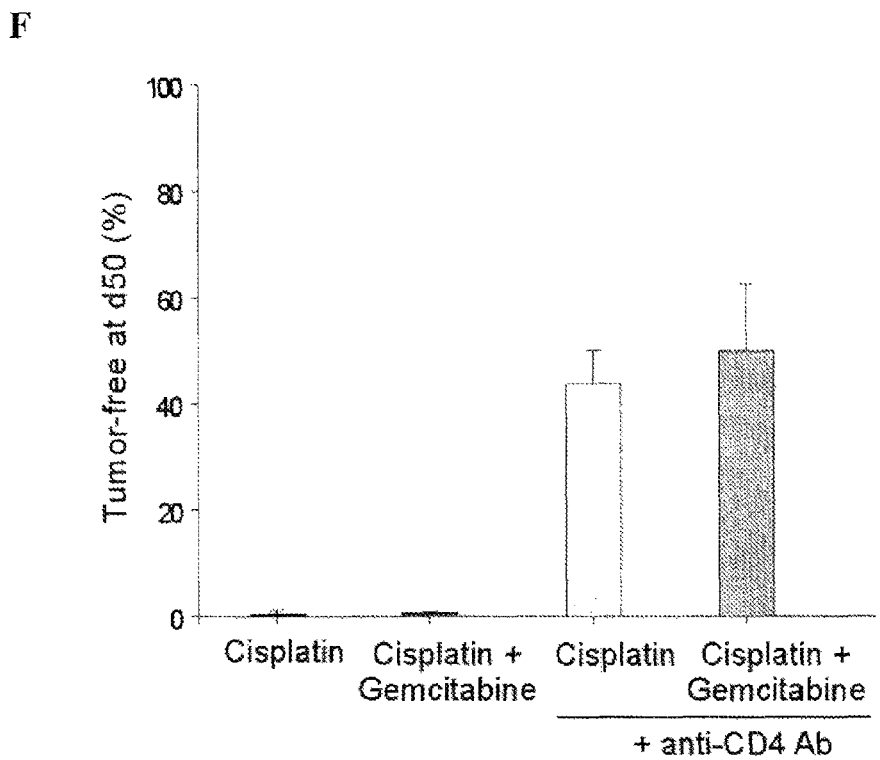
Fig. 56 E & F

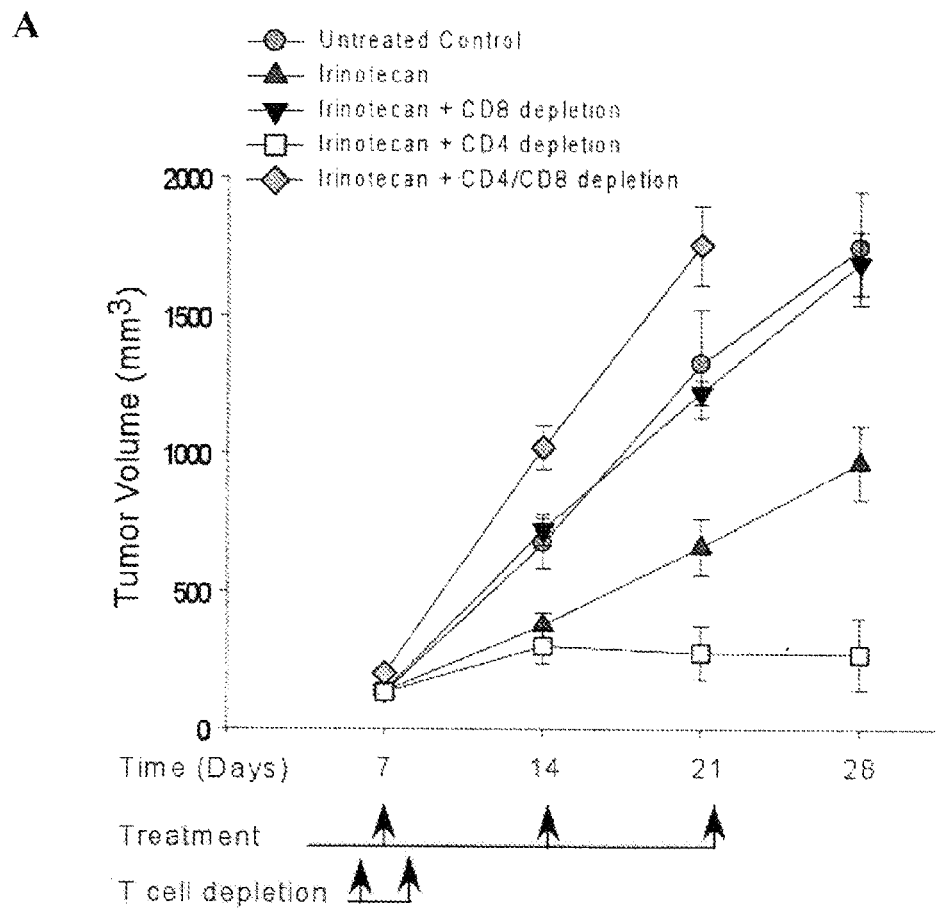
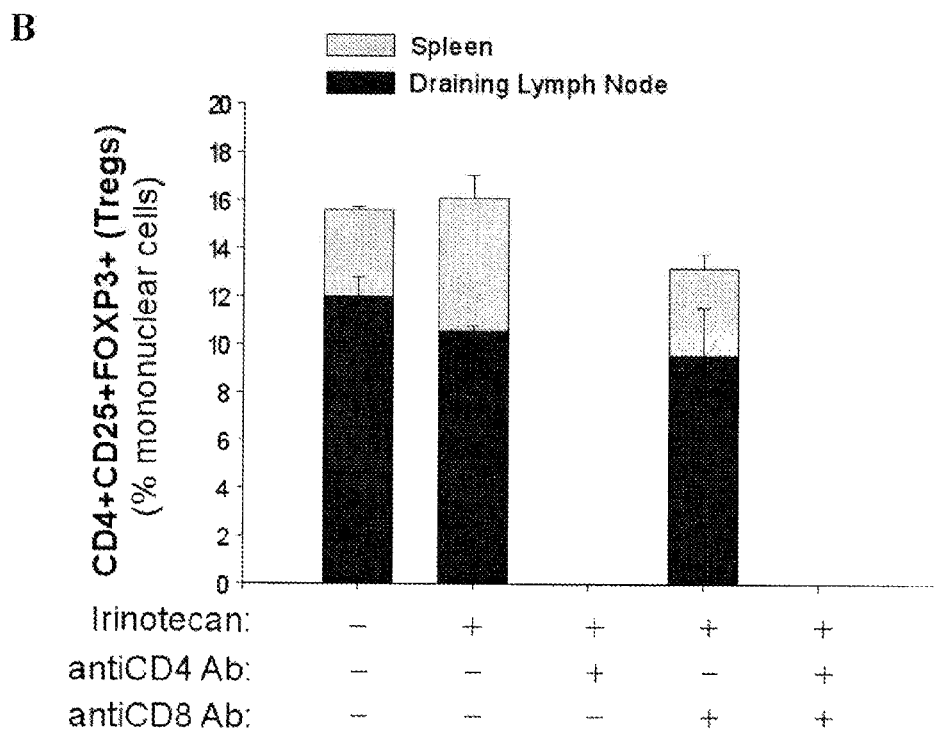
Fig. 57 A & B

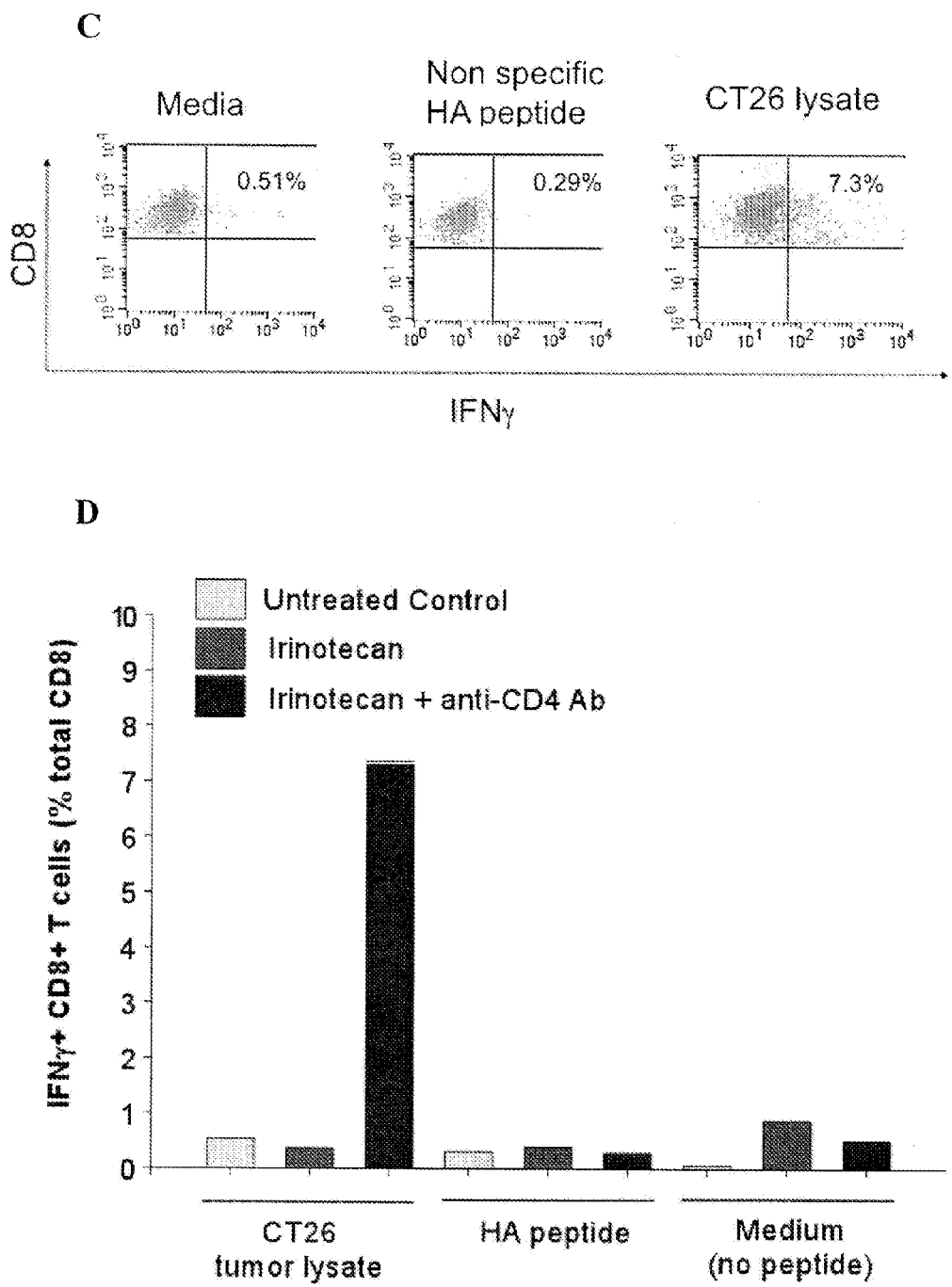
Fig. 57 C & D

E
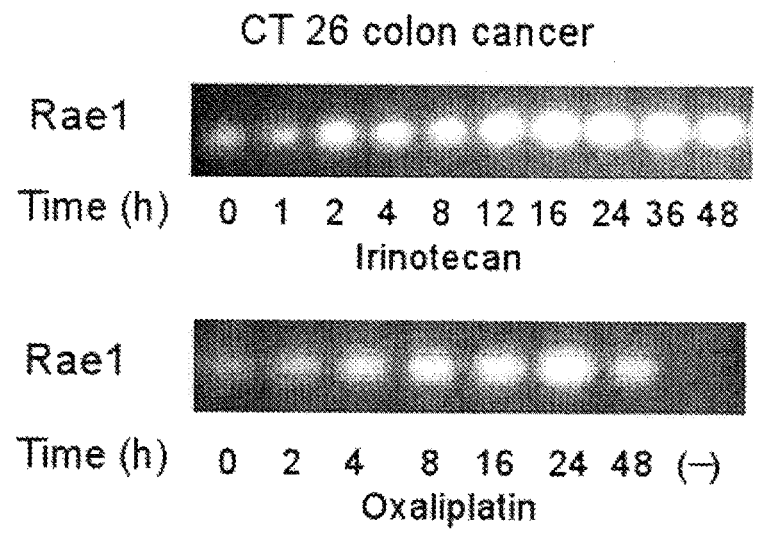
F
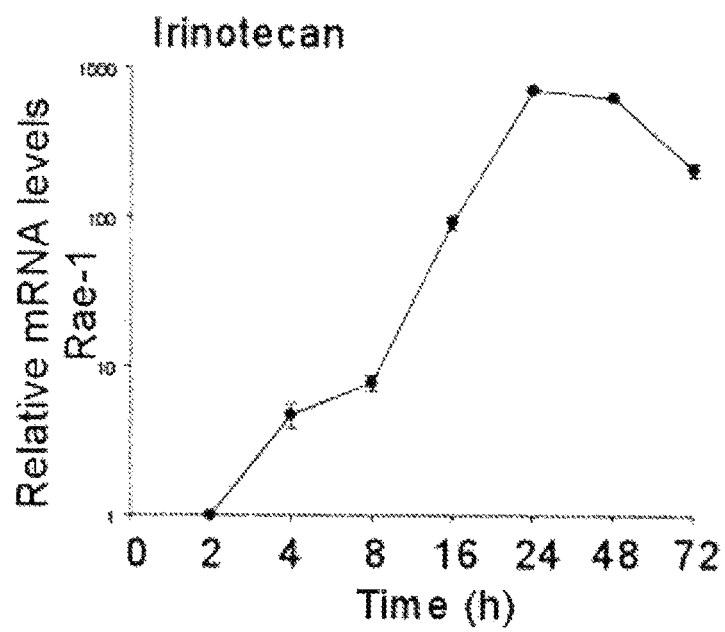
Fig. 57 E & F

G
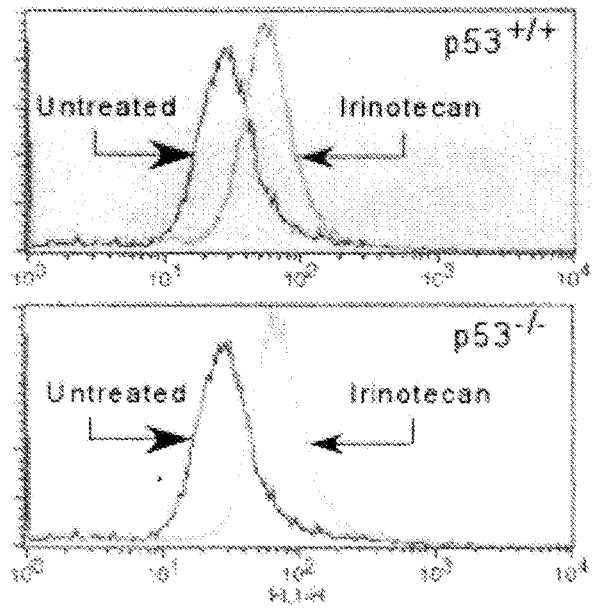
H
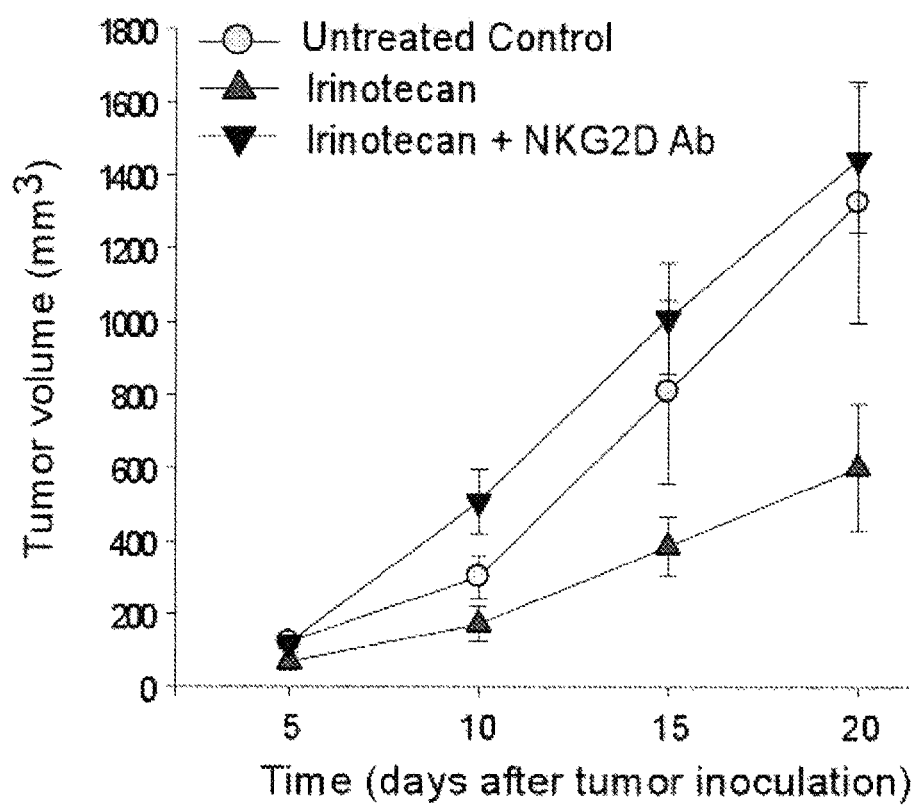
Fig. 57 G & H

COMPOSITIONS AND METHODS FOR TARGETED IMMUNOMODULATORY ANTIBODIES AND FUSION PROTEINS

CROSS-REFERENCE TO RELATED APPLICATIONS

This application is a 35 USC §371 National Stage application of International Application No. PCT/US2011/027317 filed Mar. 4, 2011, now pending; which claims the benefit under 35 USC §119(e) to U.S. Application Ser. No. 61/435,671 filed Jan. 24, 2011 and to U.S. Application Ser. No. 61/311,255 filed Mar. 5, 2010. The disclosure of each of the prior applications is considered part of and is incorporated by reference in the disclosure of this application.

BACKGROUND OF THE INVENTION

1. Field of the Invention

The present invention relates generally to the field of targeted immunomodulatory antibodies and fusion proteins for cancer therapy and more specifically to composition and methods for targeted immunostimulatory or immunosuppressive antibodies and fusion proteins to counteract or induce immune tolerance of cancer cells.

2. Background Information

The immune system provides the human body with a means to recognize and defend itself against microorganisms and substances recognized as foreign or potentially harmful. While passive immunotherapy of cancer with monoclonal antibodies and passive transfer of T cells to attack tumor cells have demonstrated clinical efficacy, the goal of active therapeutic vaccination to induce these immune effectors and establish immunological memory against tumor cells has remained challenging. Several tumor-specific and tumor-associated antigens have been identified, yet these antigens are generally weakly immunogenic and tumors employ diverse mechanisms to create a tolerogenic environment that allows them to evade immunologic attack. Strategies to overcome such immune tolerance and activating robust levels of antibody and/or T cell responses hold the key to effective cancer immunotherapy.

SUMMARY OF THE INVENTION

The present invention is based on the seminal discovery that targeted immunomodulatory antibodies and fusion proteins can counteract or reverse immune tolerance of cancer cells. Cancer cells are able to escape elimination by chemotherapeutic agents or tumor-targeted antibodies via specific immunosuppressive mechanisms in the tumor microenvironment and such ability of cancer cells is recognized as immune tolerance. Such immunosuppressive mechanisms include immunosuppressive cytokines (for example, Transforming growth factor beta (TGF-β)) and regulatory T cells and/or immunosuppressive, myeloid dendritic cells (DCs). By counteracting tumor-induced immune tolerance, the present invention provides effective compositions and methods for cancer treatment, optional in combination with another existing cancer treatment. The present invention provides strategies to counteract tumor-induced immune tolerance and enhance the antitumor efficacy of chemotherapy by activating and leveraging T cell-mediated adaptive antitumor immunity against resistant or disseminated cancer cells.

In one embodiment, the present invention provides a molecule including a targeting moiety fused with an immunomodulatory moiety. The targeting moiety specifically binds a target molecule, and the immunomodulatory moiety specifically binds one of the following molecules: (i) Transforming growth factor-beta (TGF-β); (ii) Programmed death-1 ligand 1 (PD-L1) or Programmed death-1 ligand 2 (PD-L2); (iii) Receptor activator of nuclear factor-κB (RANK) ligand (RANKL); (iv) Transforming growth factor-beta receptor (TGF-βR); (v) Programmed death-1 (PD-1); and (vi) Receptor activator of nuclear factor-κB (RANK).

In one aspect, the targeting moiety includes an antibody, antibody fragment, scFv, or Fc-containing polypeptide that specifically binds a component of a tumor cell, tumor antigen, tumor vasculature, tumor microenvironment, or tumor-infiltrating immune cell. In one aspect, the targeting moiety specifically binds epidermal growth factor receptor (EGFR1, Erb-91). HER2/neu (Erb-92), CD20, Vascular endothelial growth factor (VEGF), insulin-like growth factor receptor (IGF-1R), TRAIL-receptor, epithelial cell adhesion molecule, carcino-embryonic antigen, Prostate-specific membrane antigen, Mucin-1, CD30, CD33, or CD40.

In one aspect, the targeting moiety specifically binds a component of a regulatory T cell, myeloid suppressor cell, or dendritic cell. In another aspect, the targeting moiety specifically binds one of the following molecules: (i) CD4; (ii) CD25 (IL-2α receptor; IL-2αR); (iii) cytotoxic T-lymphocyte antigen-4 (CTLA-4; CD152); (iv) Interleukin-10 (IL-10); (v) Transforming growth factor-beta receptor (TGF-βR); (vi) Transforming growth factor-beta (TGF-β), (vii) Programmed Death-1 (PD-1); (viii) Programmed death-1 ligand (PD-L1 or PD-L2); (ix) Receptor activator of nuclear factor-κB (RANK); or (x) Receptor activator of nuclear factor-κB (RANK) ligand (RANKL).

In one aspect, the immunomodulatory moiety specifically binds one of the following molecules: (i) Transforming growth factor-beta (TGF-β); (ii) Programmed death-1 ligand (PD-L1 or PD-L2); or (iii) Receptor activator of nuclear factor-κB (RANK) ligand (RANKL).

In one aspect, the immunomodulatory moiety includes a molecule that binds TGF-β. In another aspect, the immunomodulatory moiety includes an extracellular ligand-binding domain of Transforming growth factor-beta receptor TGF-βRII, TGF-βRIIb, or TGF-βRIII. In another aspect, the immunomodulatory moiety includes an extracellular ligand-binding domain of TGF-βRII. In an additional aspect, the immunomodulatory moiety inhibits the activity or function of TGF-β.

In one aspect, the targeting moiety includes an antibody, antibody fragment, or polypeptide that specifically binds to HER2/neu, EGFR1, CD20, vascular endothelial growth factor (VEGF), cytotoxic T-lymphocyte antigen-4 (CTLA-4), CD25 (IL-2α receptor; IL-20), or CD4. In an additional aspect, the immunomodulatory moiety includes an extracellular ligand-binding domain of TGF-βRII. In another aspect, the molecule includes an amino acid sequence corresponding to SEQ ID NO 1, 2, 3, 4, 5, 6, 7, 8, 9 or 10

In one aspect, the targeting moiety includes an antibody, antibody fragment, or polypeptide that specifically binds to Programmed Death-1 (PD-1), Programmed death-1 ligand 1 (PD-L1), or Programmed death-1 ligand 2 (PD-L2). In another aspect, the targeting moiety includes an extracellular ligand-binding domain or ectodomain of Programmed Death-1 (PD-1). In an additional aspect, the immunomodulatory moiety includes an extracellular ligand-binding domain of TGF-βRII. In another aspect, the molecule includes PD-1 ectodomain, immunoglobulin Fc region, and TGFβRII ectodomain. In another aspect, the molecule includes an amino acid sequence corresponding to SEQ ID NO 11 or 12.

In one aspect, the targeting moiety includes an antibody, antibody fragment, or polypeptide that specifically binds to Receptor activator of nuclear factor-κB (RANK) or Receptor activator of nuclear factor-κB ligand (RANKL). In another aspect, the targeting moiety includes an extracellular ligand-binding domain or ectodomain of Receptor activator of nuclear factor-κB (RANK). In an additional aspect, the immunomodulatory moiety includes an extracellular ligand-binding domain of TGF-βRII. In another aspect, the molecule includes RANK ectodomain, immunoglobulin Fc region, and TGFβRII ectodomain. In another aspect, the molecule includes an amino acid sequence corresponding to SEQ ID NO 13 or 14.

In one aspect, the immunomodulatory moiety includes a molecule that specifically binds to Programmed death-1 ligand 1 (PD-L1) or Programmed death-1 ligand 2 (PD-L2). In another aspect, the immunomodulatory moiety includes an extracellular ligand-binding domain or ectodomain of Programmed Death-1 (PD-1). In an additional aspect, the immunomodulatory moiety inhibits the activity or function of Programmed death-1 ligand 1 (PD-L1).

In one aspect, the targeting moiety includes an antibody, antibody fragment, or polypeptide that specifically binds to HER2/neu, EGFR1, CD20, vascular endothelial growth factor (VEGF), cytotoxic T-lymphocyte antigen-4 (CTLA-4), CD25 (IL-2α receptor; IL-2αR), or CD4. In an additional aspect, the immunomodulatory moiety includes an extracellular ligand-binding domain or ectodomain of Programmed Death-1 (PD-1). In another aspect, the molecule includes an amino acid sequence corresponding to SEQ ID NO: 15, 16, 17, 18, 19, 20, 21, 22, 23, or 24.

In one aspect, the targeting moiety includes an antibody, antibody fragment, or polypeptide that specifically binds to Receptor activator of nuclear factor-κB (RANK) or Receptor activator of nuclear factor-κB ligand (RANKL). In another aspect, the targeting moiety includes an extracellular ligand-binding domain or ectodomain of Receptor activator of nuclear factor-κB (RANK). In an additional aspect, the immunomodulatory moiety includes an extracellular ligand-binding domain of Programmed Death-1 (PD-1). In another aspect, the molecule includes RANK ectodomain, immunoglobulin Fc region, and PD-1 ectodomain. In another aspect, the molecule includes an amino acid sequence corresponding to SEQ ID NO: 25 or 26.

In one aspect, the immunomodulatory moiety includes a molecule that specifically binds to Receptor activator of nuclear factor-κB ligand (RANKL). In another aspect, the immunomodulatory moiety includes an extracellular ligand-binding domain or ectodomain of Receptor activator of nuclear factor-κB (RANK). In an additional aspect, the immunomodulatory moiety inhibits the activity or function of Receptor activator of nuclear factor-κB ligand (RANKL).

In one aspect, the targeting moiety includes an antibody, antibody fragment, or polypeptide that specifically binds to HER2/neu, EGFR1, CD20, vascular endothelial growth factor (VEGF), cytotoxic T-lymphocyte antigen-4 (CTLA-4), CD25 (IL-2α receptor; IL-2αR), or CD4. In an additional aspect, the immunomodulatory moiety includes an extracellular ligand-binding domain or ectodomain of Receptor activator of nuclear factor-κB (RANK). In another aspect, the molecule includes an amino acid sequence corresponding to SEQ ID NO; 27, 28, 29, 30, 31, 32, 33, 34, 35, or 36.

In one aspect, the immunomodulatory moiety includes a sequence from Programmed death-1 ligand 1 (PD-L1) or Programmed death-1 ligand 2 (PD-L2). In an additional aspect, the immunomodulatory moiety increases the function of PD-1.

In one aspect, the targeting moiety specifically binds to Tumor Necrosis Factor-α (TNF-α), and the immunomodulatory moiety includes a sequence from Programmed death-1 ligand 1 (PD-L1) or Programmed death-1 ligand 2 (PD-L2). In an additional aspect, the targeting moiety includes an antibody that binds TNF-α, and the immunomodulatory moiety includes a sequence from PD-1 ligand 1 (PD-L1 or B7-H1). In another aspect, the molecule includes an amino acid sequence corresponding to SEQ ID NO: 37. In another aspect, the targeting moiety includes an extracellular ligand-binding domain of tumor necrosis factor receptor 2 (TNFR2), and the immunomodulatory moiety includes a sequence from PD-1 ligand 1 (PD-L1 or B7-H1). In another aspect, the molecule includes TNFR2 Extracellular ligand binding domain, immunoglobulin Fc region, and a sequence from PD-L1. In another aspect, the molecule includes an amino acid sequence corresponding to SEQ ID NO 38 or 39.

In one aspect, the targeting moiety includes an antibody or antibody fragment that specifically binds to CD20, CD25, or CD4, and the immunomodulatory moiety includes a sequence from Programmed death-1 ligand 1 (PD-L1) or Programmed death-1 ligand 2 (PD-L2). In another aspect, the molecule includes an amino acid sequence corresponding to SEQ ID NO: 40, 41, 42, 43, 44 or 45.

In one aspect, the targeting moiety includes the extracellular domain of CTLA-4 and immunoglobulin Fc region (IgG Cγ1), and the immunomodulatory moiety includes a sequence from Programmed death-1 ligand 1 (PD-L1) or Programmed death-1 ligand 2 (PD-L2). In another aspect, the molecule includes an amino acid sequence corresponding to SEQ ID NO: 46 or 47.

In one aspect, the targeting moiety includes transforming growth factor-β (TGF-β) and immunoglobulin Fc region (IgG Cγ1), and the immunomodulatory moiety includes a sequence from Programmed death-1 ligand 1 (PD-L1) or Programmed death-1 ligand 2 (PD-L2). In an additional aspect, the molecule includes an amino acid sequence corresponding to SEQ ID NO: 48 or 49.

In one aspect, the immunomodulatory moiety includes a sequence from transforming growth factor-β (TGF-β). In an additional aspect, the immunomodulatory moiety activates the signaling function of transforming growth factor-β (TGF-β) receptor.

In one aspect, the targeting moiety includes an antibody, antibody fragment, or polypeptide that specifically binds to Tumor Necrosis Factor-α (TNF-α), and the immunomodulatory moiety includes a sequence from transforming growth factor-β (TGF-β). In an additional aspect, the targeting moiety includes an antibody that binds TNF-α, and the immunomodulatory moiety includes a sequence from TGF-β. In another aspect, the molecule includes an amino acid sequence corresponding to SEQ ID NO: 50. In one aspect, the targeting moiety includes an extracellular ligand-binding domain of tumor necrosis factor receptor 2 (TNFR2). In another aspect, the molecule includes TNFR2 Extracellular ligand binding domain, immunoglobulin Fc region, and a sequence from transforming growth factor-β (TGF-β). In another aspect, the molecule includes an amino acid sequence corresponding to SEQ ID NO: 51 or 52.

In one aspect, the targeting moiety includes an antibody or antibody fragment that specifically binds to CD20, CD25 (IL-2α receptor; IL-2αR), or CD4, and the immunomodulatory moiety includes a sequence from transforming growth factor-β (TGF-β). In an additional aspect, the molecule includes an amino acid sequence corresponding to SEQ ID NO: 53, 54, 55, 56, 57 or 58.

In one aspect, the targeting moiety includes an extracellular domain of CTLA-4 and immunoglobulin Fc region (IgG Cγ1), and the immunomodulatory moiety includes a sequence from transforming growth factor-β (TGF-β). In another aspect, the molecule includes an amino acid sequence corresponding to SEQ ID NO 59 or 60.

In one aspect, the targeting moiety includes an antibody, antibody fragment, or polypeptide that specifically binds to Tumor Necrosis Factor-α (TNF-α), and the immunomodulatory moiety includes an extracellular RANKL-binding domain or ectodomain of Receptor activator of nuclear factor-κB (RANK). In an additional aspect, the targeting moiety includes an antibody that binds TNF-α, and the immunomodulatory moiety includes a sequence from an extracellular RANKL-binding domain or ectodomain of RANK. In another aspect, the molecule includes an amino acid sequence corresponding to SEQ ID NO: 61. In one aspect, the targeting moiety includes an extracellular ligand-binding domain of tumor necrosis factor receptor 2 (TNFR2). In another aspect, the molecule includes TNFR2 Extracellular ligand binding domain, immunoglobulin Fc region, and a sequence from an extracellular RANK-binding domain or ectodomain of RANK. In another aspect, the molecule includes an amino acid sequence corresponding to SEQ ID NO: 62 or 63.

In one aspect, the targeting moiety includes an extracellular domain of CTLA-4 and immunoglobulin Fc region (IgG Cγ1), and the immunomodulatory moiety includes an extracellular RANKL-binding domain or ectodomain of Receptor activator of nuclear factor-κB (RANK). In another aspect, the molecule includes an amino acid sequence corresponding to SEQ ID NO: 64 or 65.

In one aspect, the targeting moiety includes a sequence from transforming growth factor-β (TGF-β) and immunoglobulin Fc region (IgG Cγ1), and the immunomodulatory moiety includes an extracellular RANKL-binding domain or ectodomain of Receptor activator of nuclear factor-κB (RANK). In another aspect, the molecule includes an amino acid sequence corresponding to SEQ ID NO 66 or 67.

In one aspect, the targeting moiety includes a sequence from Programmed death-1 ligand 1 (PD-L1) and immunoglobulin Fc region (IgG Cγ1), and the immunomodulatory moiety includes an extracellular RANKL-binding domain or ectodomain of Receptor activator of nuclear factor-κB (RANK). In another aspect, the molecule includes an amino acid sequence corresponding to SEQ ID NO: 68 or 69.

In various aspects, the molecule is fused or directly linked to one or more antigen, antigenic determinant, or epitope.

In another embodiment, the present invention, provides a composition including the molecule of the invention and a cell, wherein the cell is a tumor cell, immune cell, or dendritic cell.

In another embodiment, the present invention provides a method of counteracting or overcoming immune tolerance. The method includes administering to a subject in need thereof one or more molecule of the invention.

In another embodiment, the present invention provides a method of preventing or treating a neoplastic disease. The method includes administration to a subject in need thereof one or more molecule of the invention. In various aspects, the subject is administered one or more molecule of the invention in combination with another anticancer therapy. In one aspect, the anticancer therapy includes a chemotherapeutic molecule, antibody, small molecule kinase inhibitor, hormonal agent or cytotoxic agent. In another aspect, the anticancer therapy includes ionizing radiation, ultraviolet radiation, cryoablation, thermal ablation, or radiofrequency ablation.

In another embodiment, the present invention provides a method of preventing or treating a neoplastic disease. The method includes administration to a subject in need thereof an antibody that targets and depletes CD44+ regulatory T cells (Tregs) in combination with another cytotoxic anticancer therapy. In one aspect, the antibody that targets and depletes Tregs is an anti-CD4 antibody. In various aspects, the cytotoxic anticancer therapy includes a chemotherapeutic molecule, tumor-targeted antibody, small molecule kinase inhibitor, hormonal agent or tumor-targeted cytotoxic agent. In another aspect, the cytotoxic anticancer therapy includes ionizing radiation, ultraviolet radiation, cryoablation, thermal ablation, or radiofrequency ablation.

In another embodiment, the subject is administered one or more molecule of the invention in combination with any vaccine. In another aspect, the vaccine includes a tumor antigen, tumor-associated antigen, tumor epitope, tumor antigen-containing fusion protein, tumor cell, or dendritic cell. In another aspect, the vaccine includes a pathogen antigen, pathogen-associated antigen, pathogen epitope, or pathogen antigen-containing fusion protein.

In another embodiment, the present invention provides a method for treating immune cells wherein the cells are contacted ex vivo or in vitro with a molecule of the invention. In another embodiment, the present invention provides a method of treatment of a neoplastic disease. The method includes administering to a subject in need thereof a composition of immune cells contacted with a molecule of the invention.

In another embodiment, the present invention provides a method of inducing or promoting immune tolerance. The method includes administering to a subject in need thereof one or more molecule of the invention.

In another embodiment, the present invention provides a method of preventing or treating an autoimmune or inflammatory disease including administering to a subject in need thereof one or more molecule of the invention. In one aspect, the subject is administered one or more molecule of the invention in combination with another anti-inflammatory or immunosuppressive therapy. In another embodiment, the present invention provides a method of treatment of immune cells wherein the cells are contacted ex vivo or in vitro with a molecule of the invention. In another embodiment, the present invention provides a method of treating an autoimmune or inflammatory disease or preventing rejection of grafted cells or tissue. The method includes administering to a subject in need thereof a composition of immune cells contacted with a molecule of the invention.

BRIEF DESCRIPTION OF THE DRAWINGS

FIG. 1 shows exemplary amino acid sequences of transforming growth factor beta receptor type II (TGF-β-RID or TGF-β-RIIB or a fragment thereof, including (i) Transforming growth factor beta receptor type II (TGF-β-RII) (SEQ ID NO 79), and (ii) Transforming growth factor beta receptor type IIB (TGF-β-RIIB) (SEQ ID NO 80).

Figure 53G:
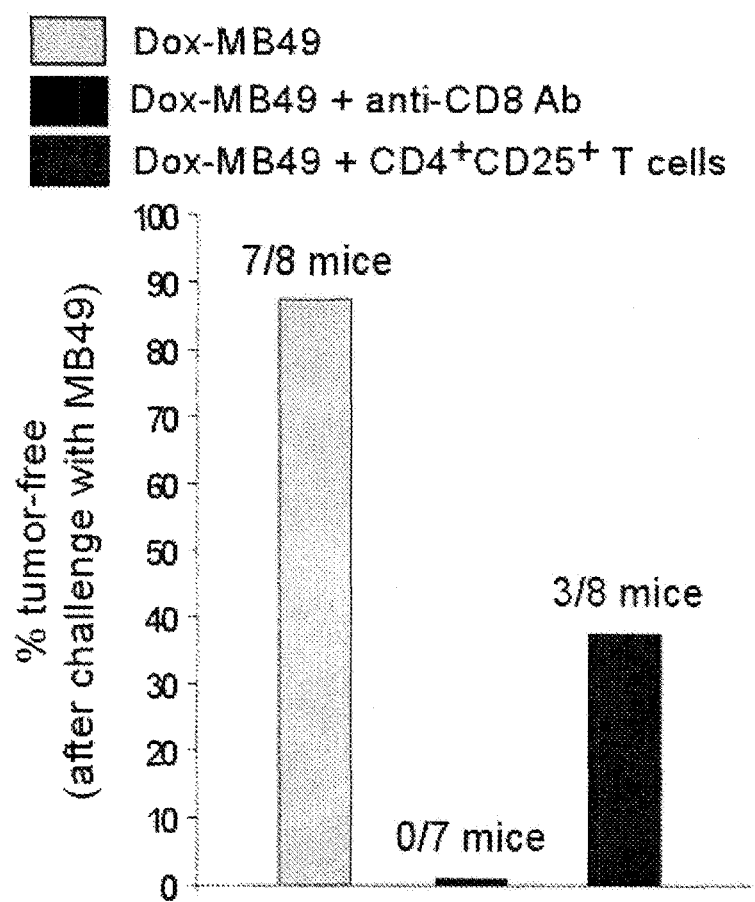

Also shown in FIG. 1 are exemplary truncated mutants of Transforming growth factor beta Receptor II (TGF-β-RII) or TGF-β-RIIB including the Extracellular domain (ECD) region that binds TGF-β, including (i) TGF-β R-II (ΔC terminus): TGFβ RII lacking the last 38 amino acids from the C-terminus (SEQ ID NO: 81) and TGF-β R-IIB (ΔC terminus): TGFβ RIIB lacking the last 38 as from the C-terminus (SEQ ID NO: 82); (ii) (Δcyt): TGFβRII lacking the kinase domain & juxtamembrane region (SEQ ID NO: 83) and TGF-βR-IIB (Δcyt): TGFβRIIB lacking the kinase domain & juxtamembrane region (SEQ ID NO: 84); (iii) TGF-β R-II containing the N-terminus region including the extracellular domain (SEQ ID NO: 85) and TGF-β R-IIB containing the N-terminus region including the extracellular domain (SEQ ID NO: 86); (iv) TGF-β R-if containing the extracellular domain that binds TGF-β (SEQ ID NO: 87) and TGF-β R-IIB containing the extracellular domain that binds TGF-β (SEQ ID NO: 88); and (v) TGF-β R-II containing the region of the extracellular domain that binds TGF-β (SEQ ID NO: 89).

In addition, FIG. 1 also shows exemplary kinase-deficient mutants, deletion mutants, or point mutants of Transforming growth factor beta Receptor II (TGFβ-RII) or TGFβ-RIIB or a fragment thereof which binds TGF-β, including (i) Transforming growth factor beta Receptor II containing point mutations-amino acid sequence of TGF-β R-II (K277R) contains a point mutation in its ATP-binding site and is inactive as a kinase (SEQ ID NO: 90); and (ii) Transforming growth factor beta Receptor II containing deletions in the amino acid sequence (deletion mutants)—Transforming growth factor beta Receptor II (Δi)-TGF-β R-II (Δi2) contains a deletion of amino acids 498 to 508 and is inactive as a kinase (SEQ ID NO: 91).

FIG. 2 shows exemplary fusion proteins including anti-HER2/neu antibody and Transforming growth factor-beta receptor II (TGFβ-RII) Extracellular domain (ECD), including anti-HER2/neu heavy chain+TGFβ-RII ECD fusion amino acid sequence (SEQ ID NO 1) and anti-HER2/neu light chain amino acid sequence (SEQ ID NO 70).

FIG. 3 shows exemplary fusion proteins including anti-EGFR1 antibody and Transforming growth factor-beta receptor II (TGFβ-RII) Extracellular domain (ECD), including anti-EGFR1 heavy chain+TGFβ-RII ECD fusion amino acid sequence (SEQ ID NO 2) and anti-EGFR1 light chain amino acid sequence (SEQ ID NO 71).

FIG. 4 shows exemplary fusion proteins including anti-CD20 antibody and Transforming growth factor-beta receptor II (TGFβ-RII) Extracellular domain (ECD), including anti-CD20 heavy chain+TGFβ-RII ECD fusion amino acid sequence (SEQ ID NO: 3) and anti-CD20 light chain amino acid sequence (SEQ ID NO: 72).

FIG. 5 shows exemplary fusion proteins including anti-VEGF antibody and Transforming growth factor-beta receptor II (TGFβ-RII) Extracellular domain (ECD), including anti-VEGF heavy chain+TGFβ-RII ECD fusion amino acid sequence (SEQ ID NO: 4) and anti-VEGF Light chain sequence (SEQ ID NO 73).

FIG. 6 shows exemplary fusion proteins including anti-human CTLA-4 antibody and Transforming growth factor-beta receptor II (TGFβ-RII) Extracellular domain (ECD), including Anti-CTLA-4 heavy chain+TGFβ-RII Extracellular domain fusion amino acid sequence (SEQ ID NO 5) and Anti-CTLA-4 light chain (SEQ ID NO 74).

FIG. 7 shows exemplary fusion proteins including IL-2, Fc, and Transforming growth factor-beta receptor II (TGFβ-RII) Extracellular domain (ECD), including IL-2+Fc+TGFβ-RII Extracellular domain (SEQ ID NO: 6) and TGFβ-RII Extracellular domain+Fc+IL-2 (SEQ ID NO: 7). The linker GGGGSGGGGSGGGGS (SEQ ID NO: 104) is optional and can be replaced with EPKSCDK (SEQ ID NO: 105) or another linker sequence well known in the art. Certain amino acid sequences can be replaced in Fc, including underlined E with D and underlined M with L.

FIG. 8 shows exemplary fusion proteins including anti-CD25 antibody and Transforming growth factor-beta receptor II (TGFβ-RII) Extracellular domain (ECD), including anti-CD25 (Daclizumab) heavy chain and TGFβ-RII Extracellular domain (SEQ ID NO 8) and anti-CD25 (Daclizumab) light chain (SEQ ID NO: 75) (FIG. 8A); and anti-CD25 (Basiliximab) heavy chain and TGFβ-RII Extracellular domain (SEQ ID NO: 9) and anti-CD25 (Basiliximab) light chain (SEQ ID NO: 76).

FIG. 9 shows exemplary fusion proteins including anti-CD4 antibody and Transforming growth factor-beta receptor II (TGFβ-RII) Extracellular domain (ECD), including anti-CD4 heavy chain and TGFβ-RII Extracellular domain (SEQ ID NO: 10) and anti-CD4 light chain (SEQ ID NO: 77)

FIG. 10 shows exemplary fusion proteins including Programmed Death-1 (PD-1) Ectodomain, Fc, and Transforming growth factor-beta receptor II (TGFβ-RII) Extracellular domain (ectodomain), including PD-1 ectodomain+Fc+TGFβRII ectodomain (SEQ ID NO: 11) and TGFβRII ectodomain+Fc+PD-1 ectodomain (SEQ ID NO: 12). The linker sequence EPKSCDK (SEQ ID NO 105) is optional and can be deleted or replaced with another linker.

FIG. 11 shows exemplary fusion proteins including Receptor activator of nuclear factor-kB (RANK) Ectodomain, Fc, and Transforming growth factor-beta receptor II (TGFβ-RII) Extracellular domain (ectodomain), including RANK ectodomain+Fc+TGFβRII ectodomain (SEQ ID NO: 13) and TGFβRII ectodomain+Fc+RANK ectodomain (SEQ ID NO: 14). The linker sequence EPKSCDK (SEQ ID NO: 105) is optional and can be deleted or replaced with another linker.

FIG. 12 shows exemplary immunomodulatory moiety that binds Programmed Death-1 ligand 1 (PD-L1 or B7-H1) or Programmed Death-1 ligand 2 (PD-L2 or B7-DC), including full-length PD-1 or fragment thereof (SEQ ID NO: 92), PD-1 extracellular domain (ectodomain) or fragment thereof (SEQ ID NO: 93), and PD-1 extracellular domain (ectodomain) ligand-binding region (SEQ ID NO 94).

FIG. 13 shows exemplary fusion proteins including anti-HER2/neu antibody and PD-1 Ectodomain, including anti-HER2/neu heavy chain+PD-1 ectodomain fusion amino acid sequence (SEQ ID NO: 15) and anti-HER2/neu light chain amino acid sequence (SEQ ID NO: 70).

FIG. 14 shows exemplary fusion proteins including anti-EGFR1 antibody and PD-1 Ectodomain, including anti-EGFR heavy chain+PD-1 ectodomain fusion amino acid sequence (SEQ ID NO 16) and anti-EGFR light chain amino acid sequence (SEQ ID NO 71).

FIG. 15 shows exemplary fusion proteins including anti-CD20 antibody and PD-1 Ectodomain, including anti-CD20 heavy chain+PD-1 ectodomain fusion amino acid sequence (SEQ ID NO 17) and anti-CD20 light chain amino acid sequence (SEQ ID NO 72).

FIG. 16 shows exemplary fusion proteins including anti-VEGF antibody and PD-1 Ectodomain, including anti-VEGF heavy chain+PD-1 ectodomain fusion amino acid sequence (SEQ ID NO 18) and anti-VEGF Light chain sequence (SEQ ID NO 73).

FIG. 17 shows exemplary fusion proteins including anti-human CTLA-4 antibody and PD-1 Ectodomain, including anti-CTLA-4 heavy chain+PD-1 ectodomain fusion amino acid sequence (SEQ ID NO 19) and anti-CTLA-4 light chain (SEQ ID NO 74).

FIG. 18 shows exemplary fusion proteins including anti-CD25 antibody and PD-1 Ectodomain, including anti-CD25 (Daclizumab) heavy chain and PD-1 ectodomain (SEQ ID NO: 20) and anti-CD25 (Daclizumab) light chain (SEQ ID NO: 75) (FIG. 18A), and anti-CD25 (Basiliximab) heavy chain and PD-1 ectodomain (SEQ ID NO: 21) and anti-CD25 (Basiliximab) light chain (SEQ ID NO: 76) (FIG. 18B).

FIG. 19 shows exemplary fusion proteins including IL-2. Fc, and PD-1 ectodomain, including IL-2+Fc+PD-1 ectodomain (SEQ ID NO: 22) and PD-1 ectodomain+Fc+IL-2 (SEQ ID NO: 23). The linker GGGGSGGGGSGGGGS SEQ ID NO: 104 is optional and can be replaced with EPKSCDK SEQ ID NO: 105 or another linker sequence well known in the art. Certain amino acid sequences can be replaced in Fc, including underlined E with D and underlined M with L.

FIG. 20 shows exemplary fusion proteins including anti-CD4 antibody and PD-1 ectodomain, including anti-CD4 heavy chain and PD-1 ectodomain (SEQ ID NO: 24) and anti-CD4 light chain (SEQ ID NO: 77)

FIG. 21 shows exemplary fusion proteins including Receptor activator of nuclear factor-kB (RANK) Ectodomain, Fc, and PD-1 ectodomain, including RANK ectodomain+Fc+PD-1 ectodomain (SEQ ID NO: 25) and PD-1 ectodomain+Fc+RANK ectodomain (SEQ ID NO: 26). The linker sequence EPKSCDK (SEQ ID NO 105) is optional and can be deleted or replaced with another linker.

FIG. 22 shows exemplary immunomodulatory moiety that binds Receptor activator of nuclear factor-kB (RANK) ligand (RANKL) including full-length RANK or fragment thereof (SEQ ID NO: 95), extracellular ligand-binding domain or ectodomain of RANK (SEQ ID NO: 96), RANKL-binding sequences or residues of RANK (SEQ ID NO: 93), or RANKL-binding sequences of Osteoprotegerin (OPG) (SEQ ID NO 98).

FIG. 23 shows exemplary fusion proteins including anti-HER2/neu antibody and RANK Ectodomain, including anti-HER2/neu heavy chain+RANK ectodomain fusion amino acid sequence (SEQ ID NO: 27) and anti-HER2/neu light chain amino acid sequence (SEQ ID NO: 70).

FIG. 24 shows exemplary fusion proteins including anti-EGFR1 antibody and RANK Ectodomain, including anti-EGFR heavy chain+RANK ectodomain fusion amino acid sequence (SEQ ID NO: 28) and anti-EGFR light chain amino acid sequence (SEQ ID NO: 71).

FIG. 25 shows exemplary fusion proteins including anti-CD20 antibody and RANK Ectodomain, including anti-CD20 heavy chain+RANK ectodomain fusion amino acid sequence (SEQ ID NO 29) and anti-CD20 light chain amino acid sequence (SEQ ID NO 72).

FIG. 26 shows exemplary fusion proteins including anti-VEGF antibody and RANK Ectodomain, including anti-VEGF heavy chain+RANK ectodomain fusion amino acid sequence (SEQ ID NO 30) and anti-VEGF Light chain sequence (SEQ ID NO 73).

FIG. 27 shows exemplary fusion proteins including anti-human CTLA-4 antibody and RANK Ectodomain, including anti-CTLA-4 heavy chain+RANK ectodomain fusion amino acid sequence (SEQ ID NO 31) and anti-CTLA-4 light chain (SEQ ID NO 74).

FIG. 28 shows exemplary fusion proteins including anti-CD25 antibody and RANK Ectodomain, including anti-CD25 (Daclizumab) heavy chain and RANK ectodomain (SEQ ID NO 32) and anti-CD25 (Daclizumab) light chain (SEQ ID NO 75) (FIG. 28A), and anti-CD25 (Basiliximab) heavy chain and RANK ectodomain (SEQ ID NO: 33) and anti-CD25 (Basiliximab) light chain (SEQ ID NO 76) (FIG. 28B).

FIG. 29 shows exemplary fusion proteins including IL-2, Fc, and RANK ectodomain, including IL-2+Fc+RANK ectodomain (SEQ ID NO: 34) and RANK ectodomain+Fc+IL-2 (SEQ ID NO: 35). The linker GGGGSGGGGSGGGGS SEQ ID NO: 104 is optional and can be replaced with EPKSCDK SEQ ID NO: 105 or another linker sequence well known in the art. Certain amino acid sequences can be replaced in Fc, including underlined E with D and underlined M with L.

FIG. 30 shows exemplary fusion proteins including anti-CD4 antibody and RANK ectodomain, including anti-CD4 heavy chain and RANK ectodomain (SEQ ID NO: 36) and anti-CD4 light chain (SEQ ID NO: 77)

FIG. 31 shows exemplary immunomodulatory moiety that binds Programmed Death-1 (PD-1) including a PD-1 ligand 1 (PD-L1 or B7-H1) or PD-1 ligand 2 (PD-L2 or B7-DC) or a fragment thereof (for example, SEQ ID NO: 101), full-length human PD-1 ligand 1 (B7-H1; PDCD1L1; PD-L1; or CD274) protein or a fragment thereof (SEQ ID NO: 99), and PD-L1 extracellular binding domain (ectodomain) or fragment thereof (SEQ ID NO: 100).

FIG. 32 shows exemplary fusion proteins including anti-tumor necrosis factor (TNFα) antibody and PD-1 ligand, including anti-TNFα heavy chain+PD-IL (SEQ ID NO: 37) and anti-TNFα light chain (SEQ ID NO: 78). The sequence KKAE (SEQ ID NO: 107) can be replaced with KRVE (SEQ ID NO 108) or KKVE (SEQ ID NO 109).

FIG. 33 shows exemplary fusion proteins including TNFR2 Extracellular ligand binding domain, Fc, and PD-1 ligand, including TNFR2 ECD+IgG Cγ1+PD-L1 (SEQ ID NO: 38) and PD-L1+IgG Cγ1-TNFR2 ECD (SEQ ID NO: 39).

FIG. 34 shows exemplary fusion proteins including anti-CD20 antibody and PD-1 ligand 1 (PD-L1), including anti-CD20 heavy chain+PD-L1 sequence (SEQ ID NO 40) and anti-CD20 light chain sequence (SEQ ID NO: 72).

FIG. 35 shows exemplary fusion proteins including anti-CD25 antibody and PD-1 ligand 1 (PD-L1), including anti-CD25 (Daclizumab) heavy chain and PD-L1 (SEQ ID NO: 41) and anti-CD25 (Daclizumab) light chain (SEQ ID NO 75) (FIG. 35A), and anti-CD25 (Basiliximab) heavy chain and PD-1 ectodomain (SEQ ID NO: 42) and anti-CD25 (Basiliximab) light chain (SEQ ID NO 76) (FIG. 35B).

FIG. 36 shows exemplary fusion proteins including IL-2, Fc, and PD-1 ligand 1 (PD-L1), including fusion protein hPD-1 ligand 1+Fc+IL-2 (SEQ ID NO: 43) and fusion protein IL-2+Fc+PD-1 ligand 1 (SEQ ID NO: 44). The linker GGGGSGGGGSGGGGS SEQ ID NO: 104 is optional and can be replaced with EPKSCDK SEQ ID NO: 105 or another linker sequence well known in the art. Certain amino acid sequences can be replaced in Fc, including underlined E with D and underlined M with L.

FIG. 37 shows exemplary fusion proteins including anti-CD4 antibody and PD-1 ligand 1 (PD-L1), including anti-CD4 heavy chain and PD-1 ligand 1 (PD-L1) (SEQ ID NO: 45) and anti-CD4 light chain (SEQ ID NO 77)

FIG. 38 shows exemplary fusion proteins including the extracellular domain of CTLA-4, Immunoglobulin Fc (IgG Cγ1), and a sequence from PD-1 ligand (PD-L1) including Oncostatin M signal peptide+CTLA-4 ECD+IgG Cγ1+PD-L1 (SEQ ID NO: 46) and PD-1L1+IgG Cγ1+CTLA-4 ECD (SEQ ID NO: 47). The IgG sequence shown can have optional C to S conversion in (bold underlined). The linker QEPKSCDK SEQ ID NO: 110 is optional and can be replaced with EPKSCDK SEQ ID NO 105 or another linker sequence.

FIG. 39 shows exemplary fusion proteins including a sequence of transforming growth factor-β (TGF-β), Immunoglobulin Fc (IgG Cγ1), and a sequence of PD-1 ligand (PD-L1) including TGFβ-1+Fc+PD-L1 (SEQ ID NO: 48), and PD-1L1+Fc+TGFβ-1 (SEQ ID NO: 49). The linker GGGGSGGGGSGGGGS SEQ ID NO: 104 is optional and can be replaced with EPKSCDK SEQ ID NO: 105 or another linker sequence well known in the art. Certain amino acid sequences can be replaced in Fc, including underlined E with D and underlined M with L.

FIG. 40 shows exemplary immunomodulatory moiety that binds Transforming growth factor-beta receptor (TGF-βR) including Transforming growth factor-beta (TGF-β1, TGF-β2, or TGF-β3 or a fragment thereof, TGF-β1 full sequence (SEQ ID NO: 102), and mature (active) TGF-β1 sequence (Ala 279-Ser 390, 112 amino acids) (SEQ ID NO 103).

FIG. 41 shows exemplary fusion proteins including an antibody that binds TNF-α, and a sequence of transforming growth factor-β (TGF-β), including anti-TNFα heavy chain+TGF-β1 (SEQ ID NO: 50) and anti-TNFα light chain (SEQ ID NO: 78). The sequence KKAE (SEQ ID NO: 107) can be replaced with KRVE (SEQ ID NO: 108) or KKVE (SEQ ID NO: 109).

FIG. 42 shows exemplary fusion proteins including TNFR2 Extracellular ligand binding domain (TNFR2 ECD), immunoglobulin Fc (IgG Cγ1), and a sequence from transforming growth factor-β (TGF-β) including TNFR2 ECD+IgG Cγ1+TGF-β1 (SEQ ID NO: 51), and TGF-β1+IgG Cγ1+TNFR2 ECD (SEQ ID NO: 52).

FIG. 43 shows exemplary fusion proteins including anti-CD20 antibody and a sequence from transforming growth factor-β (TGF-β), including anti-CD20 heavy chain+mature TGFβ1 sequence (SEQ ID NO: 53) and anti-CD20 light chain sequence (SEQ ID NO: 72).

FIG. 44 shows exemplary fusion proteins including anti-CD25 antibody and a sequence from transforming growth factor-β (TGF-β), including anti-CD25 (Daclizumab) heavy chain and TGF-β1 (SEQ ID NO: 54) and anti-CD25 (Daclizumab) light chain (SEQ ID NO: 75) (FIG. 44A), and anti-CD25 (Basiliximab) heavy chain and TGF-β1 (SEQ ID NO: 55) and anti-CD25 (Basiliximab) light chain (SEQ ID NO 76) (FIG. 44B).

FIG. 45 shows exemplary fusion proteins including IL-2, Fc, and a sequence from transforming growth factor-β (TGF-β), including TGF-β1+Fc-+IL-2 (SEQ ID NO: 56) and IL-2+Fc+TGF-β1 (SEQ ID NO: 57). The linker GGGGSGGGGSGGGGS SEQ ID NO 104 is optional and can be replaced with EPKSCDK SEQ ID NO: 105 or another linker sequence well known in the art. Certain amino acid sequences can be replaced in Fc, including underlined E with D and underlined M with L.

FIG. 46 shows exemplary fusion proteins including anti-CD4 antibody and a sequence from transforming growth factor-β (TGF-β), including anti-CD4 heavy chain and TGF-β (SEQ ID NO 58) and anti-CD4 light chain (SEQ ID NO 77)

FIG. 47 shows exemplary Fusion proteins including the extracellular domain of CTLA-4, Immunoglobulin Fc (IgG Cγ1), and a sequence from transforming growth factor-β (TGF-β) including Oncostatin M signal peptide+CTLA-4 ECD+IgG Cγ1+TGF-β1 (SEQ ID NO: 59), and TGF-β1+IgG Cγ1+CTLA-4 ECD (SEQ ID NO 60). The IgG sequence shown can have optional C to S conversion in (bold underlined). The linker QEPKSCDK SEQ ID NO: 110 is optional and can be replaced with EPKSCDK SEQ ID NO: 105 or another linker sequence.

FIG. 48 shows exemplary fusion proteins including an antibody that binds TNF-α, and a sequence of RANK ectodomain, including anti-TNFα heavy chain+RANK ectodomain (SEQ ID NO: 61) and anti-TNFα light chain (SEQ ID NO: 78). The sequence KKAE (SEQ ID NO 107) can be replaced with KRVE (SEQ ID NO 108) or KKVE (SEQ ID NO 109).

FIG. 49 shows exemplary fusion proteins including TNFR2 Extracellular ligand binding domain (TNFR2 ECD), immunoglobulin Fc (IgG Cγ1), and a sequence from RANK ectodomain including TNFR2 ECD+IgG Cγ1+RANK ectodomain (SEQ ID NO: 62), and RANK ectodomain+IgG Cγ1+TNFR2 ECD (SEQ ID NO: 63).

FIG. 50 shows exemplary Fusion proteins including the extracellular domain of CTLA-4, Immunoglobulin Fc (IgG Cγ1), and a sequence from RANK ectodomain including Oncostatin M signal peptide+CTLA-4 ECD+IgG Cγ1+RANK ectodomain (SEQ ID NO: 64), and RANK ectodomain+IgG Cγ1+CTLA-4 ECD (SEQ ID NO: 65). The IgG sequence shown can have optional C to S conversion in (bold underlined). The linker QEPKSCDK SEQ ID NO: 110 is optional and can be replaced with EPKSCDK SEQ ID NO: 105 or another linker sequence.

FIG. 51 shows exemplary fusion proteins including a sequence from transforming growth factor-β (TGF-β), immunoglobulin Fc (IgG Cγ1), and a sequence from RANK ectodomain including TGF-β-F IgG Cγ1+RANK ectodomain (SEQ ID NO: 66), and RANK ectodomain+IgG Cγ1+TGF-β (SEQ ID NO: 67).

FIG. 52 shows exemplary fusion proteins including a sequence from PD-1 ligand (PD-L1), immunoglobulin Fc (IgG Cγ1), and a sequence from RANK ectodomain including PD-L1+IgG Cγ1+RANK ectodomain (SEQ ID NO: 68), and RANK ectodomain+IgG Cγ1+PD-L1 (SEQ ID NO: 69).

FIG. 53 shows Regulatory T cells (Treg) accumulate in the tumor microenvironment and counteract the ability of chemotherapy to activate $CD8^+$ T cell-mediated antitumor immunity. (a) Surface exposure of calreticulin (CRT) in response to treatment of human (SW780) and murine (MB49) cancer cells with doxorubicin (10 μM) for 4 h. The surface exposure of CRT was determined by immunofluorescence cytometry of untreated control or doxorubicin-treated cells stained with Dylight-labeled anti-CRT antibody or an isotype control (IgG1) antibody. (b) Priming of tumor-reactive immune responses by MB49 tumor cells treated with doxorubicin ex vivo or in vivo. $5 \times 10^6$ MB49 cells that were pre-treated ex vivo with doxorubicin (10 μM) for 4 h were injected into one flank of syngeneic immunocompetent C57BL/6 mice. Alternatively, C57BL/6 mice were injected with $5 \times 10^5$ live MB49 tumor cells and then administered intratumoral doxorubicin (10 μg) at 10 d following tumor inoculation Tumor-reactive immune responses were determined by measuring production of IFN-γ by draining lymph node (DLN) cells in response to in vitro re-challenge with either MB49 cell lysates, an irrelevant peptide (Hemagglutinin-HA), or medium alone. (c) Vaccination with doxorubicin-treated tumor cells induces $CD8^+$ T cell-mediated antitumor immunity that prevents tumor formation following re-challenge with live tumor cells. MB49 cells ($5 \times 10^6$) that were pre-treated in vitro with doxorubicin (10 μM) for 4 h were injected subcutaneously into one flank of syngeneic immunocompetent C57BL/6 mice. Naïve or vaccinated mice were challenged with untreated live MB49 tumor cells injected into the opposite flank with or without pre-treatment with an anti-CD8 antibody (Clone GK2.43) (5 μg×2 doses, iv) to deplete $CD8^+$ T cells. (d) Delayed administration of chemotherapy in mice with pre-established tumors decreases its immunogenicity and antitumor efficacy. C57BL/6 mice were injected with $5 \times 10^5$ live syngeneic MB49 tumor cells and then administered intratumoral doxorubicin (10 μg) at d3, d7, or d10 following tumor inoculation. (e) Tumors foster the accumulation of $CD4^+CD25^+FoxP3^+$ cells (Tregs) in their microenvironment. Flow cytometric analyses of the percentage of $CD4^+CD25^+FoxP3^+$ cells (Tregs) among $CD4^+$ T lymphocytes isolated from the spleen, draining lymph nodes (DLN), and tumors of immunocompetent C57BL/6 mice at d0 and d14 after subcutaneous inoculation of $5 \times 10^5$ live MB49 tumor cells. (f) Tregs infiltrating the tumor microenvironment suppress priming of tumor-reactive immune responses by doxorubicin-treated tumor cells. Naïve C57BL/6 mice were vaccinated with $5\times10^6$ doxorubicin-killed MB49 cells with or without intravenous adoptive transfer of $5\times10^6$ CD4$^+$CD25$^+$ cells isolated from tumors and DLN of tumor-bearing mice via immunomagnetic separation. Tumor-reactive immune responses were determined by measuring production of IFN-γ by draining lymph node (DLN) cells in response to in vitro re-challenge with either MB49 cell lysates, an irrelevant peptide (Hemagglutinin-HA), or medium alone. (g) Tregs infiltrating the tumor microenvironment suppress the activation of adaptive antitumor immunity in response to chemotherapy-induced tumor cell death. Naïve C57BL/6 mice were vaccinated with $5\times10^6$ doxorubicin-killed MB49 cells (left flank) with or without pre-treatment with either an anti-CD8 antibody (Clone GK2.43) (5 μg×2 doses, iv) to deplete CD8$^+$ T cells or adoptive transfer of $5\times10^6$CD4$^+$CD25$^+$ cells isolated from tumors and DLN of tumor-bearing mice. Protective antitumor immunity in vaccinated mice was determined by assessment of tumor growth upon challenge with untreated live MB49 tumor cells injected into the opposite flank.

FIG. 54 shows inhibition of TGF-3 in the tumor microenvironment reduces 'adaptive' FoxP3$^+$ regulatory T cells and enhances the antitumor efficacy chemotherapy. (a) Tumor growth results in a progressive increase in the level of serum TGF-β. Levels of TGF-β in serum of mice at d0, d14, and d28 following inoculation of $5\times10^5$ live MB49 tumor cells were evaluated utilizing ELISA. (b) Tumor cell-autonomous expression of TGF-β is the dominant source of elevated TGF-β in tumor-bearing mice. Tumor cells or draining lymph node cells isolated from either tumor-bearing mice or their tumor-free counterparts were cultured ex vivo in serum-free medium for 24 h and the amount of TGF-β/$10^6$ cells in supernatants was measured by ELISA. (c) TGFβRII:Fc sequesters TGF-β in supernatants of MB49 tumor cells in a concentration-dependent manner. MB49 tumor cells were cultured in the presence of graded concentrations of TGFβRII:Fc (0-400 ng/ml) for 24 h followed by measurement of TGF-β (pg/ml/$10^6$ cells) in supernatants via ELISA. (d) TGF-β induces 'adaptive' FoxP3$^+$ regulatory T cells in the tumor microenvironment. At 5 d following inoculation of MB49 tumor cells, mice were either left untreated (control) or treated with TGF-βRII:Fc (1 μg intratumoral; twice weekly) for 3 weeks followed by flow cytometric analyses of intracellular FoxP3 expression in CD4$^+$CD25$^+$ T cells infiltrating the tumors. (e, f) Sequestration of intratumoral TGF-β with TGFβRII:Fc reduces CD4$^+$CD25'FoxP3$^+$ Tregs in tumor tissue and improves the antitumor efficacy of doxorubicin. MB49 tumor-bearing mice were administered doxorubicin (5 mg/kg i.p. weekly×3) with or without twice weekly treatment with TGFβRII:Fc (1 μg intratumoral). The percentage of CD4$^+$CD25'FoxP3$^+$ cells (Tregs) among tumor cells was assessed by flow cytometry (e), and tumor volume was monitored to determine the effect of counteracting tumor-induced TGF-β-mediated immune tolerance on the in vivo antitumor efficacy of doxorubicin (f).

FIG. 55 shows that anti-CD4 antibody-mediated depletion of CD4$^+$ regulatory T cells facilitates chemotherapy-induced activation of tumor-reactive CD8$^+$ T cells and enhances the antitumor efficacy of chemotherapy. (a) In vivo depletion of tumor-infiltrating CD4$^+$CD25$^+$FoxP3$^+$ T cells by treatment of tumor-bearing mice with anti-CD4 antibody. C57BL/6 mice injected with $5\times10^5$ MB49 tumor cells s.c. were left untreated (control) or administered an anti-CD4 antibody (Clone GK1.5) i.p. at 5 d and 9 d following tumor challenge. CD4$^+$CD25$^+$FoxP3$^+$ T cells infiltrating tumors isolated from mice at d16 following tumor challenge were detected by flow cytometry. (b) Target-specific depletion of either CD4$^4$ T cells, CD4$^+$CD25$^+$FoxP3$^+$ T cells, or CD8$^+$ T cells by treatment of tumor-bearing mice with anti-CD4 antibody or anti-CD8 antibody. C57BL/6 mice injected s.c. with $5\times10^5$ MB49 tumor cells were left untreated or treated with doxorubicin (5 mg/kg i.p. weekly×3) beginning at d7 following tumor inoculation, with or without administration of either anti-CD4 antibody (Clone GK1.5) or anti-CD8 antibody (Clone GK2.43) at d5 and d9 following tumor inoculation. Flow cytometric analyses of peripheral blood mononuclear cells isolated from mice at d16 following tumor challenge determined the percentage of CD4$^+$ T cells or CD8$^+$ T cells among total mononuclear cells, and the percentage of CD4$^+$CD25$^+$FoxP3$^+$ T cells among total CD4$^+$ T cells. (c) Depletion of CD4 regulatory T cells facilitates chemotherapy-induced activation of tumor-reactive CD8$^+$ T cells. C57BL/6 mice injected s.c. with $5\times10^5$ MB49 tumor cells were left untreated or treated with doxorubicin (5 mg/kg i.p. weekly×3) beginning at d7 following tumor inoculation, with or without administration of anti-CD4 antibody (Clone GK1.5) at d5 and d9 following tumor inoculation. Tumor-reactive immune responses were determined by flow cytometric analyses of IFN-γ expression in CD8$^+$ T cells from the tumor and draining lymph node in response to in vitro stimulation with MB49 cell lysates. (d) Depletion of CD4$^+$ regulatory T cells augments the in vivo antitumor efficacy of chemotherapy via activation of tumor-reactive CD8$^+$ T cells. C57BL/6 mice injected s.c. with $5\times10^5$ MB49 tumor cells were left untreated or treated with doxorubicin (5 mg/kg i.p. weekly×3) beginning at d7 following tumor inoculation, with or without administration of either anti-CD4 antibody (Clone GK1.5) or anti-CD8 antibody (Clone GK2.43) at d5 and d9 following tumor inoculation. Tumor volume was monitored to determine the effect of depleting either CD4$^+$ T cells or CD8$^+$ T cells on the in vivo antitumor efficacy of doxorubicin.

FIG. 56 shows anti-CD4 antibody-mediated depletion of CD4$^+$ regulatory T cells augments and sustains the antitumor effect of chemotherapy by enabling activation of adaptive antitumor immunity. (a) Surface exposure of calreticulin (CRT) in response to treatment of MB49 cancer cells with either cisplatin or the combination of cisplatin and gemcitabine for 4 h. The surface exposure of CRT was determined by immunofluorescence cytometry of untreated control or chemotherapy-treated cells stained with Dylight-labeled anti-CRT antibody or an isotype control (IgG1) antibody. (b,c) Depletion of CD4$^+$ regulatory T cells enables cisplatin-induced activation of tumor-reactive IFN-γ$^+$CD8$^+$ T cells and effector memory (CD8$^+$CD62L$^-$) T cells. C57BL/6 mice injected s.c. with $5\times10^5$ MB49 tumor cells were left untreated or treated with cisplatin (0.5 mg/kg i.p. weekly×4) beginning, at d7 following tumor inoculation, with or without administration of anti-CD4 antibody (Clone GK1.5) at d5 and d9 following tumor inoculation. Tumor-reactive immune responses were determined by flow cytometric analyses of IFN-γ expression in CD8$^+$ T cells from the tumor and draining lymph node (DLN) in response to in vitro stimulation with MB49 cell lysates (b). The percentage of effector memory $T_{EM}$ cells was determined by flow cytometric analyses of CD8$^+$CD62L$^-$ cells (c). (d,e,f) Depletion of CD4$^+$ regulatory T cells augments the in vivo antitumor efficacy of chemotherapy via activation of tumor-reactive CD8$^+$ T cells. C57BL/6 mice injected s.c. with $5\times10^5$ MB49 tumor cells were left untreated or treated with either cisplatin (0.5 mg/kg) or the combination of cisplatin and gemcitabine (i.p. weekly×4) beginning at d7 following tumor inoculation, with or without administration of either anti-CD4 antibody (Clone GK1.5) or anti-CD8 antibody (Clone GK2.43) at d5 and d9 following tumor inoculation. Tumor volume was monitored to determine the effect of depleting either CD4+ T cells or CD8+ T cells on the in vivo antitumor efficacy of chemotherapy and the percentage of mice exhibiting complete tumor-regression by d50 following tumor inoculation. Establishment of adaptive antitumor immunity following regression of primary tumors was determined by re-challenging mice with live MB49 tumor cells in the opposite flank.

FIG. 57 shows that Chemotherapy-induced expression of NKG2D ligands on tumor cells cooperates with depletion of CD4+ regulatory T cells to stimulate CD8+ T cell-mediated tumor regression. (a) Genotoxic chemotherapeutic agents induce expression of mouse NKG2D ligands (Rae-1) on cancer cells. Kinetics of the upregulation of Rae1 transcripts in mouse CT26 colon cancer cells was determined by quantitative real-time PCR following treatment with irinotecan (25 µg/ml) or oxaliplatin (10 µg/ml). Quantitative RT-PCR was carried out using, Rae-1 specific primers [sense, 5'-CTAGT-GCCACCTGGGAATTCA-3' (SEQ ID NO: 111): anti-sense, 5'-CATCATTAGCTGATCTCCAGCTCA-3' (SEQ ID NO: 112)] and probe [5'-6-FAM-CATCAGTGACAGTTACT-TCTTCACCTTCTACACAGAGA-Tamra-3" (SEQ ID NO: 113)]. (b) Genotoxic chemotherapeutic agents induce p53-independent cell surface expression of human NKG2D ligands (MHC-1-related A and B molecules—MICA/MICB) on cancer cells. Isogenic p53-proficient (p53$^{+/+}$) or p53-deficient (p53$^{-/-}$) HCT116 cells were treated with irinotecan (25 µg/ml) for 16 h or left untreated. Irinotecan-induced upregulation of cell surface expression of MICA/B was determined by flow cytometric analysis of tumor cells labeled with an anti-human MICA/B MAb (R&D Systems). (c) & (d) Induction of NKG2D ligands contributes to the antitumor effect of chemotherapy in vivo. Immunocompetent Balb/C mice injected s.c. with 2×10$^5$ syngeneic CT26 tumor cells were treated with irinotecan (50 mg/kg i.p weekly×3) beginning at d5 following tumor inoculation, with or without pre-treatment with an NKG2D blocking antibody (CX5, eBIOscience) (200 µg i.p.) at 16 h before each dose of chemotherapy. Tumor volume was monitored to determine the effect of NKG2D blockade on the in vivo antitumor efficacy of irinotecan. (e) In vivo depletion of CD4+CD25+FoxP3+ T cells by treatment of tumor-bearing mice with anti-CD4 antibody. Balb/C mice injected with 2×10$^5$ CT26 tumor cells s.c. were left untreated or treated with irinotecan (50 mg/kg i.p weekly×3) beginning at d7 following tumor inoculation, with or without administration of anti-CD4 antibody (Clone GK1.5) at d5 and d9 following tumor inoculation. CD4+CD25+FoxP3+ T cells in spleen and draining lymph node isolated from mice at d16 following tumor challenge were detected by flow cytometry. (f) Depletion of CD4+ regulatory T cells facilitates irinotecan-induced activation of tumor-reactive IFN-γ+CD8+ T cells. Balb/C mice injected with 2×10$^5$ CT26 tumor cells s.c. were left untreated or treated with irinotecan (50 mg/kg i.p weekly×3) beginning at d7 following tumor inoculation, with or without administration of anti-CD4 antibody (Clone GK1.5) at d5 and d9 following tumor inoculation. Tumor-reactive immune responses were determined by flow cytometric analyses of IFN-γ expression in CD8+ T cells from the tumor and draining lymph node (DLN) in response to in vitro stimulation with either CT26 cell lysates, an irrelevant peptide (Hemagglutinin-HA), or medium alone. (g) & (h) Chemotherapy-induced expression of NKG2D ligands on tumor cells cooperates with depletion of CD4+ regulatory T cells to stimulate CD8+ T cell-mediated tumor regression. Balb/C mice injected with 2×10$^5$ CT26 tumor cells s.c. were left untreated or treated with irinotecan (50 mg/kg i.p weekly×3) beginning at d7 following tumor inoculation, with or without administration of anti-CD4 antibody (Clone GK1.5) and/or anti-CD8 antibody (Clone GK2.43) at d5 and d9 following tumor inoculation. Tumor volume was monitored to determine the effect of depleting CD4 T cells and/or CD8+ T cells on the in vivo antitumor efficacy of irinotecan.

DETAILED DESCRIPTION OF THE INVENTION

Targeted immunostimulatory antibodies and/or fusion proteins for prevention or treatment of cancer: Chemotherapy is a cornerstone of systemic treatment of patients with most common types of advanced cancers. The vast majority of human cancers harbor genetic alterations and signaling mechanisms that impair the direct death signaling pathways entrained by chemotherapeutic agents. Although chemotherapeutic agents employ diverse mechanisms to directly kill tumor cells, the present invention provides that these agents have immuno-adjuvant effects which activate innate and adaptive antitumor immune responses that are crucial for their antitumor efficacy in vivo. The present invention also provides that antitumor CD8+ T cells play an instrumental role in the in vivo response of tumors to diverse cytotoxic chemotherapeutic agents. Although chemotherapeutic agents can induce "immunogenic" tumor cell death and facilitate cross-presentation of antigens by dendritic cells, tumors create a tolerogenic environment that allows them to suppress the activation of innate and adaptive immune responses and evade immunologic attack by immune effector cells. The present invention provides that strategies to counteract tumor-induced immune tolerance in the tumor microenvironment can enhance the antitumor efficacy of chemotherapy by activating and leveraging T cell-mediated adaptive antitumor immunity against disseminated cancer cells.

The present invention is based on the seminal discovery that targeted immunomodulatory antibodies and fusion proteins can counteract or reverse immune tolerance of cancer cells. Cancer cells are able to escape elimination by chemotherapeutic agents or tumor-targeted antibodies via specific immunosuppressive mechanisms in, the tumor microenvironment and such ability of cancer cells is recognized as immune tolerance. By counteracting tumor-induced immune tolerance, the present invention provides effective compositions and methods for cancer treatment, optional in combination with another existing cancer treatment.

The present invention provides compositions and methods for targeted immunostimulatory antibodies and fusion proteins that counteract immune tolerance in the tumor microenvironment and promote T cell-mediated adaptive antitumor immunity for maintenance of durable long-term protection against recurrent or disseminated cancers. These tumor-targeted immunostimulatory molecules are designed to facilitate effective long term T cell-mediated immune responses against tumor cells by at least one of the following:

(i) promoting death of tumor cells via enhancement of antibody-dependent cellular cytotoxicity (ADCC);

(ii) facilitating effective cross-presentation of tumor antigen(s) from dying tumor cells by augmenting maturation of dendritic cells (DCs); and (iii) increasing activation and proliferation of antitumor CD8+ T cells by negating immune suppression mediated by regulatory T cells and myeloid suppressor cells. These antitumor immune responses may be activated in tandem with the sensitization of tumor cells to immune effector-mediated cytotoxicity, thereby establishing a positive feedback loop that augments tumor cytoreduction and reinforces adaptive antitumor immunity. The tumor-targeted immunostimulatory monoclonal antibodies (mAbs) of the present invention provides the ability to generate and boost antitumor immunity to multiple cross-presented tumor antigens obtained from endogenous tumor cells during the course of therapy (as an, in situ tumor vaccine), while simultaneously leveraging the antitumor immune response to eliminate disseminated cancer cells. Accordingly, the targeted immunostimulatory antibodies and fusion proteins of the invention can integrate the hitherto distinct fields of passive and active immunotherapy and provide a novel platform for simultaneously leveraging the synergistic benefits of these strategies to entrain effective innate and adaptive immune responses against targeted cancers.

While passive immunotherapy of cancer with tumor-targeted monoclonal antibodies has demonstrated clinical efficacy, the goal of active therapeutic vaccination to induce T cell-mediated immunity and establish immunological memory against tumor cells has remained challenging. Several tumor-specific and tumor-associated antigens have been identified, yet tumors employ diverse mechanisms to create a tolerogenic environment that allows them to suppress the activation of a T cell-mediated antitumor immune response. The tumor-targeted immunostimulatory antibodies and/or fusion proteins of the invention are designed to overcome such immune tolerance in the tumor microenvironment and activate robust levels of T cell responses for effective cancer immunotherapy or chemo-immunotherapy. Accordingly, the tumor-targeted immunostimulatory antibodies and/or fusion proteins of the invention have broad clinical relevance for advancing the treatment of many types of human cancers.

The tumor-targeted immunostimulatory mAbs and/or fusion proteins of the invention provide their ability to generate and boost antitumor immunity to multiple cross-presented tumor antigens obtained from endogenous tumor cells during the course of therapy (as an in situ tumor vaccine), while simultaneously leveraging the antitumor immune response to eliminate disseminated cancer cells. Accordingly, the tumor-targeted immunostimulatory antibodies and/or fusion proteins of the invention can integrate the hitherto distinct fields of passive and active immunotherapy and provide a novel platform for simultaneously leveraging the synergistic benefits of these strategies to entrain effective innate and adaptive immune responses against targeted cancers. This approach of the present invention is distinguished from and superior to conventional tumor antigen-, allogeneic tumor cell- or DC-based vaccines in at least one of the following aspects: (i) There is no a priori requirement to define, clone and purify individual tumor antigens, since the patient's tumor itself is the in vivo source of antigens; (ii) Multivalent antitumor immune responses that are naturally tailored against antigens from the patient's own tumor are less likely to allow immune escape than a pre-selected tumor antigen; (iii) The activation of antitumor immune responses by the immuno-adjuvant effects of tumor-targeted immunostimulatory antibodies or fusion proteins occurs in tandem with the sensitization of tumor cells to immune effector-mediated cytotoxicity, thereby establishing a positive feedback loop that augments tumor cytoreduction and reinforces adaptive antitumor immunity; and (iv) The molecules of the invention have broad clinical relevance for advancing the treatment of many types of human cancers.

In addition, the targeted immunostimulatory antibodies and/or fusion proteins of the invention are distinguished from and superior to existing therapeutic molecules in at least one of the following aspects: (i) To counteract immune tolerance in the tumor microenvironment and promote T cell-mediated adaptive antitumor immunity for maintenance of long-term protection against recurrent or disseminated cancers (for prevention or treatment of diverse cancers); (ii) To produce immune cell compositions for adoptive cellular therapy of diverse cancers; and (iii) To serve as immune adjuvants or vaccines for prophylaxis of diverse cancers or infectious diseases.

The targeted immunostimulatory antibodies and/or fusion proteins of the invention provide the ability to disrupt immunosuppressive networks in the tumor microenvironment. Tumors employ a wide array of regulatory mechanisms to avoid or suppress the immune response. Cancer cells actively promote immune tolerance in the tumor microenvironment via the expression of cytokines and molecules that inhibit the differentiation and maturation of antigen-presenting dendritic cells. The immunosuppressive cytokines and ligands produced by tumor cells include the following: (i) Transforming growth factor-beta (TGF-$\beta$); (ii) Programmed death-1 ligand 1 (PD-L1; B7-H1); (iii) Vascular endothelial growth factor (VEGF); and (iv) Interleukin-10 (IL-10). In addition to blocking dendritic cell (DC) maturation, these molecules promote the development of specialized subsets of immunosuppressive $CD4^+$ T cells (regulatory T cells; Treg cells) and myeloid-derived suppressor cells (MDSC). Tregs are a minority sub-population of $CD4^+$ T cells that constitutively express CD25 [the interleukin-2 (IL-2) receptor $\alpha$-chain] and the forkhead box P3 (FOXP3) transcription factor, Tregs (CD4+CD25+FoxP3+ cells) maintain immune tolerance by restraining the activation, proliferation, and effector functions of a wide range of immune cells, including $CD4^+$ and $CD8^+$ T cells, natural killer (NK) and NKT cells. B cells and antigen presenting cells (APCs) in vitro and in vivo. The accumulation of Treg cells in the tumor microenvironment re-inforces tumor immune tolerance and facilitates tumor progression and metastases. The increased expression of immunosuppressive cytokines (TGF-$\beta$; PD-L1) and tumor-infiltrating Tregs is correlated with a reduction of survival of patients with diverse types of cancers. The present invention provides that tumor-induced immune tolerance mediated via Tregs is a crucial determinant of the resistance of cancers to cytotoxic chemotherapeutic agents and tumor-targeted antibodies. The targeted immunostimulatory antibodies and/or fusion proteins of the invention inhibit key immunosuppressive molecules expressed by the targeted tumor cell or tumor-infiltrating Treg cells and myeloid suppressor cells (DCs or MDSC). As such, they provide the targeted ability to inhibit the development or function of Tregs within the tumor microenvironment. In another aspect, they provide the ability to counteract Treg-induced immune suppression in the tumor microenvironment.

The targeted immunostimulatory antibodies and/or fusion proteins of the invention provide the ability to inhibit the development or function of Tregs and myeloid suppressor cells (DCs or MDSC) within the tumor microenvironment. Tregs (CD4+CD25+FoxP3+ cells) express an array of immunosuppressive cytokines and molecules which act in concert to induce immune tolerance and promote tumor progression and metastases. These include: (1) Cytotoxic T-lymphocyte associated protein 4 (CTLA-4; CD152), a co-inhibitory receptor that binds to the ligands CD80 (B7-1) or CD86 (B7-2) on the antigen presenting cell (APC) and inhibits co-stimulation of T cells; (ii) Programmed death-1 ligand 1 (PD-L1; B7-H1), a ligand which engages the co-inhibitory receptor Programmed death-1 (PD-1) and inhibits T cell activation and proliferation. (iii) Transforming growth factor-beta (TGF-$\beta$), a cytokine which regulates immune responses by restricting the maturation and antigen-presenting function of dendritic cells, inhibiting the proliferation and activation of naïve T cells, suppressing the expression of cytotoxic molecules (Granzyme A/B, FasL, Apo2L/TRAIL, IFN-γ) in immune effector cells, and promoting the development and function of Tregs; (iv) Receptor activator of nuclear factor-κB ligand (RANKL), a ligand which engages Receptor activator of nuclear factor-κB (RANK) and promotes osteoclast differentiation. Treg development, and tumor metastases. In addition, Tregs express other surface molecules; (v) LAG-3, a CD4-related molecule that hinds MI-IC class IL (vi) glucocorticoid-induced tumor necrosis factor receptor family-related gene (GITR; TNFRSF18); and (vii) IL-10. The targeted immunostimulatory antibodies and/or fusion proteins of the invention provide the ability to bind a targeted molecule expressed by Tregs or myeloid suppressor cells while concurrently sequestering and inhibiting one or more immunosuppressive molecule that promotes their development, survival or function. In one aspect, the targeted immunostimulatory antibodies and/or fusion proteins directly deplete the number of Tregs.

In one embodiment, the present invention provides a molecule including a targeting moiety fused with an immunomodulatory moiety. The targeting moiety specifically binds a target molecule on the tumor cell or tumor microenvironment (tumor stroma, tumor vasculature, or tumor infiltrating immune cell), and the immunomodulatory moiety specifically binds an immunosuppressive molecule expressed by the targeted tumor cell or tumor-infiltrating Treg cells and myeloid suppressor cells (DC or MDSC).

In one embodiment, the present invention provides a molecule including a targeting moiety fused with an immunomodulatory moiety. The targeting moiety specifically binds a target molecule expressed by Treg cells, myeloid suppressor cells (MDSC), or dendritic cells (DC), and the immunomodulatory moiety specifically binds an immunosuppressive molecule that promotes their development, survival or function.

In one embodiment, the present invention provides a molecule including a targeting moiety fused with an immunomodulatory moiety. The targeting moiety specifically binds a target molecule, and the immunomodulatory moiety specifically binds one of the following molecules: (i) Transforming growth factor-beta (TGF-β); (ii) Programmed death-1 ligand 1 (PD-L1) or Programmed death-1 ligand 2 (PD-L2); (iii) Receptor activator of nuclear factor-κB (RANK) ligand (RANKL); (iv) Vascular endothelial growth factor (VEGF); (v) Transforming growth factor-beta receptor (TGF-βR); (vi) Programmed death-1 (PD-1); and (vii) Receptor activator of nuclear factor-κB (RANK).

In one aspect, the targeting moiety includes an antibody, antibody fragment, scFv, or Fc-containing polypeptide that specifically binds a component of a tumor cell, tumor antigen, tumor vasculature, tumor microenvironment, or tumor-infiltrating immune cell. In one aspect, the targeting moiety specifically binds epidermal growth factor receptor (EGFR1, Erb-B1), HER2/neu (Erb-B2), CD20, Vascular endothelial growth factor (VEGF), insulin-like growth factor receptor (IGF-1R), TRAIL-receptor, epithelial cell adhesion molecule, carcino-embryonic antigen, Prostate-specific membrane antigen, Mucin-1, CD30, CD33, or CD40.

In one aspect, the targeting moiety specifically binds a component of a regulatory T cell myeloid suppressor cell or dendritic cell. In another aspect, the targeting moiety specifically binds one of the following molecules: (i) CD4; (ii) CD25 (IL-2α receptor; IL-2αR); (iii) cytotoxic T-lymphocyte antigen-4 (CTLA-4; CD152): (iv) Interleukin-10 (IL-10); (v) Transforming growth factor-beta receptor (TGF-βR); (vi) Transforming growth factor-beta (TGF-β); (vii) Programmed Death-1 (PD-1); (viii) Programmed death-1 ligand (PD-L1 or PD-L2); (ix) Receptor activator of nuclear factor-κB (RANK): (x) Receptor activator of nuclear factor-κB (RANK) ligand (RANKL); (xi) LAG-3: or ND glucocorticoid-induced tumor necrosis factor receptor family-related gene (GITR; TNFRSF18).

In one aspect, the immunomodulatory moiety specifically binds one of the following molecules: (i) Transforming growth factor-beta (TGF-β); (ii) Programmed death-1 ligand (PD-L1 or PD-L2): (iii) Receptor activator of nuclear factor-κB (RANK) ligand (RANKL); or (iv) vascular endothelial growth factor (VEGF).

In one aspect, the immunomodulatory moiety includes a molecule that binds TGF-β. In another aspect, the immunomodulatory moiety includes an extracellular ligand-binding domain of Transforming growth factor-beta receptor TGF-βRII, TGF-βRIIb, or TGF-βRIII. In another aspect, the immunomodulatory moiety includes an extracellular ligand-binding domain of TGF-βRII. In another aspect, the molecule includes a TGF-β-binding amino acid sequence corresponding to SEQ ID NOs: 79-91. In an additional aspect, the immunomodulatory moiety inhibits the activity or function of TGF-β.

In one aspect, the targeting moiety includes an antibody, antibody fragment, or polypeptide that specifically binds to HER2/neu, EGFR1, CD20, vascular endothelial growth factor (VEGF), cytotoxic T-lymphocyte antigen-4 (CTLA-4), CD25 (IL-2α receptor; IL-2αR), or CD4. In an additional aspect, the immunomodulatory moiety includes an extracellular ligand-binding domain of TGF-βRII. In another aspect, the molecule includes an amino acid sequence corresponding to SEQ ID NO 1, 2, 3, 4, 5, 6, 7, 8, 9 or 10.

In one aspect, the targeting moiety includes an antibody, antibody fragment, or polypeptide that specifically binds to Programmed Death-1 (PD-1), Programmed death-1 ligand 1 (PD-L1), or Programmed death-1 ligand 2 (PD-L2). In another aspect the targeting moiety includes an extracellular ligand-binding domain or ectodomain of Programmed Death-1 (PD-1). In an additional aspect, the immunomodulatory moiety includes an extracellular ligand-binding domain of TGF-βRII. In another aspect, the molecule includes PD-1 ectodomain, immunoglobulin Fc region, and TGFβRII ectodomain. In another aspect, the molecule includes an amino acid sequence corresponding to SEQ ID NO 11 or 12.

In one aspect, the targeting moiety includes an antibody, antibody fragment, or polypeptide that specifically binds to Receptor activator of nuclear factor-κB (RANK) or Receptor activator of nuclear factor-κB ligand (RANKL). In another aspect, the targeting moiety includes an extracellular ligand-binding domain or ectodomain of Receptor activator of nuclear factor-κB (RANK). In an additional aspect, the immunomodulatory moiety includes an extracellular ligand-binding domain of TGF-βRII. In another aspect, the molecule includes RANK ectodomain, immunoglobulin Fc region, and TGF-βRII ectodomain. In another aspect, the molecule includes an amino acid sequence corresponding to SEQ ID NO 13 or 14.

In one aspect, the immunomodulatory moiety includes a molecule that specifically binds to Programmed death-1 ligand 1 (PD-L1) or Programmed death-1 ligand 2 (PD-L2). In another aspect, the immunomodulatory moiety includes an extracellular ligand-binding domain or ectodomain of Programmed Death-1 (PD-1). In another aspect, the molecule includes a PD-L1-binding amino acid sequence corresponding to SEQ ID NO: 92, 93, or 94. In an additional aspect, the immunomodulatory moiety inhibits the activity or function of Programmed death-1 ligand 1 (PD-L1).

In one aspect, the targeting, moiety includes an antibody, antibody fragment, or polypeptide that specifically binds to HER2/neu, EGFR1, CD20, vascular endothelial growth factor (VEGF), cytotoxic T-lymphocyte antigen-4 (CTLA-4), CD25 (IL-2α receptor; IL-2αR), or CD4. In an additional aspect, the immunomodulatory moiety includes an extracellular ligand-binding domain or ectodomain of Programmed Death-1 (PD-1). In another aspect, the molecule includes an amino acid sequence corresponding to SEQ ID NO: 15, 16, 17, 18, 19, 20, 21, 22, 23, or 24.

In one aspect, the targeting moiety includes an antibody, antibody fragment, or polypeptide that specifically binds to Receptor activator of nuclear factor-κB (RANK) or Receptor activator of nuclear factor-κB ligand (RANKL). In another aspect the targeting moiety includes an extracellular ligand-binding domain or ectodomain of Receptor activator of nuclear factor-κB (RANK). In an additional aspect the immunomodulatory moiety includes an extracellular ligand-binding domain of Programmed Death-1 (PD-1). In another aspect, the molecule includes RANK ectodomain, immunoglobulin Fc region, and PD-1 ectodomain. In another aspect, the molecule includes an amino acid sequence corresponding to SEQ ID NO 25 or 26.

In one aspect, the immunomodulatory moiety includes a molecule that specifically binds to Receptor activator of nuclear factor-κB ligand (RANKL). In another aspect, the immunomodulatory moiety includes an extracellular ligand-binding domain or ectodomain of Receptor activator of nuclear factor-κB (RANK). In another aspect, the molecule includes a RANKL-binding amino acid sequence corresponding to SEQ ID NO: 95, 96, 97, or 98. In an additional aspect, the immunomodulatory moiety inhibits the activity or function of Receptor activator of nuclear factor-κB ligand (RANKL).

In one aspect, the targeting moiety includes an antibody, antibody fragment, or polypeptide that specifically binds to HER2/neu, EGFR1, CD20, vascular endothelial growth factor (VEGF), cytotoxic T-lymphocyte antigen-4 (CTLA-4), CD25 (IL-2α receptor; IL-2αR), or CD4. In an additional aspect, the immunomodulatory moiety includes an extracellular ligand-binding domain or ectodomain of Receptor activator of nuclear factor-κB (RANK). In another aspect, the molecule includes an amino acid sequence corresponding to SEQ ID NO: 27, 28, 29, 30, 31, 32, 33, 34, 35, or 36.

The present invention provides novel targeted immunosuppressive antibodies and fusion proteins that induce or promote immune tolerance by at least one of the following:
(i) inhibiting the activation of dendritic cells, T cells, and/or B cells; and
(ii) promoting the development and/or suppressor function of regulatory T cells and immunosuppressive myeloid DCs. These targeted immunosuppressive molecules of the invention are designed to suppress unwanted or excessive immune or inflammatory responses in order to treat autoimmune or inflammatory diseases or prevent the rejection of a transplanted cell, tissue, or organ.

Targeted immunosuppressive antibodies and/or fusion proteins: The aberrant activation of self-reactive T cells and/or breakdown of the mechanisms of immune tolerance promotes the development of autoimmunity that results in various diseases including type I diabetes mellitus, multiple sclerosis, systemic lupus erythematosus, inflammatory bowel disease, and rheumatoid arthritis. The targeted immunosuppressive antibodies and/or fusion proteins of the invention are designed to suppress unwanted or excessive immune or inflammatory responses and restore or promote immune tolerance. Accordingly, the compositions and methods of the invention have broad clinical relevance for the treatment of diverse autoimmune or inflammatory diseases and preventing the rejection of a transplanted cell, tissue, or organ grafts.

The targeted immunosuppressive antibodies and/or fusion proteins of the invention provides their ability to inhibit the activity of targeted pro-inflammatory cytokines or immune cells while simultaneously promoting immune tolerance via the targeted delivery of immunosuppressive molecules that facilitate the development and/or function of regulatory T cells. These molecules of the present invention are distinguished from and superior to existing therapeutic molecules in at least one of the following aspects: (i) The molecules of the invention enable targeted delivery of immunosuppressive molecules to immune cells or pro-inflammatory molecules in the milieu of the affected cell, tissue or organ; (ii) The molecules of the invention can couple the inhibition of the targeted pro-inflammatory molecule or immune cell with the simultaneous delivery of an immunosuppressive molecule that promotes immune tolerance, thereby improving the suppression of immune effector cells; and (iii) The molecules of the invention can provide a mechanism of simultaneously engaging two independent or synergistic mechanisms of immune tolerance or immune suppression.

Further, the targeted immunosuppressive antibodies and/or fusion proteins of the invention are distinguished from and superior to existing therapeutic molecules in at least one of the following aspects: (i) To suppress unwanted or excessive immune or inflammatory responses in order to treat autoimmune or inflammatory diseases; and (ii) To prevent the rejection of a transplanted cell, tissue, or organ grafts.

In one aspect, the immunomodulatory moiety includes a sequence from Programmed death-1 ligand 1 (PD-L1) or Programmed death-1 ligand 2 (PD-L2). In another aspect, the molecule includes a PD-1-binding amino acid sequence corresponding to SEQ ID NO 99, 100, or 101. In an additional aspect, the immunomodulatory moiety increases the function of PD-1.

In one aspect, the targeting moiety specifically binds to Tumor Necrosis Factor-α (TNF-α), and the immunomodulatory moiety includes a sequence from Programmed death-1 ligand 1 (PD-L1) or Programmed death-1 ligand 2 (PD-L2). In an additional aspect, the targeting moiety includes an antibody that binds TNF-α, and the immunomodulatory moiety includes a sequence from PD-1 ligand 1 (PD-L1 or B7-H1). In another aspect, the molecule includes an amino acid sequence corresponding to SEQ ID NO 37. In another aspect, the targeting moiety includes an extracellular ligand-binding domain of tumor necrosis factor receptor 2 (TNFR2), and the immunomodulatory moiety includes a sequence from PD-1 ligand 1 (PD-L1 or B7-H1). In another aspect, the molecule includes TNFR2 Extracellular ligand binding domain, immunoglobulin Fc region, and a sequence from PD-L1. In another aspect, the molecule includes an amino acid sequence corresponding to SEQ ID NO: 38 or 39.

In one aspect, the targeting moiety includes an antibody or antibody fragment that specifically binds to CD20, CD25, or CD4, and the immunomodulatory moiety includes a sequence from Programmed death-1 ligand 1 (PD-L1) or Programmed death-1 ligand 2 (PD-L2). In another aspect, the molecule includes an amino acid sequence corresponding to SEQ ID NO 40, 41, 42, 43, 44, or 45.

In one aspect, the targeting moiety includes the extracellular domain of CTLA-4 and immunoglobulin Fc region (IgG Cγ1), and the immunomodulatory moiety includes a sequence from Programmed death-1 ligand 1 (PD-L1) or Programmed death-1 ligand 2 (PD-L2). In another aspect, the molecule includes an amino acid sequence corresponding to SEQ ID NO 46 or 47.

In one aspect, the targeting moiety includes transforming growth factor-β (TGF-β) and immunoglobulin Fc region (IgG Cγ1), and the immunomodulatory moiety includes a sequence from Programmed death-1 ligand 1 (PD-L1) or Programmed death-1 ligand 2 (PD-L2). In an additional aspect, the molecule includes an amino acid sequence corresponding to SEQ ID NO: 48 or 49.

In one aspect, the immunomodulatory moiety includes a sequence from transforming growth factor-β (TGF-β). In another aspect, the molecule includes an amino acid sequence corresponding to SEQ ID NO 99, 100, or 101. In an additional aspect, the immunomodulatory moiety activates the signaling function of transforming growth factor-β (TGF-β) receptor.

In one aspect, the targeting moiety includes an antibody, antibody fragment, or polypeptide that specifically binds to Tumor Necrosis Factor-α (TNF-α), and the immunomodulatory moiety includes a sequence from transforming growth factor-β (TGF-β). In an additional aspect, the targeting moiety includes an antibody that binds TNF-α, and the immunomodulatory moiety includes a sequence from TGF-β. In another aspect, the molecule includes an amino acid sequence corresponding to SEQ ID NO: 50. In one aspect, the targeting moiety includes an extracellular ligand-binding domain of tumor necrosis factor receptor 2 (TNFR2). In another aspect, the molecule includes TNFR2 Extracellular ligand binding domain, immunoglobulin Fc region, and a sequence from transforming growth factor-β (TGF-β). In another aspect, the molecule includes an amino acid sequence corresponding to SEQ ID NO: 51 or 52.

In one aspect, the targeting moiety includes an antibody or antibody fragment that specifically binds to CD20, CD25 (IL-2α receptor; IL-2αR), or CD4, and the immunomodulatory moiety includes a sequence from transforming growth factor-β (IGF-β). In an additional aspect, the molecule includes an amino acid sequence corresponding to SEQ ID NO: 53, 54, 55, 56, 57 or 58.

In one aspect, the targeting moiety includes an extracellular domain of CTLA-4 and immunoglobulin Fc region (IgG Cγ1), and the immunomodulatory moiety includes a sequence from transforming growth factor-β (TGF-β). In another aspect, the molecule includes an amino acid sequence corresponding to SEQ ID NO: 59 or 60.

In one aspect, the targeting moiety includes an antibody, antibody fragment, or polypeptide that specifically binds to Tumor Necrosis Factor-α (TNF-α), and the immunomodulatory moiety includes an extracellular RANKL-binding domain or ectodomain of Receptor activator of nuclear factor-κB (RANK) or Osteoprotegerin (OPG). In an additional aspect, the targeting moiety includes an antibody that binds TNF-α, and the immunomodulatory moiety includes a sequence from an extracellular RANKL-binding domain or ectodomain of RANK. In another aspect, the molecule includes an amino acid sequence corresponding to SEQ ID NO: 61. In one aspect, the targeting moiety includes an extracellular ligand-binding domain of tumor necrosis factor receptor 2 (TNFR2). In another aspect, the molecule includes TNFR2 Extracellular ligand binding domain, immunoglobulin Fc region, and a sequence from an extracellular RANK-binding domain or ectodomain of RANK. In another aspect, the molecule includes an amino acid sequence corresponding to SEQ ID NO: 62 or 63.

In one aspect, the targeting moiety includes an extracellular domain of CTLA-4 and immunoglobulin Fc region (IgG Cγ1), and the immunomodulatory moiety includes an extracellular RANKL-binding domain or ectodomain of Receptor activator of nuclear factor-κB (RANK) or Osteoprotegerin (OPG). In another aspect, the molecule includes an amino acid sequence corresponding to SEQ ID NO: 64 or 65.

In one aspect, the targeting moiety includes a sequence from transforming growth factor-β (TGF-β) and immunoglobulin Fc region (IgG Cγ1), and the immunomodulatory moiety includes an extracellular RANKL-binding domain or ectodomain of Receptor activator of nuclear factor-κB (RANK). In another aspect, the molecule includes an amino acid sequence corresponding to SEQ ID NO 66 or 67.

In one aspect, the targeting moiety includes a sequence from Programmed death-1 ligand 1 (PD-L1) and immunoglobulin Fc region (IgG Cγ1), and the immunomodulatory moiety includes an extracellular RANKL-binding domain or ectodomain of Receptor activator of nuclear factor-κB (RANK). In another aspect, the molecule includes an amino acid sequence corresponding to SEQ ID NO: 68 or 69.

In various aspects, the molecule is fused or directly linked to one or more antigen, antigenic determinant, or epitope.

In another embodiment, the present invention provides a composition including the molecule of the invention and a cell, wherein the cell is a tumor cell, immune cell, or dendritic cell.

In another embodiment, the present invention provides a method of counteracting or overcoming immune tolerance. The method includes administering to a subject in need thereof one or more molecule of the invention.

In another embodiment, the present invention provides a method of preventing or treating a neoplastic disease. In one aspect, the neoplastic disease is a non-T cell malignancy which does not express CD4 on the tumor cell. In one embodiment, the method includes administration to a subject in need thereof an antibody that targets and depletes CD4+ regulatory T cells (Tregs) in combination with a cytotoxic anticancer therapy. In one aspect, the antibody that targets and depletes Tregs is an anti-CD4 antibody. In various aspects, the cytotoxic anticancer therapy includes a chemotherapeutic molecule, tumor-targeted antibody, small molecule kinase inhibitor, hormonal agent, or tumor-targeted cytotoxic agent, anti-angiogenic agent or any combination thereof. In another aspect, the cytotoxic anticancer therapy includes ionizing radiation, ultraviolet radiation, cryoablation, thermal ablation, or radiofrequency ablation.

In another embodiment, the method includes administration to a subject in need thereof an antibody or molecule that targets and depletes CD4+ regulatory T cells (Tregs) in combination with an immunostimulatory antibody, fusion protein, peptide or ligand that targets CTLA-4. PD1, PD-1L, RANKL, TGF-β, GITR, 4-1BB, OX-40, or Toll-like receptors (TLR 1-10). In one aspect, the TLR-agonist comprises an activator of TLR-8 or TLR-9. In one aspect, the TLR agonist comprises an immunostimulatory nucleic acid sequence containing CpG nucleotides. In one aspect, the antibody that targets and depletes Tregs is an anti-CD4 antibody.

In another embodiment, the present invention provides a method of preventing or treating a neoplastic disease. The method includes administration to a subject in need thereof one or more molecule of the invention. In various aspects, the subject is administered one or more molecule of the invention in combination with another anticancer therapy. In one aspect, the anticancer therapy includes a chemotherapeutic molecule, antibody, small molecule kinase inhibitor, hormonal agent, cytotoxic agent, targeted therapeutic agent, or anti-angiogenic agent. In another aspect, the anticancer therapy includes ionizing radiation, ultraviolet radiation, cryoablation, thermal ablation, or radiofrequency ablation. In another aspect, the subject is administered one or more molecule of the invention in combination with an antibody or molecule that inhibits the production or function of regulatory T cells (Tregs) or depletes the number of Tregs. In one aspect, the antibody that targets and depletes Tregs is an anti-CD4 antibody. In another aspect, the molecule that counteracts the function of Tregs is an antibody, fusion protein, peptide or ligand that targets CTLA-4, PD1, PD-1L, RANKL, TGF-β, GITR. In another aspect, the molecule that counteracts the function of Tregs is an antibody or fusion protein or ligand that targets 4-1BB or OX-40. In another aspect, the molecule that counteracts the function of Tregs is an agonist of Toll-like receptors (TLR 1-10). In one aspect, the TLR-agonist comprises an activator of TLR-8 or TLR-9. In one aspect, the TLR agonist is an immunostimulatory nucleic acid sequence containing CpG nucleotides.

In one aspect the chemotherapeutic agent is a topoisomerase-interacting agent, anthracycline, doxorubicin, mitoxantrone, camptothecin, camptothecin analogue, irinotecan, epipodophyilotoxin, etoposide, alkylating agent, cyclophosphamide, cisplatin, cisplatin analogue, oxaliplatin, antimetabolite, fluoropyrimidine analogue, 5-fluorouracil, gemcitabine, azacytidine, antimicrotubule agent, taxane, paclitaxel, or docetaxel.

In another embodiment, the subject is administered one or more molecule of the invention in combination with any vaccine. In another aspect, the vaccine includes a tumor antigen, tumor-associated antigen, tumor epitope, tumor antigen-containing fusion protein, tumor cell, or dendritic cell. In another aspect, the vaccine includes a pathogen antigen, pathogen-associated antigen, pathogen epitope, or pathogen antigen-containing fusion protein. In one aspect, the vaccine includes a surrogate CD4+ T cell helper epitope from tetanus toxin. In one aspect, the CD4+ T helper sequence contains a domain of tetanus toxin fragment C (pDOM1). In one aspect, the pDOM sequence is fused to a cell-permeabilizing cationic polypeptide (e.g. Arginine-9). In another aspect, the Arg9-pDOM sequence is fused to a specific antigen comprising the vaccine.

In another embodiment, the present invention provides a method for treating immune cells wherein the cells are contacted ex vivo or in vitro with a molecule of the invention. In another embodiment, the present invention provides a method of treatment of a neoplastic disease. The method includes administering to a subject in need thereof a composition of immune cells contacted with a molecule of the invention.

In another embodiment, the present invention provides a method of inducing or promoting immune tolerance. The method includes administering to a subject in need thereof one or more molecule of the invention.

In another embodiment, the present invention provides a method of preventing or treating an autoimmune or inflammatory disease including administering to a subject in need thereof one or more molecule of the invention. In one aspect, the subject is administered one or more molecule of the invention in combination with another anti-inflammatory or immunosuppressive therapy. In another embodiment, the present invention provides a method of treatment of immune cells wherein the cells are contacted ex vivo or in vitro with a molecule of the invention. In another embodiment, the present invention provides a method of treating an autoimmune or inflammatory disease or preventing rejection of grafted cells or tissue. The method includes administering to a subject in need thereof a composition of immune cells contacted with a molecule of the invention.

All publications, patents, and patent applications mentioned in this specification are herein incorporated by reference to the same extent as if each individual publication, patent, or patent application was specifically and individually indicated to be incorporated by reference.

As used in this specification and the appended claims, the singular forms "a," "an," and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As used herein "immune cells" or "immune effector cells" include T lymphocytes, B lymphocytes, natural killer (NK) cells, NKT cells, monocytes, macrophages, dendritic cells (DC), antigen presenting cells (APC).

As used herein, "neoplasm" or "tumor" including grammatical variations thereof, means new and abnormal growth of tissue, which may be benign or cancerous. In a related aspect, the neoplasm is indicative of a neoplastic disease or disorder, including but not limited, to various cancers. For example, such cancers can include prostate, pancreatic, biliary, colon, rectal, liver, kidney, lung, testicular, breast, ovarian, pancreatic, brain, and head and neck cancers, melanoma, sarcoma, multiple myeloma, leukemia, lymphoma, and the like.

A used herein, "subject," including grammatical variations thereof, means a human or vertebrate animal including a dog, cat, horse, cow, pig, sheep, goat, chicken, monkey, rat, and mouse.

As used herein, "targeting moiety" refers to a molecule that has the ability to localize and bind to a specific molecule or cellular component. The targeting moiety can be an antibody, antibody fragment, scFv. Fc-containing polypeptide, fusion antibody, polypeptide, peptide, aptamer, ligand, nucleic acid, or any combination thereof. In one embodiment, a targeting moiety can bind to a molecule present in a cell or tissue. In one aspect, the targeting moiety can bind a molecule in a diseased cell or tissue, such as a cancer cell or tumor. In, another aspect, the targeting molecule can bind a normal cell or tissue, such as an immune cell. In another aspect, the targeting moiety can bind a cellular or extracellular molecule that modulates the immune response. In another aspect, the targeting moiety binds a growth factor receptor, growth factor, cytokine receptor, cytokine, or cell surface molecule.

In another embodiment, the targeting moiety is a tumor-targeting moiety. The tumor-targeting moiety can bind a component of a tumor cell or bind in the vicinity of a tumor cell (e.g., tumor vasculature or tumor microenvironment). In one embodiment, the tumor targeting moiety binds to a component of a tumor cell, tumor microenvironment, tumor vasculature, tumor-associated lymphocyte, tumor antigen, tumor-associated antigen, tumor cell surface molecule, tumor antigenic determinant, tumor antigen-containing fusion protein, tumor-associated cell, tumor-associated immune cell, or tumor vaccine.

For example, in various embodiments, a targeting moiety is specific for or binds to a molecule or component, which includes but is not limited to, epidermal growth factor receptor (EGFR, EGFR1, ErbB-1, HER1). ErbB-2 (HER2/neu), ErbB-3/HER3. ErbB-4/HER4, EGFR ligand family; insulin-like growth factor receptor (IGFR) family, IGF-binding proteins (IGFBPs), IGFR ligand family (IGF-1R); platelet derived growth factor receptor (PDGFR) family, PDGFR ligand family; fibroblast growth factor receptor (FGFR) family, FGFR ligand family, vascular endothelial growth factor receptor (VEGFR) family, VEGF family; HGF receptor family: TRK receptor family; ephrin (EPH) receptor family: AXL receptor family; leukocyte tyrosine kinase (LTK) receptor family; TIE receptor family, angiopoietin 1, 2; receptor tyrosine kinase-like orphan receptor (ROR) receptor family; discoidin domain receptor (DDR) family; RET receptor family; KLG receptor family; RYK receptor family; MuSK receptor family; Transforming growth factor alpha (TGF-α), TGF-α receptor; Transforming growth factor-beta (TGF-β), TGF-β receptor; Interleukin β receptor alpha2 chain (IL13Ralpha2), Interleukin-6 (IL-6), 1L-6 receptor, interleukin-4, IL-4 receptor, Cytokine receptors, Class I (hematopoietin family) and Class II (interferon/1L-10 family) receptors, tumor necrosis factor (TNF) family, TNF-α, tumor necrosis factor (TNF) receptor superfamily (TNTRSF), death receptor family, TRAIL-receptor; cancer-testis (CT) antigens, lineage-specific antigens, differentiation antigens, alpha-actinin-4, ARTC1, breakpoint cluster region-Abelson (Bcr-abl) fusion products, B-RAF, caspase-5 (CASP-5), caspase-8 (CASP-8), beta-catenin (CTNNB1), cell division cycle 27 (CDC27), cyclin-dependent kinase 4 (CDK4), CDKN2A, COA-1, dek-can fusion protein, EFTUD-2. Elongation factor 2 (ELF2), Ets variant gene 6/acute myeloid leukemia 1 gene ETS (ETC6-AML1) fusion protein, fibronectin (FN), GPNMB, low density lipid receptor/GDP-L fucose: beta-Dgalactose 2-alpha-Lfucosyltraosferase (LDLR/FUT) fusion protein. HLA-A2, arginine to isoleucine exchange at residue 170 of the alpha-helix of the alpha2-domain in the HLA-A2 gene (HLA-A*201-R170I), MLA-A11, heat shock protein 70-2 mutated (HSP70-2M), KIAA0205, MART2, melanoma ubiquitous mutated 1, 2, 3 (MUM-1, 2, 3), prostatic acid phosphatase (PAP), neo-PAP, Myosin class 1, NFYC, OGT, OS-9, pml-RARalpha fusion protein, PRDX5, PTPRK, K-ras (KRAS2), N-ras (NRAS), HRAS, RBAF600, SIRT2. SNRPD1, SYT-SSX1 or -SSX2 fusion protein, Triosephosphate Isomerase, BAGE, BAGE-1. BAGE-2, 3, 4, 5, GAGE-1, 2, 3, 4, 5, 6, 7, 8, GnT-V (aberrant N-acetyl glucosaminyl transferase V, MGAT5), HERV-K MEL, KK-LC, KM-HN-1, LAGE, LAGE-1, CTL-recognixed antigen on melanoma (CAMEL), MAGE-A1 (MAGE-1). MAGE-A2, MAGE-A3, MAGE-A4, MAGE-AS, MAGE-A6, MAGE-A8, MAGE-A9, MAGE-A10. MAGE-A11, MAGE-A12, MAGE-3, MAGE-B1, MAGE-B2, MAGE-B5. MAGE-B6, MAGE-C1, MAGE-C2, mucin 1 (MUC1), MART-1/Melan-A (MLANA), gp100, gp100/Pme117 (S1LV), tyrosinase (TYR), TRP-1, HAGE, NA-88, NY-ESO-1, NY-ESO-1/LAGE-2, SAGE, Sp17. SSX-1, 2, 3, 4, TRP2-1NT2, carcinoembryonic antigen (CEA), Kallikfein 4, mammaglobm-A, OA1, prostate specific antigen (PSA), prostate specific membrane antigen, TRP-1/, 75. TRP-2 adipophilin, interferon inducible protein absent in nielanorna 2 (AIM-2). BING-4, CPSF, cyclin D1, epithelial cell adhesion molecule (EpCAM), EpbA3, fibroblast growth factor-5 (FGF-5), glycoprotein 250 (gp250intestinal carboxyl esterase (iCE), alpha-feto protein (AFP), M-CSF, mdm-2, MUCI, p53 (TP53), PBF, FRAME, PSMA, RAGE-1. RNF43, RU2AS, SOX10, STEAP1, survivin (BIRCS), human telomerase reverse transcriptase (hTERT), telomerase, Wilms' tumor gene (WT1), SYCP1, BRDT, SPANX, XAGE, ADAM2, PAGE-5, LIP1, CTAGE-1, CSAGE, MMA1, CAGE, BORIS, HOM-TES-85, AF15q14, HCA66I, LDHC, MORC, SGY-1, SPO11, TPX1, NY-SAR-35, FTHLI7, NXF2 TDRD1, TEX 15, FATE, TPTE, immunoglobulin idiotypes, Bence-Jones protein, estrogen receptors (ER), androgen receptors (AR), CD40, CD30, CD20, CD19, CD33, CD4, CD25, CD3, cancer antigen 72-4 (CA 72-4), cancer antigen 15-3 (CA 15-3), cancer antigen 27-29 (CA 27-29), cancer antigen 125 (CA 125), cancer antigen 19-9 (CA 19-9), beta-human chorionic gonadotropin, 1-2 microglobulin, squamous cell carcinoma antigen, neuron-specific enoJase, heat shock protein gp96. GM2, sargramostim, CTLA-4, 707 alanine proline (707-AP), adenocarcinoma antigen recognized by T cells 4 (ART-4), carcinoembryogenic antigen peptide-1 (CAP-1), calcium-activated chloride channel-2 (CLCA2), cyclophilin B (Cyp-B), human signet ring tumor-2 (HST-2), Human papilloma virus (HPV) proteins (HPV-E6, HPV-E7, major or minor capsid antigens, others), Epstein-Barr virus (EBV) proteins (EBV latent membrane proteins—LMP1, LMP2; others), Hepatitis B or C virus proteins, and HIV proteins. A composition of the invention can further include the foregoing as a peptide/polypeptide and/or encoding the same.

In one aspect, the targeting moiety includes an antibody, antibody fragment, scFv, or Fc-containing polypeptide that specifically binds a component of a tumor cell, tumor antigen, tumor vasculature, tumor microenvironment, or tumor-infiltrating immune cell. In one aspect, the targeting moiety specifically binds epidermal growth factor receptor (EGFR1, Erb-B1), HER2/neu (Erb-B2), CD20. Vascular endothelial growth factor (VEGF), insulin-like growth factor receptor (IGF-1R). TRAIL-receptor, epithelial cell adhesion molecule, carcino-embryonic antigen, Prostate-specific membrane antigen. Mucin-1, CD30, CD33. CD40, or a combination thereof.

Examples of antibodies which can be incorporated into compositions and methods disclosed herein include, but are not limited, to antibodies such as trastuzumab (anti-HER2/neu antibody); Pertuzumab (anti-HER2 mAb); cetuximab (chimeric monoclonal antibody to epidermal growth factor receptor EGFR); panitumumab (anti-EGFR antibody); nimotuzumab (anti-EGFR antibody); Zalutumumab (anti-EGFR mAb); Necitumumab (anti-EGFR mAb); MDX-210 (humanized anti-HER-2 bispecific antibody); MDX-210 (humanized anti-HER-2 bispecific antibody); MDX-447 (humanized anti-EGF receptor bispecific antibody); Rituximab (chimeric murine/human anti-CD20 mAb); Obinutuzumab (anti-CD20 mAb); Ofatumumab (anti-CD20 mAb); Tositumumab-1131 (anti-CD20 mAb); Ibritumomab tiuxetan (anti-CD20 mAb); Bevacizumab (anti-VEGF mAb); Ramucirumab (anti-VEGFR2 mAb); Ranibizumab (anti-VEGF mAb); Aflibercept (extracellular domains of VEGFR1 and VEGFR2 fused to IgG1 Fc); AMG386 (angiopoietin-1 and -2 binding peptide fused to IgG1 Fc); Dalotuzumab (anti-IGF-1R mAb); Gemtuzumab ozogamicin (anti-CD33 mAb); Alemtuzumab (anti-Campath-1/CD52 mAb); Brentuximab vedotin (anti-CD30 mAb); Catumaxomab (bispecific mAb that targets epithelial cell adhesion molecule and CD3); Naptumomab (anti-5T4 mAb); Girentuximab (anti-Carbonic anhydrase ix); or Farletuzumab (anti-folate receptor). Other examples include antibodies such as Panorex™ (17-1A) (murine monoclonal antibody); Panorex (@(17-1A) (chimeric murine monoclonal antibody); BEC2 (ami-idiotypic mAb, mimics the GD epitope) (with BCG); Oncolym (Lym-1 monoclonal antibody); SMART M195 Ab, humanized 13' 1 LYM-1 (Oncolym). Ovarex (B43.13, anti-idiotypic mouse mAb); 3622W94 mAb that binds to EGP40 (17-1A) pancarcinoma antigen on adenocarcinomas; Zenapax (SMART Anti-Tac (IL-2 receptor); SMART M195 Ab, humanized Ab, humanized); NovoMAb-G2 (pancarcinoma specific Ab); TNT (chimeric mAb to histone antigens); TNT (chimeric mAb to histone antigens); Gliomab-H (Monoclonals—Humanized Abs);

GNI-250 Mab; EMD-72000 (chimeric-EGF antagonist); LymphoCide (humanized IL.L.2 antibody); and MDX-260 bispecific, targets GD-2, ANA Ab, SMART IDIO Ab, SMART ABL 364 Ab or ImmuRAIT-CEA. Examples of antibodies include those disclosed in U.S. Pat. No. 5,736,167. U.S. Pat. No. 7,060,808, and U.S. Pat. No. 5,821,337.

In one embodiment, the targeting moiety specifically binds a component of a regulatory T cell, myeloid suppressor cell, or dendritic cell. In another aspect, the targeting moiety specifically binds one of the following molecules: CD4; CD25 (IL-2α receptor; IL-2αR); cytotoxic T-lymphocyte antigen-4 (CTLA-4; CD152); Interleukin-10 (IL-10); Transforming growth factor-beta receptor (TGF-βR); Transforming growth factor-beta (TGF-β); Programmed Death-1 (PD-1); Programmed death-1 ligand (PD-L1 or PD-L2); Receptor activator of nuclear factor-κB (RANK); Receptor activator of nuclear factor-κB (RANK) ligand (RANKL); LAG-3; glucocorticoid-induced tumor necrosis factor receptor family-related gene (GITR; TNFRSF18); or Interleukin-4 receptor (IL-4R). In one aspect, the targeting moiety is an agonist that increases the function of the targeted molecule. In another aspect, the targeting moiety is an antagonist that inhibits the function of the targeted molecule.

In one aspect, the targeting moiety binds a specific cytokine, cytokine receptor, co-stimulatory molecule, co-inhibitory molecule, or immunomodulatory receptor that modulates the immune system. In another aspect, the targeting moiety specifically binds one of the following molecules: tumor necrosis factor (TNF) superfamily; tumor necrosis factor-α (TNF-α); tumor necrosis factor receptor (TNFR) superfamily; Interleukin-12 (IL-12); IL-12 receptor; 4-1BB (CD137); 4-1BB ligand (4-1BBL; CD137L); OX40 (CD134; TNR4); OX40 ligand (OX40L; CD40; CD40 ligand (CD40L); CTLA-4; Programmed death-1 (PD-1); PD-1 ligand 1 (PD-L1: B7-H1); or PD-1 ligand 2 (PD-L2; B7-DC); B7 family; B7-1 (CD80); B7-2 (CD86); B7-H3; B7-H4; GITR/AITR; GITRL/AITRL; BTLA; CD70; CD27; LIGHT; HVEM; Toll-like receptor (TLR) (TLR 1, 2, 3, 4, 5, 6, 7, 8, 9, 10). In one aspect, the targeting moiety is an agonist that increases the function of the targeted molecule. In another aspect, the targeting moiety is an antagonist that inhibits the function of the targeted molecule.

In one aspect, the targeting moiety includes an antibody, antibody fragment, scFv, Fc-containing polypeptide, or peptide that specifically binds a component of a regulatory T cell, myeloid suppressor cell, or dendritic cell. In another aspect, the targeting moiety includes an antibody, antibody fragment, scFv, or Fc-containing polypeptide that specifically binds a cytokine, cytokine receptor, co-stimulatory molecule, or co-inhibitory molecule that modulates the immune system. In another aspect, the targeting moiety specifically binds one of the following molecules: CD4; CD25 (IL-2α receptor; IL-2αR); cytotoxic T-lymphocyte antigen-4 (CTLA-4; CD152); Interleukin-10 (IL-10); Transforming growth factor-beta receptor (TGF-βR); Transforming growth factor-beta (TGF-β); Programmed Death-1 (PD-1); PD-1 ligand 1 (PD-L1; B7-H1); PD-1 ligand 2 (PD-L2; B7-DC); Receptor activator of nuclear factor-κB (RANK); Receptor activator of nuclear factor-κB (RANK) ligand (RANKL); LAG-3; glucocorticoid-induced tumor necrosis factor receptor family-related gene (GITR; TNFRSF18); Interleukin-4 receptor (IL-4R); tumor necrosis factor (TNF) superfamily; tumor necrosis factor-α (TNF-α); tumor necrosis factor receptor (TNFR) superfamily; interleukin-12 (IL-12); IL-12 receptor; 4-1BB (CD137); 4-1BB ligand (4-1BBL; CD137L); OX40 (CD134; TNR4): OX40 ligand (OX40L; CD40: CD40 ligand (CD40L); CTLA-4; B7 family; B7-1 (CD80); B7-2 (CD86); B7-H3; B7-H4; GITR/AITR; GITRL/AITRL; BTLA; CD70; CD27; LIGHT; or HVEM. In one aspect, the targeting moiety is an agonist that increases the function of the targeted molecule, in another aspect, the targeting moiety is an antagonist that inhibits the function of the targeted molecule.

Examples of antibodies which can be incorporated into compositions and methods disclosed herein include, but are not limited, to antibodies such as Zanulimumab (anti-CD4 mAb), Keliximab (anti-CD4 mAb); Ipilimumab (MDX-101; anti-CTLA-4 mAb); Tremilimumab (anti-CTLA-4 mAb); (Daclizumab (anti-CD25/IL-2R mAb); Basiliximab (anti-CD25/IL-2R mAb); MDX-1106 (anti-PD1 mAb); antibody to GITR; GC1008 (anti-TGF-β antibody); metelimumab/CAT-192 (anti-TGF-β antibody); Ierdelimumab/CAT-152 (anti-TGF-β antibody): ID11 (anti-TGF-β antibody); Denosumab (anti-RANKL mAb); BMS-663513 (humanized anti-4-1BB mAb); SGN-40 (humanized anti-CD40 mAb); CP870,893 (human anti-CD40 mAb); Infliximab (chimeric anti-TNF mAb; Adalimumab (human anti-TNF mAb): Certolizumab (humanized Fab anti-TNF); Golimumab (anti-TUNE); Etanercept (Extracellular domain of TNFR fused to IgG1 Fc); Belatacept (Extracellular domain of CTLA-4 fused to Fe); Abatacept (Extracellular domain of CTLA-4 fused to Fc); Belimumab (anti-B Lymphocyte stimulator); Muromonab-CD3 (anti-CD3 mAb); Otelixizumab (anti-CD3 mAb); Teplizumab (anti-CD3 mAb); Tocilizumab (anti-IL6R mAb); REGN88 (anti-IL6R mAb); Ustekinumab (anti-IL-12/23 mAb); Briakinumab (anti-IL-12/23 mAb); Natalizumab (anti-α4 integrin); Vedolizumab (anti-α4 β7 integrin mAb); T1h (anti-CD6 mAb); Epratuzumab (anti-CD22 mAb); Efalizumab (anti-CD11a mAb); and Atacicept (extracellular domain of transmembrane activator and calcium-modulating ligand interactor fused with Fe).

In one embodiment, the present invention provides a molecule including a targeting moiety fused with an "immunomodulatory moiety". As used herein, "immunomodulatory moiety" refers to a ligand peptide, polypeptide, or Fc-containing polypeptide that binds a specific component of a regulatory T cell, myeloid suppressor cell, or dendritic cell and modulates the number or function of Tregs or myeloid suppressor cells. In an additional aspect, the "immunomodulatory moiety" specifically binds a cytokine, cytokine receptor, co-stimulatory molecule, or co-inhibitory molecule that modulates the immune system. In another aspect, the immunomodulatory moiety specifically binds one of the following molecules: Transforming growth factor-beta receptor (TGFβR): Transforming growth factor-beta (TGF-β); Programmed Death-1 (PD-1); PD-1 ligand 1 (PD-L1; B7-H1); PD-1 ligand 2 (PD-L2; B7-DC); Receptor activator of nuclear factor-κB (RANK); or Receptor activator of nuclear factor-κB (RANK) ligand (RANKL); or vascular endothelial growth factor (VEGF). In another aspect, the immunomodulatory moiety specifically binds one of the following molecules: glucocorticoid-induced tumor necrosis factor receptor family-related gene (GITR; AITR; TNFRSF18); GITRL/AITRL; 4-1BB (CD137); 4-1BB ligand (4-1BBL; CD137L); OX40 (CD134; TNR4); OX40 ligand (OX40L); B7-H3; B7-H4; BTLA; CD40; CD40 ligand (CD40L); CD70; CD27; LIGHT; or HVEM. In another aspect, the immunomodulatory moiety specifically binds one of the following molecules: tumor necrosis factor-α (TNF-α); Interleukin-12 (IL-12); IL-12R; Interleukin-10 (IL-10); IL-10R. In another aspect, the immunomodulatory moiety comprises an extracellular domain of CTLA-4. In one aspect, the immunomodulatory moiety is an agonist that increases the function of the bound molecule. In another aspect, the immunomodulatory moiety is an antagonist that inhibits the function of the targeted molecule.

In another aspect, the immunomodulatory moiety comprises an extracellular domain or ligand-binding sequence of one of the following receptors: Transforming growth factor-beta receptor (TGF-βRII, TGF-βRIIb, or TGF-βRIII); Programmed Death-1 (PD-1); Receptor activator of nuclear factor-κB (RANK); vascular endothelial growth factor receptor (VEGFR1 or VEGFR2); or IL-10R. In another aspect, the immunomodulatory moiety comprises an extracellular domain or ligand-binding sequence of one of the following receptors: tumor necrosis factor receptor 2 (TNFR2); 4-1BB (CD137); OX40 (CD134; TNR4); CD40; IL-12R; or glucocorticoid-induced tumor necrosis factor receptor family-related gene (GITR; AITR; TNFRSF18). In an additional aspect, the extracellular domain of the specific receptor binds the cognate ligand and inhibits the interaction of the ligand with its native receptor.

In another aspect, the immunomodulatory moiety comprises one or more of the following ligands or active ligand fragments: Transforming growth factor-beta (TGF-β); PD-1 ligand 1 (PD-L1); PD-1 ligand 2 (PD-L2); or IL-10. In another aspect, the immunomodulatory moiety comprises one or more of the following ligands or active ligand fragments: 4-1BB ligand (4-1BBL; CD137L); OX40 ligand (OX40L); IL-12; CD40L; or GITRL/AITRL.

In another aspect, the immunomodulatory moiety is fused to the C-terminus of the targeting moiety. In another aspect, the immunomodulatory moiety is fused to the N-terminus of the targeting moiety. In one aspect, the fusion molecule is represented by X-Fc-Y, wherein X is the targeting moiety, Fc is an immunoglobulin Fc region, and Y is the immunomodulatory moiety. In another aspect, the fusion molecule is represented by Y-Fc-X, wherein X is the targeting moiety, and Y is the immunomodulatory moiety. In one aspect, the targeting moiety may additionally be an immunomodulatory moiety.

In one aspect, the targeting moiety includes an antibody, antibody fragment, scFv, or Fc-containing polypeptide that specifically binds a component of a tumor cell, tumor antigen, tumor vasculature, tumor microenvironment, or tumor-infiltrating immune cell, and the immunomodulatory moiety comprises an extracellular domain or ligand-binding sequence of one of the following receptors: Transforming growth factor-beta receptor (TGF-βRII, TGF-βRIIb, or TGF-βRIII); Programmed Death-1 (PD-1); Receptor activator of nuclear factor-κB (RANK); vascular endothelial growth factor receptor (VEGFR1 or VEGFR2); or IL-10R.

In one aspect, the targeting moiety includes an antibody, antibody fragment, scFv, or Fc-containing polypeptide that specifically binds a component of a tumor cell, tumor antigen, tumor vasculature, tumor microenvironment, or tumor-infiltrating immune cell, and the immunomodulatory moiety comprises one or more of the following ligands or active ligand fragments: 4-1BB ligand (4-1BBL; CD137L); OX40 ligand (OX40L); IL-12; CD40L; or GITRL/AITRL.

In another aspect, the targeting moiety includes an antibody, antibody fragment, scFv, Fc-containing polypeptide or ligand that binds a specific component of a regulatory T cell, myeloid suppressor cell, or dendritic cell, and the immunomodulatory moiety comprises an extracellular domain or ligand-binding sequence of one of the following receptors: Transforming growth factor-beta receptor (TGF-βRII, TGF-βRIIb, or TGF-βRIII); Programmed Death-1 (PD-1); Receptor activator of nuclear factor-κB (RANK); or IL-10R. In another aspect, the immunomodulatory moiety comprises one or more of the following ligands or active ligand fragments: 4-1BB ligand (4-1BBL; CD137L); OX40 ligand (OX40L); IL-12; CD40L; or GITRL/AITRL. In another aspect, the specific targeted component of a regulatory T cell, myeloid suppressor cell, or dendritic cell is one of the following molecules: CD4; CD25 (IL-2α receptor; IL-2αR); cytotoxic T-lymphocyte antigen-4 (CTLA-4; CD152); Interleukin-10 (IL-10); Transforming growth factor-beta (TGF-β): Programmed Death-1 (PD-1); Programmed death-1 ligand (PD-L1 or PD-L2); Receptor activator of nuclear factor-κB (RANK) ligand (RANKL): LAG-3; glucocorticoid-induced tumor necrosis factor receptor family-related gene (GITR: TNFRSF18); or Interleukin-4 receptor (IL-4R).

In another aspect, the targeting moiety includes an antibody, antibody fragment, scFv, Fc-containing poly peptide or ligand that binds one of the following: CTLA-4; 4-1BB (CD137); OX40 (CD134; TNR4); CD40; IL-12R; or glucocorticoid-induced tumor necrosis factor receptor family-related gene (GITR; AITR; TNFRSF18); and the immunomodulatory moiety comprises a different molecule selected from the following: (i) an extracellular domain or ligand-binding sequence of one of the following receptors; Transforming growth factor-beta receptor (TGF-βRII, TGF-βRIIb, or TGF-βRIII); Programmed Death-1 (PD-1); Receptor activator of nuclear factor-κB (RANK); or IL-10R; or (ii) Fc-containing polypeptide or ligand that binds one of the following: CTLA-4: 4-1BB (CD137); OX40 (CD134; TNR4); CD40; IL-12R; or GITR (AITR; TNFRSF18).

In another aspect, the targeting moiety and immunomodulatory moiety are two different molecules selected from any of the following: an antibody, antibody fragment, scFv, Fc-containing polypeptide or ligand that binds TGF-β, CTLA-4, PD-1, 4-1BB (CD137), OX40 (CD134; TNR4). CD40; IL-12R, or GITR/AITR (TNFRSF18), or Toll-like receptor (TLR); an extracellular domain or ligand-binding sequence of Transforming growth factor-beta receptor (TGF-βRII, TGF-βRIIb, or TGF-βRIII). Programmed Death-1 (PD-1), Receptor activator of nuclear factor-κB (RANK), or IL-10R. In one aspect the fusion molecule is represented by X-Fc-Y, wherein X is an immunomodulatory targeting moiety and Y is a different immunomodulatory moiety.

In another aspect, the targeting moiety includes an antibody, antibody fragment, scFv, Fc-containing polypeptide that binds one of the following molecules: CD4: CD25 (IL-2α receptor; IL-2R); or CD20; and the immunomodulatory moiety comprises one of the following ligands or active ligand fragments: Transforming growth factor-beta (TGF-β); PD-1 ligand 1 (PD-L1); PD-1 ligand 2 (PD-L2); or IL-10.

In another aspect, the targeting moiety includes an antibody, antibody fragment, scFv, Fc-containing polypeptide that binds tumor necrosis factor-α (TNF-α), Interleukin-12 (IL-12). IL-6R, B-lymphocyte stimulator, CD11a, CD6, or CD22; and the immunomodulatory moiety comprises one of the following: (i) ligands or active ligand fragments of Transforming growth factor-beta (TGF-β). PD-1 ligand 1 (PD-L1), or IL-10; or (ii) an extracellular domain or ligand-binding fragment of RANK, 4-1BB (CD137), OX40 (CD134; TNR4), CD40, IL-12R or GITR/AITR (TNFRSF18).

In another aspect, the targeting moiety comprises the extracellular domain of CTLA-4 fused to immunoglobulin Fc, and the immunomodulatory moiety comprises one of the following: (i) ligands or active ligand fragments of Transforming growth factor-beta (TGF-β). PD-1 ligand 1 (PD-L1), or IL-10; or (ii) ligand-binding fragment of TNFR2, RANK, 4-1BB (CD137), OX40 (CD134; TNR4), CD40, IL-12R or GITR/AITR (TNFRSF18).

In another aspect, the targeting moiety and immunomodulatory moiety are two different molecules selected from any of the following: an antibody, antibody fragment, scFv, Fc-containing polypeptide that binds tumor necrosis factor-α (TNF-α), interleukin-12 (IL-12), IL-6R. B-lymphocyte stimulator, CD11a, CD6, or CD22; a ligand-binding fragment of TNFR2, RANK, 4-1BB (CD137), OX40 (CD134; TNR4), CD40, IL-12R or GITR/AITR (TNFRSF18); ligands or active ligand fragments of Transforming growth factor-beta (TGF-β), PD-1 ligand 1 (PD-L1), or IL-10; or CTLA-4-Fc. In one aspect, the fusion molecule is represented by X-Fc-Y, wherein X is the immunomodulatory targeting moiety and Y is a different immunomodulatory moiety.

Antibodies: In one embodiment, the targeting moiety or fusion protein is an immunoglobulin. As used herein, the term "immunoglobulin" includes natural or artificial mono- or polyvalent antibodies including, but not limited to polyclonal, monoclonal, multispecific, human, humanized or chimeric antibodies, single chain antibodies. Fab fragments. F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin ion can be of any type (e.g., IgG IgE, IgM. IgD, IgA, and IgY), class (e.g., IgG1, IgG2, IgG3, IgG4, IgA1, and IgA2) or subclass of immunoglobulin molecule.

An antibody as disclosed herein includes an antibody fragment, such as, but not limited to, Fab, Fab' and F(ab')2, Fd, single-chain Fvs (scFv), single-chain antibodies, disulfide-linked Fvs (sdfv) and fragments including either a VL or VH domain. In one embodiment, the targeting moiety is an antibody or scFv.

An antigen-binding antibody fragment, including single-chain antibody, may include the variable region(s) alone or in combination with the entirety or a portion of the following: hinge region, CH1, CH2, and CH3 domains. An antigen-binding fragment can also include any combination of variable region(s) with a hinge region, CH1, CH2, and CH3 domains. Also includes is a Fc fragment, antigen-Fc fusion proteins, and Fc-targeting moiety. The antibody may be from any animal origin including birds and mammals. In one aspect, the antibody is, or derived from, a human, murine (e.g., mouse and rat), donkey, sheep, rabbit, goat, guinea pig, camel, horse, or chicken. Further, such antibody may be a humanized version of an antibody. The antibody may be monospecific, bispecific, trispecific, or of greater multispecificity.

The antibody herein specifically include a "chimeric" antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA. 81:6851-6855). A chimeric antibody of interest herein includes "primatized" antibodies including variable domain antigen-binding sequences derived from a non-human primate (e.g., Old World Monkey, Ape etc) and human constant region sequences.

Various methods have been employed to produce antibodies. Hybridoma technology, which refers to a cloned cell line that produces a single type of antibody, uses the cells of various species, including mice (murine), hamsters, rats, and humans. Another method to prepare an antibody uses genetic engineering including recombinant DNA techniques. For example, antibodies made from these techniques include, among others, chimeric antibodies and humanized antibodies. A chimeric antibody combines DNA encoding regions from more than one type of species. For example, a chimeric antibody may derive the variable region from a mouse and the constant region from a human. A humanized antibody comes predominantly from a human, even though it contains non-human portions. Like a chimeric antibody, a humanized antibody may contain a completely human constant region. But unlike a chimeric antibody, the variable region may be partially derived from a human. The nonhuman, synthetic portions of a humanized antibody often come from CDRs in murine antibodies. In any event, these regions are crucial to allow the antibody to recognize and bind to a specific antigen.

In one embodiment, a hybridoma can produce a targeted fusion protein comprising a targeting moiety and an immunomodulatory moiety. In one embodiment, a targeting moiety comprising an antibody, antibody fragment, or polypeptide is linked or fused to an immunomodulatory moiety consisting of a polypeptide, with a linker or without a linker. The linker can be an amino acid linker. In one embodiment, a linker is (GGGGS)n wherein n is 1, 2, 3, 4, 5, 6, 7, or 8. For example, GGGGSGGGGSGGGGS (SEQ ID NO: 104). In another embodiment, a linker is EPKSCDK (SEQ ID NO: 105). In another embodiment, a linker is IEGRDMD (SEQ. ID. NO: 106). In various aspects, the length of the linker may be modified to optimize binding of the target moiety or the function of the immunomodulatory moiety. In various aspects, the immunomodulatory moiety is a polypeptide that is fused to the C-terminus of the Fc region of the heavy chain of a targeting antibody or Fc-containing fusion protein. In another aspect, the immunomodulatory moiety is a polypeptide that is fused to the C-terminus of the light chain of a targeting antibody. In another aspect, the fusion protein comprises an X-Fc-Y sequence, wherein X is a targeting polypeptide and Y is an immunomodulatory polypeptide.

For example, a hybridoma can produce the polypeptides corresponding to SEQ. ID. NO: 1-69.

An antibody fragment can include a portion of an intact, antibody, e.g. including the antigen-binding or variable region thereof. Examples of antibody fragments include Fab, Fab', F(ab')2, and Fv fragments; Fc fragments or Fc-fusion products; diabodies; linear antibodies; single-chain antibody molecules; and multispecific antibodies formed from antibody fragment(s).

An intact antibody is one which includes an antigen-binding variable region as well as a light chain constant domain (CL) and heavy chain constant domains, CH1, CH2 and CH3. The constant domains may be native sequence constant domains (e.g. human native sequence constant domains) or amino acid sequence variant thereof for any other modified Fc (e.g. glycosylation or other engineered Fc).

The intact antibody may have one or more "effector functions" which refer to those biological activities attributable to the Fc region (a native sequence Fc region or amino acid sequence variant Fc region or any other modified Fc region) of an antibody. Examples of antibody effector functions include C1q binding; complement dependent cytotoxicity; Fc receptor binding; antibody-dependent cell-mediated cytotoxicity (ADCC): phagocytosis; down regulation of cell surface receptors (e.g., B cell receptor (BCR); and cross-presentation of antigens by antigen presenting cells or dendritic cells. In one embodiment, the targeting antibody or Fc-containing fusion protein facilitates focused or preferential delivery of a immunomodulatory moiety to a target cell. In another aspect, a targeting antibody can induce death of the targeted cell or sensitize it to immune cell-mediated cytotoxicity. In another aspect, the Fc-fusion protein or antibody can facilitate delivery of the immunomodulatory moiety or immunogenic apoptotic material from antibody-bound tumor targets, or both, to an antigen presenting cells (APC) via interactions between their Fc and Fc receptors (on APC).

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgC3, IgG4. IgA, and IgA2. The heavy-chain constant domains (hat correspond to the different classes of antibodies are called alpha (α), delta (δ), epsilon (ε), gamma (γ), and mu (μ) respectively. The subunit structures and three-dimensional configurations of different classes of immunoglobulins are well known.

Peptides: In some aspects of the invention the targeting, moiety or immunomodulatory moiety is a peptide or polypeptide. A peptide includes any analog, fragment or chemical derivative of a peptide whose amino acid residue sequence is shown herein. Therefore, a present peptide can be subject to various changes, substitutions, insertions, and deletions where such changes provide for certain advantages in its use. In this regard, a peptide of this invention corresponds to, rather than is identical to, the sequence of a recited peptide where one or more changes are made and it retains the ability to function as the unmodified peptide in one or more of the assays.

The term "analog" includes any peptide having an amino acid residue sequence substantially identical to a sequence specifically shown herein in which one or more residues have been conservatively substituted with a functionally similar residue and which displays the activity as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The term "fragment" refers to any subject polypeptide having an amino acid residue sequence shorter than that of a polypeptide whose amino acid residue sequence is disclosed herein.

As used herein "a tumor targeting peptide" includes polymers containing fewer than 100 amino acids, where the polymer specifically binds to a cellular component of a tumor cell, tumor vasculature, and/or a component of a tumor microenvironment.

A peptide of the present invention can be synthesized by any of the techniques that are known to those skilled in "the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al., "Solid Phase Peptide Synthesis"* W. H. Freeman Co., San Francisco, 1969; Bodanszky, et al., "Peptide Synthesis", John Wiley & Sons, Second Edition, 1976; J. Meienhofer, "Hormonal Proteins and Peptides". Vol. 2. p. 46, Academic Press (New York), 1983; Merrifield, Adv. Enzymol., 32:221-96, 1969: Fields et al. Int. J. Peptide Protein Res., 35:161-214, 1990; and U.S. Pat. No. 4,244,946 for solid phase peptide synthesis, and Schroder et al. "The Peptides", Vol. 1, Academic Press (New York), 1965 for classical solution synthesis. Appropriate protective groups usable in such synthesis are described in the above texts and in J. F. W. McOmie, "Protective Groups in Organic Chemistry", Plenum Press, New York, 1973.

Aptamers: In one aspect of the invention, the targeting moiety is an aptamer. In various embodiments, an aptamer is specific for a molecule on a tumor cell, tumor vasculature, and/or a tumor microenvironment. The term "aptamer" includes DNA, RNA or peptides that are selected based on specific binding properties to a particular molecule. For example, an aptamer(s) can be selected for binding a particular gene product in a tumor cell, tumor vasculature, tumor microenvironment, and/or an immune cell, as disclosed herein, where selection is made by methods known in the art and familiar to one of skill in the art. Subsequently, said aptamer(s) can be administered to a subject to modulate or regulate an immune response.

Some aptamers having affinity to a specific protein, DNA, amino acid and nucleotides have been described (e.g., K. Y. Wang, et al., Biochemistry 32:1899-1904 (1993): Pitney et al., U.S. Pat. No. 5,691,145: Gold, et al. Ann. Rev. Biochem. 64:763-797 (1995); Szostak et al., U.S. Pat. No. 5,631,146). High affinity and high specificity binding aptamers have been derived from combinatorial libraries (supra, Gold, et al.). Aptamers may have high affinities, with equilibrium dissociation constants ranging from micromolar to sub-nanomolar depending on the selection used, aptamers may also exhibit high selectivity, for example, showing a thousand fold, discrimination between 7-methyl G and G (Haller and Sarnow, Proc. Natl. Acad. Sci. USA 94:8521-8526 (1997)) or between D and L-tryptophan (supra, Gold et al.). An aptamer can be selected based on the particular molecule targeted (e.g., aptamer targeting EGFR or other cancer markers). Standard procedures for in vitro selection are known, such as SELEX experiments, described at Science 249 (4968) 505-510 (1990), and Nature (London), 346 (6287) 818-822 (1990) which can be followed throughout, or with modifications and improvements known in the art.

The term "therapeutically effective amount" means the amount of the subject compound that will elicit the biological or medical response of a tissue, system, animal or human that is being sought by the researcher, veterinarian, medical doctor or other clinician.

By "pharmaceutically acceptable" it is meant the carrier, diluent or excipient must be compatible with the other ingredients of the formulation and not deleterious to the recipient thereof.

The terms "administration of" and or "administering" should be understood to mean providing a composition in a therapeutically effective amount to the individual in need of treatment. Administration can be intratumoral or systemic (intravenous) administration. Furthermore, in conjunction with vaccination of recipient with pathogen antigen vaccine (e.g. tetanus toxoid). In addition, in conjunction with agent to deplete or inactivate regulatory T cells (e.g. cyclophosphamide) or myeloid suppressor cells (e.g. gemcitabine). In a further example, ex vivo treatment of immune cells and tumor cells for generation of tumor reactive or pathogen antigen reactive immune cells—for adoptive cellular immunotherapy. Administration can be intradermal or subcutaneous.

Furthermore, administration can be in combination with one or more additional therapeutic agents deplete or inactivate regulatory T cells (cyclophosphamide) or myeloid suppressor cells (e.g. gemcitabine). The pharmaceutical compositions of the invention identified herein are useful for parenteral topical, oral, nasal (or otherwise inhaled), rectal, or local administration, such as by aerosol or transdermally, for prophylactic and/or therapeutic treatment of one or more of the pathologies/indications described herein (e.g., cancer, pathogenic infectious agents, associated conditions thereof). The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, lipid complexes, etc.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLE 1

Counteracting Tumor Immune Tolerance Via Antibody-Mediated Depletion of $CD4^+$ Regulatory T Cells Facilitates the Activation of Tumor-Reactive $CD8^+$ T Cells and Enhances the In Vivo Antitumor Efficacy of Cytotoxic Anticancer Agents Immunogenic death of tumor cells by chemotherapeutic agents can induce $CD8^+$ T cell-mediated antitumor immunity. In response to specific chemotherapeutic agents, tumor cells exhibit the rapid translocation of intracellular calreticulin (CRT) to the cell surface where its aggregation provides a signal for the recognition and engulfment of dying tumor cells by antigen presenting dendritic cells (DCs). Treatment of mouse MB49 or human SW780 bladder cancer cells with doxorubicin, an anthracycline chemotherapeutic agent, induced rapid surface exposure of CRT that was detected by immunofluorescence cytometry of cells stained with Dylight 488-labeled anti-CRT antibody (FIG. 1a). To determine whether ex vivo treatment with doxorubicin induced an immunogenic death of tumor cells, either untreated live MB49 cells or an equivalent number of MB49 cells that were pre-treated in vitro with doxorubicin were injected into one flank of syngeneic immunocompetent C57BL/6 mice. Unlike mice injected with live tumor cells, mice injected with doxorubicin-treated tumor cells exhibited increased production of IFN-γ by draining lymph node (DLN) cells in response to in vitro re-challenge with MB49 cell lysates (FIG. 1b). Vaccination with doxorubicin-killed MB49 cells generated a tumor-specific immune response since no corresponding increase in IFN-γ secretion by DLN cells was observed following in vitro exposure to an irrelevant peptide (Hemagglutinin-HA). Injection of doxorubicin-treated MB49 tumor cells protected mice against tumor growth upon challenge with untreated live MB49 tumor cells injected into the opposite flank. (FIG. 1c). The protection against tumor growth by vaccination with doxorubicin-treated tumor cells was not observed in mice that were depleted of $CD8^+$ T cells with an anti-CD8 antibody before challenge with live tumor cells (FIG. 1c). These observations indicate that ex vivo treatment with chemotherapeutic agents can induce an immunogenic death of tumor cells that generates $CD8^+$ T cell-mediated adaptive antitumor immunity.

Tumor-induced immune tolerance inhibits activation of $CD8^+$ T cells in response to chemotherapy. To examine whether in vivo treatment with chemotherapeutic agents can activate $CD8^+$ T cell-mediated immune responses in mice with pre-established tumors, C57BL/6 mice were injected with live syngeneic MB49 tumor cells and then administered intratumoral doxorubicin at various time points following tumor inoculation. In contrast to vaccination of naïve mice with doxorubicin-killed MB49 cells, in vivo treatment of mice with established MB49 tumors at d10 following tumor inoculation failed to induce a corresponding increase in IFN-γ secretion by DLN cells in response to in vitro re-challenge with MB49 cell lysates (FIG. 1b). Whereas treatment with doxorubicin on d3 following tumor inoculation was able to arrest tumor growth, delayed administration of the same dose of doxorubicin on d10 failed to inhibit the progressive growth of established MB49 tumors (FIG. 1d). These results indicate that tumor-induced immune tolerance in the microenvironment of established cancers counteracts the activation of adaptive antitumor immunity in response to chemotherapy-induced tumor cell death.

Regulatory T cells (Treg) accumulate in the tumor microenvironment and counteract the ability of chemotherapy to activate $CD8^+$ T cell mediated antitumor immunity. To investigate whether $FoxP3^+$ Tregs are involved in enforcing immune tolerance in the tumor microenvironment, we examined the percentage of $CD4^+CD25^+FoxP3^+$ cells (Tregs) among $CD4^+$ T lymphocytes in the spleen, draining lymph nodes (DLN), and tumors of immunocompetent C57BL/6 mice at d0 and d14 after tumor inoculation. Whereas tumor-bearing mice exhibited only a minor increase in the percentage of Tregs among $CD4^+$ T cells in the spleen and DLN at d14 following tumor inoculation, a majority of tumor-infiltrating $CD4^+$ T cells at this time were $CD4^+CD25^+FoxP3^+$ cells (FIG. 1e). To investigate whether Tregs infiltrating the tumor microenvironment can suppress the activation of adaptive antitumor immunity in response to chemotherapy-induced tumor cell death, $CD4^+CD25^+$ cells isolated from tumors and DLN of tumor-bearing mice were adoptively transferred into syngeneic C57BL/6 naïve mice before vaccination with doxorubicin-killed MB49 cells. The adoptive transfer of tumor-infiltrating $CD4^+CD25^+$ cells into naïve mice inhibited the ability of subsequent in vivo vaccination with doxorubicin-treated MB49 tumor cells to increase production of IFN-γ by draining lymph node (DLN) cells in response to in vitro re-challenge with MB49 cell lysates (FIG. 1f). Consistent with the ability of tumor-infiltrating $CD4^+CD25^+$ cells to suppress the tumor-specific immune response, the adoptive transfer of these cells counteracted the protection conferred by vaccination with doxorubicin-treated MB49 cells against tumor growth upon challenge with untreated live MB49 tumor cells (FIG. 1g). These results indicate that the tumor microenvironment fosters the accumulation of $FoxP3^+$ Tregs which counteract the activation of $CD8^+$ T cell mediated antitumor immunity in response to chemotherapy-induced tumor cell death.

Inhibition of TGF-β in the tumor microenvironment reduces tumor-infiltrating $FoxP3^+$ regulatory T cells and enhances the antitumor efficacy chemotherapy. TGF-β induces FoxP3 expression in naïve peripheral $CD4^+$ $CD25^-$ $FoxP3^-$ T cells and facilitates their conversion into 'adaptive'

FoxP3⁺ Tregs that share the immunosuppressive ability of natural FoxP3⁺ Tregs generated in the thymus. Since human cancers frequently become refractory to the growth-inhibitory effect of TGF-β and acquire an ability to increase expression and secretion of TGF-β, we investigated whether this switch enables tumor cells to increase the number of adaptive Tregs in the tumor microenvironment. Examination of serum levels of TGF-β in mice at d0, d14, and d28 following inoculation of live MB49 tumor cells demonstrated that, tumor growth resulted in a progressive increase in the level of serum TGF-β (FIG. 2a). To assess the precise source of TGF-β in tumor-bearing mice, the total amount of TGF-β in supernatants of tumor cells or draining lymph node cells isolated from tumor-bearing mice were measured following ex vivo culture in serum-free medium for 24 h. Measurement of the level of TGF-β/$10^6$ cells showed that tumor cells were the dominant source of the increased level of TGF-β in tumor-bearing mice (FIG. 2b). In addition to tumor cell-autonomous expression of TGF-β, T cells from tumor-bearing mice also expressed higher levels of TGF-β compared to their counterparts from tumor-free mice (FIG. 2b). To determine whether the elevation of TGF-β is responsible for the upregulation of Tregs in the tumor microenvironment, tumor-bearing mice were treated with a soluble chimeric protein comprising the extracellular domain of TGFβRII and the Fc portion of the murine IgG1 heavy chain (TGFβRII:Fc). This fusion protein interferes with the binding of TGF-β to endogenous TGFβRII and functions as a stable TGF-β antagonist. ELISA assays confirmed the ability of TGFβRII:Fc to sequester TGF-β in supernatants of MB49 tumor cells in a concentration-dependent manner (FIG. 2c). At 5 d following inoculation of MB49 tumor cells, mice were either left untreated or treated with TGFβRII:Fc (1 µg intratumoral; twice weekly) for 3 weeks followed by flow cytometric analyses of intracellular FoxP3 expression in CD4⁺CD25⁺ T cells infiltrating the tumors. In vivo treatment of tumors with TGFβRII:Fc resulted in a significant decline in FoxP3 expression in tumor-infiltrating CD4⁺ T cells (FIG. 2d) and a dramatic reduction of CD4⁺CD25⁺FoxP3⁺ Tregs in tumor tissue (FIG. 2e). To determine whether inhibition of TGF-β in the tumor microenvironment can improve the antitumor efficacy of chemotherapy, MB49 tumor-bearing mice were administered doxorubicin (5 mg/kg i.p. weekly×3) with or without twice weekly treatment with TGFβRII:Fc (1 µg intratumoral). In contrast to treatment with either doxorubicin or TGFβRII:Fc alone, combined treatment with both agents was able to arrest the growth of MB49 tumors. These results indicate that tumor cell autonomous expression of TGF-β in the tumor microenvironment induces 'adaptive' FoxP3⁺ Tregs and that counteracting tumor-induced TGF-β-mediated immune tolerance enhances the antitumor efficacy of chemotherapy.

Anti-CD4 antibody-mediated depletion of CD4⁺ regulatory T cells facilitates chemotherapy-induced activation of tumor-reactive CD8⁺ T cells and enhances the antitumor efficacy of chemotherapy. To determine whether depletion of CD4⁺ regulatory T cells can improve the antitumor efficacy of chemotherapy by enhancing the activity of CD8⁺ T cells in the tumor microenvironment, immunocompetent mice bearing syngeneic tumors were administered an anti-CD4 antibody (Clone GK1.5) to deplete CD4⁺ T cells or an anti-CD8 antibody (Clone GK2.43) to deplete CD8⁺ T cells and then treated with specific chemotherapeutic agents. Flow cytometric analyses of peripheral blood mononuclear cells from MB49 tumor-bearing mice at d7 following administration of anti-CD4 antibody or anti-CD8 antibody confirmed the target-specific depletion of either CD4⁺ T cells or CD8⁺ T cells, respectively (FIG. 3a). Mice treated with anti-CD4 antibody showed loss of CD4⁺CD25⁺FoxP3⁺ T cells in the peripheral blood as well as among tumor-infiltrating cells (FIG. 3a, b). To determine whether antibody-mediated depletion of CD4⁺CD25⁺FoxP3⁺ cells facilitates chemotherapy-induced activation of tumor-reactive CD8⁺ T cells in the tumor microenvironment, we evaluated the expression of IFN-γ in CD8⁺ T cells extracted from the tumor and draining lymph node of MB49 tumor-bearing mice that were left untreated or treated with doxorubicin (with or without anti-CD4 antibody). Flow cytometric analyses showed that CD8 T cells from untreated mice did not express IFN-γ in response to in vitro re-challenge with MB49 cell lysates (FIG. 3c). Whereas IFN-γ⁺CD8⁺ T cells became evident in mice treated with doxorubicin alone, antibody-mediated depletion of CD4 T cells further enhanced the percentage of tumor-reactive CD8⁺ T cells that expressed IFN-γ in doxorubicin-treated animals (FIG. 3c). To directly evaluate whether the activation of tumor-reactive CD8⁺ T cells determines the in vivo antitumor efficacy of chemotherapy, we examined the effect of antibody-mediated depletion of CD8⁺ T cells or CD4⁺ T cells on the response of MB49 tumor-bearing mice to systemic treatment with doxorubicin (5 mg/kg). Treatment with doxorubicin alone inhibited the growth of MB49 tumors but failed to arrest tumor progression. Whereas depletion of CD8⁺ T cells completely impaired the in vivo antitumor efficacy of doxorubicin, depletion of CD4⁺ T cells enhanced the response to doxorubicin and resulted in tumor regression (FIG. 3d).

Anti-CD4 antibody-mediated depletion of CD4⁺ regulatory T cells augments and sustains the antitumor effect of chemotherapy by enabling activation of adaptive antitumor immunity. Whereas tumor cells treated with anthracyclins, such as doxorubicin, are particularly effective in eliciting an antitumor immune response, other chemotherapeutic agents are less effective in inducing immunogenic tumor cell death. The surface exposure of calreticulin is a key determinant of the immunogenicity of tumor cell death in response to chemotherapeutic agents. Compared to the efficient translocation of CRT to the cell surface in response to treatment with doxorubicin (FIG. 1a), treatment of MB49 tumor cells with equitoxic doses of either cisplatin or the combination of cisplatin and gemcitabine was less effective in increasing CRT exposure (FIG. 4a). Whereas tumor-reactive IFN-γ⁺CD8⁺ T cells were evident in tumors of MB49 tumor-bearing mice treated with doxorubicin (FIG. 3c), treatment with cisplatin was unable to induce a corresponding elevation of IFN-γ expression in CD8⁺ T cells in response to in vitro re-challenge with MB49 cell lysates (FIG. 4b). To examine whether counteraction of Treg-mediated immune tolerance enables the activation of antitumor immunity by cisplatin, immunocompetent tumor-bearing mice were treated with cisplatin following depletion of Tregs with anti-CD4 antibody. Antibody-mediated depletion of CD4⁺ T cells enhanced the percentage of tumor-reactive IFN-γ⁺CD8⁺ T cells as well as CD8⁺CD62L⁻ T cells in cisplatin-treated animals (FIG. 4b,c). Treatment of MB49 tumor-bearing mice with cisplatin partially inhibited tumor growth but failed to arrest tumor progression. Whereas depletion of CD8⁺ T cells completely negated the in vivo antitumor effect of cisplatin, depletion of CD4⁺ T cells enhanced the response to cisplatin and arrested tumor growth (FIG. 4d). Although treatment of tumor-bearing mice with the combination of cisplatin and gemcitabine was also able to arrest tumor growth, tumor growth rapidly resumed following termination of therapy with none of the animals (0/8) being tumor-free at d50 following tumor inoculation (FIG. 4e). In contrast, mice depleted of CD4⁺ T cells exhibited a more sustained response to either single agent or combination chemotherapy, with 7/16 mice exhibiting complete tumor regression. The complete regression of tumors was attended with establishment of adaptive antitumor immunity since none of the cured mice (7/7) developed tumors when re-challenged with live MB49 tumor cells in the opposite flank.

Chemotherapy-induced expression of NKG2D ligands on tumor cells cooperates with depletion of CD4+ regulatory T cells to stimulate CD8+ T cell-mediated tumor regression. NKG2D (NK group 2, member D) is a lectin-like type II transmembrane stimulatory receptor used by NK cells, γδ-TC$^{R+}$ T cells and αβ-TC$^{R+}$ T cells for immune surveillance of tumors. Expression of mouse and human ligands for NKG2D is upregulated in transformed epithelial cell lines in response to genotoxic stress or stalled DNA replication, via activation of a DNA damage checkpoint pathway initiated by ATM (ataxia telengiectasia, mutated) or ATR (ATM- and Rad3-related) protein kinases. Treatment of CT26 mouse colon cancer cells with genotoxic chemotherapeutic agents resulted in upregulation of mouse NKG2D ligands of the retinoic acid inducible gene family (Rae1) (FIG. 5a). RT-PCR showed that Rae1 mRNA was induced in CT26 cells by 2-4-h, reached a plateau after 16-24 h, and began to decline after 48 h of treatment with either the irinotecan or oxaliplatin (FIG. 5a). Flow cytometric analysis demonstrated that cell surface expression of human NKG2D ligands (MHC-1-related A and B molecules—MICA, MICB) was also upregulated on human colorectal cancer cells (HCT116) in response to treatment with irinotecan (FIG. 1b). Isogenic HCT116 cells that differ only in their p53 status demonstrated that p53 is not required for irinotecan-induced upregulation of MICA/B (FIG. 1b). To examine whether the induction of NKG2D ligands contributes to the antitumor effect of chemotherapy in vivo, immunocompetent Balb/C mice inoculated with syngeneic CT26 tumor cells were treated with irinotecan (50 mg/kg i.p) with or without pre-treatment with an NKG2D blocking antibody (200 μg i.p.). Whereas treatment with irinotecan alone inhibited the growth of CT26 tumors, the antitumor effect of irinotecan was negated by pre-treatment with the NKG2D blocking antibody (FIG. 1c). Since engagement of NKG2D by its ligands provides a costimulatory signal for the activation of CD8+ T cells, we investigated whether DNA damage-induced expression of NKG2D ligands on tumor cells cooperates with depletion of CD4+ regulatory T cells to stimulate CD8+ T cell-mediated tumor regression. Balb/C mice bearing CT26 tumors were administered an anti-CD4 antibody (Clone GK1.5) to deplete CD4+ T cells and/or an anti-CD8 antibody (Clone GK2.43) to deplete CD8+ T cells and then treated with irinotecan. Flow cytometric analyses confirmed the loss of CD4+CD25+FoxP3+ T cells in the spleen and draining lymph node of mice treated with anti-CD4 antibody (FIG. 5d). Antibody-mediated depletion of CD4+ T cells enhanced the percentage of tumor-reactive IFN-γ$^{+}$CD8+ T cells in irinotecan-treated animals (FIG. 5e). Whereas treatment of CT26 tumor-bearing mice with irinotecan only slowed tumor growth, depletion of CD4+ T cells enhanced the response to irinotecan and arrested tumor growth (FIG. 5c. The ability of CD4+ T cell depletion to augment the antitumor efficacy of irinotecan was mediated by CD8+ T cells since antibody-mediated depletion of CD8+ T cells completely negated the in vivo antitumor effect of chemotherapy in CD4+ T cell-depleted mice (FIG. 5c.

These data provide the following insights: (i) activation of tumor-reactive CD8+ T cells in response to immunogenic tumor cell death is a crucial determinant of the antitumor efficacy of chemotherapy in vivo; (ii) tumor-induced Tregs impair the antitumor efficacy of chemotherapy by inhibiting the activation of CD8+ T cells in the tumor microenvironment; and (iii) Counteracting tumor-induced immune tolerance via antibody-mediated depletion of CD4+ regulatory T cells facilitates chemotherapy-induced activation of antitumor immunity with memory, thereby enhancing the antitumor efficacy of chemotherapy; (iv) Strategies to decrease the number or function of CD4+ regulatory T cells in the tumor microenvironment can increase the activation of CD8+ T cells and improve the response of tumors to cytotoxic anti-cancer agents (chemotherapy, tumor-targeted antibodies, targeted therapeutics, kinase inhibitors) or chemoimmunotherapy (combination of chemotherapeutic agent with immunotherapeutic agents).

EXAMPLE 2

Exemplary Targeted Immunomodulatory Antibodies & Fusion Proteins

A targeting moiety, including an antibody, can be coupled to an immunomodulatory moiety including a polypeptide derived from the extracellular domain of TGFBR2. Crosslinkers or activating agents for such coupling or conjugation are well known in the art. Alternatively, the fusion proteins of the invention can be synthesized using recombination DNA technology well known in the art where the coding sequences of various portions of the fusion proteins can be linked together at the nucleic acid level. Subsequently the fusion proteins of the invention can be produced using a host cell well known in the art. Examples of targeted immunomodulatory antibodies and fusion proteins are shown in FIGS. 1-33 and briefly described below.

In one embodiment, the present invention provides a molecule including a targeting moiety fused with an immunomodulatory moiety, wherein the targeting moiety specifically binds to a target molecule, and the immunomodulatory moiety specifically binds to Transforming growth factor-beta (TGF-β). SEQ ID NO: 1 provides a fusion protein including anti-HER2/neu antibody and Transforming growth factor-beta receptor II (TGFβ-RII) Extracellular domain (ECD) (FIG. 2). SEQ ID NO: 2 provides a fusion protein including anti-EGFR1 antibody and Transforming growth factor-beta receptor II (TGFβ-RII) Extracellular domain (ECD) (FIG. 3). SEQ ID NO: 3 provides a fusion protein including anti-CD20 antibody and Transforming growth factor-beta receptor II (TGFβ-RII) Extracellular domain (ECD) (FIG. 4). SEQ ID NO: 4 provides a fusion protein including anti-VEGF antibody and Transforming growth factor-beta receptor II (TGFβ-RII) Extracellular domain (ECD) (FIG. 5). SEQ ID NO: 5 provides a fusion protein including anti-human CTLA-4 antibody and Transforming growth factor-beta receptor II (TGFβ-RII) Extracellular domain (ECD) (FIG. 6). SEQ ID NO: 6 provides a fusion protein including IL-2. Fc, and Transforming growth factor-beta receptor II (TGFβ-RII) Extracellular domain (ECD) (FIG. 7). SEQ ID NO: 7 provides a fusion protein including Transforming growth factor-beta receptor II (TGFβ-RII) Extracellular domain (ECD), Fc, and IL-2 (FIG. 7). SEQ ID NO 8 provides a fusion protein including anti-CD25 antibody and Transforming growth factor-beta receptor II (TGFβ-RII) Extracellular domain (ECD) (FIG. 8A). SEQ ID NO: 9 provides a fusion protein including anti-CD25 antibody and Transforming growth factor-beta receptor II (TGFβ-RII) Extracellular domain (ECD) (FIG. 8B). SEQ ID NO: 10 provides a fusion protein including anti-CD4 antibody and Transforming growth factor-beta receptor II (TGFβ-RII) Extracellular domain (ECD) (FIG. 9). SEQ ID NO: 11 provides a fusion protein including PD-1 Ectodomain, Fc, and Transforming growth factor-beta receptor II (TGFβ-RII) Extracellular domain (ectodomain) (PD-1 ectodomain+Fc+TGFβRII ectodomain; FIG. 10). SEQ ID NO: 12 provides a fusion protein including Transforming growth factor-beta receptor II (TGFβ-RII) Extracellular domain (ectodomain), Fc, and PD-1 Ectodomain (TGFβ-RII ectodomain+Fc+PD-1 ectodomain; FIG. 10). SEQ ID NO: 13 provides a fusion protein including RANK Ectodomain, Fc, and Transforming growth factor-beta receptor (TGFβ-RII) Extracellular domain (ectodomain) (RANK ectodomain+Fc+TGFβRII ectodomain; FIG. 11). SEQ ID NO: 14 provides a fusion protein including Transforming growth factor-beta receptor II (TGFβ-RII) Extracellular domain (ectodomain), Fc, and RANK Ectodomain (TGFβRII ectodomain+Fc+RANK ectodomain; FIG. 11).

In another embodiment, the present invention provides a molecule including a targeting moiety fused with an immunomodulatory moiety, wherein the targeting moiety specifically binds to a target molecule, and the immunomodulatory moiety is a molecule that specifically binds to Programmed Death-1 ligand 1 (PD-L1 or B7-H1) or Programmed Death-1 ligand 2 (PD-L2 or B7-DC). SEQ ID NO 15 provides a fusion protein including anti-HER2/neu antibody and PD-1 Ectodomain (FIG. 13). SEQ ID NO 16 provides a fusion protein including anti-EGFR1 antibody and PD-1 Ectodomain (FIG. 14). SEQ ID NO 17 provides a fusion protein including anti-CD20 antibody and PD-1 Ectodomain (FIG. 15). SEQ ID NO 18 provides a fusion protein including anti-VEGF antibody and PD-1 Ectodomain (FIG. 16). SEQ ID NO: 19 provides a fusion protein including anti-human CTLA-4 antibody and PD-1 Ectodomain (FIG. 17). SEQ ID NO: 20 provides a fusion protein including anti-CD25 antibody and PD-1 Ectodomain (FIG. 18A). SEQ ID NO: 21 provides a fusion protein including anti-CD25 antibody and PD-1 Ectodomain (FIG. 18B). SEQ ID NO: 22 provides a fusion protein including IL-2, Fc, and PD-1 ectodomain (IL-2+Fc+PD-1 ectodomain; FIG. 19). SEQ ID NO: 23 provides a fusion protein including PD-1 ectodomain, Fc, and IL-2 (PD-1 ectodomain+Fc+IL-2; FIG. 19). SEQ ID NO: 24 provides a fusion protein including anti-CD4 antibody and PD-1 Ectodomain (FIG. 20). SEQ ID NO: 25 provides a fusion protein including RANK Ectodomain. Fc, and PD-1 ectodomain (RANK ectodomain+Fc+PD-1 ectodomain; FIG. 21). SEQ ID NO: 26 provides a fusion protein including PD-1 ectodomain, Fc, and RANK Ectodomain (PD-1 ectodomain+Fc+RANK ectodomain; FIG. 21).

In another embodiment, the present invention provides a molecule including a targeting moiety fused with an immunomodulatory moiety, wherein the targeting moiety specifically binds to a target molecule, and the immunomodulatory moiety is a molecule that specifically binds to Receptor activator of NF-kB ligand (RANKL). SEQ ID NO: 27 provides a fusion protein including anti-HER2/neu antibody and RANK Ectodomain (FIG. 23). SEQ ID NO: 28 provides a fusion protein including anti-EGFR1 antibody and RANK Ectodomain (FIG. 24). SEQ ID NO: 29 provides a fusion protein including anti-CD20 antibody and RANK Ectodomain (FIG. 25). SEQ ID NO: 30 provides a fusion protein including anti VEGF antibody and RANK Ectodomain (FIG. 26). SEQ ID NO: 31 provides a fusion protein including anti-human CTLA-4 antibody and RANK Ectodomain (FIG. 27). SEQ ID NO: 32 provides a fusion protein including anti-CD25 antibody and RANK Ectodomain (FIG. 28A). SEQ ID NO: 33 provides a fusion protein including anti-CD25 antibody and RANK Ectodomain (FIG. 28B). SEQ ID NO: 34 provides a fusion protein including IL-2, Fc, and RANK ectodomain (IL-2+Fc+RANK ectodomain; FIG. 29). SEQ ID NO: 35 provides a fusion protein including RANK ectodomain, Fc, and IL-2 (RANK ectodomain+Fc+IL-2; FIG. 29). SEQ ID NO: 36 provides a fusion protein including anti-CD4 antibody and RANK Ectodomain (FIG. 30).

In another embodiment, the present invention provides a molecule including a targeting moiety fused with an immunomodulatory moiety, wherein the targeting moiety specifically binds to a target molecule, and the immunomodulatory moiety includes a molecule that specifically binds to Programmed death-1 (PD-1). SEQ ID NO: 37 provides a fusion protein including anti-tumor necrosis factor (TNFα) antibody and PD-1 ligand 1 (FIG. 32). SEQ ID NO: 38 provides a fusion protein including TNFR2 Extracellular ligand binding domain, Fc, and PD-1 ligand: (TNFR2 ECD+IgG Cγ1+PD-L1; FIG. 33). SEQ ID NO: 39 provides a fusion protein including PD-1 ligand, Fc, and TNFR2 Extracellular ligand binding domain: (PD-L1+IgG Cγ1-TNFR2 ECD; FIG. 33). SEQ ID NO: 40 provides a fusion protein including anti-CD20 antibody and PD-1 ligand 1 (PD-L1) (FIG. 34). SEQ ID NO: 41 provides a fusion protein including anti-CD25 antibody and PD-1 ligand 1 (PD-L1) (FIG. 35A). SEQ ID NO: 42 provides a fusion protein including anti-CD25 antibody and PD-1 ligand 1 (PD-L1) (FIG. 35B). SEQ ID NO: 43 provides a fusion protein including PD-1 ligand 1 (PD-L1), Fc, and IL-2 (PD-L1-Fc-IL2; FIG. 36). SEQ ID NO: 44 provides a fusion protein including IL-2, Fc, and PD-1 ligand 1 (PD-L1) (IL-2-Fc-PD-L1; FIG. 36). SEQ ID NO: 45 provides a fusion protein including anti-CD4 antibody and PD-1 ligand 1 (PD-L1) (FIG. 37). SEQ ID NO: 46 provides a fusion protein including the extracellular domain of CTLA-4, Immunoglobulin Fc (IgG Cγ1), and a sequence from PD-1 ligand (PD-L1) (Oncostatin M signal peptide+CTLA-4 ECD+IgG Cγ1+PD-L1; FIG. 38). SEQ ID NO: 47 provides a fusion protein including the extracellular domain of PD-1 ligand (PD-L1), immunoglobulin Fc (IgG Cγ1), and a sequence from the extracellular domain of CTLA-4: (PD-L1+IgG Cγ1+CTLA-4 ECD; FIG. 38). SEQ ID NO: 48 provides a fusion protein including Transforming growth factor-β (TGF-β), immunoglobulin Fc (IgG1), and a sequence from PD-1 ligand 1 (PD-L1) (TGFβ-1+Fc+PD-L1; FIG. 39). SEQ ID NO: 49 provides a fusion protein including a sequence from PD-1 ligand 1 (PD-L1), immunoglobulin Fc (IgG Cγ1), and Transforming growth factor beta (TGF-β) (PD-L1+Fc+TGF-1; FIG. 39).

In another embodiment, the present invention provides a molecule including a targeting moiety fused with an immunomodulatory moiety, wherein the targeting moiety specifically binds to a target molecule, and the immunomodulatory moiety includes a molecule that specifically binds to Transforming growth factor-beta receptor (TGF-βR). SEQ ID NO 50 provides a fusion protein including an antibody that binds TNF-α, and a sequence from Transforming growth factor-β (TGF-β) (FIG. 41). SEQ ID NO: 51 provides a fusion protein including TNFR2 Extracellular ligand binding domain, Fc, and a sequence from Transforming growth factor-β (TGF-β) (TNFR2 ECD+IgG Cγ1+TGF-β; FIG. 42). SEQ ID NO 52 provides a fusion protein including a sequence from Transforming growth factor-β (TGF-β), Fc, and TNFR2 Extracellular ligand binding domain: (TGF-β+IgG Cγ1+TNFR2 ECD; FIG. 42). SEQ ID NO: 53 provides a fusion protein including anti-CD20 antibody and a sequence from Transforming growth factor-β (TGF-β) (FIG. 43). SEQ ID NO: 54 provides a fusion protein including anti-CD25 antibody and a sequence from transforming growth factor-β (TGF-β) (FIG. 44A). SEQ ID NO: 55 provides a fusion protein including anti-CD25 antibody and a sequence from transforming growth factor-β (TGF-β) (FIG. 44B). SEQ ID NO: 56 provides a fusion protein including a sequence from Transforming growth factor-β (TGF-β), Fc, and IL-2 (TGF-β+Fc+IL-2; FIG. 45). SEQ ID NO: 57 provides a fusion protein including IL-2, Fc, and Transforming growth factor-β (TGF-β) (IL-2+Fc+TGF-β; FIG. 45). SEQ ID NO: 58 provides a fusion protein including anti-CD4 antibody and a sequence from transforming growth factor-3 (TGF-β) (FIG. 46). SEQ ID NO: 59 provides a fusion protein including the extracellular domain of CTLA-4, immunoglobulin Fc (IgG Cγ1), and a sequence from a sequence from transforming growth factor-β (TGF-β) (Oncostatin M signal peptide+CTLA-4 ECD+IgG Cγ1+TGF-1; FIG. 47). SEQ ID NO: 60 provides a fusion protein including a sequence from Transforming growth factor-3 (TGF-13, immunoglobulin Fc (IgG Cγ1), and a sequence from the extracellular domain of CTLA-4: (TGF-β1+IgG Cγ1+CTLA-4 ECD) (FIG. 47).

In another embodiment, the present invention provides a molecule including a targeting moiety fused with an immunomodulatory moiety, wherein the targeting moiety specifically binds to a target molecule, and the immunomodulatory moiety is a molecule that specifically binds to Receptor activator of NF-kB ligand (RANKL). SEQ ID NO: 61 provides a fusion protein including an antibody that binds TNT-α, and a sequence from RANK Ectodomain (FIG. 48). SEQ ID NO: 62 provides a fusion protein including TNFR2 Extracellular ligand binding domain, Fc, and a sequence from RANK Ectodomain (TNFR2 ECD+IgG Cγ1+RANK Ectodomain; FIG. 49). SEQ ID NO: 63 provides a fusion protein including a sequence from RANK Ectodomain, Fc, and TNFR2 Extracellular ligand binding domain: (RANK Ectodomain+IgG Cγ1+TNFR2 ECD; FIG. 49). SEQ ID NO: 64 provides a fusion protein including the extracellular domain of CTLA-4, immunoglobulin Fc (IgG Cγ1), and a sequence from a sequence from RANK Ectodomain (Oncostatin M signal peptide+CTLA-4 ECD+IgG Cγ1+RANK Ectodomain; FIG. 50). SEQ ID NO: 65 provides a fusion protein including a sequence from RANK Ectodomain, immunoglobulin Fc (IgG Cγ1), and a sequence from the extracellular domain of CTLA-4: (RANK Ectodomain+IgG Cγ1+CTLA-4 ECD) (FIG. 50). SEQ ID NO: 66 provides a fusion protein including a sequence from transforming growth factor-β (TGF-β), immunoglobulin Fc region (IgG Cγ1), and an extracellular ligand-binding domain or ectodomain of Receptor activator of nuclear factor-κB (RANK) (TGF-β+IgG Cγ1+RANK Ectodomain; FIG. 51). SEQ ID NO: 67 provides a fusion protein including a sequence from RANK Ectodomain, immunoglobulin Fc (IgG Cγ1), and a sequence from transforming growth factor-β (TGF-β): (RANK Ectodomain+IgG Cγ1+TGF-β) (FIG. 51). SEQ ID NO: 68 provides a fusion protein including a sequence from Programmed death-1 ligand 1 (PD-L1), immunoglobulin Fc region (IgG Cγ1), and an extracellular ligand-binding domain or ectodomain of Receptor activator of nuclear factor-κB (RANK) (PD-L1+IgG Cγ1+RANK Ectodomain; FIG. 52). SEQ ID NO: 69 provides a fusion protein including a sequence from RANK Ectodomain, immunoglobulin Fc (IgG Cγ1), and a sequence from Programmed death-1 ligand 1 (PD-L1): (RANK Ectodomain+IgG Cγ1+PD-L1) (FIG. 52).

Although the invention has been described with reference to the above example, it will be understood that modifications and variations are encompassed within the spirit and scope of the invention. Accordingly, the invention is limited only by the following claims.

What is claimed is:

1. An isolated molecule comprising a targeting moiety fused with an immunomodulatory moiety, wherein:
    (a) the targeting moiety specifically binds Cytotoxic T-lymphocyte associated antigen-4 (CTLA-4); and
    (b) the immunomodulatory moiety comprises an amino acid sequence of the extracellular domain of Transforming growth factor-beta receptor (TGF-βR).

2. The molecule of claim 1, wherein the targeting moiety comprises an antibody, antibody fragment, scFv, or Fc-containing polypeptide that specifically binds CTLA-4.

3. The molecule of claim 1, wherein the immunomodulatory moiety comprises an amino acid sequence of the extracellular domain of Transforming growth factor-beta receptor selected from the group consisting of SEQ ID NO: 79-91.

4. The molecule of claim 3, wherein the immunomodulatory moiety comprises an amino acid sequence of the extracellular domain of Transforming growth factor-beta receptor II (TGF-βRII).

5. The molecule of claim 4, wherein the immunomodulatory moiety comprises the amino acid sequence corresponding to SEQ ID NO: 87 or a binding fragment thereof.

6. The molecule of claim 5, wherein the molecule comprises the amino acid sequence corresponding to SEQ ID NO: 5 or a binding fragment thereof.

7. The molecule of claim 6, wherein the molecule comprises the amino acid sequence corresponding to SEQ ID NO: 5 or a binding fragment thereof and the amino acid sequence corresponding to SEQ ID NO: 74 or a binding fragment thereof.

8. A method of treating a neoplastic disease comprising: administration to a subject in need thereof one or more molecules of claim 1, wherein the neoplastic disease is bladder cancer or melanoma.

9. The method of claim 8, wherein the subject is administered in combination with another anticancer therapy.

10. The method of claim 8, wherein the anticancer therapy comprises a chemotherapeutic molecule, antibody, small molecule kinase inhibitor, hormonal agent, ionizing radiation, ultraviolet radiation, cryoablation, thermal ablation, or radiofrequency ablation.

11. The method of claim 8, wherein the subject is administered in combination with a vaccine.

12. The method of claim 8, wherein the subject is human.

13. The isolated molecule of claim 1, further comprising a linker at the $C_H3$ region of the Fc.

14. The isolated molecule of claim 13, wherein the linker is (GGGGS)n (SEQ ID NO:104), and wherein n is 1, 2, 3, 4, 5, 6, 7 or 8.

15. The isolated molecule of claim 13, wherein the linker comprises the amino acid sequence GGGGSGGGGSGGGGS (SEQ ID NO:104).

* * * * *

SEQUENCE LISTING

```
<160> NUMBER OF SEQ ID NOS: 122

<210> SEQ ID NO 1
<211> LENGTH: 602
<212> TYPE: PRT
<213> ORGANISM: Homo sapiens

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
                145                 150                 155                 160
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys Gly Gly Gly Gly Ser Gly Gly Gly Ser Gly Gly Gly Gly
                450                 455                 460

Ser Thr Ile Pro Pro His Val Gln Lys Ser Val Asn Asn Asp Met Ile
465                 470                 475                 480

Val Thr Asp Asn Asn Gly Ala Val Lys Phe Pro Gln Leu Cys Lys Phe
                485                 490                 495

Cys Asp Val Arg Phe Ser Thr Cys Asp Asn Gln Lys Ser Cys Met Ser
                500                 505                 510

Asn Cys Ser Ile Thr Ser Ile Cys Glu Lys Pro Gln Glu Val Cys Val
                515                 520                 525

Ala Val Trp Arg Lys Asn Asp Glu Asn Ile Thr Leu Glu Thr Val Cys
                530                 535                 540

His Asp Pro Lys Leu Pro Tyr His Asp Phe Ile Leu Glu Asp Ala Ala
545                 550                 555                 560

Ser Pro Lys Cys Ile Met Lys Glu Lys Lys Pro Gly Glu Thr Phe
                565                 570                 575
```

```
Phe Met Cys Ser Cys Ser Ser Asp Glu Cys Asn Asp Asn Ile Ile Phe
            580                 585                 590

Ser Glu Glu Tyr Asn Thr Ser Asn Pro Asp
            595                 600

<210> SEQ ID NO 2
<211> LENGTH: 601
<212> TYPE: PRT
<213> ORGANISM: Homo sapiens

<400> SEQUENCE: 2

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
```

```
            340                 345                 350
Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Gly Gly Gly Gly Ser
    450                 455                 460

Thr Ile Pro Pro His Val Gln Lys Ser Val Asn Asn Asp Met Ile Val
465                 470                 475                 480

Thr Asp Asn Asn Gly Ala Val Lys Phe Pro Gln Leu Cys Lys Phe Cys
                485                 490                 495

Asp Val Arg Phe Ser Thr Cys Asp Asn Gln Lys Ser Cys Met Ser Asn
            500                 505                 510

Cys Ser Ile Thr Ser Ile Cys Glu Lys Pro Gln Glu Val Cys Val Ala
        515                 520                 525

Val Trp Arg Lys Asn Asp Glu Asn Ile Thr Leu Glu Thr Val Cys His
    530                 535                 540

Asp Pro Lys Leu Pro Tyr His Asp Phe Ile Leu Glu Asp Ala Ala Ser
545                 550                 555                 560

Pro Lys Cys Ile Met Lys Glu Lys Lys Pro Gly Glu Thr Phe Phe
                565                 570                 575

Met Cys Ser Cys Ser Ser Asp Glu Cys Asn Asp Asn Ile Ile Phe Ser
            580                 585                 590

Glu Glu Tyr Asn Thr Ser Asn Pro Asp
        595                 600

<210> SEQ ID NO 3
<211> LENGTH: 603
<212> TYPE: PRT
<213> ORGANISM: Homo sapiens

<400> SEQUENCE: 3

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110
```

-continued

```
Ala Gly Thr Thr Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Ser Gly Gly Gly Gly
    450                 455                 460

Gly Ser Thr Ile Pro Pro His Val Gln Lys Ser Val Asn Asn Asp Met
465                 470                 475                 480

Ile Val Thr Asp Asn Asn Gly Ala Val Lys Phe Pro Gln Leu Cys Lys
                485                 490                 495

Phe Cys Asp Val Arg Phe Ser Thr Cys Asp Asn Gln Lys Ser Cys Met
            500                 505                 510

Ser Asn Cys Ser Ile Thr Ser Ile Cys Glu Lys Pro Gln Glu Val Cys
        515                 520                 525

Val Ala Val Trp Arg Lys Asn Asp Glu Asn Ile Thr Leu Glu Thr Val
```

-continued

```
                530                 535                 540
Cys His Asp Pro Lys Leu Pro Tyr His Asp Phe Ile Leu Glu Asp Ala
545                 550                 555                 560

Ala Ser Pro Lys Cys Ile Met Lys Glu Lys Lys Pro Gly Glu Thr
                565                 570                 575

Phe Phe Met Cys Ser Cys Ser Ser Asp Glu Cys Asn Asp Asn Ile Ile
                580                 585                 590

Phe Ser Glu Glu Tyr Asn Thr Ser Asn Pro Asp
                595                 600

<210> SEQ ID NO 4
<211> LENGTH: 605
<212> TYPE: PRT
<213> ORGANISM: Homo sapiens

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys Gly Gly Gly Ser Gly Gly Gly Gly Ser Gly
450                 455                 460

Gly Gly Gly Ser Thr Ile Pro Pro His Val Gln Lys Ser Val Asn Asn
465                 470                 475                 480

Asp Met Ile Val Thr Asp Asn Asn Gly Ala Val Lys Phe Pro Gln Leu
            485                 490                 495

Cys Lys Phe Cys Asp Val Arg Phe Ser Thr Cys Asp Asn Gln Lys Ser
            500                 505                 510

Cys Met Ser Asn Cys Ser Ile Thr Ser Ile Cys Glu Lys Pro Gln Glu
            515                 520                 525

Val Cys Val Ala Val Trp Arg Lys Asn Asp Glu Asn Ile Thr Leu Glu
530                 535                 540

Thr Val Cys His Asp Pro Lys Leu Pro Tyr His Asp Phe Ile Leu Glu
545                 550                 555                 560

Asp Ala Ala Ser Pro Lys Cys Ile Met Lys Glu Lys Lys Lys Pro Gly
            565                 570                 575

Glu Thr Phe Phe Met Cys Ser Cys Ser Ser Asp Glu Cys Asn Asp Asn
            580                 585                 590

Ile Ile Phe Ser Glu Glu Tyr Asn Thr Ser Asn Pro Asp
            595                 600                 605

<210> SEQ ID NO 5
<211> LENGTH: 600
<212> TYPE: PRT
<213> ORGANISM: Homo sapiens

<400> SEQUENCE: 5

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

Gly Gly Gly Gly Ser Gly Gly Gly Ser Gly Gly Gly Gly Ser Gly Thr
450                 455                 460

Ile Pro Pro His Val Gln Lys Ser Val Asn Asn Asp Met Ile Val Thr
465                 470                 475                 480

Asp Asn Asn Gly Ala Val Lys Phe Pro Gln Leu Cys Lys Phe Cys Asp
                485                 490                 495
```

Val Arg Phe Ser Thr Cys Asp Asn Gln Lys Ser Cys Met Ser Asn Cys
            500                 505                 510

Ser Ile Thr Ser Ile Cys Glu Lys Pro Gln Glu Val Cys Val Ala Val
            515                 520                 525

Trp Arg Lys Asn Asp Glu Asn Ile Thr Leu Glu Thr Val Cys His Asp
    530                 535                 540

Pro Lys Leu Pro Tyr His Asp Phe Ile Leu Glu Asp Ala Ala Ser Pro
545                 550                 555                 560

Lys Cys Ile Met Lys Glu Lys Lys Pro Gly Glu Thr Phe Phe Met
                565                 570                 575

Cys Ser Cys Ser Ser Asp Glu Cys Asn Asp Asn Ile Ile Phe Ser Glu
            580                 585                 590

Glu Tyr Asn Thr Ser Asn Pro Asp
            595                 600

<210> SEQ ID NO 6
<211> LENGTH: 525
<212> TYPE: PRT
<213> ORGANISM: Homo sapiens

<400> SEQUENCE: 6

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Gly Gly Gly Gly Ser Gly Gly Gly Ser Gly
    130                 135                 140

Gly Gly Ser Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
            195                 200                 205

Glu Val His Asn Ala Lys Thr Lys Pro Arg Glu Glu Gln Tyr Asn Ser
    210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
            260                 265                 270

Gln Val Tyr Thr Leu Pro Pro Ser Arg Glu Glu Met Thr Lys Asn Gln
              275                 280                 285

Val Ser Leu Thr Cys Leu Val Lys Gly Phe Tyr Pro Ser Asp Ile Ala
        290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
                325                 330                 335

Thr Val Asp Lys Ser Arg Trp Gln Gln Gly Asn Val Phe Ser Cys Ser
                340                 345                 350

Val Met His Glu Ala Leu His Asn His Tyr Thr Gln Lys Ser Leu Ser
                355                 360                 365

Leu Ser Pro Gly Lys Gly Gly Gly Gly Ser Gly Gly Gly Gly Ser Gly
            370                 375                 380

Gly Gly Gly Ser Thr Ile Pro Pro His Val Gln Lys Ser Val Asn Asn
385                 390                 395                 400

Asp Met Ile Val Thr Asp Asn Asn Gly Ala Val Lys Phe Pro Gln Leu
                405                 410                 415

Cys Lys Phe Cys Asp Val Arg Phe Ser Thr Cys Asp Asn Gln Lys Ser
                420                 425                 430

Cys Met Ser Asn Cys Ser Ile Thr Ser Ile Cys Glu Lys Pro Gln Glu
                435                 440                 445

Val Cys Val Ala Val Trp Arg Lys Asn Asp Glu Asn Ile Thr Leu Glu
            450                 455                 460

Thr Val Cys His Asp Pro Lys Leu Pro Tyr His Asp Phe Ile Leu Glu
465                 470                 475                 480

Asp Ala Ala Ser Pro Lys Cys Ile Met Lys Glu Lys Lys Lys Pro Gly
                485                 490                 495

Glu Thr Phe Phe Met Cys Ser Cys Ser Ser Asp Glu Cys Asn Asp Asn
                500                 505                 510

Ile Ile Phe Ser Glu Glu Tyr Asn Thr Ser Asn Pro Asp
            515                 520                 525

<210> SEQ ID NO 7
<211> LENGTH: 525
<212> TYPE: PRT
<213> ORGANISM: Homo sapiens

<400> SEQUENCE: 7

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
                20                  25                  30

Asp Val Arg Phe Ser Thr Cys Asp Asn Gln Lys Ser Cys Met Ser Asn
            35                  40                  45

Cys Ser Ile Thr Ser Ile Cys Glu Lys Pro Gln Glu Val Cys Val Ala
        50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser

```
            115                 120                 125
Glu Glu Tyr Asn Thr Ser Asn Pro Asp Gly Gly Gly Ser Gly Gly
        130                 135                 140
Gly Gly Ser Gly Gly Gly Gly Ser Thr His Thr Cys Pro Cys Pro
145                 150                 155                 160
Ala Pro Glu Leu Leu Gly Gly Pro Ser Val Phe Leu Phe Pro Lys
                165                 170                 175
Pro Lys Asp Thr Leu Met Ile Ser Arg Thr Pro Glu Val Thr Cys Val
            180                 185                 190
Val Val Asp Val Ser His Glu Asp Pro Glu Val Lys Phe Asn Trp Tyr
            195                 200                 205
Val Asp Gly Val Glu Val His Asn Ala Lys Thr Lys Pro Arg Glu Glu
        210                 215                 220
Gln Tyr Asn Ser Thr Tyr Arg Val Val Ser Val Leu Thr Val Leu His
225                 230                 235                 240
Gln Asp Trp Leu Asn Gly Lys Glu Tyr Lys Cys Lys Val Ser Asn Lys
                245                 250                 255
Ala Leu Pro Ala Pro Ile Glu Lys Thr Ile Ser Lys Ala Lys Gly Gln
        260                 265                 270
Pro Arg Glu Pro Gln Val Tyr Thr Leu Pro Pro Ser Arg Glu Glu Met
        275                 280                 285
Thr Lys Asn Gln Val Ser Leu Thr Cys Leu Val Lys Gly Phe Tyr Pro
        290                 295                 300
Ser Asp Ile Ala Val Glu Trp Glu Ser Asn Gly Gln Pro Glu Asn Asn
305                 310                 315                 320
Tyr Lys Thr Thr Pro Pro Val Leu Asp Ser Asp Gly Ser Phe Phe Leu
                325                 330                 335
Tyr Ser Lys Leu Thr Val Asp Lys Ser Arg Trp Gln Gln Gly Asn Val
            340                 345                 350
Phe Ser Cys Ser Val Met His Glu Ala Leu His Asn His Tyr Thr Gln
            355                 360                 365
Lys Ser Leu Ser Leu Ser Pro Gly Lys Gly Gly Gly Ser Gly Gly
        370                 375                 380
Gly Gly Ser Gly Gly Gly Gly Ser Ala Pro Thr Ser Ser Ser Thr Lys
385                 390                 395                 400
Lys Thr Gln Leu Gln Leu Glu His Leu Leu Asp Leu Gln Met Ile
                405                 410                 415
Leu Asn Gly Ile Asn Asn Tyr Lys Asn Pro Lys Leu Thr Arg Met Leu
        420                 425                 430
Thr Phe Lys Phe Tyr Met Pro Lys Lys Ala Thr Glu Leu Lys His Leu
        435                 440                 445
Gln Cys Leu Glu Glu Glu Leu Lys Pro Leu Glu Val Leu Asn Leu
        450                 455                 460
Ala Gln Ser Lys Asn Phe His Leu Arg Pro Arg Asp Leu Ile Ser Asn
465                 470                 475                 480
Ile Asn Val Ile Val Leu Glu Leu Lys Gly Ser Glu Thr Thr Phe Met
                485                 490                 495
Cys Glu Tyr Ala Asp Glu Thr Ala Thr Ile Val Glu Phe Leu Asn Arg
            500                 505                 510
Trp Ile Thr Phe Cys Gln Ser Ile Ile Ser Thr Leu Thr
            515                 520                 525

<210> SEQ ID NO 8
```

<211> LENGTH: 598
<212> TYPE: PRT
<213> ORGANISM: Homo sapiens

<400> SEQUENCE: 8

```
Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Thr Ser Tyr
            20                  25                  30
Arg Met His Trp Val Arg Gln Ala Pro Gly Gln Gly Leu Glu Trp Ile
        35                  40                  45
Gly Tyr Ile Asn Pro Ser Thr Gly Tyr Thr Tyr Asn Gln Lys Phe
    50                  55                  60
Lys Asp Lys Ala Thr Ile Thr Ala Asp Glu Ser Thr Asn Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Gly Gly Val Phe Asp Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
```

```
                385             390             395             400
        Gly Ser Phe Phe Leu Tyr Ser Lys Leu Thr Val Asp Lys Ser Arg Trp
                        405             410             415

Gln Gln Gly Asn Val Phe Ser Cys Ser Val Met His Glu Ala Leu His
                    420             425             430

Asn His Tyr Thr Gln Lys Ser Leu Ser Leu Ser Pro Gly Lys Gly Gly
                    435             440             445

Gly Gly Ser Gly Gly Gly Ser Gly Gly Gly Ser Thr Ile Pro
                450             455             460

Pro His Val Gln Lys Ser Val Asn Asn Asp Met Ile Val Thr Asp Asn
        465             470             475             480

Asn Gly Ala Val Lys Phe Pro Gln Leu Cys Lys Phe Cys Asp Val Arg
                        485             490             495

Phe Ser Thr Cys Asp Asn Gln Lys Ser Cys Met Ser Asn Cys Ser Ile
                        500             505             510

Thr Ser Ile Cys Glu Lys Pro Gln Glu Val Cys Val Ala Val Trp Arg
                    515             520             525

Lys Asn Asp Glu Asn Ile Thr Leu Glu Thr Val Cys His Asp Pro Lys
        530             535             540

Leu Pro Tyr His Asp Phe Ile Leu Glu Asp Ala Ala Ser Pro Lys Cys
        545             550             555             560

Ile Met Lys Glu Lys Lys Lys Pro Gly Glu Thr Phe Phe Met Cys Ser
                        565             570             575

Cys Ser Ser Asp Glu Cys Asn Asp Asn Ile Ile Phe Ser Glu Glu Tyr
                    580             585             590

Asn Thr Ser Asn Pro Asp
                    595

<210> SEQ ID NO 9
<211> LENGTH: 597
<212> TYPE: PRT
<213> ORGANISM: Homo sapiens

<400> SEQUENCE: 9

Gln Leu Gln Gln Ser Gly Thr Val Leu Ala Arg Pro Gly Ala Ser Val
        1               5                   10                  15

Lys Met Ser Cys Lys Ala Ser Gly Tyr Ser Phe Thr Arg Tyr Trp Met
                        20                  25                  30

His Trp Ile Lys Gln Arg Pro Gly Gln Gly Leu Glu Trp Ile Gly Ala
                    35                  40                  45

Ile Tyr Pro Gly Asn Ser Asp Thr Ser Tyr Asn Gln Lys Phe Glu Gly
                50                  55                  60

Lys Ala Lys Leu Thr Ala Val Thr Ser Ala Ser Thr Ala Tyr Met Glu
        65                  70                  75                  80

Leu Ser Ser Leu Thr His Glu Asp Ser Ala Val Tyr Tyr Cys Ser Arg
                        85                  90                  95

Asp Tyr Gly Tyr Tyr Phe Asp Phe Trp Gly Gln Gly Thr Thr Leu Thr
                        100                 105                 110

Val Ser Ser Ala Ser Thr Lys Gly Pro Ser Val Phe Pro Leu Ala Pro
                    115                 120                 125

Ser Ser Lys Ser Thr Ser Gly Gly Thr Ala Ala Leu Gly Cys Leu Val
                130                 135                 140

Lys Asp Tyr Phe Pro Glu Pro Val Thr Val Ser Trp Asn Ser Gly Ala
        145                 150                 155                 160
```

```
Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Gly Gly Gly
        435                 440                 445

Gly Ser Gly Gly Gly Ser Gly Gly Gly Ser Thr Ile Pro Pro
    450                 455                 460

His Val Gln Lys Ser Val Asn Asn Asp Met Ile Val Thr Asp Asn Asn
465                 470                 475                 480

Gly Ala Val Lys Phe Pro Gln Leu Cys Lys Phe Cys Asp Val Arg Phe
                485                 490                 495

Ser Thr Cys Asp Asn Gln Lys Ser Cys Met Ser Asn Cys Ser Ile Thr
            500                 505                 510

Ser Ile Cys Glu Lys Pro Gln Glu Val Cys Val Ala Val Trp Arg Lys
        515                 520                 525

Asn Asp Glu Asn Ile Thr Leu Glu Thr Val Cys His Asp Pro Lys Leu
    530                 535                 540

Pro Tyr His Asp Phe Ile Leu Glu Asp Ala Ala Ser Pro Lys Cys Ile
545                 550                 555                 560

Met Lys Glu Lys Lys Pro Gly Glu Thr Phe Phe Met Cys Ser Cys
                565                 570                 575

Ser Ser Asp Glu Cys Asn Asp Asn Ile Ile Phe Ser Glu Glu Tyr Asn
```

```
                    580                 585                 590
Thr Ser Asn Pro Asp
            595

<210> SEQ ID NO 10
<211> LENGTH: 603
<212> TYPE: PRT
<213> ORGANISM: Homo sapiens

<400> SEQUENCE: 10

Gln Val Gln Leu Gln Glu Ala Gly Pro Gly Leu Val Lys Pro Ser Glu
1               5                   10                  15

Thr Leu Ser Leu Thr Cys Ser Val Ser Gly Ser Ile Ser Gly Asp
            20                  25                  30

Tyr Tyr Trp Phe Trp Ile Arg Gln Ser Pro Gly Lys Gly Leu Glu Trp
        35                  40                  45

Ile Gly Tyr Ile Tyr Gly Ser Gly Gly Thr Asn Tyr Asn Pro Ser
    50                  55                  60

Leu Asn Asn Arg Val Ser Ile Ser Ile Asp Thr Ser Lys Asn Leu Phe
65                  70                  75                  80

Ser Leu Lys Leu Arg Ser Val Thr Ala Ala Asp Thr Ala Val Tyr Tyr
                85                  90                  95

Cys Ala Ser Asn Ile Leu Lys Tyr Leu His Trp Leu Leu Tyr Trp Gly
            100                 105                 110

Gln Gly Val Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Thr Ile Pro Pro His Val Gln Lys Ser Val Asn Asn Asp Met
465                 470                 475                 480

Ile Val Thr Asp Asn Asn Gly Ala Val Lys Phe Pro Gln Leu Cys Lys
                485                 490                 495

Phe Cys Asp Val Arg Phe Ser Thr Cys Asp Asn Gln Lys Ser Cys Met
            500                 505                 510

Ser Asn Cys Ser Ile Thr Ser Ile Cys Glu Lys Pro Gln Glu Val Cys
        515                 520                 525

Val Ala Val Trp Arg Lys Asn Asp Glu Asn Ile Thr Leu Glu Thr Val
    530                 535                 540

Cys His Asp Pro Lys Leu Pro Tyr His Asp Phe Ile Leu Glu Asp Ala
545                 550                 555                 560

Ala Ser Pro Lys Cys Ile Met Lys Glu Lys Lys Lys Pro Gly Glu Thr
                565                 570                 575

Phe Phe Met Cys Ser Cys Ser Ser Asp Glu Cys Asn Asp Asn Ile Ile
            580                 585                 590

Phe Ser Glu Glu Tyr Asn Thr Ser Asn Pro Asp
        595                 600

<210> SEQ ID NO 11
<211> LENGTH: 542
<212> TYPE: PRT
<213> ORGANISM: Homo sapiens

<400> SEQUENCE: 11

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

```
Ala Glu Val Pro Thr Ala His Pro Ser Pro Ser Pro Arg Pro Ala Gly
            130                 135                 140

Gln Phe Gln Thr Leu Val Gly Gly Gly Ser Gly Gly Gly Gly Ser
145                 150                 155                 160

Gly Gly Gly Gly Ser Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
            195                 200                 205

Val Ser His Glu Asp Pro Glu Val Lys Phe Asn Trp Tyr Val Asp Gly
210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
            245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
            275                 280                 285

Pro Gln Val Tyr Thr Leu Pro Pro Ser Arg Glu Glu Met Thr Lys Asn
290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
            325                 330                 335

Thr Pro Pro Val Leu Asp Ser Asp Gly Ser Phe Phe Leu Tyr Ser Lys
            340                 345                 350

Leu Thr Val Asp Lys Ser Arg Trp Gln Gln Gly Asn Val Phe Ser Cys
            355                 360                 365

Ser Val Met His Glu Ala Leu His Asn His Tyr Thr Gln Lys Ser Leu
            370                 375                 380

Ser Leu Ser Pro Gly Lys Gly Gly Gly Ser Gly Gly Gly Gly Ser
385                 390                 395                 400

Gly Gly Gly Gly Ser Thr Ile Pro Pro His Val Gln Lys Ser Val Asn
                405                 410                 415

Asn Asp Met Ile Val Thr Asp Asn Asn Gly Ala Val Lys Phe Pro Gln
            420                 425                 430

Leu Cys Lys Phe Cys Asp Val Arg Phe Ser Thr Cys Asp Asn Gln Lys
            435                 440                 445

Ser Cys Met Ser Asn Cys Ser Ile Thr Ser Ile Cys Glu Lys Pro Gln
450                 455                 460

Glu Val Cys Val Ala Val Trp Arg Lys Asn Asp Glu Asn Ile Thr Leu
465                 470                 475                 480

Glu Thr Val Cys His Asp Pro Lys Leu Pro Tyr His Asp Phe Ile Leu
            485                 490                 495

Glu Asp Ala Ala Ser Pro Lys Cys Ile Met Lys Glu Lys Lys Lys Pro
            500                 505                 510

Gly Glu Thr Phe Phe Met Cys Ser Cys Ser Ser Asp Glu Cys Asn Asp
            515                 520                 525

Asn Ile Ile Phe Ser Glu Glu Tyr Asn Thr Ser Asn Pro Asp
530                 535                 540
```

<210> SEQ ID NO 12
<211> LENGTH: 542
<212> TYPE: PRT
<213> ORGANISM: Homo sapiens

<400> SEQUENCE: 12

```
Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Gly Gly Gly Ser Gly Gly
    130                 135                 140

Gly Gly Ser Gly Gly Gly Gly Ser Thr His Thr Cys Pro Pro Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Val
            340                 345                 350

Phe Ser Cys Ser Val Met His Glu Ala Leu His Asn His Tyr Thr Gln
        355                 360                 365

Lys Ser Leu Ser Leu Ser Pro Gly Lys Gly Gly Gly Gly Ser Gly Gly
    370                 375                 380
```

```
Gly Gly Ser Gly Gly Gly Ser Pro Gly Trp Phe Leu Asp Ser Pro
385                 390                 395                 400

Asp Arg Pro Trp Asn Pro Pro Thr Phe Ser Pro Ala Leu Leu Val Val
            405                 410                 415

Thr Glu Gly Asp Asn Ala Thr Phe Thr Cys Ser Phe Ser Asn Thr Ser
        420                 425                 430

Glu Ser Phe Val Leu Asn Trp Tyr Arg Met Ser Pro Ser Asn Gln Thr
    435                 440                 445

Asp Lys Leu Ala Ala Phe Pro Glu Asp Arg Ser Gln Pro Gly Gln Asp
    450                 455                 460

Cys Arg Phe Arg Val Thr Gln Leu Pro Asn Gly Arg Asp Phe His Met
465                 470                 475                 480

Ser Val Val Arg Ala Arg Arg Asn Asp Ser Gly Thr Tyr Leu Cys Gly
                485                 490                 495

Ala Ile Ser Leu Ala Pro Lys Ala Gln Ile Lys Glu Ser Leu Arg Ala
            500                 505                 510

Glu Leu Arg Val Thr Glu Arg Ala Glu Val Pro Thr Ala His Pro
        515                 520                 525

Ser Pro Ser Pro Arg Pro Ala Gly Gln Phe Gln Thr Leu Val
    530                 535                 540

<210> SEQ ID NO 13
<211> LENGTH: 577
<212> TYPE: PRT
<213> ORGANISM: Homo sapiens

<400> SEQUENCE: 13

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Gly Gly Gly Ser Gly Gly
    130                 135                 140

Gly Gly Ser Gly Gly Gly Gly Ser Thr His Thr Cys Pro Pro Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
        195                 200                 205

Val Asp Gly Val Glu Val His Asn Ala Lys Thr Lys Pro Arg Glu Glu
```

```
                210                 215                 220
Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Val
            340                 345                 350

Phe Ser Cys Ser Val Met His Glu Ala Leu His Asn His Tyr Thr Gln
        355                 360                 365

Lys Ser Leu Ser Leu Ser Pro Gly Lys Gly Gly Gly Ser Gly Gly
370                 375                 380

Gly Gly Ser Gly Gly Gly Ser Gln Ile Ala Pro Pro Cys Thr Ser
385                 390                 395                 400

Glu Lys His Tyr Glu His Leu Gly Arg Cys Cys Asn Lys Cys Glu Pro
                405                 410                 415

Gly Lys Tyr Met Ser Ser Lys Cys Thr Thr Thr Ser Asp Ser Val Cys
            420                 425                 430

Leu Pro Cys Gly Pro Asp Glu Tyr Leu Asp Ser Trp Asn Glu Glu Asp
        435                 440                 445

Lys Cys Leu Leu His Lys Val Cys Asp Thr Gly Lys Ala Leu Val Ala
450                 455                 460

Val Val Ala Gly Asn Ser Thr Thr Pro Arg Arg Cys Ala Cys Thr Ala
465                 470                 475                 480

Gly Tyr His Trp Ser Gln Asp Cys Glu Cys Cys Arg Arg Asn Thr Glu
                485                 490                 495

Cys Ala Pro Gly Leu Gly Ala Gln His Pro Leu Gln Leu Asn Lys Asp
            500                 505                 510

Thr Val Cys Lys Pro Cys Leu Ala Gly Tyr Phe Ser Asp Ala Phe Ser
        515                 520                 525

Ser Thr Asp Lys Cys Arg Pro Trp Thr Asn Cys Thr Phe Leu Gly Lys
530                 535                 540

Arg Val Glu His His Gly Thr Glu Lys Ser Asp Ala Val Cys Ser Ser
545                 550                 555                 560

Ser Leu Pro Ala Arg Lys Pro Pro Asn Glu Pro His Val Tyr Leu Pro
                565                 570                 575

Gly

<210> SEQ ID NO 14
<211> LENGTH: 577
<212> TYPE: PRT
<213> ORGANISM: Homo sapiens

<400> SEQUENCE: 14

Gln Ile Ala Pro Pro Cys Thr Ser Glu Lys His Tyr Glu His Leu Gly
```

-continued

```
1               5                   10                  15
Arg Cys Cys Asn Lys Cys Glu Pro Gly Lys Tyr Met Ser Ser Lys Cys
                20                  25                  30

Thr Thr Thr Ser Asp Ser Val Cys Leu Pro Cys Gly Pro Asp Glu Tyr
            35                  40                  45

Leu Asp Ser Trp Asn Glu Glu Asp Lys Cys Leu Leu His Lys Val Cys
        50                  55                  60

Asp Thr Gly Lys Ala Leu Val Ala Val Ala Gly Asn Ser Thr Thr
65                  70                  75                  80

Pro Arg Arg Cys Ala Cys Thr Ala Gly Tyr His Trp Ser Gln Asp Cys
                85                  90                  95

Glu Cys Cys Arg Arg Asn Thr Glu Cys Ala Pro Gly Leu Gly Ala Gln
                100                 105                 110

His Pro Leu Gln Leu Asn Lys Asp Thr Val Cys Lys Pro Cys Leu Ala
            115                 120                 125

Gly Tyr Phe Ser Asp Ala Phe Ser Ser Thr Asp Lys Cys Arg Pro Trp
        130                 135                 140

Thr Asn Cys Thr Phe Leu Gly Lys Arg Val Glu His His Gly Thr Glu
145                 150                 155                 160

Lys Ser Asp Ala Val Cys Ser Ser Ser Leu Pro Ala Arg Lys Pro Pro
                165                 170                 175

Asn Glu Pro His Val Tyr Leu Pro Gly Gly Gly Gly Ser Gly Gly
            180                 185                 190

Gly Gly Ser Gly Gly Gly Gly Ser Thr His Thr Cys Pro Pro Cys Pro
        195                 200                 205

Ala Pro Glu Leu Leu Gly Gly Pro Ser Val Phe Leu Phe Pro Pro Lys
210                 215                 220

Pro Lys Asp Thr Leu Met Ile Ser Arg Thr Pro Glu Val Thr Cys Val
225                 230                 235                 240

Val Val Asp Val Ser His Glu Asp Pro Glu Val Lys Phe Asn Trp Tyr
                245                 250                 255

Val Asp Gly Val Glu Val His Asn Ala Lys Thr Lys Pro Arg Glu Glu
            260                 265                 270

Gln Tyr Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
    290                 295                 300

Ala Leu Pro Ala Pro Ile Glu Lys Thr Ile Ser Lys Ala Lys Gly Gln
305                 310                 315                 320

Pro Arg Glu Pro Gln Val Tyr Thr Leu Pro Pro Ser Arg Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Phe Leu
    370                 375                 380

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Pro Gly Lys Gly Gly Gly Gly Ser Gly Gly
            420                 425                 430
```

-continued

Gly Gly Ser Gly Gly Gly Ser Thr Ile Pro Pro His Val Gln Lys
        435                 440                 445

Ser Val Asn Asn Asp Met Ile Val Thr Asp Asn Asn Gly Ala Val Lys
450                 455                 460

Phe Pro Gln Leu Cys Lys Phe Cys Asp Val Arg Phe Ser Thr Cys Asp
465                 470                 475                 480

Asn Gln Lys Ser Cys Met Ser Asn Cys Ser Ile Thr Ser Ile Cys Glu
            485                 490                 495

Lys Pro Gln Glu Val Cys Val Ala Val Trp Arg Lys Asn Asp Glu Asn
            500                 505                 510

Ile Thr Leu Glu Thr Val Cys His Asp Pro Lys Leu Pro Tyr His Asp
        515                 520                 525

Phe Ile Leu Glu Asp Ala Ala Ser Pro Lys Cys Ile Met Lys Glu Lys
        530                 535                 540

Lys Lys Pro Gly Glu Thr Phe Phe Met Cys Ser Cys Ser Ser Asp Glu
545                 550                 555                 560

Cys Asn Asp Asn Ile Ile Phe Ser Glu Glu Tyr Asn Thr Ser Asn Pro
                565                 570                 575

Asp

<210> SEQ ID NO 15
<211> LENGTH: 615
<212> TYPE: PRT
<213> ORGANISM: Homo sapiens

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

```
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Gly Gly Gly Ser Gly Gly Gly Gly Ser Gly Gly Gly Gly
    450                 455                 460

Ser Pro Gly Trp Phe Leu Asp Ser Pro Asp Arg Pro Trp Asn Pro Pro
465                 470                 475                 480

Thr Phe Ser Pro Ala Leu Leu Val Val Thr Glu Gly Asp Asn Ala Thr
                485                 490                 495

Phe Thr Cys Ser Phe Ser Asn Thr Ser Glu Ser Phe Val Leu Asn Trp
            500                 505                 510

Tyr Arg Met Ser Pro Ser Asn Gln Thr Asp Lys Leu Ala Ala Phe Pro
        515                 520                 525

Glu Asp Arg Ser Gln Pro Gly Gln Asp Cys Arg Phe Arg Val Thr Gln
    530                 535                 540

Leu Pro Asn Gly Arg Asp Phe His Met Ser Val Val Arg Ala Arg Arg
545                 550                 555                 560

Asn Asp Ser Gly Thr Tyr Leu Cys Gly Ala Ile Ser Leu Ala Pro Lys
                565                 570                 575

Ala Gln Ile Lys Glu Ser Leu Arg Ala Glu Leu Arg Val Thr Glu Arg
            580                 585                 590

Arg Ala Glu Val Pro Thr Ala His Pro Ser Pro Ser Pro Arg Pro Ala
        595                 600                 605

Gly Gln Phe Gln Thr Leu Val
    610                 615

<210> SEQ ID NO 16
<211> LENGTH: 614
```

-continued

<212> TYPE: PRT
<213> ORGANISM: Homo sapiens

<400> SEQUENCE: 16

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Gly Ser Gly Gly Gly Ser Gly Gly Gly Gly Ser
450                 455                 460

Pro Gly Trp Phe Leu Asp Ser Pro Asp Arg Pro Trp Asn Pro Pro Thr
465                 470                 475                 480

Phe Ser Pro Ala Leu Leu Val Val Thr Glu Gly Asp Asn Ala Thr Phe
            485                 490                 495

Thr Cys Ser Phe Ser Asn Thr Ser Glu Ser Phe Val Leu Asn Trp Tyr
            500                 505                 510

Arg Met Ser Pro Ser Asn Gln Thr Asp Lys Leu Ala Ala Phe Pro Glu
            515                 520                 525

Asp Arg Ser Gln Pro Gly Gln Asp Cys Arg Phe Arg Val Thr Gln Leu
            530                 535                 540

Pro Asn Gly Arg Asp Phe His Met Ser Val Val Arg Ala Arg Arg Asn
545                 550                 555                 560

Asp Ser Gly Thr Tyr Leu Cys Gly Ala Ile Ser Leu Ala Pro Lys Ala
            565                 570                 575

Gln Ile Lys Glu Ser Leu Arg Ala Glu Leu Arg Val Thr Glu Arg Arg
            580                 585                 590

Ala Glu Val Pro Thr Ala His Pro Ser Pro Ser Pro Arg Pro Ala Gly
            595                 600                 605

Gln Phe Gln Thr Leu Val
            610

<210> SEQ ID NO 17
<211> LENGTH: 616
<212> TYPE: PRT
<213> ORGANISM: Homo sapiens

<400> SEQUENCE: 17

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
```

```
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Lys Ala Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
                290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
                355                 360                 365
Leu Thr Cys Leu Val Lys Gly Phe Tyr Pro Ser Asp Ile Ala Val Glu
                370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
Pro Gly Lys Gly Gly Gly Ser Gly Gly Gly Ser Gly Gly Gly
                450                 455                 460
Gly Ser Pro Gly Trp Phe Leu Asp Ser Pro Asp Arg Pro Trp Asn Pro
465                 470                 475                 480
Pro Thr Phe Ser Pro Ala Leu Leu Val Val Thr Glu Gly Asp Asn Ala
                485                 490                 495
Thr Phe Thr Cys Ser Phe Ser Asn Thr Ser Glu Ser Phe Val Leu Asn
                500                 505                 510
Trp Tyr Arg Met Ser Pro Ser Asn Gln Thr Asp Lys Leu Ala Ala Phe
                515                 520                 525
Pro Glu Asp Arg Ser Gln Pro Gly Gln Asp Cys Arg Phe Arg Val Thr
                530                 535                 540
Gln Leu Pro Asn Gly Arg Asp Phe His Met Ser Val Val Arg Ala Arg
545                 550                 555                 560
Arg Asn Asp Ser Gly Thr Tyr Leu Cys Gly Ala Ile Ser Leu Ala Pro
                565                 570                 575
```

```
Lys Ala Gln Ile Lys Glu Ser Leu Arg Ala Glu Leu Arg Val Thr Glu
                575                 580                 585                 590

Arg Arg Ala Glu Val Pro Thr Ala His Pro Ser Pro Ser Pro Arg Pro
                595                 600                 605

Ala Gly Gln Phe Gln Thr Leu Val
                610                 615

<210> SEQ ID NO 18
<211> LENGTH: 618
<212> TYPE: PRT
<213> ORGANISM: Homo sapiens

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
                20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
```

```
                    325                 330                 335
Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys Gly Gly Gly Ser Gly Gly Gly Ser Gly
            450                 455                 460

Gly Gly Gly Ser Pro Gly Trp Phe Leu Asp Ser Pro Asp Arg Pro Trp
465                 470                 475                 480

Asn Pro Pro Thr Phe Ser Pro Ala Leu Leu Val Val Thr Glu Gly Asp
            485                 490                 495

Asn Ala Thr Phe Thr Cys Ser Phe Ser Asn Thr Ser Glu Ser Phe Val
            500                 505                 510

Leu Asn Trp Tyr Arg Met Ser Pro Ser Asn Gln Thr Asp Lys Leu Ala
            515                 520                 525

Ala Phe Pro Glu Asp Arg Ser Gln Pro Gly Gln Asp Cys Arg Phe Arg
            530                 535                 540

Val Thr Gln Leu Pro Asn Gly Arg Asp Phe His Met Ser Val Val Arg
545                 550                 555                 560

Ala Arg Arg Asn Asp Ser Gly Thr Tyr Leu Cys Gly Ala Ile Ser Leu
            565                 570                 575

Ala Pro Lys Ala Gln Ile Lys Glu Ser Leu Arg Ala Glu Leu Arg Val
            580                 585                 590

Thr Glu Arg Arg Ala Glu Val Pro Thr Ala His Pro Ser Pro Ser Pro
            595                 600                 605

Arg Pro Ala Gly Gln Phe Gln Thr Leu Val
            610                 615

<210> SEQ ID NO 19
<211> LENGTH: 613
<212> TYPE: PRT
<213> ORGANISM: Homo sapiens

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80
```

-continued

Leu Gln Met Asn Ser Leu Arg Ala Glu Asp Thr Ala Ile Tyr Tyr Cys
                85                  90                  95
Ala Arg Thr Gly Trp Leu Gly Pro Phe Asp Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Arg Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
Gly Gly Gly Gly Ser Gly Gly Gly Ser Gly Gly Gly Ser Pro
    450                 455                 460
Gly Trp Phe Leu Asp Ser Pro Asp Arg Pro Trp Asn Pro Pro Thr Phe
465                 470                 475                 480
Ser Pro Ala Leu Leu Val Val Thr Glu Gly Asp Asn Ala Thr Phe Thr
                485                 490                 495
Cys Ser Phe Ser Asn Thr Ser Glu Ser Phe Val Leu Asn Trp Tyr Arg

```
                    500                 505                 510
Met Ser Pro Ser Asn Gln Thr Asp Lys Leu Ala Ala Phe Pro Glu Asp
            515                 520                 525

Arg Ser Gln Pro Gly Gln Asp Cys Arg Phe Arg Val Thr Gln Leu Pro
        530                 535                 540

Asn Gly Arg Asp Phe His Met Ser Val Val Arg Ala Arg Arg Asn Asp
545                 550                 555                 560

Ser Gly Thr Tyr Leu Cys Gly Ala Ile Ser Leu Ala Pro Lys Ala Gln
            565                 570                 575

Ile Lys Glu Ser Leu Arg Ala Glu Leu Arg Val Thr Glu Arg Arg Ala
        580                 585                 590

Glu Val Pro Thr Ala His Pro Ser Pro Ser Pro Arg Pro Ala Gly Gln
            595                 600                 605

Phe Gln Thr Leu Val
        610

<210> SEQ ID NO 20
<211> LENGTH: 611
<212> TYPE: PRT
<213> ORGANISM: Homo sapiens

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Gly Gly
        435                 440                 445

Gly Gly Ser Gly Gly Gly Ser Gly Gly Gly Ser Pro Gly Trp
450                 455                 460

Phe Leu Asp Ser Pro Asp Arg Pro Trp Asn Pro Pro Thr Phe Ser Pro
465                 470                 475                 480

Ala Leu Leu Val Val Thr Glu Gly Asp Asn Ala Thr Phe Thr Cys Ser
                485                 490                 495

Phe Ser Asn Thr Ser Glu Ser Phe Val Leu Asn Trp Tyr Arg Met Ser
            500                 505                 510

Pro Ser Asn Gln Thr Asp Lys Leu Ala Ala Phe Pro Glu Asp Arg Ser
        515                 520                 525

Gln Pro Gly Gln Asp Cys Arg Phe Arg Val Thr Gln Leu Pro Asn Gly
530                 535                 540

Arg Asp Phe His Met Ser Val Val Arg Ala Arg Arg Asn Asp Ser Gly
545                 550                 555                 560

Thr Tyr Leu Cys Gly Ala Ile Ser Leu Ala Pro Lys Ala Gln Ile Lys
                565                 570                 575

Glu Ser Leu Arg Ala Glu Leu Arg Val Thr Glu Arg Arg Ala Glu Val
            580                 585                 590

Pro Thr Ala His Pro Ser Pro Ser Pro Arg Pro Ala Gly Gln Phe Gln
        595                 600                 605

Thr Leu Val
    610

<210> SEQ ID NO 21
<211> LENGTH: 610
<212> TYPE: PRT
<213> ORGANISM: Homo sapiens

<400> SEQUENCE: 21

Gln Leu Gln Gln Ser Gly Thr Val Leu Ala Arg Pro Gly Ala Ser Val
1               5                   10                  15
```

```
Lys Met Ser Cys Lys Ala Ser Gly Tyr Ser Phe Thr Arg Tyr Trp Met
             20                  25                  30
His Trp Ile Lys Gln Arg Pro Gly Gln Gly Leu Glu Trp Ile Gly Ala
         35                  40                  45
Ile Tyr Pro Gly Asn Ser Asp Thr Ser Tyr Asn Gln Lys Phe Glu Gly
 50                  55                  60
Lys Ala Lys Leu Thr Ala Val Thr Ser Ala Ser Thr Ala Tyr Met Glu
65                  70                  75                  80
Leu Ser Ser Leu Thr His Glu Asp Ser Ala Val Tyr Tyr Cys Ser Arg
                 85                  90                  95
Asp Tyr Gly Tyr Tyr Phe Asp Phe Trp Gly Gln Gly Thr Thr Leu Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Arg Val Glu Pro Lys Ser Cys Asp Lys Thr His Thr Cys
210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
```

His Tyr Thr Gln Lys Ser Leu Ser Leu Ser Pro Gly Lys Gly Gly
            435                 440                 445

Gly Ser Gly Gly Gly Ser Gly Gly Gly Ser Pro Gly Trp Phe
450                 455                 460

Leu Asp Ser Pro Asp Arg Pro Trp Asn Pro Thr Phe Ser Pro Ala
465                 470                 475                 480

Leu Leu Val Val Thr Glu Gly Asp Asn Ala Thr Phe Thr Cys Ser Phe
                485                 490                 495

Ser Asn Thr Ser Glu Ser Phe Val Leu Asn Trp Tyr Arg Met Ser Pro
            500                 505                 510

Ser Asn Gln Thr Asp Lys Leu Ala Ala Phe Pro Glu Asp Arg Ser Gln
            515                 520                 525

Pro Gly Gln Asp Cys Arg Phe Arg Val Thr Gln Leu Pro Asn Gly Arg
            530                 535                 540

Asp Phe His Met Ser Val Val Arg Ala Arg Arg Asn Asp Ser Gly Thr
545                 550                 555                 560

Tyr Leu Cys Gly Ala Ile Ser Leu Ala Pro Lys Ala Gln Ile Lys Glu
                565                 570                 575

Ser Leu Arg Ala Glu Leu Arg Val Thr Glu Arg Arg Ala Glu Val Pro
            580                 585                 590

Thr Ala His Pro Ser Pro Ser Pro Arg Pro Ala Gly Gln Phe Gln Thr
            595                 600                 605

Leu Val
    610

<210> SEQ ID NO 22
<211> LENGTH: 538
<212> TYPE: PRT
<213> ORGANISM: Homo sapiens

<400> SEQUENCE: 22

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly
    130                 135                 140

Gly Gly Gly Ser Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

```
Ser His Glu Asp Pro Glu Val Lys Phe Asn Trp Tyr Val Asp Gly Val
        195                 200                 205
Glu Val His Asn Ala Lys Thr Lys Pro Arg Glu Glu Gln Tyr Asn Ser
210                 215                 220
Thr Tyr Arg Val Val Ser Val Leu Thr Val Leu His Gln Asp Trp Leu
225                 230                 235                 240
Asn Gly Lys Glu Tyr Lys Cys Lys Val Ser Asn Lys Ala Leu Pro Ala
                245                 250                 255
Pro Ile Glu Lys Thr Ile Ser Lys Ala Lys Gly Gln Pro Arg Glu Pro
                260                 265                 270
Gln Val Tyr Thr Leu Pro Pro Ser Arg Glu Glu Met Thr Lys Asn Gln
                275                 280                 285
Val Ser Leu Thr Cys Leu Val Lys Gly Phe Tyr Pro Ser Asp Ile Ala
                290                 295                 300
Val Glu Trp Glu Ser Asn Gly Gln Pro Glu Asn Asn Tyr Lys Thr Thr
305                 310                 315                 320
Pro Pro Val Leu Asp Ser Asp Gly Ser Phe Phe Leu Tyr Ser Lys Leu
                325                 330                 335
Thr Val Asp Lys Ser Arg Trp Gln Gln Gly Asn Val Phe Ser Cys Ser
                340                 345                 350
Val Met His Glu Ala Leu His Asn His Tyr Thr Gln Lys Ser Leu Ser
                355                 360                 365
Leu Ser Pro Gly Lys Gly Gly Gly Ser Gly Gly Gly Ser Gly
                370                 375                 380
Gly Gly Gly Ser Pro Gly Trp Phe Leu Asp Ser Pro Asp Arg Pro Trp
385                 390                 395                 400
Asn Pro Pro Thr Phe Ser Pro Ala Leu Leu Val Val Thr Glu Gly Asp
                405                 410                 415
Asn Ala Thr Phe Thr Cys Ser Phe Ser Asn Thr Ser Glu Ser Phe Val
                420                 425                 430
Leu Asn Trp Tyr Arg Met Ser Pro Ser Asn Gln Thr Asp Lys Leu Ala
                435                 440                 445
Ala Phe Pro Glu Asp Arg Ser Gln Pro Gly Gln Asp Cys Arg Phe Arg
                450                 455                 460
Val Thr Gln Leu Pro Asn Gly Arg Asp Phe His Met Ser Val Val Arg
465                 470                 475                 480
Ala Arg Arg Asn Asp Ser Gly Thr Tyr Leu Cys Gly Ala Ile Ser Leu
                485                 490                 495
Ala Pro Lys Ala Gln Ile Lys Glu Ser Leu Arg Ala Glu Leu Arg Val
                500                 505                 510
Thr Glu Arg Arg Ala Glu Val Pro Thr Ala His Pro Ser Pro Ser Pro
                515                 520                 525
Arg Pro Ala Gly Gln Phe Gln Thr Leu Val
                530                 535

<210> SEQ ID NO 23
<211> LENGTH: 538
<212> TYPE: PRT
<213> ORGANISM: Homo sapiens

<400> SEQUENCE: 23

Pro Gly Trp Phe Leu Asp Ser Pro Asp Arg Pro Trp Asn Pro Pro Thr
1               5                   10                  15
Phe Ser Pro Ala Leu Leu Val Val Thr Glu Gly Asp Asn Ala Thr Phe
```

-continued

```
                20                  25                  30
Thr Cys Ser Phe Ser Asn Thr Ser Glu Ser Phe Val Leu Asn Trp Tyr
            35                  40                  45
Arg Met Ser Pro Ser Asn Gln Thr Asp Lys Leu Ala Ala Phe Pro Glu
        50                  55                  60
Asp Arg Ser Gln Pro Gly Gln Asp Cys Arg Phe Arg Val Thr Gln Leu
 65                  70                  75                  80
Pro Asn Gly Arg Asp Phe His Met Ser Val Val Arg Ala Arg Arg Asn
                85                  90                  95
Asp Ser Gly Thr Tyr Leu Cys Gly Ala Ile Ser Leu Ala Pro Lys Ala
            100                 105                 110
Gln Ile Lys Glu Ser Leu Arg Ala Glu Leu Arg Val Thr Glu Arg Arg
        115                 120                 125
Ala Glu Val Pro Thr Ala His Pro Ser Pro Ser Pro Arg Pro Ala Gly
        130                 135                 140
Gln Phe Gln Thr Leu Val Gly Gly Gly Ser Gly Gly Gly Gly Gly Ser
145                 150                 155                 160
Gly Gly Gly Gly Ser Thr His Thr Cys Pro Pro Cys Pro Ala Pro Glu
                165                 170                 175
Leu Leu Gly Gly Pro Ser Val Phe Leu Phe Pro Pro Lys Pro Lys Asp
            180                 185                 190
Thr Leu Met Ile Ser Arg Thr Pro Glu Val Thr Cys Val Val Val Asp
        195                 200                 205
Val Ser His Glu Asp Pro Glu Val Lys Phe Asn Trp Tyr Val Asp Gly
        210                 215                 220
Val Glu Val His Asn Ala Lys Thr Lys Pro Arg Glu Glu Gln Tyr Asn
225                 230                 235                 240
Ser Thr Tyr Arg Val Val Ser Val Leu Thr Val Leu His Gln Asp Trp
                245                 250                 255
Leu Asn Gly Lys Glu Tyr Lys Cys Lys Val Ser Asn Lys Ala Leu Pro
            260                 265                 270
Ala Pro Ile Glu Lys Thr Ile Ser Lys Ala Lys Gly Gln Pro Arg Glu
        275                 280                 285
Pro Gln Val Tyr Thr Leu Pro Pro Ser Arg Glu Glu Met Thr Lys Asn
        290                 295                 300
Gln Val Ser Leu Thr Cys Leu Val Lys Gly Phe Tyr Pro Ser Asp Ile
305                 310                 315                 320
Ala Val Glu Trp Glu Ser Asn Gly Gln Pro Glu Asn Asn Tyr Lys Thr
                325                 330                 335
Thr Pro Pro Val Leu Asp Ser Asp Gly Ser Phe Phe Leu Tyr Ser Lys
            340                 345                 350
Leu Thr Val Asp Lys Ser Arg Trp Gln Gln Gly Asn Val Phe Ser Cys
        355                 360                 365
Ser Val Met His Glu Ala Leu His Asn His Tyr Thr Gln Lys Ser Leu
        370                 375                 380
Ser Leu Ser Pro Gly Lys Gly Gly Gly Ser Gly Gly Gly Gly Ser
385                 390                 395                 400
Gly Gly Gly Gly Ser Ala Pro Thr Ser Ser Ser Thr Lys Lys Thr Gln
                405                 410                 415
Leu Gln Leu Glu His Leu Leu Leu Asp Leu Gln Met Ile Leu Asn Gly
            420                 425                 430
Ile Asn Asn Tyr Lys Asn Pro Lys Leu Thr Arg Met Leu Thr Phe Lys
        435                 440                 445
```

```
Phe Tyr Met Pro Lys Lys Ala Thr Glu Leu Lys His Leu Gln Cys Leu
            450                 455                 460
Glu Glu Glu Leu Lys Pro Leu Glu Glu Val Leu Asn Leu Ala Gln Ser
465                 470                 475                 480
Lys Asn Phe His Leu Arg Pro Arg Asp Leu Ile Ser Asn Ile Asn Val
            485                 490                 495
Ile Val Leu Glu Leu Lys Gly Ser Glu Thr Thr Phe Met Cys Glu Tyr
            500                 505                 510
Ala Asp Glu Thr Ala Thr Ile Val Glu Phe Leu Asn Arg Trp Ile Thr
            515                 520                 525
Phe Cys Gln Ser Ile Ile Ser Thr Leu Thr
            530                 535

<210> SEQ ID NO 24
<211> LENGTH: 616
<212> TYPE: PRT
<213> ORGANISM: Homo sapiens

<400> SEQUENCE: 24

Gln Val Gln Leu Gln Glu Ala Gly Pro Gly Leu Val Lys Pro Ser Glu
1               5                   10                  15
Thr Leu Ser Leu Thr Cys Ser Val Ser Gly Gly Ser Ile Ser Gly Asp
            20                  25                  30
Tyr Tyr Trp Phe Trp Ile Arg Gln Ser Pro Gly Lys Gly Leu Glu Trp
            35                  40                  45
Ile Gly Tyr Ile Tyr Gly Ser Gly Gly Thr Asn Tyr Asn Pro Ser
        50                  55                  60
Leu Asn Asn Arg Val Ser Ile Ser Ile Asp Thr Ser Lys Asn Leu Phe
65                  70                  75                  80
Ser Leu Lys Leu Arg Ser Val Thr Ala Ala Asp Thr Ala Val Tyr Tyr
            85                  90                  95
Cys Ala Ser Asn Ile Leu Lys Tyr Leu His Trp Leu Leu Tyr Trp Gly
            100                 105                 110
Gln Gly Val Leu Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
            165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Arg Val Glu Pro Lys Ser Cys
            210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
            245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
```

```
                    275                 280                 285
His Asn Ala Lys Thr Lys Pro Arg Glu Glu Gln Tyr Asn Ser Thr Tyr
290                 295                 300

Arg Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Ser Gly Gly Gly Ser Gly Gly Gly
450                 455                 460

Gly Ser Pro Gly Trp Phe Leu Asp Ser Pro Asp Arg Pro Trp Asn Pro
465                 470                 475                 480

Pro Thr Phe Ser Pro Ala Leu Leu Val Val Thr Glu Gly Asp Asn Ala
                485                 490                 495

Thr Phe Thr Cys Ser Phe Ser Asn Thr Ser Glu Ser Phe Val Leu Asn
            500                 505                 510

Trp Tyr Arg Met Ser Pro Ser Asn Gln Thr Asp Lys Leu Ala Ala Phe
        515                 520                 525

Pro Glu Asp Arg Ser Gln Pro Gly Gln Asp Cys Arg Phe Arg Val Thr
530                 535                 540

Gln Leu Pro Asn Gly Arg Asp Phe His Met Ser Val Val Arg Ala Arg
545                 550                 555                 560

Arg Asn Asp Ser Gly Thr Tyr Leu Cys Gly Ala Ile Ser Leu Ala Pro
                565                 570                 575

Lys Ala Gln Ile Lys Glu Ser Leu Arg Ala Glu Leu Arg Val Thr Glu
            580                 585                 590

Arg Arg Ala Glu Val Pro Thr Ala His Pro Ser Pro Ser Pro Arg Pro
        595                 600                 605

Ala Gly Gln Phe Gln Thr Leu Val
610                 615

<210> SEQ ID NO 25
<211> LENGTH: 590
<212> TYPE: PRT
<213> ORGANISM: Homo sapiens

<400> SEQUENCE: 25

Gln Ile Ala Pro Pro Cys Thr Ser Glu Lys His Tyr Glu His Leu Gly
1               5                   10                  15

Arg Cys Cys Asn Lys Cys Glu Pro Gly Lys Tyr Met Ser Ser Lys Cys
            20                  25                  30
```

-continued

```
Thr Thr Thr Ser Asp Ser Val Cys Leu Pro Cys Gly Pro Asp Glu Tyr
            35                  40                  45

Leu Asp Ser Trp Asn Glu Glu Asp Lys Cys Leu Leu His Lys Val Cys
 50                  55                  60

Asp Thr Gly Lys Ala Leu Val Ala Val Ala Gly Asn Ser Thr Thr
 65                  70                  75                  80

Pro Arg Arg Cys Ala Cys Thr Ala Gly Tyr His Trp Ser Gln Asp Cys
                 85                  90                  95

Glu Cys Cys Arg Arg Asn Thr Glu Cys Ala Pro Gly Leu Gly Ala Gln
             100                 105                 110

His Pro Leu Gln Leu Asn Lys Asp Thr Val Cys Lys Pro Cys Leu Ala
             115                 120                 125

Gly Tyr Phe Ser Asp Ala Phe Ser Ser Thr Asp Lys Cys Arg Pro Trp
         130                 135                 140

Thr Asn Cys Thr Phe Leu Gly Lys Arg Val Glu His His Gly Thr Glu
145                 150                 155                 160

Lys Ser Asp Ala Val Cys Ser Ser Ser Leu Pro Ala Arg Lys Pro Pro
                 165                 170                 175

Asn Glu Pro His Val Tyr Leu Pro Gly Gly Gly Gly Ser Gly Gly
             180                 185                 190

Gly Gly Ser Gly Gly Gly Gly Ser Thr His Thr Cys Pro Pro Cys Pro
         195                 200                 205

Ala Pro Glu Leu Leu Gly Gly Pro Ser Val Phe Leu Phe Pro Pro Lys
         210                 215                 220

Pro Lys Asp Thr Leu Met Ile Ser Arg Thr Pro Glu Val Thr Cys Val
225                 230                 235                 240

Val Val Asp Val Ser His Glu Asp Pro Glu Val Lys Phe Asn Trp Tyr
                 245                 250                 255

Val Asp Gly Val Glu Val His Asn Ala Lys Thr Lys Pro Arg Glu Glu
             260                 265                 270

Gln Tyr Asn Ser Thr Tyr Arg Val Val Ser Val Leu Thr Val Leu His
         275                 280                 285

Gln Asp Trp Leu Asn Gly Lys Glu Tyr Lys Cys Lys Val Ser Asn Lys
     290                 295                 300

Ala Leu Pro Ala Pro Ile Glu Lys Thr Ile Ser Lys Ala Lys Gly Gln
305                 310                 315                 320

Pro Arg Glu Pro Gln Val Tyr Thr Leu Pro Pro Ser Arg Glu Glu Met
                 325                 330                 335

Thr Lys Asn Gln Val Ser Leu Thr Cys Leu Val Lys Gly Phe Tyr Pro
             340                 345                 350

Ser Asp Ile Ala Val Glu Trp Glu Ser Asn Gly Gln Pro Glu Asn Asn
         355                 360                 365

Tyr Lys Thr Thr Pro Pro Val Leu Asp Ser Asp Gly Ser Phe Phe Leu
     370                 375                 380

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                 405                 410                 415

Lys Ser Leu Ser Leu Ser Pro Gly Lys Gly Gly Gly Gly Ser Gly Gly
             420                 425                 430

Gly Gly Ser Gly Gly Gly Gly Ser Pro Gly Trp Phe Leu Asp Ser Pro
         435                 440                 445

Asp Arg Pro Trp Asn Pro Pro Thr Phe Ser Pro Ala Leu Leu Val Val
```

```
                    450                 455                 460
Thr Glu Gly Asp Asn Ala Thr Phe Thr Cys Ser Phe Ser Asn Thr Ser
465                 470                 475                 480

Glu Ser Phe Val Leu Asn Trp Tyr Arg Met Ser Pro Ser Asn Gln Thr
                485                 490                 495

Asp Lys Leu Ala Ala Phe Pro Glu Asp Arg Ser Gln Pro Gly Gln Asp
                500                 505                 510

Cys Arg Phe Arg Val Thr Gln Leu Pro Asn Gly Arg Asp Phe His Met
                515                 520                 525

Ser Val Val Arg Ala Arg Arg Asn Asp Ser Gly Thr Tyr Leu Cys Gly
                530                 535                 540

Ala Ile Ser Leu Ala Pro Lys Ala Gln Ile Lys Glu Ser Leu Arg Ala
545                 550                 555                 560

Glu Leu Arg Val Thr Glu Arg Arg Ala Glu Val Pro Thr Ala His Pro
                565                 570                 575

Ser Pro Ser Pro Arg Pro Ala Gly Gln Phe Gln Thr Leu Val
                580                 585                 590
```

<210> SEQ ID NO 26
<211> LENGTH: 590
<212> TYPE: PRT
<213> ORGANISM: Homo sapiens

<400> SEQUENCE: 26

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
                35                  40                  45

Arg Met Ser Pro Ser Asn Gln Thr Asp Lys Leu Ala Ala Phe Pro Glu
            50                  55                  60

Asp Arg Ser Gln Pro Gly Gln Asp Cys Arg Phe Arg Val Thr Gln Leu
65              70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Gly Gly Gly Ser Gly Gly Gly Ser
145                 150                 155                 160

Gly Gly Gly Gly Ser Thr His Thr Cys Pro Pro Cys Pro Ala Pro Glu
                165                 170                 175

Leu Leu Gly Gly Pro Ser Val Phe Leu Phe Pro Pro Lys Pro Lys Asp
                180                 185                 190

Thr Leu Met Ile Ser Arg Thr Pro Glu Val Thr Cys Val Val Val Asp
            195                 200                 205

Val Ser His Glu Asp Pro Glu Val Lys Phe Asn Trp Tyr Val Asp Gly
    210                 215                 220

Val Glu Val His Asn Ala Lys Thr Lys Pro Arg Glu Glu Gln Tyr Asn
225                 230                 235                 240
```

-continued

```
Ser Thr Tyr Arg Val Val Ser Val Leu Thr Val Leu His Gln Asp Trp
            245                 250                 255
Leu Asn Gly Lys Glu Tyr Lys Cys Lys Val Ser Asn Lys Ala Leu Pro
        260                 265                 270
Ala Pro Ile Glu Lys Thr Ile Ser Lys Ala Lys Gly Gln Pro Arg Glu
    275                 280                 285
Pro Gln Val Tyr Thr Leu Pro Pro Ser Arg Glu Glu Met Thr Lys Asn
290                 295                 300
Gln Val Ser Leu Thr Cys Leu Val Lys Gly Phe Tyr Pro Ser Asp Ile
305                 310                 315                 320
Ala Val Glu Trp Glu Ser Asn Gly Gln Pro Glu Asn Asn Tyr Lys Thr
                325                 330                 335
Thr Pro Pro Val Leu Asp Ser Asp Gly Ser Phe Phe Leu Tyr Ser Lys
            340                 345                 350
Leu Thr Val Asp Lys Ser Arg Trp Gln Gln Gly Asn Val Phe Ser Cys
        355                 360                 365
Ser Val Met His Glu Ala Leu His Asn His Tyr Thr Gln Lys Ser Leu
    370                 375                 380
Ser Leu Ser Pro Gly Lys Gly Gly Gly Ser Gly Gly Gly Gly Ser
385                 390                 395                 400
Gly Gly Gly Gly Ser Gln Ile Ala Pro Pro Cys Thr Ser Glu Lys His
                405                 410                 415
Tyr Glu His Leu Gly Arg Cys Cys Asn Lys Cys Glu Pro Gly Lys Tyr
            420                 425                 430
Met Ser Ser Lys Cys Thr Thr Thr Ser Asp Ser Val Cys Leu Pro Cys
        435                 440                 445
Gly Pro Asp Glu Tyr Leu Asp Ser Trp Asn Glu Glu Asp Lys Cys Leu
    450                 455                 460
Leu His Lys Val Cys Asp Thr Gly Lys Ala Leu Val Ala Val Val Ala
465                 470                 475                 480
Gly Asn Ser Thr Thr Pro Arg Arg Cys Ala Cys Thr Ala Gly Tyr His
                485                 490                 495
Trp Ser Gln Asp Cys Glu Cys Cys Arg Arg Asn Thr Glu Cys Ala Pro
            500                 505                 510
Gly Leu Gly Ala Gln His Pro Leu Gln Leu Asn Lys Asp Thr Val Cys
        515                 520                 525
Lys Pro Cys Leu Ala Gly Tyr Phe Ser Asp Ala Phe Ser Ser Thr Asp
    530                 535                 540
Lys Cys Arg Pro Trp Thr Asn Cys Thr Phe Leu Gly Lys Arg Val Glu
545                 550                 555                 560
His His Gly Thr Glu Lys Ser Asp Ala Val Cys Ser Ser Ser Leu Pro
                565                 570                 575
Ala Arg Lys Pro Pro Asn Glu Pro His Val Tyr Leu Pro Gly
            580                 585                 590

<210> SEQ ID NO 27
<211> LENGTH: 650
<212> TYPE: PRT
<213> ORGANISM: Homo sapiens

<400> SEQUENCE: 27

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
```

```
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
```

-continued

```
Gly Lys Gly Gly Gly Ser Gly Gly Gly Ser Gly Gly Gly Gly
    450                 455                 460

Ser Gln Ile Ala Pro Pro Cys Thr Ser Glu Lys His Tyr Glu His Leu
465                 470                 475                 480

Gly Arg Cys Cys Asn Lys Cys Glu Pro Gly Lys Tyr Met Ser Ser Lys
                485                 490                 495

Cys Thr Thr Thr Ser Asp Ser Val Cys Leu Pro Cys Gly Pro Asp Glu
            500                 505                 510

Tyr Leu Asp Ser Trp Asn Glu Glu Asp Lys Cys Leu Leu His Lys Val
        515                 520                 525

Cys Asp Thr Gly Lys Ala Leu Val Ala Val Ala Gly Asn Ser Thr
    530                 535                 540

Thr Pro Arg Arg Cys Ala Cys Thr Ala Gly Tyr His Trp Ser Gln Asp
545                 550                 555                 560

Cys Glu Cys Cys Arg Arg Asn Thr Glu Cys Ala Pro Gly Leu Gly Ala
                565                 570                 575

Gln His Pro Leu Gln Leu Asn Lys Asp Thr Val Cys Lys Pro Cys Leu
            580                 585                 590

Ala Gly Tyr Phe Ser Asp Ala Phe Ser Ser Thr Asp Lys Cys Arg Pro
        595                 600                 605

Trp Thr Asn Cys Thr Phe Leu Gly Lys Arg Val Glu His His Gly Thr
    610                 615                 620

Glu Lys Ser Asp Ala Val Cys Ser Ser Ser Leu Pro Ala Arg Lys Pro
625                 630                 635                 640

Pro Asn Glu Pro His Val Tyr Leu Pro Gly
                645                 650

<210> SEQ ID NO 28
<211> LENGTH: 649
<212> TYPE: PRT
<213> ORGANISM: Homo sapiens

<400> SEQUENCE: 28

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Gly Gly Ser Gly Gly Gly Gly Ser Gly Gly Gly Gly Ser
450                 455                 460

Gln Ile Ala Pro Pro Cys Thr Ser Glu Lys His Tyr Glu His Leu Gly
465                 470                 475                 480

Arg Cys Cys Asn Lys Cys Glu Pro Gly Lys Tyr Met Ser Ser Lys Cys
                485                 490                 495

Thr Thr Thr Ser Asp Ser Val Cys Leu Pro Cys Gly Pro Asp Glu Tyr
            500                 505                 510

Leu Asp Ser Trp Asn Glu Glu Asp Lys Cys Leu Leu His Lys Val Cys
            515                 520                 525

Asp Thr Gly Lys Ala Leu Val Ala Val Ala Gly Asn Ser Thr Thr
            530                 535                 540

Pro Arg Arg Cys Ala Cys Thr Ala Gly Tyr His Trp Ser Gln Asp Cys
545                 550                 555                 560

Glu Cys Cys Arg Arg Asn Thr Glu Cys Ala Pro Gly Leu Gly Ala Gln
                565                 570                 575

His Pro Leu Gln Leu Asn Lys Asp Thr Val Cys Lys Pro Cys Leu Ala
            580                 585                 590
```

```
Gly Tyr Phe Ser Asp Ala Phe Ser Thr Asp Lys Cys Arg Pro Trp
            595                 600                 605

Thr Asn Cys Thr Phe Leu Gly Lys Arg Val Glu His His Gly Thr Glu
610                 615                 620

Lys Ser Asp Ala Val Cys Ser Ser Ser Leu Pro Ala Arg Lys Pro Pro
625                 630                 635                 640

Asn Glu Pro His Val Tyr Leu Pro Gly
                645

<210> SEQ ID NO 29
<211> LENGTH: 651
<212> TYPE: PRT
<213> ORGANISM: Homo sapiens

<400> SEQUENCE: 29

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Ser Gly Gly Gly Gly
    450                 455                 460

Gly Ser Gln Ile Ala Pro Pro Cys Thr Ser Glu Lys His Tyr Glu His
465                 470                 475                 480

Leu Gly Arg Cys Cys Asn Lys Cys Glu Pro Gly Lys Tyr Met Ser Ser
                485                 490                 495

Lys Cys Thr Thr Thr Ser Asp Ser Val Cys Leu Pro Cys Gly Pro Asp
            500                 505                 510

Glu Tyr Leu Asp Ser Trp Asn Glu Asp Lys Cys Leu Leu His Lys
        515                 520                 525

Val Cys Asp Thr Gly Lys Ala Leu Val Ala Val Ala Gly Asn Ser
    530                 535                 540

Thr Thr Pro Arg Arg Cys Ala Cys Thr Ala Gly Tyr His Trp Ser Gln
545                 550                 555                 560

Asp Cys Glu Cys Cys Arg Arg Asn Thr Glu Cys Ala Pro Gly Leu Gly
                565                 570                 575

Ala Gln His Pro Leu Gln Leu Asn Lys Asp Thr Val Cys Lys Pro Cys
            580                 585                 590

Leu Ala Gly Tyr Phe Ser Asp Ala Phe Ser Ser Thr Asp Lys Cys Arg
        595                 600                 605

Pro Trp Thr Asn Cys Thr Phe Leu Gly Lys Arg Val Glu His His Gly
    610                 615                 620

Thr Glu Lys Ser Asp Ala Val Cys Ser Ser Ser Leu Pro Ala Arg Lys
625                 630                 635                 640

Pro Pro Asn Glu Pro His Val Tyr Leu Pro Gly
                645                 650

<210> SEQ ID NO 30
<211> LENGTH: 653
<212> TYPE: PRT
<213> ORGANISM: Homo sapiens

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val

```
            35                  40                  45
Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Ser Gly Gly Gly Ser Gly
    450                 455                 460
```

Gly Gly Gly Ser Gln Ile Ala Pro Pro Cys Thr Ser Glu Lys His Tyr
465                 470                 475                 480

Glu His Leu Gly Arg Cys Cys Asn Lys Cys Glu Pro Gly Lys Tyr Met
                485                 490                 495

Ser Ser Lys Cys Thr Thr Thr Ser Asp Ser Val Cys Leu Pro Cys Gly
            500                 505                 510

Pro Asp Glu Tyr Leu Asp Ser Trp Asn Glu Glu Asp Lys Cys Leu Leu
        515                 520                 525

His Lys Val Cys Asp Thr Gly Lys Ala Leu Val Ala Val Ala Gly
    530                 535                 540

Asn Ser Thr Thr Pro Arg Arg Cys Ala Cys Thr Ala Gly Tyr His Trp
545                 550                 555                 560

Ser Gln Asp Cys Glu Cys Cys Arg Arg Asn Thr Glu Cys Ala Pro Gly
                565                 570                 575

Leu Gly Ala Gln His Pro Leu Gln Leu Asn Lys Asp Thr Val Cys Lys
            580                 585                 590

Pro Cys Leu Ala Gly Tyr Phe Ser Asp Ala Phe Ser Ser Thr Asp Lys
        595                 600                 605

Cys Arg Pro Trp Thr Asn Cys Thr Phe Leu Gly Lys Arg Val Glu His
610                 615                 620

His Gly Thr Glu Lys Ser Asp Ala Val Cys Ser Ser Ser Leu Pro Ala
625                 630                 635                 640

Arg Lys Pro Pro Asn Glu Pro His Val Tyr Leu Pro Gly
                645                 650

<210> SEQ ID NO 31
<211> LENGTH: 648
<212> TYPE: PRT
<213> ORGANISM: Homo sapiens

<400> SEQUENCE: 31

Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser

```
            180                 185                 190
Ser Leu Gly Thr Gln Thr Tyr Ile Cys Asn Val Asn His Lys Pro Ser
            195                 200                 205
Asn Thr Lys Val Asp Lys Arg Val Glu Pro Lys Ser Cys Asp Lys Thr
            210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
            435                 440                 445
Gly Gly Gly Gly Ser Gly Gly Gly Gly Ser Gly Gly Gly Gly Ser Gln
            450                 455                 460
Ile Ala Pro Pro Cys Thr Ser Glu Lys His Tyr Glu His Leu Gly Arg
465                 470                 475                 480
Cys Cys Asn Lys Cys Glu Pro Gly Lys Tyr Met Ser Ser Lys Cys Thr
                485                 490                 495
Thr Thr Ser Asp Ser Val Cys Leu Pro Cys Gly Pro Asp Glu Tyr Leu
            500                 505                 510
Asp Ser Trp Asn Glu Glu Asp Lys Cys Leu Leu His Lys Val Cys Asp
            515                 520                 525
Thr Gly Lys Ala Leu Val Ala Val Val Ala Gly Asn Ser Thr Thr Pro
            530                 535                 540
Arg Arg Cys Ala Cys Thr Ala Gly Tyr His Trp Ser Gln Asp Cys Glu
545                 550                 555                 560
Cys Cys Arg Arg Asn Thr Glu Cys Ala Pro Gly Leu Gly Ala Gln His
                565                 570                 575
Pro Leu Gln Leu Asn Lys Asp Thr Val Cys Lys Pro Cys Leu Ala Gly
            580                 585                 590
Tyr Phe Ser Asp Ala Phe Ser Ser Thr Asp Lys Cys Arg Pro Trp Thr
            595                 600                 605
```

```
Asn Cys Thr Phe Leu Gly Lys Arg Val Glu His His Gly Thr Glu Lys
610                 615                 620

Ser Asp Ala Val Cys Ser Ser Leu Pro Ala Arg Lys Pro Pro Asn
625                 630                 635                 640

Glu Pro His Val Tyr Leu Pro Gly
                645

<210> SEQ ID NO 32
<211> LENGTH: 646
<212> TYPE: PRT
<213> ORGANISM: Homo sapiens

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Arg Met His Trp Val Arg Gln Ala Pro Gly Gln Gly Leu Glu Trp Ile
            35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
```

```
                    325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys Gly Gly
        435                 440                 445
Gly Gly Ser Gly Gly Gly Ser Gly Gly Gly Ser Gln Ile Ala
    450                 455                 460
Pro Pro Cys Thr Ser Glu Lys His Tyr Glu His Leu Gly Arg Cys Cys
465                 470                 475                 480
Asn Lys Cys Glu Pro Gly Lys Tyr Met Ser Ser Lys Cys Thr Thr Thr
                485                 490                 495
Ser Asp Ser Val Cys Leu Pro Cys Gly Pro Asp Glu Tyr Leu Asp Ser
            500                 505                 510
Trp Asn Glu Glu Asp Lys Cys Leu Leu His Lys Val Cys Asp Thr Gly
        515                 520                 525
Lys Ala Leu Val Ala Val Ala Gly Asn Ser Thr Thr Pro Arg Arg
    530                 535                 540
Cys Ala Cys Thr Ala Gly Tyr His Trp Ser Gln Asp Cys Glu Cys Cys
545                 550                 555                 560
Arg Arg Asn Thr Glu Cys Ala Pro Gly Leu Gly Ala Gln His Pro Leu
                565                 570                 575
Gln Leu Asn Lys Asp Thr Val Cys Lys Pro Cys Leu Ala Gly Tyr Phe
            580                 585                 590
Ser Asp Ala Phe Ser Ser Thr Asp Lys Cys Arg Pro Trp Thr Asn Cys
        595                 600                 605
Thr Phe Leu Gly Lys Arg Val Glu His His Gly Thr Glu Lys Ser Asp
    610                 615                 620
Ala Val Cys Ser Ser Ser Leu Pro Ala Arg Lys Pro Pro Asn Glu Pro
625                 630                 635                 640
His Val Tyr Leu Pro Gly
                645

<210> SEQ ID NO 33
<211> LENGTH: 645
<212> TYPE: PRT
<213> ORGANISM: Homo sapiens

<400> SEQUENCE: 33

Gln Leu Gln Gln Ser Gly Thr Val Leu Ala Arg Pro Gly Ala Ser Val
1               5                   10                  15
Lys Met Ser Cys Lys Ala Ser Gly Tyr Ser Phe Thr Arg Tyr Trp Met
            20                  25                  30
His Trp Ile Lys Gln Arg Pro Gly Gln Gly Leu Glu Trp Ile Gly Ala
        35                  40                  45
```

-continued

```
Ile Tyr Pro Gly Asn Ser Asp Thr Ser Tyr Asn Gln Lys Phe Glu Gly
 50                  55                  60

Lys Ala Lys Leu Thr Ala Val Thr Ser Ala Ser Thr Ala Tyr Met Glu
 65                  70                  75                  80

Leu Ser Ser Leu Thr His Glu Asp Ser Ala Val Tyr Tyr Cys Ser Arg
                 85                  90                  95

Asp Tyr Gly Tyr Tyr Phe Asp Phe Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Gly Gly Gly
        435                 440                 445

Gly Ser Gly Gly Gly Gly Ser Gly Gly Gly Gly Ser Gln Ile Ala Pro
450                 455                 460

Pro Cys Thr Ser Glu Lys His Tyr Glu His Leu Gly Arg Cys Cys Asn
```

```
              465                 470                 475                 480
Lys Cys Glu Pro Gly Lys Tyr Met Ser Ser Lys Cys Thr Thr Thr Ser
                    485                 490                 495

Asp Ser Val Cys Leu Pro Cys Gly Pro Asp Glu Tyr Leu Asp Ser Trp
                500                 505                 510

Asn Glu Glu Asp Lys Cys Leu Leu His Lys Val Cys Asp Thr Gly Lys
            515                 520                 525

Ala Leu Val Ala Val Val Ala Gly Asn Ser Thr Thr Pro Arg Arg Cys
        530                 535                 540

Ala Cys Thr Ala Gly Tyr His Trp Ser Gln Asp Cys Glu Cys Cys Arg
545                 550                 555                 560

Arg Asn Thr Glu Cys Ala Pro Gly Leu Gly Ala Gln His Pro Leu Gln
                565                 570                 575

Leu Asn Lys Asp Thr Val Cys Lys Pro Cys Leu Ala Gly Tyr Phe Ser
            580                 585                 590

Asp Ala Phe Ser Ser Thr Asp Lys Cys Arg Pro Trp Thr Asn Cys Thr
        595                 600                 605

Phe Leu Gly Lys Arg Val Glu His His Gly Thr Glu Lys Ser Asp Ala
610                 615                 620

Val Cys Ser Ser Ser Leu Pro Ala Arg Lys Pro Pro Asn Glu Pro His
625                 630                 635                 640

Val Tyr Leu Pro Gly
                645

<210> SEQ ID NO 34
<211> LENGTH: 573
<212> TYPE: PRT
<213> ORGANISM: Homo sapiens

<400> SEQUENCE: 34

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Ser Gly
    130                 135                 140

Gly Gly Gly Ser Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190
```

Ser His Glu Asp Pro Glu Val Lys Phe Asn Trp Tyr Val Asp Gly Val
          195                 200                 205

Glu Val His Asn Ala Lys Thr Lys Pro Arg Glu Glu Gln Tyr Asn Ser
210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
              245                 250                 255

Pro Ile Glu Lys Thr Ile Ser Lys Ala Lys Gly Gln Pro Arg Glu Pro
          260                 265                 270

Gln Val Tyr Thr Leu Pro Pro Ser Arg Glu Glu Met Thr Lys Asn Gln
      275                 280                 285

Val Ser Leu Thr Cys Leu Val Lys Gly Phe Tyr Pro Ser Asp Ile Ala
290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
              325                 330                 335

Thr Val Asp Lys Ser Arg Trp Gln Gln Gly Asn Val Phe Ser Cys Ser
          340                 345                 350

Val Met His Glu Ala Leu His Asn His Tyr Thr Gln Lys Ser Leu Ser
      355                 360                 365

Leu Ser Pro Gly Lys Gly Gly Gly Ser Gly Gly Gly Ser Gly
370                 375                 380

Gly Gly Ser Gln Ile Ala Pro Pro Cys Thr Ser Glu Lys His Tyr
385                 390                 395                 400

Glu His Leu Gly Arg Cys Cys Asn Lys Cys Glu Pro Gly Lys Tyr Met
              405                 410                 415

Ser Ser Lys Cys Thr Thr Thr Ser Asp Ser Val Cys Leu Pro Cys Gly
          420                 425                 430

Pro Asp Glu Tyr Leu Asp Ser Trp Asn Glu Glu Asp Lys Cys Leu Leu
      435                 440                 445

His Lys Val Cys Asp Thr Gly Lys Ala Leu Val Ala Val Ala Gly
450                 455                 460

Asn Ser Thr Thr Pro Arg Arg Cys Ala Cys Thr Ala Gly Tyr His Trp
465                 470                 475                 480

Ser Gln Asp Cys Glu Cys Cys Arg Arg Asn Thr Glu Cys Ala Pro Gly
              485                 490                 495

Leu Gly Ala Gln His Pro Leu Gln Leu Asn Lys Asp Thr Val Cys Lys
          500                 505                 510

Pro Cys Leu Ala Gly Tyr Phe Ser Asp Ala Phe Ser Ser Thr Asp Lys
      515                 520                 525

Cys Arg Pro Trp Thr Asn Cys Thr Phe Leu Gly Lys Arg Val Glu His
530                 535                 540

His Gly Thr Glu Lys Ser Asp Ala Val Cys Ser Ser Ser Leu Pro Ala
545                 550                 555                 560

Arg Lys Pro Pro Asn Glu Pro His Val Tyr Leu Pro Gly
              565                 570

<210> SEQ ID NO 35
<211> LENGTH: 573
<212> TYPE: PRT
<213> ORGANISM: Homo sapiens

<400> SEQUENCE: 35

```
Gln Ile Ala Pro Pro Cys Thr Ser Glu Lys His Tyr Glu His Leu Gly
  1               5                  10                  15

Arg Cys Cys Asn Lys Cys Glu Pro Gly Lys Tyr Met Ser Ser Lys Cys
             20                  25                  30

Thr Thr Thr Ser Asp Ser Val Cys Leu Pro Cys Gly Pro Asp Glu Tyr
         35                  40                  45

Leu Asp Ser Trp Asn Glu Glu Asp Lys Cys Leu Leu His Lys Val Cys
     50                  55                  60

Asp Thr Gly Lys Ala Leu Val Ala Val Val Ala Gly Asn Ser Thr Thr
 65                  70                  75                  80

Pro Arg Arg Cys Ala Cys Thr Ala Gly Tyr His Trp Ser Gln Asp Cys
                 85                  90                  95

Glu Cys Cys Arg Arg Asn Thr Glu Cys Ala Pro Gly Leu Gly Ala Gln
             100                 105                 110

His Pro Leu Gln Leu Asn Lys Asp Thr Val Cys Lys Pro Cys Leu Ala
             115                 120                 125

Gly Tyr Phe Ser Asp Ala Phe Ser Ser Thr Asp Lys Cys Arg Pro Trp
         130                 135                 140

Thr Asn Cys Thr Phe Leu Gly Lys Arg Val Glu His Gly Thr Glu
145                 150                 155                 160

Lys Ser Asp Ala Val Cys Ser Ser Ser Leu Pro Ala Arg Lys Pro Pro
                 165                 170                 175

Asn Glu Pro His Val Tyr Leu Pro Gly Gly Gly Gly Ser Gly Gly
             180                 185                 190

Gly Gly Ser Gly Gly Gly Gly Ser Thr His Thr Cys Pro Pro Cys Pro
         195                 200                 205

Ala Pro Glu Leu Leu Gly Gly Pro Ser Val Phe Leu Phe Pro Pro Lys
210                 215                 220

Pro Lys Asp Thr Leu Met Ile Ser Arg Thr Pro Glu Val Thr Cys Val
225                 230                 235                 240

Val Val Asp Val Ser His Glu Asp Pro Glu Val Lys Phe Asn Trp Tyr
                 245                 250                 255

Val Asp Gly Val Glu Val His Asn Ala Lys Thr Lys Pro Arg Glu Glu
             260                 265                 270

Gln Tyr Asn Ser Thr Tyr Arg Val Val Ser Val Leu Thr Val Leu His
         275                 280                 285

Gln Asp Trp Leu Asn Gly Lys Glu Tyr Lys Cys Lys Val Ser Asn Lys
     290                 295                 300

Ala Leu Pro Ala Pro Ile Glu Lys Thr Ile Ser Lys Ala Lys Gly Gln
305                 310                 315                 320

Pro Arg Glu Pro Gln Val Tyr Thr Leu Pro Pro Ser Arg Glu Glu Met
                 325                 330                 335

Thr Lys Asn Gln Val Ser Leu Thr Cys Leu Val Lys Gly Phe Tyr Pro
             340                 345                 350

Ser Asp Ile Ala Val Glu Trp Glu Ser Asn Gly Gln Pro Glu Asn Asn
         355                 360                 365

Tyr Lys Thr Thr Pro Pro Val Leu Asp Ser Asp Gly Ser Phe Phe Leu
     370                 375                 380

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                 405                 410                 415
```

```
Lys Ser Leu Ser Leu Ser Pro Gly Lys Gly Gly Gly Ser Gly Gly
                420                 425                 430

Gly Gly Ser Gly Gly Gly Ser Ala Pro Thr Ser Ser Ser Thr Lys
            435                 440                 445

Lys Thr Gln Leu Gln Leu Glu His Leu Leu Leu Asp Leu Gln Met Ile
450                 455                 460

Leu Asn Gly Ile Asn Asn Tyr Lys Asn Pro Lys Leu Thr Arg Met Leu
465                 470                 475                 480

Thr Phe Lys Phe Tyr Met Pro Lys Lys Ala Thr Glu Leu Lys His Leu
                485                 490                 495

Gln Cys Leu Glu Glu Glu Leu Lys Pro Leu Glu Glu Val Leu Asn Leu
            500                 505                 510

Ala Gln Ser Lys Asn Phe His Leu Arg Pro Arg Asp Leu Ile Ser Asn
            515                 520                 525

Ile Asn Val Ile Val Leu Glu Leu Lys Gly Ser Glu Thr Thr Phe Met
530                 535                 540

Cys Glu Tyr Ala Asp Glu Thr Ala Thr Ile Val Glu Phe Leu Asn Arg
545                 550                 555                 560

Trp Ile Thr Phe Cys Gln Ser Ile Ile Ser Thr Leu Thr
                565                 570

<210> SEQ ID NO 36
<211> LENGTH: 651
<212> TYPE: PRT
<213> ORGANISM: Homo sapiens

<400> SEQUENCE: 36

Gln Val Gln Leu Gln Glu Ala Gly Pro Gly Leu Val Lys Pro Ser Glu
1               5                   10                  15

Thr Leu Ser Leu Thr Cys Ser Val Ser Gly Gly Ser Ile Ser Gly Asp
                20                  25                  30

Tyr Tyr Trp Phe Trp Ile Arg Gln Ser Pro Gly Lys Gly Leu Glu Trp
            35                  40                  45

Ile Gly Tyr Ile Tyr Gly Ser Gly Gly Thr Asn Tyr Asn Pro Ser
        50                  55                  60

Leu Asn Asn Arg Val Ser Ile Ser Ile Asp Thr Ser Lys Asn Leu Phe
65                  70                  75                  80

Ser Leu Lys Leu Arg Ser Val Thr Ala Ala Asp Thr Ala Val Tyr Tyr
                85                  90                  95

Cys Ala Ser Asn Ile Leu Lys Tyr Leu His Trp Leu Leu Tyr Trp Gly
            100                 105                 110

Gln Gly Val Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220
```

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys Gly Gly Gly Gly Ser Gly Gly Gly Gly Ser Gly Gly Gly
    450                 455                 460

Gly Ser Gln Ile Ala Pro Pro Cys Thr Ser Glu Lys His Tyr Glu His
465                 470                 475                 480

Leu Gly Arg Cys Cys Asn Lys Cys Glu Pro Gly Lys Tyr Met Ser Ser
                485                 490                 495

Lys Cys Thr Thr Thr Ser Asp Ser Val Cys Leu Pro Cys Gly Pro Asp
            500                 505                 510

Glu Tyr Leu Asp Ser Trp Asn Glu Glu Asp Lys Cys Leu Leu His Lys
        515                 520                 525

Val Cys Asp Thr Gly Lys Ala Leu Val Ala Val Ala Gly Asn Ser
    530                 535                 540

Thr Thr Pro Arg Arg Cys Ala Cys Thr Ala Gly Tyr His Trp Ser Gln
545                 550                 555                 560

Asp Cys Glu Cys Cys Arg Arg Asn Thr Glu Cys Ala Pro Gly Leu Gly
                565                 570                 575

Ala Gln His Pro Leu Gln Leu Asn Lys Asp Thr Val Cys Lys Pro Cys
            580                 585                 590

Leu Ala Gly Tyr Phe Ser Asp Ala Phe Ser Ser Thr Asp Lys Cys Arg
        595                 600                 605

Pro Trp Thr Asn Cys Thr Phe Leu Gly Lys Arg Val Glu His His Gly
    610                 615                 620

Thr Glu Lys Ser Asp Ala Val Cys Ser Ser Ser Leu Pro Ala Arg Lys
625                 630                 635                 640
```

```
Pro Pro Asn Glu Pro His Val Tyr Leu Pro Gly
                645                 650

<210> SEQ ID NO 37
<211> LENGTH: 755
<212> TYPE: PRT
<213> ORGANISM: Homo sapiens

<400> SEQUENCE: 37

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Leu Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Ser Gly Gly Gly Ser Gly Gly Gly
    450                 455                 460

Gly Ser Arg Ile Phe Ala Val Phe Ile Phe Met Thr Tyr Trp His Leu
465                 470                 475                 480

Leu Asn Ala Phe Thr Val Thr Val Pro Lys Asp Leu Tyr Val Val Glu
                485                 490                 495

Tyr Gly Ser Asn Met Thr Ile Glu Cys Lys Phe Pro Val Glu Lys Gln
                500                 505                 510

Leu Asp Leu Ala Ala Leu Ile Val Tyr Trp Glu Met Glu Asp Lys Asn
            515                 520                 525

Ile Ile Gln Phe Val His Gly Glu Glu Asp Leu Lys Val Gln His Ser
        530                 535                 540

Ser Tyr Arg Gln Arg Ala Arg Leu Leu Lys Asp Gln Leu Ser Leu Gly
545                 550                 555                 560

Asn Ala Ala Leu Gln Ile Thr Asp Val Lys Leu Gln Asp Ala Gly Val
                565                 570                 575

Tyr Arg Cys Met Ile Ser Tyr Gly Gly Ala Asp Tyr Lys Arg Ile Thr
                580                 585                 590

Val Lys Val Asn Ala Pro Tyr Asn Lys Ile Asn Gln Arg Ile Leu Val
            595                 600                 605

Val Asp Pro Val Thr Ser Glu His Glu Leu Thr Cys Gln Ala Glu Gly
        610                 615                 620

Tyr Pro Lys Ala Glu Val Ile Trp Thr Ser Ser Asp His Gln Val Leu
625                 630                 635                 640

Ser Gly Lys Thr Thr Thr Thr Asn Ser Lys Arg Glu Glu Lys Leu Phe
                645                 650                 655

Asn Val Thr Ser Thr Leu Arg Ile Asn Thr Thr Thr Asn Glu Ile Phe
                660                 665                 670

Tyr Cys Thr Phe Arg Arg Leu Asp Pro Glu Glu Asn His Thr Ala Glu
            675                 680                 685

Leu Val Ile Pro Glu Leu Pro Leu Ala His Pro Pro Asn Glu Arg Thr
        690                 695                 700

His Leu Val Ile Leu Gly Ala Ile Leu Leu Cys Leu Gly Val Ala Leu
705                 710                 715                 720

Thr Phe Ile Phe Arg Leu Arg Lys Gly Arg Met Met Asp Val Lys Lys
                725                 730                 735

Cys Gly Ile Gln Asp Thr Asn Ser Lys Lys Gln Ser Asp Thr His Leu
                740                 745                 750

Glu Glu Thr
        755

<210> SEQ ID NO 38
<211> LENGTH: 771
```

<212> TYPE: PRT
<213> ORGANISM: Homo sapiens

<400> SEQUENCE: 38

```
Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400
```

```
Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys Gly Gly Gly Gly Ser Gly Gly Gly Gly Ser Gly Gly Gly
465                 470                 475                 480

Gly Ser Arg Ile Phe Ala Val Phe Ile Phe Met Thr Tyr Trp His Leu
                485                 490                 495

Leu Asn Ala Phe Thr Val Thr Val Pro Lys Asp Leu Tyr Val Val Glu
                500                 505                 510

Tyr Gly Ser Asn Met Thr Ile Glu Cys Lys Phe Pro Val Glu Lys Gln
                515                 520                 525

Leu Asp Leu Ala Ala Leu Ile Val Tyr Trp Glu Met Glu Asp Lys Asn
            530                 535                 540

Ile Ile Gln Phe Val His Gly Glu Glu Asp Leu Lys Val Gln His Ser
545                 550                 555                 560

Ser Tyr Arg Gln Arg Ala Arg Leu Leu Lys Asp Gln Leu Ser Leu Gly
                565                 570                 575

Asn Ala Ala Leu Gln Ile Thr Asp Val Lys Leu Gln Asp Ala Gly Val
                580                 585                 590

Tyr Arg Cys Met Ile Ser Tyr Gly Gly Ala Asp Tyr Lys Arg Ile Thr
                595                 600                 605

Val Lys Val Asn Ala Pro Tyr Asn Lys Ile Asn Gln Arg Ile Leu Val
            610                 615                 620

Val Asp Pro Val Thr Ser Glu His Glu Leu Thr Cys Gln Ala Glu Gly
625                 630                 635                 640

Tyr Pro Lys Ala Glu Val Ile Trp Thr Ser Ser Asp His Gln Val Leu
                645                 650                 655

Ser Gly Lys Thr Thr Thr Thr Asn Ser Lys Arg Glu Glu Lys Leu Phe
                660                 665                 670

Asn Val Thr Ser Thr Leu Arg Ile Asn Thr Thr Thr Asn Glu Ile Phe
                675                 680                 685

Tyr Cys Thr Phe Arg Arg Leu Asp Pro Glu Glu Asn His Thr Ala Glu
            690                 695                 700

Leu Val Ile Pro Glu Leu Pro Leu Ala His Pro Pro Asn Glu Arg Thr
705                 710                 715                 720

His Leu Val Ile Leu Gly Ala Ile Leu Leu Cys Leu Gly Val Ala Leu
                725                 730                 735

Thr Phe Ile Phe Arg Leu Arg Lys Gly Arg Met Met Asp Val Lys Lys
                740                 745                 750

Cys Gly Ile Gln Asp Thr Asn Ser Lys Lys Gln Ser Asp Thr His Leu
                755                 760                 765

Glu Glu Thr
    770

<210> SEQ ID NO 39
<211> LENGTH: 787
<212> TYPE: PRT
<213> ORGANISM: Homo sapiens
```

```
<400> SEQUENCE: 39

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
        195                 200                 205

Cys Thr Phe Arg Arg Leu Asp Pro Glu Glu Asn His Thr Ala Glu Leu
        210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr Gly Gly Gly Gly Ser Gly Gly Gly Gly Ser Gly Gly Gly Gly
        290                 295                 300

Ser Glu Pro Lys Ser Cys Asp Lys Thr His Thr Cys Pro Pro Cys Pro
305                 310                 315                 320

Ala Pro Glu Leu Leu Gly Gly Pro Ser Val Phe Leu Phe Pro Pro Lys
                325                 330                 335

Pro Lys Asp Thr Leu Met Ile Ser Arg Thr Pro Glu Val Thr Cys Val
            340                 345                 350

Val Val Asp Val Ser His Glu Asp Pro Glu Val Lys Phe Asn Trp Tyr
        355                 360                 365

Val Asp Gly Val Glu Val His Asn Ala Lys Thr Lys Pro Arg Glu Glu
    370                 375                 380

Gln Tyr Asn Ser Thr Tyr Arg Val Val Ser Val Leu Thr Val Leu His
385                 390                 395                 400

Gln Asp Trp Leu Asn Gly Lys Glu Tyr Lys Cys Lys Val Ser Asn Lys
                405                 410                 415
```

Ala Leu Pro Ala Pro Ile Glu Lys Thr Ile Ser Lys Ala Lys Gly Gln
            420                 425                 430

Pro Arg Glu Pro Gln Val Tyr Thr Leu Pro Pro Ser Arg Glu Glu Met
            435                 440                 445

Thr Lys Asn Gln Val Ser Leu Thr Cys Leu Val Lys Gly Phe Tyr Pro
        450                 455                 460

Ser Asp Ile Ala Val Glu Trp Glu Ser Asn Gly Gln Pro Glu Asn Asn
465                 470                 475                 480

Tyr Lys Thr Thr Pro Pro Val Leu Asp Ser Asp Gly Ser Phe Phe Leu
                485                 490                 495

Tyr Ser Lys Leu Thr Val Asp Lys Ser Arg Trp Gln Gln Gly Asn Val
            500                 505                 510

Phe Ser Cys Ser Val Met His Glu Ala Leu His Asn His Tyr Thr Gln
            515                 520                 525

Lys Ser Leu Ser Leu Ser Pro Gly Lys Gly Gly Gly Ser Gly Gly
        530                 535                 540

Gly Gly Ser Gly Gly Gly Gly Ser Leu Pro Ala Gln Val Ala Phe Thr
545                 550                 555                 560

Pro Tyr Ala Pro Glu Pro Gly Ser Thr Cys Arg Leu Arg Glu Tyr Tyr
                565                 570                 575

Asp Gln Thr Ala Gln Met Cys Cys Ser Lys Cys Ser Pro Gly Gln His
            580                 585                 590

Ala Lys Val Phe Cys Thr Lys Thr Ser Asp Thr Val Cys Asp Ser Cys
            595                 600                 605

Glu Asp Ser Thr Tyr Thr Gln Leu Trp Asn Trp Val Pro Glu Cys Leu
            610                 615                 620

Ser Cys Gly Ser Arg Cys Ser Ser Asp Gln Val Glu Thr Gln Ala Cys
625                 630                 635                 640

Thr Arg Glu Gln Asn Arg Ile Cys Thr Cys Arg Pro Gly Trp Tyr Cys
                645                 650                 655

Ala Leu Ser Lys Gln Glu Gly Cys Arg Leu Cys Ala Pro Leu Arg Lys
            660                 665                 670

Cys Arg Pro Gly Phe Gly Val Ala Arg Pro Gly Thr Glu Thr Ser Asp
            675                 680                 685

Val Val Cys Lys Pro Cys Ala Pro Gly Thr Phe Ser Asn Thr Thr Ser
        690                 695                 700

Ser Thr Asp Ile Cys Arg Pro His Gln Ile Cys Asn Val Val Ala Ile
705                 710                 715                 720

Pro Gly Asn Ala Ser Met Asp Ala Val Cys Thr Ser Thr Ser Pro Thr
                725                 730                 735

Arg Ser Met Ala Pro Gly Ala Val His Leu Pro Gln Pro Val Ser Thr
            740                 745                 750

Arg Ser Gln His Thr Gln Pro Thr Pro Glu Pro Ser Thr Ala Pro Ser
            755                 760                 765

Thr Ser Phe Leu Leu Pro Met Gly Pro Ser Pro Ala Glu Gly Ser
        770                 775                 780

Thr Gly Asp
785

<210> SEQ ID NO 40
<211> LENGTH: 755
<212> TYPE: PRT
<213> ORGANISM: Homo sapiens

```
<400> SEQUENCE: 40

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Ser Gly Gly Gly Ser Gly Gly Gly
    450                 455                 460

Gly Ser Arg Ile Phe Ala Val Phe Ile Phe Met Thr Tyr Trp His Leu
465                 470                 475                 480

Leu Asn Ala Phe Thr Val Thr Val Pro Lys Asp Leu Tyr Val Val Glu
                485                 490                 495

Tyr Gly Ser Asn Met Thr Ile Glu Cys Lys Phe Pro Val Glu Lys Gln
            500                 505                 510

Leu Asp Leu Ala Ala Leu Ile Val Tyr Trp Glu Met Glu Asp Lys Asn
        515                 520                 525

Ile Ile Gln Phe Val His Gly Glu Glu Asp Leu Lys Val Gln His Ser
    530                 535                 540

Ser Tyr Arg Gln Arg Ala Arg Leu Leu Lys Asp Gln Leu Ser Leu Gly
545                 550                 555                 560

Asn Ala Ala Leu Gln Ile Thr Asp Val Lys Leu Gln Asp Ala Gly Val
                565                 570                 575

Tyr Arg Cys Met Ile Ser Tyr Gly Gly Ala Asp Tyr Lys Arg Ile Thr
            580                 585                 590

Val Lys Val Asn Ala Pro Tyr Asn Lys Ile Asn Gln Arg Ile Leu Val
        595                 600                 605

Val Asp Pro Val Thr Ser Glu His Glu Leu Thr Cys Gln Ala Glu Gly
    610                 615                 620

Tyr Pro Lys Ala Glu Val Ile Trp Thr Ser Ser Asp His Gln Val Leu
625                 630                 635                 640

Ser Gly Lys Thr Thr Thr Thr Asn Ser Lys Arg Glu Glu Lys Leu Phe
                645                 650                 655

Asn Val Thr Ser Thr Leu Arg Ile Asn Thr Thr Thr Asn Glu Ile Phe
            660                 665                 670

Tyr Cys Thr Phe Arg Arg Leu Asp Pro Glu Glu Asn His Thr Ala Glu
        675                 680                 685

Leu Val Ile Pro Glu Leu Pro Leu Ala His Pro Pro Asn Glu Arg Thr
    690                 695                 700

His Leu Val Ile Leu Gly Ala Ile Leu Leu Cys Leu Gly Val Ala Leu
705                 710                 715                 720

Thr Phe Ile Phe Arg Leu Arg Lys Gly Arg Met Met Asp Val Lys Lys
                725                 730                 735

Cys Gly Ile Gln Asp Thr Asn Ser Lys Lys Gln Ser Asp Thr His Leu
            740                 745                 750

Glu Glu Thr
        755

<210> SEQ ID NO 41
<211> LENGTH: 750
<212> TYPE: PRT
<213> ORGANISM: Homo sapiens

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr

```
              20                  25                  30
Arg Met His Trp Val Arg Gln Ala Pro Gly Gln Gly Leu Glu Trp Ile
            35                  40                  45
Gly Tyr Ile Asn Pro Ser Thr Gly Tyr Thr Glu Tyr Asn Gln Lys Phe
         50                  55                  60
Lys Asp Lys Ala Thr Ile Thr Ala Asp Glu Ser Thr Asn Thr Ala Tyr
 65                  70                  75                  80
Met Glu Leu Ser Ser Leu Arg Ser Glu Asp Thr Ala Val Tyr Tyr Cys
                 85                  90                  95
Ala Arg Gly Gly Gly Val Phe Asp Tyr Trp Gly Gln Gly Thr Leu Val
             100                 105                 110
Thr Val Ser Ser Ala Ser Thr Lys Gly Pro Ser Val Phe Pro Leu Ala
         115                 120                 125
Pro Ser Ser Lys Ser Thr Ser Gly Gly Thr Ala Ala Leu Gly Cys Leu
     130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
             165                 170                 175
Gly Leu Tyr Ser Leu Ser Ser Val Val Thr Val Pro Ser Ser Ser Leu
             180                 185                 190
Gly Thr Gln Thr Tyr Ile Cys Asn Val Asn His Lys Pro Ser Asn Thr
         195                 200                 205
Lys Val Asp Lys Lys Val Glu Pro Lys Ser Cys Asp Lys Thr His Thr
     210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                 245                 250                 255
Glu Val Thr Cys Val Val Val Asp Val Ser His Glu Asp Pro Glu Val
             260                 265                 270
Lys Phe Asn Trp Tyr Val Asp Gly Val Glu Val His Asn Ala Lys Thr
         275                 280                 285
Lys Pro Arg Glu Glu Gln Tyr Asn Ser Thr Tyr Arg Val Val Ser Val
     290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                 325                 330                 335
Lys Ala Lys Gly Gln Pro Arg Glu Pro Gln Val Tyr Thr Leu Pro Pro
             340                 345                 350
Ser Arg Asp Glu Leu Thr Lys Asn Gln Val Ser Leu Thr Cys Leu Val
         355                 360                 365
Lys Gly Phe Tyr Pro Ser Asp Ile Ala Val Glu Trp Glu Ser Asn Gly
     370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                 405                 410                 415
Gln Gln Gly Asn Val Phe Ser Cys Ser Val Met His Glu Ala Leu His
             420                 425                 430
Asn His Tyr Thr Gln Lys Ser Leu Ser Leu Ser Pro Gly Lys Gly Gly
         435                 440                 445
```

Gly Gly Ser Gly Gly Gly Ser Gly Gly Gly Ser Arg Ile Phe
            450                 455                 460

Ala Val Phe Ile Phe Met Thr Tyr Trp His Leu Leu Asn Ala Phe Thr
465                 470                 475                 480

Val Thr Val Pro Lys Asp Leu Tyr Val Glu Tyr Gly Ser Asn Met
                485                 490                 495

Thr Ile Glu Cys Lys Phe Pro Val Lys Gln Leu Asp Leu Ala Ala
                500                 505                 510

Leu Ile Val Tyr Trp Glu Met Glu Asp Lys Asn Ile Ile Gln Phe Val
                515                 520                 525

His Gly Glu Glu Asp Leu Lys Val Gln His Ser Ser Tyr Arg Gln Arg
                530                 535                 540

Ala Arg Leu Leu Lys Asp Gln Leu Ser Leu Gly Asn Ala Ala Leu Gln
545                 550                 555                 560

Ile Thr Asp Val Lys Leu Gln Asp Ala Gly Val Tyr Arg Cys Met Ile
                565                 570                 575

Ser Tyr Gly Gly Ala Asp Tyr Lys Arg Ile Thr Val Lys Val Asn Ala
                580                 585                 590

Pro Tyr Asn Lys Ile Asn Gln Arg Ile Leu Val Val Asp Pro Val Thr
                595                 600                 605

Ser Glu His Glu Leu Thr Cys Gln Ala Glu Gly Tyr Pro Lys Ala Glu
610                 615                 620

Val Ile Trp Thr Ser Ser Asp His Gln Val Leu Ser Gly Lys Thr Thr
625                 630                 635                 640

Thr Thr Asn Ser Lys Arg Glu Glu Lys Leu Phe Asn Val Thr Ser Thr
                645                 650                 655

Leu Arg Ile Asn Thr Thr Thr Asn Glu Ile Phe Tyr Cys Thr Phe Arg
                660                 665                 670

Arg Leu Asp Pro Glu Glu Asn His Thr Ala Glu Leu Val Ile Pro Glu
                675                 680                 685

Leu Pro Leu Ala His Pro Pro Asn Glu Arg Thr His Leu Val Ile Leu
690                 695                 700

Gly Ala Ile Leu Leu Cys Leu Gly Val Ala Leu Thr Phe Ile Phe Arg
705                 710                 715                 720

Leu Arg Lys Gly Arg Met Met Asp Val Lys Lys Cys Gly Ile Gln Asp
                725                 730                 735

Thr Asn Ser Lys Lys Gln Ser Asp Thr His Leu Glu Glu Thr
                740                 745                 750

<210> SEQ ID NO 42
<211> LENGTH: 749
<212> TYPE: PRT
<213> ORGANISM: Homo sapiens

<400> SEQUENCE: 42

Gln Leu Gln Gln Ser Gly Thr Val Leu Ala Arg Pro Gly Ala Ser Val
1               5                   10                  15

Lys Met Ser Cys Lys Ala Ser Gly Tyr Ser Phe Thr Arg Tyr Trp Met
                20                  25                  30

His Trp Ile Lys Gln Arg Pro Gly Gln Gly Leu Glu Trp Ile Gly Ala
                35                  40                  45

Ile Tyr Pro Gly Asn Ser Asp Thr Ser Tyr Asn Gln Lys Phe Glu Gly
                50                  55                  60

Lys Ala Lys Leu Thr Ala Val Thr Ser Ala Ser Thr Ala Tyr Met Glu

```
                65                  70                  75                  80
Leu Ser Ser Leu Thr His Glu Asp Ser Ala Val Tyr Tyr Cys Ser Arg
                    85                  90                  95

Asp Tyr Gly Tyr Tyr Phe Asp Phe Trp Gly Gln Gly Thr Thr Leu Thr
                    100                 105                 110

Val Ser Ser Ala Ser Thr Lys Gly Pro Ser Val Phe Pro Leu Ala Pro
                    115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                    165                 170                 175

Leu Tyr Ser Leu Ser Ser Val Val Thr Val Pro Ser Ser Ser Leu Gly
                    180                 185                 190

Thr Gln Thr Tyr Ile Cys Asn Val Asn His Lys Pro Ser Asn Thr Lys
                    195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                    245                 250                 255

Val Thr Cys Val Val Val Asp Val Ser His Glu Asp Pro Glu Val Lys
                    260                 265                 270

Phe Asn Trp Tyr Val Asp Gly Val Glu Val His Asn Ala Lys Thr Lys
                    275                 280                 285

Pro Arg Glu Glu Gln Tyr Asn Ser Thr Tyr Arg Val Val Ser Val Leu
                    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                    325                 330                 335

Ala Lys Gly Gln Pro Arg Glu Pro Gln Val Tyr Thr Leu Pro Pro Ser
                    340                 345                 350

Arg Asp Glu Leu Thr Lys Asn Gln Val Ser Leu Thr Cys Leu Val Lys
                    355                 360                 365

Gly Phe Tyr Pro Ser Asp Ile Ala Val Glu Trp Glu Ser Asn Gly Gln
                    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                    405                 410                 415

Gln Gly Asn Val Phe Ser Cys Ser Val Met His Glu Ala Leu His Asn
                    420                 425                 430

His Tyr Thr Gln Lys Ser Leu Ser Leu Ser Pro Gly Lys Gly Gly Gly
                    435                 440                 445

Gly Ser Gly Gly Gly Gly Ser Gly Gly Gly Gly Ser Arg Ile Phe Ala
    450                 455                 460

Val Phe Ile Phe Met Thr Tyr Trp His Leu Leu Asn Ala Phe Thr Val
465                 470                 475                 480

Thr Val Pro Lys Asp Leu Tyr Val Val Glu Tyr Gly Ser Asn Met Thr
                    485                 490                 495
```

```
Ile Glu Cys Lys Phe Pro Val Glu Lys Gln Leu Asp Leu Ala Ala Leu
            500                 505                 510

Ile Val Tyr Trp Glu Met Glu Asp Lys Asn Ile Ile Gln Phe Val His
            515                 520                 525

Gly Glu Glu Asp Leu Lys Val Gln His Ser Ser Tyr Arg Gln Arg Ala
            530                 535                 540

Arg Leu Leu Lys Asp Gln Leu Ser Leu Gly Asn Ala Ala Leu Gln Ile
545                 550                 555                 560

Thr Asp Val Lys Leu Gln Asp Ala Gly Val Tyr Arg Cys Met Ile Ser
            565                 570                 575

Tyr Gly Gly Ala Asp Tyr Lys Arg Ile Thr Val Lys Val Asn Ala Pro
            580                 585                 590

Tyr Asn Lys Ile Asn Gln Arg Ile Leu Val Val Asp Pro Val Thr Ser
            595                 600                 605

Glu His Glu Leu Thr Cys Gln Ala Glu Gly Tyr Pro Lys Ala Glu Val
            610                 615                 620

Ile Trp Thr Ser Ser Asp His Gln Val Leu Ser Gly Lys Thr Thr Thr
625                 630                 635                 640

Thr Asn Ser Lys Arg Glu Glu Lys Leu Phe Asn Val Thr Ser Thr Leu
            645                 650                 655

Arg Ile Asn Thr Thr Thr Asn Glu Ile Phe Tyr Cys Thr Phe Arg Arg
            660                 665                 670

Leu Asp Pro Glu Glu Asn His Thr Ala Glu Leu Val Ile Pro Glu Leu
            675                 680                 685

Pro Leu Ala His Pro Pro Asn Glu Arg Thr His Leu Val Ile Leu Gly
            690                 695                 700

Ala Ile Leu Leu Cys Leu Gly Val Ala Leu Thr Phe Ile Phe Arg Leu
705                 710                 715                 720

Arg Lys Gly Arg Met Met Asp Val Lys Lys Cys Gly Ile Gln Asp Thr
            725                 730                 735

Asn Ser Lys Lys Gln Ser Asp Thr His Leu Glu Glu Thr
            740                 745

<210> SEQ ID NO 43
<211> LENGTH: 678
<212> TYPE: PRT
<213> ORGANISM: Homo sapiens

<400> SEQUENCE: 43

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
            50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
            85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
```

```
            115                 120                 125
Lys Val Asn Ala Pro Tyr Asn Lys Ile Asn Gln Arg Ile Leu Val Val
            130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
                195                 200                 205

Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
            275                 280                 285

Glu Thr Gly Gly Gly Gly Ser Gly Gly Gly Gly Ser Gly Gly Gly Gly
            290                 295                 300

Ser Thr His Thr Cys Pro Pro Cys Pro Ala Pro Glu Leu Leu Gly Gly
305                 310                 315                 320

Pro Ser Val Phe Leu Phe Pro Pro Lys Pro Lys Asp Thr Leu Met Ile
                325                 330                 335

Ser Arg Thr Pro Glu Val Thr Cys Val Val Val Asp Val Ser His Glu
                340                 345                 350

Asp Pro Glu Val Lys Phe Asn Trp Tyr Val Asp Gly Val Glu Val His
            355                 360                 365

Asn Ala Lys Thr Lys Pro Arg Glu Glu Gln Tyr Asn Ser Thr Tyr Arg
370                 375                 380

Val Val Ser Val Leu Thr Val Leu His Gln Asp Trp Leu Asn Gly Lys
385                 390                 395                 400

Glu Tyr Lys Cys Lys Val Ser Asn Lys Ala Leu Pro Ala Pro Ile Glu
                405                 410                 415

Lys Thr Ile Ser Lys Ala Lys Gly Gln Pro Arg Glu Pro Gln Val Tyr
                420                 425                 430

Thr Leu Pro Pro Ser Arg Glu Glu Met Thr Lys Asn Gln Val Ser Leu
            435                 440                 445

Thr Cys Leu Val Lys Gly Phe Tyr Pro Ser Asp Ile Ala Val Glu Trp
            450                 455                 460

Glu Ser Asn Gly Gln Pro Glu Asn Asn Tyr Lys Thr Thr Pro Pro Val
465                 470                 475                 480

Leu Asp Ser Asp Gly Ser Phe Phe Leu Tyr Ser Lys Leu Thr Val Asp
                485                 490                 495

Lys Ser Arg Trp Gln Gln Gly Asn Val Phe Ser Cys Ser Val Met His
                500                 505                 510

Glu Ala Leu His Asn His Tyr Thr Gln Lys Ser Leu Ser Leu Ser Pro
            515                 520                 525

Gly Lys Gly Gly Gly Gly Ser Gly Gly Gly Gly Ser Gly Gly Gly Gly
            530                 535                 540
```

```
Ser Ala Pro Thr Ser Ser Thr Lys Lys Thr Gln Leu Gln Leu Glu
545                 550                 555                 560

His Leu Leu Leu Asp Leu Gln Met Ile Leu Asn Gly Ile Asn Asn Tyr
                565                 570                 575

Lys Asn Pro Lys Leu Thr Arg Met Leu Thr Phe Lys Phe Tyr Met Pro
            580                 585                 590

Lys Lys Ala Thr Glu Leu Lys His Leu Gln Cys Leu Glu Glu Glu Leu
        595                 600                 605

Lys Pro Leu Glu Glu Val Leu Asn Leu Ala Gln Ser Lys Asn Phe His
    610                 615                 620

Leu Arg Pro Arg Asp Leu Ile Ser Asn Ile Asn Val Ile Val Leu Glu
625                 630                 635                 640

Leu Lys Gly Ser Glu Thr Thr Phe Met Cys Glu Tyr Ala Asp Glu Thr
                645                 650                 655

Ala Thr Ile Val Glu Phe Leu Asn Arg Trp Ile Thr Phe Cys Gln Ser
            660                 665                 670

Ile Ile Ser Thr Leu Thr
            675

<210> SEQ ID NO 44
<211> LENGTH: 677
<212> TYPE: PRT
<213> ORGANISM: Homo sapiens

<400> SEQUENCE: 44

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly
    130                 135                 140

Gly Gly Gly Ser Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
        195                 200                 205

Glu Val His Asn Ala Lys Thr Lys Pro Arg Glu Glu Gln Tyr Asn Ser
    210                 215                 220

Thr Tyr Arg Val Val Ser Val Leu Thr Val Leu His Gln Asp Trp Leu
```

```
                225                 230                 235                 240
Asn Gly Lys Glu Tyr Lys Cys Lys Val Ser Asn Lys Ala Leu Pro Ala
                    245                 250                 255
Pro Ile Glu Lys Thr Ile Ser Lys Ala Lys Gly Gln Pro Arg Glu Pro
                260                 265                 270
Gln Val Tyr Thr Leu Pro Pro Ser Arg Glu Met Thr Lys Asn Gln
                275                 280                 285
Val Ser Leu Thr Cys Leu Val Lys Gly Phe Tyr Pro Ser Asp Ile Ala
    290                 295                 300
Val Glu Trp Glu Ser Asn Gly Gln Pro Glu Asn Asn Tyr Lys Thr Thr
305                 310                 315                 320
Pro Pro Val Leu Asp Ser Asp Gly Ser Phe Phe Leu Tyr Ser Lys Leu
                325                 330                 335
Thr Val Asp Lys Ser Arg Trp Gln Gln Gly Asn Val Phe Ser Cys Ser
                340                 345                 350
Val Met His Glu Ala Leu His Asn His Tyr Thr Gln Lys Ser Leu Ser
                355                 360                 365
Leu Ser Pro Gly Lys Gly Gly Gly Ser Gly Gly Gly Ser Gly
    370                 375                 380
Gly Gly Gly Ser Arg Ile Phe Ala Val Phe Ile Phe Met Thr Tyr Trp
385                 390                 395                 400
His Leu Leu Asn Ala Phe Thr Val Thr Val Pro Lys Asp Leu Tyr Val
                405                 410                 415
Val Glu Tyr Gly Ser Asn Met Thr Ile Glu Cys Lys Phe Pro Val Glu
                420                 425                 430
Lys Gln Leu Asp Leu Ala Ala Leu Ile Val Tyr Trp Glu Met Glu Asp
            435                 440                 445
Lys Asn Ile Ile Gln Phe Val His Gly Glu Glu Asp Leu Lys Val Gln
        450                 455                 460
His Ser Ser Tyr Arg Gln Arg Ala Arg Leu Leu Lys Asp Gln Leu Ser
465                 470                 475                 480
Leu Gly Asn Ala Ala Leu Gln Ile Thr Asp Val Lys Leu Gln Asp Ala
                485                 490                 495
Gly Val Tyr Arg Cys Met Ile Ser Tyr Gly Gly Ala Asp Tyr Lys Arg
                500                 505                 510
Ile Thr Val Lys Val Asn Ala Pro Tyr Asn Lys Ile Asn Gln Arg Ile
            515                 520                 525
Leu Val Val Asp Pro Val Thr Ser Glu His Glu Leu Thr Cys Gln Ala
        530                 535                 540
Glu Gly Tyr Pro Lys Ala Glu Val Ile Trp Thr Ser Ser Asp His Gln
545                 550                 555                 560
Val Leu Ser Gly Lys Thr Thr Thr Asn Ser Lys Arg Glu Glu Lys
                565                 570                 575
Leu Phe Asn Val Thr Ser Thr Leu Arg Ile Asn Thr Thr Thr Asn Glu
                580                 585                 590
Ile Phe Tyr Cys Thr Phe Arg Arg Leu Asp Pro Glu Glu Asn His Thr
                595                 600                 605
Ala Glu Leu Val Ile Pro Glu Leu Pro Leu Ala His Pro Pro Asn Glu
        610                 615                 620
Arg Thr His Leu Val Ile Leu Gly Ala Ile Leu Leu Cys Leu Gly Val
625                 630                 635                 640
Ala Leu Thr Phe Ile Phe Arg Leu Arg Lys Gly Arg Met Met Asp Val
                645                 650                 655
```

-continued

```
Lys Lys Cys Gly Ile Gln Asp Thr Asn Ser Lys Lys Gln Ser Asp Thr
            660                 665                 670

His Leu Glu Glu Thr
        675

<210> SEQ ID NO 45
<211> LENGTH: 755
<212> TYPE: PRT
<213> ORGANISM: Homo sapiens

<400> SEQUENCE: 45

Gln Val Gln Leu Gln Glu Ala Gly Pro Gly Leu Val Lys Pro Ser Glu
1               5                   10                  15

Thr Leu Ser Leu Thr Cys Ser Val Ser Gly Gly Ser Ile Ser Gly Asp
            20                  25                  30

Tyr Tyr Trp Phe Trp Ile Arg Gln Ser Pro Gly Lys Gly Leu Glu Trp
        35                  40                  45

Ile Gly Tyr Ile Tyr Gly Ser Gly Gly Thr Asn Tyr Asn Pro Ser
    50                  55                  60

Leu Asn Asn Arg Val Ser Ile Ser Ile Asp Thr Ser Lys Asn Leu Phe
65                  70                  75                  80

Ser Leu Lys Leu Arg Ser Val Thr Ala Ala Asp Thr Ala Val Tyr Tyr
            85                  90                  95

Cys Ala Ser Asn Ile Leu Lys Tyr Leu His Trp Leu Tyr Trp Gly
        100                 105                 110

Gln Gly Val Leu Val Thr Val Ser Ala Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
```

-continued

Tyr Thr Leu Pro Pro Ser Arg Asp Glu Leu Thr Lys Asn Gln Val Ser
            340                 345                 350
                355                     360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                     390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys Gly Gly Gly Gly Ser Gly Gly Gly Gly Ser Gly Gly Gly
            450                 455                 460

Gly Ser Arg Ile Phe Ala Val Phe Ile Phe Met Thr Tyr Trp His Leu
465                     470                 475                 480

Leu Asn Ala Phe Thr Val Thr Val Pro Lys Asp Leu Tyr Val Val Glu
                485                 490                 495

Tyr Gly Ser Asn Met Thr Ile Glu Cys Lys Phe Pro Val Glu Lys Gln
                500                 505                 510

Leu Asp Leu Ala Ala Leu Ile Val Tyr Trp Glu Met Glu Asp Lys Asn
            515                 520                 525

Ile Ile Gln Phe Val His Gly Glu Glu Asp Leu Lys Val Gln His Ser
            530                 535                 540

Ser Tyr Arg Gln Arg Ala Arg Leu Leu Lys Asp Gln Leu Ser Leu Gly
545                 550                 555                 560

Asn Ala Ala Leu Gln Ile Thr Asp Val Lys Leu Gln Asp Ala Gly Val
                565                 570                 575

Tyr Arg Cys Met Ile Ser Tyr Gly Gly Ala Asp Tyr Lys Arg Ile Thr
            580                 585                 590

Val Lys Val Asn Ala Pro Tyr Asn Lys Ile Asn Gln Arg Ile Leu Val
            595                 600                 605

Val Asp Pro Val Thr Ser Glu His Glu Leu Thr Cys Gln Ala Glu Gly
            610                 615                 620

Tyr Pro Lys Ala Glu Val Ile Trp Thr Ser Ser Asp His Gln Val Leu
625                 630                 635                 640

Ser Gly Lys Thr Thr Thr Thr Asn Ser Lys Arg Glu Glu Lys Leu Phe
                645                 650                 655

Asn Val Thr Ser Thr Leu Arg Ile Asn Thr Thr Thr Asn Glu Ile Phe
                660                 665                 670

Tyr Cys Thr Phe Arg Arg Leu Asp Pro Glu Glu Asn His Thr Ala Glu
            675                 680                 685

Leu Val Ile Pro Glu Leu Pro Leu Ala His Pro Pro Asn Glu Arg Thr
            690                 695                 700

His Leu Val Ile Leu Gly Ala Ile Leu Leu Cys Leu Gly Val Ala Leu
705                 710                 715                 720

Thr Phe Ile Phe Arg Leu Arg Lys Gly Arg Met Met Asp Val Lys Lys
                725                 730                 735

Cys Gly Ile Gln Asp Thr Asn Ser Lys Lys Gln Ser Asp Thr His Leu
                740                 745                 750

Glu Glu Thr
            755

-continued

<210> SEQ ID NO 46
<211> LENGTH: 687
<212> TYPE: PRT
<213> ORGANISM: Homo sapiens

<400> SEQUENCE: 46

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Gln Glu Pro Lys Ser Cys Asp Lys Thr His
145                 150                 155                 160

Thr Cys Pro Pro Cys Pro Ala Pro Glu Leu Leu Gly Gly Pro Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys Gly

```
                370              375              380
Gly Gly Ser Gly Gly Gly Ser Gly Gly Gly Ser Arg Ile
385             390             395             400

Phe Ala Val Phe Ile Phe Met Thr Tyr Trp His Leu Leu Asn Ala Phe
                405                 410                 415

Thr Val Thr Val Pro Lys Asp Leu Tyr Val Val Glu Tyr Gly Ser Asn
                420                 425                 430

Met Thr Ile Glu Cys Lys Phe Pro Val Glu Lys Gln Leu Asp Leu Ala
            435                 440                 445

Ala Leu Ile Val Tyr Trp Glu Met Glu Asp Lys Asn Ile Ile Gln Phe
    450                 455                 460

Val His Gly Glu Glu Asp Leu Lys Val Gln His Ser Ser Tyr Arg Gln
465                 470                 475                 480

Arg Ala Arg Leu Leu Lys Asp Gln Leu Ser Leu Gly Asn Ala Ala Leu
                485                 490                 495

Gln Ile Thr Asp Val Lys Leu Gln Asp Ala Gly Val Tyr Arg Cys Met
            500                 505                 510

Ile Ser Tyr Gly Gly Ala Asp Tyr Lys Arg Ile Thr Val Lys Val Asn
    515                 520                 525

Ala Pro Tyr Asn Lys Ile Asn Gln Arg Ile Leu Val Val Asp Pro Val
530                 535                 540

Thr Ser Glu His Glu Leu Thr Cys Gln Ala Glu Gly Tyr Pro Lys Ala
545                 550                 555                 560

Glu Val Ile Trp Thr Ser Ser Asp His Gln Val Leu Ser Gly Lys Thr
                565                 570                 575

Thr Thr Thr Asn Ser Lys Arg Glu Glu Lys Leu Phe Asn Val Thr Ser
            580                 585                 590

Thr Leu Arg Ile Asn Thr Thr Thr Asn Glu Ile Phe Tyr Cys Thr Phe
    595                 600                 605

Arg Arg Leu Asp Pro Glu Glu Asn His Thr Ala Glu Leu Val Ile Pro
610                 615                 620

Glu Leu Pro Leu Ala His Pro Pro Asn Glu Arg Thr His Leu Val Ile
625                 630                 635                 640

Leu Gly Ala Ile Leu Leu Cys Leu Gly Val Ala Leu Thr Phe Ile Phe
                645                 650                 655

Arg Leu Arg Lys Gly Arg Met Met Asp Val Lys Lys Cys Gly Ile Gln
            660                 665                 670

Asp Thr Asn Ser Lys Lys Gln Ser Asp Thr His Leu Glu Glu Thr
    675                 680                 685

<210> SEQ ID NO 47
<211> LENGTH: 678
<212> TYPE: PRT
<213> ORGANISM: Homo sapiens

<400> SEQUENCE: 47

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
    50                  55                  60
```

-continued

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr Gly Gly Gly Gly Ser Gly Gly Gly Gly Ser Gly Gly Gly Gly
    290                 295                 300

Ser Gln Glu Pro Lys Ser Cys Asp Lys Thr His Thr Cys Pro Pro Cys
305                 310                 315                 320

Pro Ala Pro Glu Leu Leu Gly Gly Pro Ser Val Phe Leu Phe Pro Pro
                325                 330                 335

Lys Pro Lys Asp Thr Leu Met Ile Ser Arg Thr Pro Glu Val Thr Cys
            340                 345                 350

Val Val Val Asp Val Ser His Glu Asp Pro Glu Val Lys Phe Asn Trp
        355                 360                 365

Tyr Val Asp Gly Val Glu Val His Asn Ala Lys Thr Lys Pro Arg Glu
    370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Pro Ile Glu Lys Thr Ile Ser Lys Ala Lys Gly
            420                 425                 430

Gln Pro Arg Glu Pro Gln Val Tyr Thr Leu Pro Pro Ser Arg Asp Glu
        435                 440                 445

Leu Thr Lys Asn Gln Val Ser Leu Thr Cys Leu Val Lys Gly Phe Tyr
    450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe

```
                    485                 490                 495
Leu Tyr Ser Lys Leu Thr Val Asp Lys Ser Arg Trp Gln Gln Gly Asn
                500                 505                 510

Val Phe Ser Cys Ser Val Met His Glu Ala Leu His Asn His Tyr Thr
            515                 520                 525

Gln Lys Ser Leu Ser Leu Ser Pro Gly Lys Gly Gly Gly Ser Gly
        530                 535                 540

Gly Gly Gly Ser Gly Gly Gly Ser Ala Met His Val Ala Gln Pro
545                 550                 555                 560

Ala Val Val Leu Ala Ser Ser Arg Gly Ile Ala Ser Phe Val Cys Glu
                565                 570                 575

Tyr Ala Ser Pro Gly Lys Ala Thr Glu Val Arg Val Thr Val Leu Arg
                580                 585                 590

Gln Ala Asp Ser Gln Val Thr Glu Val Cys Ala Ala Thr Tyr Met Met
                595                 600                 605

Gly Asn Glu Leu Thr Phe Leu Asp Asp Ser Ile Cys Thr Gly Thr Ser
                610                 615                 620

Ser Gly Asn Gln Val Asn Leu Thr Ile Gln Gly Leu Arg Ala Met Asp
625                 630                 635                 640

Thr Gly Leu Tyr Ile Cys Lys Val Glu Leu Met Tyr Pro Pro Pro Tyr
                    645                 650                 655

Tyr Leu Gly Ile Gly Asn Gly Thr Gln Ile Tyr Val Ile Asp Pro Glu
                660                 665                 670

Pro Cys Pro Asp Ser Asp
            675

<210> SEQ ID NO 48
<211> LENGTH: 656
<212> TYPE: PRT
<213> ORGANISM: Homo sapiens

<400> SEQUENCE: 48

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
                20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
        50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

Gly Gly Gly Gly Ser Gly Gly Gly Ser Gly Gly Gly Ser Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Asp Val Ser His Glu Asp Pro
                165                 170                 175
```

```
Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

Gly Gly Gly Gly Ser Gly Gly Gly Ser Gly Gly Gly Gly Ser Arg
        355                 360                 365

Ile Phe Ala Val Phe Ile Phe Met Thr Tyr Trp His Leu Leu Asn Ala
370                 375                 380

Phe Thr Val Thr Val Pro Lys Asp Leu Tyr Val Val Glu Tyr Gly Ser
385                 390                 395                 400

Asn Met Thr Ile Glu Cys Lys Phe Pro Val Glu Lys Gln Leu Asp Leu
                405                 410                 415

Ala Ala Leu Ile Val Tyr Trp Glu Met Glu Asp Lys Asn Ile Ile Gln
            420                 425                 430

Phe Val His Gly Glu Glu Asp Leu Lys Val Gln His Ser Ser Tyr Arg
        435                 440                 445

Gln Arg Ala Arg Leu Leu Lys Asp Gln Leu Ser Leu Gly Asn Ala Ala
    450                 455                 460

Leu Gln Ile Thr Asp Val Lys Leu Gln Asp Ala Gly Val Tyr Arg Cys
465                 470                 475                 480

Met Ile Ser Tyr Gly Gly Ala Asp Tyr Lys Arg Ile Thr Val Lys Val
                485                 490                 495

Asn Ala Pro Tyr Asn Lys Ile Asn Gln Arg Ile Leu Val Val Asp Pro
            500                 505                 510

Val Thr Ser Glu His Glu Leu Thr Cys Gln Ala Glu Gly Tyr Pro Lys
        515                 520                 525

Ala Glu Val Ile Trp Thr Ser Ser Asp His Gln Val Leu Ser Gly Lys
    530                 535                 540

Thr Thr Thr Thr Asn Ser Lys Arg Glu Glu Lys Leu Phe Asn Val Thr
545                 550                 555                 560

Ser Thr Leu Arg Ile Asn Thr Thr Thr Asn Glu Ile Phe Tyr Cys Thr
                565                 570                 575

Phe Arg Arg Leu Asp Pro Glu Glu Asn His Thr Ala Glu Leu Val Ile
            580                 585                 590

Pro Glu Leu Pro Leu Ala His Pro Pro Asn Glu Arg Thr His Leu Val
```

```
                595                 600                 605
Ile Leu Gly Ala Ile Leu Leu Cys Leu Gly Val Ala Leu Thr Phe Ile
    610                 615                 620

Phe Arg Leu Arg Lys Gly Arg Met Met Asp Val Lys Lys Cys Gly Ile
625                 630                 635                 640

Gln Asp Thr Asn Ser Lys Lys Gln Ser Asp Thr His Leu Glu Glu Thr
                645                 650                 655

<210> SEQ ID NO 49
<211> LENGTH: 657
<212> TYPE: PRT
<213> ORGANISM: Homo sapiens

<400> SEQUENCE: 49

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
    115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
    195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
    275                 280                 285

Glu Thr Gly Gly Gly Gly Ser Gly Gly Gly Ser Gly Gly Gly Gly
290                 295                 300

Ser Thr His Thr Cys Pro Pro Cys Pro Ala Pro Glu Leu Leu Gly Gly
305                 310                 315                 320
```

```
Pro Ser Val Phe Leu Phe Pro Pro Lys Pro Lys Asp Thr Leu Met Ile
                325                 330                 335

Ser Arg Thr Pro Glu Val Thr Cys Val Val Asp Val Ser His Glu
            340                 345                 350

Asp Pro Glu Val Lys Phe Asn Trp Tyr Val Asp Gly Val Glu Val His
        355                 360                 365

Asn Ala Lys Thr Lys Pro Arg Glu Glu Gln Tyr Asn Ser Thr Tyr Arg
370                 375                 380

Val Val Ser Val Leu Thr Val Leu His Gln Asp Trp Leu Asn Gly Lys
385                 390                 395                 400

Glu Tyr Lys Cys Lys Val Ser Asn Lys Ala Leu Pro Ala Pro Ile Glu
                405                 410                 415

Lys Thr Ile Ser Lys Ala Lys Gly Gln Pro Arg Glu Pro Gln Val Tyr
            420                 425                 430

Thr Leu Pro Pro Ser Arg Glu Glu Met Thr Lys Asn Gln Val Ser Leu
        435                 440                 445

Thr Cys Leu Val Lys Gly Phe Tyr Pro Ser Asp Ile Ala Val Glu Trp
450                 455                 460

Glu Ser Asn Gly Gln Pro Glu Asn Asn Tyr Lys Thr Thr Pro Pro Val
465                 470                 475                 480

Leu Asp Ser Asp Gly Ser Phe Phe Leu Tyr Ser Lys Leu Thr Val Asp
                485                 490                 495

Lys Ser Arg Trp Gln Gln Gly Asn Val Phe Ser Cys Ser Val Met His
            500                 505                 510

Glu Ala Leu His Asn His Tyr Thr Gln Lys Ser Leu Ser Leu Ser Pro
        515                 520                 525

Gly Lys Gly Gly Gly Gly Ser Gly Gly Gly Gly Ser Gly Gly Gly Gly
530                 535                 540

Ser Ala Leu Asp Thr Asn Tyr Cys Phe Ser Ser Thr Glu Lys Asn Cys
545                 550                 555                 560

Cys Val Arg Gln Leu Tyr Ile Asp Phe Arg Lys Asp Leu Gly Trp Lys
                565                 570                 575

Trp Ile His Glu Pro Lys Gly Tyr His Ala Asn Phe Cys Leu Gly Pro
            580                 585                 590

Cys Pro Tyr Ile Trp Ser Leu Asp Thr Gln Tyr Ser Lys Val Leu Ala
        595                 600                 605

Leu Tyr Asn Gln His Asn Pro Gly Ala Ser Ala Ala Pro Cys Cys Val
610                 615                 620

Pro Gln Ala Leu Glu Pro Leu Pro Ile Val Tyr Tyr Val Gly Arg Lys
625                 630                 635                 640

Pro Lys Val Glu Gln Leu Ser Asn Met Ile Val Arg Ser Cys Lys Cys
                645                 650                 655

Ser

<210> SEQ ID NO 50
<211> LENGTH: 578
<212> TYPE: PRT
<213> ORGANISM: Homo sapiens

<400> SEQUENCE: 50

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30
```

-continued

```
Ala Met His Trp Val Arg Gln Ala Pro Gly Lys Gly Leu Glu Trp Val
         35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Leu Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
```

```
                450             455             460
Gly Ser Ala Leu Asp Thr Asn Tyr Cys Phe Ser Ser Thr Glu Lys Asn
465                     470                 475                 480

Cys Cys Val Arg Gln Leu Tyr Ile Asp Phe Arg Lys Asp Leu Gly Trp
                485                 490                 495

Lys Trp Ile His Glu Pro Lys Gly Tyr His Ala Asn Phe Cys Leu Gly
                500                 505                 510

Pro Cys Pro Tyr Ile Trp Ser Leu Asp Thr Gln Tyr Ser Lys Val Leu
                515                 520                 525

Ala Leu Tyr Asn Gln His Asn Pro Gly Ala Ser Ala Ala Pro Cys Cys
                530                 535                 540

Val Pro Gln Ala Leu Glu Pro Leu Pro Ile Val Tyr Tyr Val Gly Arg
545                 550                 555                 560

Lys Pro Lys Val Glu Gln Leu Ser Asn Met Ile Val Arg Ser Cys Lys
                565                 570                 575

Cys Ser

<210> SEQ ID NO 51
<211> LENGTH: 594
<212> TYPE: PRT
<213> ORGANISM: Homo sapiens

<400> SEQUENCE: 51

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
                20                  25                  30

Ser Lys Cys Ser Pro Gly Gln His Ala Lys Val Phe Cys Thr Lys Thr
                35                  40                  45

Ser Asp Thr Val Cys Asp Ser Cys Glu Asp Ser Thr Tyr Thr Gln Leu
            50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
                100                 105                 110

Arg Leu Cys Ala Pro Leu Arg Lys Cys Arg Pro Gly Phe Gly Val Ala
                115                 120                 125

Arg Pro Gly Thr Glu Thr Ser Asp Val Val Cys Lys Pro Cys Ala Pro
            130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
                180                 185                 190

His Leu Pro Gln Pro Val Ser Thr Arg Ser Gln His Thr Gln Pro Thr
                195                 200                 205

Pro Glu Pro Ser Thr Ala Pro Ser Thr Ser Phe Leu Leu Pro Met Gly
                210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
```

Gly Pro Ser Val Phe Leu Phe Pro Pro Lys Pro Lys Asp Thr Leu Met
            245                 250                 255
Ile Ser Arg Thr Pro Glu Val Thr Cys Val Val Val Asp Val Ser His
        260                 265                 270
Glu Asp Pro Glu Val Lys Phe Asn Trp Tyr Val Asp Gly Val Glu Val
    275                 280                 285
His Asn Ala Lys Thr Lys Pro Arg Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
            325                 330                 335
Glu Lys Thr Ile Ser Lys Ala Lys Gly Gln Pro Arg Glu Pro Gln Val
        340                 345                 350
Tyr Thr Leu Pro Pro Ser Arg Glu Glu Met Thr Lys Asn Gln Val Ser
    355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
            405                 410                 415
Asp Lys Ser Arg Trp Gln Gln Gly Asn Val Phe Ser Cys Ser Val Met
        420                 425                 430
His Glu Ala Leu His Asn His Tyr Thr Gln Lys Ser Leu Ser Leu Ser
    435                 440                 445
Pro Gly Lys Gly Gly Gly Ser Gly Gly Gly Ser Gly Gly Gly
450                 455                 460
Gly Ser Ala Leu Asp Thr Asn Tyr Cys Phe Ser Ser Thr Glu Lys Asn
465                 470                 475                 480
Cys Cys Val Arg Gln Leu Tyr Ile Asp Phe Arg Lys Asp Leu Gly Trp
            485                 490                 495
Lys Trp Ile His Glu Pro Lys Gly Tyr His Ala Asn Phe Cys Leu Gly
        500                 505                 510
Pro Cys Pro Tyr Ile Trp Ser Leu Asp Thr Gln Tyr Ser Lys Val Leu
    515                 520                 525
Ala Leu Tyr Asn Gln His Asn Pro Gly Ala Ser Ala Ala Pro Cys Cys
530                 535                 540
Val Pro Gln Ala Leu Glu Pro Leu Pro Ile Val Tyr Tyr Val Gly Arg
545                 550                 555                 560
Lys Pro Lys Val Glu Gln Leu Ser Asn Met Ile Val Arg Ser Cys Lys
            565                 570                 575
Cys Ser
        580                 585                 590

<210> SEQ ID NO 52
<211> LENGTH: 602
<212> TYPE: PRT
<213> ORGANISM: Homo sapiens

<400> SEQUENCE: 52

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp

```
                    20                  25                  30
Ile His Glu Pro Lys Gly Tyr His Ala Asn Phe Cys Leu Gly Pro Cys
            35                  40                  45
Pro Tyr Ile Trp Ser Leu Asp Thr Gln Tyr Ser Lys Val Leu Ala Leu
            50                  55                  60
Tyr Asn Gln His Asn Pro Gly Ala Ser Ala Ala Pro Cys Cys Val Pro
 65                  70                  75                  80
Gln Ala Leu Glu Pro Leu Pro Ile Val Tyr Tyr Val Gly Arg Lys Pro
                    85                  90                  95
Lys Val Glu Gln Leu Ser Asn Met Ile Val Arg Ser Cys Lys Cys Ser
                100                 105                 110
Gly Gly Gly Gly Ser Gly Gly Gly Ser Gly Gly Gly Ser Thr
                115                 120                 125
His Thr Cys Pro Pro Cys Pro Ala Pro Glu Leu Leu Gly Gly Pro Ser
                130                 135                 140
Val Phe Leu Phe Pro Pro Lys Pro Lys Asp Thr Leu Met Ile Ser Arg
145                 150                 155                 160
Thr Pro Glu Val Thr Cys Val Val Asp Val Ser His Glu Asp Pro
                    165                 170                 175
Glu Val Lys Phe Asn Trp Tyr Val Asp Gly Val Glu Val His Asn Ala
                180                 185                 190
Lys Thr Lys Pro Arg Glu Glu Gln Tyr Asn Ser Thr Tyr Arg Val Val
                195                 200                 205
Ser Val Leu Thr Val Leu His Gln Asp Trp Leu Asn Gly Lys Glu Tyr
                210                 215                 220
Lys Cys Lys Val Ser Asn Lys Ala Leu Pro Ala Pro Ile Glu Lys Thr
225                 230                 235                 240
Ile Ser Lys Ala Lys Gly Gln Pro Arg Glu Pro Gln Val Tyr Thr Leu
                245                 250                 255
Pro Pro Ser Arg Glu Glu Met Thr Lys Asn Gln Val Ser Leu Thr Cys
                260                 265                 270
Leu Val Lys Gly Phe Tyr Pro Ser Asp Ile Ala Val Glu Trp Glu Ser
                275                 280                 285
Asn Gly Gln Pro Glu Asn Asn Tyr Lys Thr Thr Pro Pro Val Leu Asp
                290                 295                 300
Ser Asp Gly Ser Phe Phe Leu Tyr Ser Lys Leu Thr Val Asp Lys Ser
305                 310                 315                 320
Arg Trp Gln Gln Gly Asn Val Phe Ser Cys Ser Val Met His Glu Ala
                325                 330                 335
Leu His Asn His Tyr Thr Gln Lys Ser Leu Ser Leu Ser Pro Gly Lys
                340                 345                 350
Gly Gly Gly Gly Ser Gly Gly Gly Ser Gly Gly Gly Gly Ser Leu
                355                 360                 365
Pro Ala Gln Val Ala Phe Thr Pro Tyr Ala Pro Glu Pro Gly Ser Thr
                370                 375                 380
Cys Arg Leu Arg Glu Tyr Tyr Asp Gln Thr Ala Gln Met Cys Cys Ser
385                 390                 395                 400
Lys Cys Ser Pro Gly Gln His Ala Lys Val Phe Cys Thr Lys Thr Ser
                405                 410                 415
Asp Thr Val Cys Asp Ser Cys Glu Asp Ser Thr Tyr Thr Gln Leu Trp
                420                 425                 430
Asn Trp Val Pro Glu Cys Leu Ser Cys Gly Ser Arg Cys Ser Ser Asp
                435                 440                 445
```

```
Gln Val Glu Thr Gln Ala Cys Thr Arg Glu Gln Asn Arg Ile Cys Thr
        450                 455                 460

Cys Arg Pro Gly Trp Tyr Cys Ala Leu Ser Lys Gln Glu Gly Cys Arg
465                 470                 475                 480

Leu Cys Ala Pro Leu Arg Lys Cys Arg Pro Gly Phe Gly Val Ala Arg
                485                 490                 495

Pro Gly Thr Glu Thr Ser Asp Val Val Cys Lys Pro Cys Ala Pro Gly
            500                 505                 510

Thr Phe Ser Asn Thr Thr Ser Ser Thr Asp Ile Cys Arg Pro His Gln
        515                 520                 525

Ile Cys Asn Val Val Ala Ile Pro Gly Asn Ala Ser Met Asp Ala Val
    530                 535                 540

Cys Thr Ser Thr Ser Pro Thr Arg Ser Met Ala Pro Gly Ala Val His
545                 550                 555                 560

Leu Pro Gln Pro Val Ser Thr Arg Ser Gln His Thr Gln Pro Thr Pro
                565                 570                 575

Glu Pro Ser Thr Ala Pro Ser Thr Ser Phe Leu Leu Pro Met Gly Pro
            580                 585                 590

Ser Pro Pro Ala Glu Gly Ser Thr Gly Asp
        595                 600

<210> SEQ ID NO 53
<211> LENGTH: 578
<212> TYPE: PRT
<213> ORGANISM: Homo sapiens

<400> SEQUENCE: 53

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
```

```
        210                 215                 220
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Ser Gly Gly Gly Ser Gly Gly Gly
            450                 455                 460

Gly Ser Ala Leu Asp Thr Asn Tyr Cys Phe Ser Ser Thr Glu Lys Asn
465                 470                 475                 480

Cys Cys Val Arg Gln Leu Tyr Ile Asp Phe Arg Lys Asp Leu Gly Trp
                485                 490                 495

Lys Trp Ile His Glu Pro Lys Gly Tyr His Ala Asn Phe Cys Leu Gly
            500                 505                 510

Pro Cys Pro Tyr Ile Trp Ser Leu Asp Thr Gln Tyr Ser Lys Val Leu
        515                 520                 525

Ala Leu Tyr Asn Gln His Asn Pro Gly Ala Ser Ala Ala Pro Cys Cys
530                 535                 540

Val Pro Gln Ala Leu Glu Pro Leu Pro Ile Val Tyr Tyr Val Gly Arg
545                 550                 555                 560

Lys Pro Lys Val Glu Gln Leu Ser Asn Met Ile Val Arg Ser Cys Lys
                565                 570                 575

Cys Ser

<210> SEQ ID NO 54
<211> LENGTH: 573
<212> TYPE: PRT
<213> ORGANISM: Homo sapiens

<400> SEQUENCE: 54

Gln Val Gln Leu Val Gln Ser Gly Ala Glu Val Lys Lys Pro Gly Ser
```

-continued

```
1               5                   10                  15
Ser Val Lys Val Ser Cys Lys Ala Ser Gly Tyr Thr Phe Thr Ser Tyr
                20                  25                  30

Arg Met His Trp Val Arg Gln Ala Pro Gly Gln Gly Leu Glu Trp Ile
            35                  40                  45

Gly Tyr Ile Asn Pro Ser Thr Gly Tyr Thr Glu Tyr Asn Gln Lys Phe
        50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430
```

```
Asn His Tyr Thr Gln Lys Ser Leu Ser Leu Ser Pro Gly Lys Gly Gly
            435                 440                 445

Gly Gly Ser Gly Gly Gly Ser Gly Gly Gly Ser Ala Leu Asp
        450                 455                 460

Thr Asn Tyr Cys Phe Ser Ser Thr Glu Lys Asn Cys Cys Val Arg Gln
465                 470                 475                 480

Leu Tyr Ile Asp Phe Arg Lys Asp Leu Gly Trp Lys Trp Ile His Glu
                485                 490                 495

Pro Lys Gly Tyr His Ala Asn Phe Cys Leu Gly Pro Cys Pro Tyr Ile
            500                 505                 510

Trp Ser Leu Asp Thr Gln Tyr Ser Lys Val Leu Ala Leu Tyr Asn Gln
            515                 520                 525

His Asn Pro Gly Ala Ser Ala Ala Pro Cys Cys Val Pro Gln Ala Leu
        530                 535                 540

Glu Pro Leu Pro Ile Val Tyr Tyr Val Gly Arg Lys Pro Lys Val Glu
545                 550                 555                 560

Gln Leu Ser Asn Met Ile Val Arg Ser Cys Lys Cys Ser
                565                 570

<210> SEQ ID NO 55
<211> LENGTH: 572
<212> TYPE: PRT
<213> ORGANISM: Homo sapiens

<400> SEQUENCE: 55

Gln Leu Gln Gln Ser Gly Thr Val Leu Ala Arg Pro Gly Ala Ser Val
1               5                   10                  15

Lys Met Ser Cys Lys Ala Ser Gly Tyr Ser Phe Thr Arg Tyr Trp Met
                20                  25                  30

His Trp Ile Lys Gln Arg Pro Gly Gln Gly Leu Glu Trp Ile Gly Ala
            35                  40                  45

Ile Tyr Pro Gly Asn Ser Asp Thr Ser Tyr Asn Gln Lys Phe Glu Gly
        50                  55                  60

Lys Ala Lys Leu Thr Ala Val Thr Ser Ala Ser Thr Ala Tyr Met Glu
65                  70                  75                  80

Leu Ser Ser Leu Thr His Glu Asp Ser Ala Val Tyr Tyr Cys Ser Arg
                85                  90                  95

Asp Tyr Gly Tyr Tyr Phe Asp Phe Trp Gly Gln Gly Thr Thr Leu Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
```

```
            225                 230                 235                 240

Phe Pro Pro Lys Pro Lys Asp Thr Leu Met Ile Ser Arg Thr Pro Glu
                        245                 250                 255

Val Thr Cys Val Val Val Asp Val Ser His Glu Asp Pro Glu Val Lys
                    260                 265                 270

Phe Asn Trp Tyr Val Asp Gly Val Glu Val His Asn Ala Lys Thr Lys
                    275                 280                 285

Pro Arg Glu Glu Gln Tyr Asn Ser Thr Tyr Arg Val Val Ser Val Leu
                290                 295                 300

Thr Val Leu His Gln Asp Trp Leu Asn Gly Lys Glu Tyr Lys Cys Lys
        305                 310                 315                 320

Val Ser Asn Lys Ala Leu Pro Ala Pro Ile Glu Lys Thr Ile Ser Lys
                        325                 330                 335

Ala Lys Gly Gln Pro Arg Glu Pro Gln Val Tyr Thr Leu Pro Pro Ser
                    340                 345                 350

Arg Asp Glu Leu Thr Lys Asn Gln Val Ser Leu Thr Cys Leu Val Lys
                    355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
        385                 390                 395                 400

Ser Phe Phe Leu Tyr Ser Lys Leu Thr Val Asp Lys Ser Arg Trp Gln
                        405                 410                 415

Gln Gly Asn Val Phe Ser Cys Ser Val Met His Glu Ala Leu His Asn
                    420                 425                 430

His Tyr Thr Gln Lys Ser Leu Ser Leu Ser Pro Gly Lys Gly Gly Gly
                    435                 440                 445

Gly Ser Gly Gly Gly Ser Gly Gly Gly Ser Ala Leu Asp Thr
                450                 455                 460

Asn Tyr Cys Phe Ser Ser Thr Glu Lys Asn Cys Cys Val Arg Gln Leu
        465                 470                 475                 480

Tyr Ile Asp Phe Arg Lys Asp Leu Gly Trp Lys Trp Ile His Glu Pro
                        485                 490                 495

Lys Gly Tyr His Ala Asn Phe Cys Leu Gly Pro Cys Pro Tyr Ile Trp
                    500                 505                 510

Ser Leu Asp Thr Gln Tyr Ser Lys Val Leu Ala Leu Tyr Asn Gln His
                    515                 520                 525

Asn Pro Gly Ala Ser Ala Ala Pro Cys Cys Val Pro Gln Ala Leu Glu
                530                 535                 540

Pro Leu Pro Ile Val Tyr Tyr Val Gly Arg Lys Pro Lys Val Glu Gln
        545                 550                 555                 560

Leu Ser Asn Met Ile Val Arg Ser Cys Lys Cys Ser
                        565                 570

<210> SEQ ID NO 56
<211> LENGTH: 500
<212> TYPE: PRT
<213> ORGANISM: Homo sapiens

<400> SEQUENCE: 56

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30
```

-continued

```
Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
 50                  55                  60

Tyr Asn Gln His Asn Pro Gly Ala Ser Ala Ala Pro Cys Cys Val Pro
 65                  70                  75                  80

Gln Ala Leu Glu Pro Leu Pro Ile Val Tyr Tyr Val Gly Arg Lys Pro
                 85                  90                  95

Lys Val Glu Gln Leu Ser Asn Met Ile Val Arg Ser Cys Lys Cys Ser
                100                 105                 110

Gly Gly Gly Gly Ser Gly Gly Gly Ser Gly Gly Gly Gly Ser Thr
                115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
                180                 185                 190

Lys Thr Lys Pro Arg Glu Glu Gln Tyr Asn Ser Thr Tyr Arg Val Val
            195                 200                 205

Ser Val Leu Thr Val Leu His Gln Asp Trp Leu Asn Gly Lys Glu Tyr
        210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

Gly Gly Gly Gly Ser Gly Gly Gly Gly Ser Gly Gly Gly Gly Ser Ala
        355                 360                 365

Pro Thr Ser Ser Ser Thr Lys Lys Thr Gln Leu Gln Leu Glu His Leu
    370                 375                 380

Leu Leu Asp Leu Gln Met Ile Leu Asn Gly Ile Asn Asn Tyr Lys Asn
385                 390                 395                 400

Pro Lys Leu Thr Arg Met Leu Thr Phe Lys Phe Tyr Met Pro Lys Lys
                405                 410                 415

Ala Thr Glu Leu Lys His Leu Gln Cys Leu Glu Glu Glu Leu Lys Pro
            420                 425                 430

Leu Glu Glu Val Leu Asn Leu Ala Gln Ser Lys Asn Phe His Leu Arg
        435                 440                 445

Pro Arg Asp Leu Ile Ser Asn Ile Asn Val Ile Val Leu Glu Leu Lys
```

```
                    450                 455                 460

Gly Ser Glu Thr Thr Phe Met Cys Glu Tyr Ala Asp Glu Thr Ala Thr
465                 470                 475                 480

Ile Val Glu Phe Leu Asn Arg Trp Ile Thr Phe Cys Gln Ser Ile Ile
                    485                 490                 495

Ser Thr Leu Thr
                500

<210> SEQ ID NO 57
<211> LENGTH: 500
<212> TYPE: PRT
<213> ORGANISM: Homo sapiens

<400> SEQUENCE: 57

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr Gly Gly Gly Gly Ser Gly Gly Gly Gly Ser Gly
130                 135                 140

Gly Gly Gly Ser Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
                180                 185                 190

Ser His Glu Asp Pro Glu Val Lys Phe Asn Trp Tyr Val Asp Gly Val
                195                 200                 205

Glu Val His Asn Ala Lys Thr Lys Pro Arg Glu Glu Gln Tyr Asn Ser
                210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
                260                 265                 270

Gln Val Tyr Thr Leu Pro Pro Ser Arg Glu Glu Met Thr Lys Asn Gln
                275                 280                 285

Val Ser Leu Thr Cys Leu Val Lys Gly Phe Tyr Pro Ser Asp Ile Ala
                290                 295                 300

Val Glu Trp Glu Ser Asn Gly Gln Pro Glu Asn Asn Tyr Lys Thr Thr
305                 310                 315                 320
```

-continued

Pro Pro Val Leu Asp Ser Asp Gly Ser Phe Leu Tyr Ser Lys Leu
                325                 330                 335

Thr Val Asp Lys Ser Arg Trp Gln Gln Gly Asn Val Phe Ser Cys Ser
            340                 345                 350

Val Met His Glu Ala Leu His Asn His Tyr Thr Gln Lys Ser Leu Ser
            355                 360                 365

Leu Ser Pro Gly Lys Gly Gly Gly Ser Gly Gly Gly Ser Gly
        370                 375                 380

Gly Gly Gly Ser Ala Leu Asp Thr Asn Tyr Cys Phe Ser Ser Thr Glu
385                 390                 395                 400

Lys Asn Cys Cys Val Arg Gln Leu Tyr Ile Asp Phe Arg Lys Asp Leu
                405                 410                 415

Gly Trp Lys Trp Ile His Glu Pro Lys Gly Tyr His Ala Asn Phe Cys
            420                 425                 430

Leu Gly Pro Cys Pro Tyr Ile Trp Ser Leu Asp Thr Gln Tyr Ser Lys
            435                 440                 445

Val Leu Ala Leu Tyr Asn Gln His Asn Pro Gly Ala Ser Ala Ala Pro
        450                 455                 460

Cys Cys Val Pro Gln Ala Leu Glu Pro Leu Pro Ile Val Tyr Tyr Val
465                 470                 475                 480

Gly Arg Lys Pro Lys Val Glu Gln Leu Ser Asn Met Ile Val Arg Ser
                485                 490                 495

Cys Lys Cys Ser
        500

<210> SEQ ID NO 58
<211> LENGTH: 578
<212> TYPE: PRT
<213> ORGANISM: Homo sapiens

<400> SEQUENCE: 58

Gln Val Gln Leu Gln Glu Ala Gly Pro Gly Leu Val Lys Pro Ser Glu
1               5                   10                  15

Thr Leu Ser Leu Thr Cys Ser Val Ser Gly Gly Ser Ile Ser Gly Asp
            20                  25                  30

Tyr Tyr Trp Phe Trp Ile Arg Gln Ser Pro Gly Lys Gly Leu Glu Trp
        35                  40                  45

Ile Gly Tyr Ile Tyr Gly Ser Gly Gly Thr Asn Tyr Asn Pro Ser
    50                  55                  60

Leu Asn Asn Arg Val Ser Ile Ser Ile Asp Thr Ser Lys Asn Leu Phe
65                  70                  75                  80

Ser Leu Lys Leu Arg Ser Val Thr Ala Ala Asp Thr Ala Val Tyr Tyr
                85                  90                  95

Cys Ala Ser Asn Ile Leu Lys Tyr Leu His Trp Leu Leu Tyr Trp Gly
            100                 105                 110

Gln Gly Val Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

```
Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Ser Gly Gly Gly Gly
    450                 455                 460

Gly Ser Ala Leu Asp Thr Asn Tyr Cys Phe Ser Ser Thr Glu Lys Asn
465                 470                 475                 480

Cys Cys Val Arg Gln Leu Tyr Ile Asp Phe Arg Lys Asp Leu Gly Trp
                485                 490                 495

Lys Trp Ile His Glu Pro Lys Gly Tyr His Ala Asn Phe Cys Leu Gly
            500                 505                 510

Pro Cys Pro Tyr Ile Trp Ser Leu Asp Thr Gln Tyr Ser Lys Val Leu
        515                 520                 525

Ala Leu Tyr Asn Gln His Asn Pro Gly Ala Ser Ala Ala Pro Cys Cys
    530                 535                 540

Val Pro Gln Ala Leu Glu Pro Leu Pro Ile Val Tyr Tyr Val Gly Arg
545                 550                 555                 560

Lys Pro Lys Val Glu Gln Leu Ser Asn Met Ile Val Arg Ser Cys Lys
                565                 570                 575

Cys Ser
```

<210> SEQ ID NO 59
<211> LENGTH: 510
<212> TYPE: PRT

<213> ORGANISM: Homo sapiens

<400> SEQUENCE: 59

```
Met Gly Val Leu Leu Thr Gln Arg Thr Leu Leu Ser Leu Val Leu Ala
1               5                   10                  15
Leu Leu Phe Pro Ser Met Ala Ser Met Ala Met His Val Ala Gln Pro
            20                  25                  30
Ala Val Val Leu Ala Ser Ser Arg Gly Ile Ala Ser Phe Val Cys Glu
        35                  40                  45
Tyr Ala Ser Pro Gly Lys Ala Thr Glu Val Arg Val Thr Val Leu Arg
50                  55                  60
Gln Ala Asp Ser Gln Val Thr Glu Val Cys Ala Ala Thr Tyr Met Met
65                  70                  75                  80
Gly Asn Glu Leu Thr Phe Leu Asp Asp Ser Ile Cys Thr Gly Thr Ser
                85                  90                  95
Ser Gly Asn Gln Val Asn Leu Thr Ile Gln Gly Leu Arg Ala Met Asp
            100                 105                 110
Thr Gly Leu Tyr Ile Cys Lys Val Glu Leu Met Tyr Pro Pro Pro Tyr
        115                 120                 125
Tyr Leu Gly Ile Gly Asn Gly Thr Gln Ile Tyr Val Ile Asp Pro Glu
130                 135                 140
Pro Cys Pro Asp Ser Asp Gln Glu Pro Lys Ser Cys Asp Lys Thr His
145                 150                 155                 160
Thr Cys Pro Pro Cys Pro Ala Pro Glu Leu Leu Gly Gly Pro Ser Val
                165                 170                 175
Phe Leu Phe Pro Pro Lys Pro Lys Asp Thr Leu Met Ile Ser Arg Thr
            180                 185                 190
Pro Glu Val Thr Cys Val Val Val Asp Val Ser His Glu Asp Pro Glu
        195                 200                 205
Val Lys Phe Asn Trp Tyr Val Asp Gly Val Glu Val His Asn Ala Lys
210                 215                 220
Thr Lys Pro Arg Glu Glu Gln Tyr Asn Ser Thr Tyr Arg Val Val Ser
225                 230                 235                 240
Val Leu Thr Val Leu His Gln Asp Trp Leu Asn Gly Lys Glu Tyr Lys
                245                 250                 255
Cys Lys Val Ser Asn Lys Ala Leu Pro Ala Pro Ile Glu Lys Thr Ile
            260                 265                 270
Ser Lys Ala Lys Gly Gln Pro Arg Glu Pro Gln Val Tyr Thr Leu Pro
        275                 280                 285
Pro Ser Arg Asp Glu Leu Thr Lys Asn Gln Val Ser Leu Thr Cys Leu
290                 295                 300
Val Lys Gly Phe Tyr Pro Ser Asp Ile Ala Val Glu Trp Glu Ser Asn
305                 310                 315                 320
Gly Gln Pro Glu Asn Asn Tyr Lys Thr Thr Pro Pro Val Leu Asp Ser
                325                 330                 335
Asp Gly Ser Phe Phe Leu Tyr Ser Lys Leu Thr Val Asp Lys Ser Arg
            340                 345                 350
Trp Gln Gln Gly Asn Val Phe Ser Cys Ser Val Met His Glu Ala Leu
        355                 360                 365
His Asn His Tyr Thr Gln Lys Ser Leu Ser Leu Ser Pro Gly Lys Gly
370                 375                 380
Gly Gly Gly Ser Gly Gly Gly Ser Gly Gly Gly Gly Ser Ala Leu
385                 390                 395                 400
```

```
Asp Thr Asn Tyr Cys Phe Ser Ser Thr Glu Lys Asn Cys Cys Val Arg
                405                 410                 415

Gln Leu Tyr Ile Asp Phe Arg Lys Asp Leu Gly Trp Lys Trp Ile His
        420                 425                 430

Glu Pro Lys Gly Tyr His Ala Asn Phe Cys Leu Gly Pro Cys Pro Tyr
            435                 440                 445

Ile Trp Ser Leu Asp Thr Gln Tyr Ser Lys Val Leu Ala Leu Tyr Asn
    450                 455                 460

Gln His Asn Pro Gly Ala Ser Ala Ala Pro Cys Cys Val Pro Gln Ala
465                 470                 475                 480

Leu Glu Pro Leu Pro Ile Val Tyr Tyr Val Gly Arg Lys Pro Lys Val
                485                 490                 495

Glu Gln Leu Ser Asn Met Ile Val Arg Ser Cys Lys Cys Ser
                500                 505                 510

<210> SEQ ID NO 60
<211> LENGTH: 484
<212> TYPE: PRT
<213> ORGANISM: Homo sapiens

<400> SEQUENCE: 60

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
                20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
                100                 105                 110

Glu Pro Lys Ser Cys Asp Lys Thr His Thr Cys Pro Pro Cys Pro Ala
            115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
                180                 185                 190

Tyr Asn Ser Thr Tyr Arg Val Val Ser Val Leu Thr Val Leu His Gln
            195                 200                 205

Asp Trp Leu Asn Gly Lys Glu Tyr Lys Cys Lys Val Ser Asn Lys Ala
    210                 215                 220

Leu Pro Ala Pro Ile Glu Lys Thr Ile Ser Lys Ala Lys Gly Gln Pro
225                 230                 235                 240

Arg Glu Pro Gln Val Tyr Thr Leu Pro Pro Ser Arg Asp Glu Leu Thr
                245                 250                 255

Lys Asn Gln Val Ser Leu Thr Cys Leu Val Lys Gly Phe Tyr Pro Ser
                260                 265                 270
```

```
Asp Ile Ala Val Glu Trp Glu Ser Asn Gly Gln Pro Glu Asn Asn Tyr
            275                 280                 285

Lys Thr Thr Pro Pro Val Leu Asp Ser Asp Gly Ser Phe Phe Leu Tyr
        290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys Gly Gly Gly Ser Gly Gly Gly
            340                 345                 350

Gly Ser Gly Gly Gly Ser Ala Met His Val Ala Gln Pro Ala Val
            355                 360                 365

Val Leu Ala Ser Ser Arg Gly Ile Ala Ser Phe Val Cys Glu Tyr Ala
        370                 375                 380

Ser Pro Gly Lys Ala Thr Glu Val Arg Val Thr Val Leu Arg Gln Ala
385                 390                 395                 400

Asp Ser Gln Val Thr Glu Val Cys Ala Ala Thr Tyr Met Met Gly Asn
                405                 410                 415

Glu Leu Thr Phe Leu Asp Asp Ser Ile Cys Thr Gly Thr Ser Ser Gly
            420                 425                 430

Asn Gln Val Asn Leu Thr Ile Gln Gly Leu Arg Ala Met Asp Thr Gly
            435                 440                 445

Leu Tyr Ile Cys Lys Val Glu Leu Met Tyr Pro Pro Pro Tyr Tyr Leu
            450                 455                 460

Gly Ile Gly Asn Gly Thr Gln Ile Tyr Val Ile Asp Pro Glu Pro Cys
465                 470                 475                 480

Pro Asp Ser Asp

<210> SEQ ID NO 61
<211> LENGTH: 651
<212> TYPE: PRT
<213> ORGANISM: Homo sapiens

<400> SEQUENCE: 61

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Leu Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys Gly Gly Gly Gly Ser Gly Gly Gly Ser Gly Gly Gly Gly
        450                 455                 460

Gly Ser Gln Ile Ala Pro Pro Cys Thr Ser Glu Lys His Tyr Glu His
465                 470                 475                 480

Leu Gly Arg Cys Cys Asn Lys Cys Glu Pro Gly Lys Tyr Met Ser Ser
                485                 490                 495

Lys Cys Thr Thr Thr Ser Asp Ser Val Cys Leu Pro Cys Gly Pro Asp
                500                 505                 510

Glu Tyr Leu Asp Ser Trp Asn Glu Glu Asp Lys Cys Leu Leu His Lys
            515                 520                 525

Val Cys Asp Thr Gly Lys Ala Leu Val Ala Val Ala Gly Asn Ser
        530                 535                 540

Thr Thr Pro Arg Arg Cys Ala Cys Thr Ala Gly Tyr His Trp Ser Gln
545                 550                 555                 560

Asp Cys Glu Cys Cys Arg Arg Asn Thr Glu Cys Ala Pro Gly Leu Gly
                565                 570                 575
```

```
Ala Gln His Pro Leu Gln Leu Asn Lys Asp Thr Val Cys Lys Pro Cys
            580                 585                 590

Leu Ala Gly Tyr Phe Ser Asp Ala Phe Ser Ser Thr Asp Lys Cys Arg
        595                 600                 605

Pro Trp Thr Asn Cys Thr Phe Leu Gly Lys Arg Val Glu His His Gly
    610                 615                 620

Thr Glu Lys Ser Asp Ala Val Cys Ser Ser Ser Leu Pro Ala Arg Lys
625                 630                 635                 640

Pro Pro Asn Glu Pro His Val Tyr Leu Pro Gly
                645                 650

<210> SEQ ID NO 62
<211> LENGTH: 667
<212> TYPE: PRT
<213> ORGANISM: Homo sapiens

<400> SEQUENCE: 62

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300
```

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys Gly Gly Gly Gly Ser Gly Gly Gly Gly Ser Gly Gly Gly
465                 470                 475                 480

Gly Ser Gln Ile Ala Pro Pro Cys Thr Ser Glu Lys His Tyr Glu His
                485                 490                 495

Leu Gly Arg Cys Cys Asn Lys Cys Glu Pro Gly Lys Tyr Met Ser Ser
            500                 505                 510

Lys Cys Thr Thr Thr Ser Asp Ser Val Cys Leu Pro Cys Gly Pro Asp
        515                 520                 525

Glu Tyr Leu Asp Ser Trp Asn Glu Glu Asp Lys Cys Leu Leu His Lys
    530                 535                 540

Val Cys Asp Thr Gly Lys Ala Leu Val Ala Val Ala Gly Asn Ser
545                 550                 555                 560

Thr Thr Pro Arg Arg Cys Ala Cys Thr Ala Gly Tyr His Trp Ser Gln
                565                 570                 575

Asp Cys Glu Cys Cys Arg Arg Asn Thr Glu Cys Ala Pro Gly Leu Gly
            580                 585                 590

Ala Gln His Pro Leu Gln Leu Asn Lys Asp Thr Val Cys Lys Pro Cys
        595                 600                 605

Leu Ala Gly Tyr Phe Ser Asp Ala Phe Ser Ser Thr Asp Lys Cys Arg
    610                 615                 620

Pro Trp Thr Asn Cys Thr Phe Leu Gly Lys Arg Val Glu His His Gly
625                 630                 635                 640

Thr Glu Lys Ser Asp Ala Val Cys Ser Ser Ser Leu Pro Ala Arg Lys
                645                 650                 655

Pro Pro Asn Glu Pro His Val Tyr Leu Pro Gly
            660                 665

<210> SEQ ID NO 63
<211> LENGTH: 675
<212> TYPE: PRT
<213> ORGANISM: Homo sapiens

<400> SEQUENCE: 63

Gln Ile Ala Pro Pro Cys Thr Ser Glu Lys His Tyr Glu His Leu Gly

-continued

```
1               5                   10                  15
Arg Cys Cys Asn Lys Cys Glu Pro Gly Lys Tyr Met Ser Ser Lys Cys
                20                  25                  30

Thr Thr Thr Ser Asp Ser Val Cys Leu Pro Cys Gly Pro Asp Glu Tyr
            35                  40                  45

Leu Asp Ser Trp Asn Glu Glu Asp Lys Cys Leu Leu His Lys Val Cys
        50                  55                  60

Asp Thr Gly Lys Ala Leu Val Ala Val Ala Gly Asn Ser Thr Thr
65                  70                  75                  80

Pro Arg Arg Cys Ala Cys Thr Ala Gly Tyr His Trp Ser Gln Asp Cys
                85                  90                  95

Glu Cys Cys Arg Arg Asn Thr Glu Cys Ala Pro Gly Leu Gly Ala Gln
                100                 105                 110

His Pro Leu Gln Leu Asn Lys Asp Thr Val Cys Lys Pro Cys Leu Ala
            115                 120                 125

Gly Tyr Phe Ser Asp Ala Phe Ser Ser Thr Asp Lys Cys Arg Pro Trp
        130                 135                 140

Thr Asn Cys Thr Phe Leu Gly Lys Arg Val Glu His His Gly Thr Glu
145                 150                 155                 160

Lys Ser Asp Ala Val Cys Ser Ser Ser Leu Pro Ala Arg Lys Pro Pro
                165                 170                 175

Asn Glu Pro His Val Tyr Leu Pro Gly Gly Gly Gly Ser Gly Gly
            180                 185                 190

Gly Gly Ser Gly Gly Gly Gly Ser Thr His Thr Cys Pro Pro Cys Pro
        195                 200                 205

Ala Pro Glu Leu Leu Gly Gly Pro Ser Val Phe Leu Phe Pro Pro Lys
210                 215                 220

Pro Lys Asp Thr Leu Met Ile Ser Arg Thr Pro Glu Val Thr Cys Val
225                 230                 235                 240

Val Val Asp Val Ser His Glu Asp Pro Glu Val Lys Phe Asn Trp Tyr
                245                 250                 255

Val Asp Gly Val Glu Val His Asn Ala Lys Thr Lys Pro Arg Glu Glu
            260                 265                 270

Gln Tyr Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
    290                 295                 300

Ala Leu Pro Ala Pro Ile Glu Lys Thr Ile Ser Lys Ala Lys Gly Gln
305                 310                 315                 320

Pro Arg Glu Pro Gln Val Tyr Thr Leu Pro Pro Ser Arg Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Phe Leu
    370                 375                 380

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Pro Gly Lys Gly Gly Gly Gly Ser Gly Gly
            420                 425                 430
```

Gly Gly Ser Gly Gly Gly Ser Leu Pro Ala Gln Val Ala Phe Thr
            435                 440                 445

Pro Tyr Ala Pro Glu Pro Gly Ser Thr Cys Arg Leu Arg Glu Tyr Tyr
450                 455                 460

Asp Gln Thr Ala Gln Met Cys Cys Ser Lys Cys Ser Pro Gly Gln His
465                 470                 475                 480

Ala Lys Val Phe Cys Thr Lys Thr Ser Asp Thr Val Cys Asp Ser Cys
            485                 490                 495

Glu Asp Ser Thr Tyr Thr Gln Leu Trp Asn Trp Val Pro Glu Cys Leu
            500                 505                 510

Ser Cys Gly Ser Arg Cys Ser Ser Asp Gln Val Glu Thr Gln Ala Cys
            515                 520                 525

Thr Arg Glu Gln Asn Arg Ile Cys Thr Cys Arg Pro Gly Trp Tyr Cys
            530                 535                 540

Ala Leu Ser Lys Gln Glu Gly Cys Arg Leu Cys Ala Pro Leu Arg Lys
545                 550                 555                 560

Cys Arg Pro Gly Phe Gly Val Ala Arg Pro Gly Thr Glu Thr Ser Asp
                565                 570                 575

Val Val Cys Lys Pro Cys Ala Pro Gly Thr Phe Ser Asn Thr Thr Ser
            580                 585                 590

Ser Thr Asp Ile Cys Arg Pro His Gln Ile Cys Asn Val Val Ala Ile
            595                 600                 605

Pro Gly Asn Ala Ser Met Asp Ala Val Cys Thr Ser Thr Ser Pro Thr
610                 615                 620

Arg Ser Met Ala Pro Gly Ala Val His Leu Pro Gln Pro Val Ser Thr
625                 630                 635                 640

Arg Ser Gln His Thr Gln Pro Thr Pro Glu Pro Ser Thr Ala Pro Ser
                645                 650                 655

Thr Ser Phe Leu Leu Pro Met Gly Pro Ser Pro Pro Ala Glu Gly Ser
            660                 665                 670

Thr Gly Asp
        675

<210> SEQ ID NO 64
<211> LENGTH: 583
<212> TYPE: PRT
<213> ORGANISM: Homo sapiens

<400> SEQUENCE: 64

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr

-continued

```
            115                 120                 125
Tyr Leu Gly Ile Gly Asn Gly Thr Gln Ile Tyr Val Ile Asp Pro Glu
        130                 135                 140
Pro Cys Pro Asp Ser Asp Gln Glu Pro Lys Ser Cys Asp Lys Thr His
145                 150                 155                 160
Thr Cys Pro Pro Cys Pro Ala Pro Glu Leu Leu Gly Gly Pro Ser Val
                165                 170                 175
Phe Leu Phe Pro Pro Lys Pro Lys Asp Thr Leu Met Ile Ser Arg Thr
            180                 185                 190
Pro Glu Val Thr Cys Val Val Val Asp Val Ser His Glu Asp Pro Glu
        195                 200                 205
Val Lys Phe Asn Trp Tyr Val Asp Gly Val Glu Val His Asn Ala Lys
    210                 215                 220
Thr Lys Pro Arg Glu Glu Gln Tyr Asn Ser Thr Tyr Arg Val Val Ser
225                 230                 235                 240
Val Leu Thr Val Leu His Gln Asp Trp Leu Asn Gly Lys Glu Tyr Lys
                245                 250                 255
Cys Lys Val Ser Asn Lys Ala Leu Pro Ala Pro Ile Glu Lys Thr Ile
            260                 265                 270
Ser Lys Ala Lys Gly Gln Pro Arg Glu Pro Gln Val Tyr Thr Leu Pro
        275                 280                 285
Pro Ser Arg Asp Glu Leu Thr Lys Asn Gln Val Ser Leu Thr Cys Leu
    290                 295                 300
Val Lys Gly Phe Tyr Pro Ser Asp Ile Ala Val Glu Trp Glu Ser Asn
305                 310                 315                 320
Gly Gln Pro Glu Asn Asn Tyr Lys Thr Thr Pro Pro Val Leu Asp Ser
                325                 330                 335
Asp Gly Ser Phe Phe Leu Tyr Ser Lys Leu Thr Val Asp Lys Ser Arg
            340                 345                 350
Trp Gln Gln Gly Asn Val Phe Ser Cys Ser Val Met His Glu Ala Leu
        355                 360                 365
His Asn His Tyr Thr Gln Lys Ser Leu Ser Leu Ser Pro Gly Lys Gly
    370                 375                 380
Gly Gly Gly Ser Gly Gly Gly Ser Gly Gly Gly Ser Gln Ile
385                 390                 395                 400
Ala Pro Pro Cys Thr Ser Glu Lys His Tyr Glu His Leu Gly Arg Cys
                405                 410                 415
Cys Asn Lys Cys Glu Pro Gly Lys Tyr Met Ser Ser Lys Cys Thr Thr
            420                 425                 430
Thr Ser Asp Ser Val Cys Leu Pro Cys Gly Pro Asp Glu Tyr Leu Asp
        435                 440                 445
Ser Trp Asn Glu Glu Asp Lys Cys Leu Leu His Lys Val Cys Asp Thr
    450                 455                 460
Gly Lys Ala Leu Val Ala Val Val Ala Gly Asn Ser Thr Thr Pro Arg
465                 470                 475                 480
Arg Cys Ala Cys Thr Ala Gly Tyr His Trp Ser Gln Asp Cys Glu Cys
                485                 490                 495
Cys Arg Arg Asn Thr Glu Cys Ala Pro Gly Leu Gly Ala Gln His Pro
            500                 505                 510
Leu Gln Leu Asn Lys Asp Thr Val Cys Lys Pro Cys Leu Ala Gly Tyr
        515                 520                 525
Phe Ser Asp Ala Phe Ser Ser Thr Asp Lys Cys Arg Pro Trp Thr Asn
    530                 535                 540
```

```
Cys Thr Phe Leu Gly Lys Arg Val Glu His His Gly Thr Glu Lys Ser
545                 550                 555                 560

Asp Ala Val Cys Ser Ser Ser Leu Pro Ala Arg Lys Pro Pro Asn Glu
            565                 570                 575

Pro His Val Tyr Leu Pro Gly
            580
```

<210> SEQ ID NO 65
<211> LENGTH: 557
<212> TYPE: PRT
<213> ORGANISM: Homo sapiens

<400> SEQUENCE: 65

```
Gln Ile Ala Pro Pro Cys Thr Ser Glu Lys His Tyr Glu His Leu Gly
1               5                   10                  15

Arg Cys Cys Asn Lys Cys Glu Pro Gly Lys Tyr Met Ser Ser Lys Cys
                20                  25                  30

Thr Thr Thr Ser Asp Ser Val Cys Leu Pro Cys Gly Pro Asp Glu Tyr
            35                  40                  45

Leu Asp Ser Trp Asn Glu Glu Asp Lys Cys Leu Leu His Lys Val Cys
50                  55                  60

Asp Thr Gly Lys Ala Leu Val Ala Val Ala Gly Asn Ser Thr Thr
65                  70                  75                  80

Pro Arg Arg Cys Ala Cys Thr Ala Gly Tyr His Trp Ser Gln Asp Cys
                85                  90                  95

Glu Cys Cys Arg Arg Asn Thr Glu Cys Ala Pro Gly Leu Gly Ala Gln
            100                 105                 110

His Pro Leu Gln Leu Asn Lys Asp Thr Val Cys Lys Pro Cys Leu Ala
            115                 120                 125

Gly Tyr Phe Ser Asp Ala Phe Ser Ser Thr Asp Lys Cys Arg Pro Trp
130                 135                 140

Thr Asn Cys Thr Phe Leu Gly Lys Arg Val Glu His His Gly Thr Glu
145                 150                 155                 160

Lys Ser Asp Ala Val Cys Ser Ser Ser Leu Pro Ala Arg Lys Pro Pro
                165                 170                 175

Asn Glu Pro His Val Tyr Leu Pro Gly Glu Pro Lys Ser Cys Asp Lys
            180                 185                 190

Thr His Thr Cys Pro Pro Cys Pro Ala Pro Glu Leu Leu Gly Gly Pro
            195                 200                 205

Ser Val Phe Leu Phe Pro Pro Lys Pro Lys Asp Thr Leu Met Ile Ser
210                 215                 220

Arg Thr Pro Glu Val Thr Cys Val Val Val Asp Val Ser His Glu Asp
225                 230                 235                 240

Pro Glu Val Lys Phe Asn Trp Tyr Val Asp Gly Val Glu Val His Asn
                245                 250                 255

Ala Lys Thr Lys Pro Arg Glu Glu Gln Tyr Asn Ser Thr Tyr Arg Val
            260                 265                 270

Val Ser Val Leu Thr Val Leu His Gln Asp Trp Leu Asn Gly Lys Glu
        275                 280                 285

Tyr Lys Cys Lys Val Ser Asn Lys Ala Leu Pro Ala Pro Ile Glu Lys
290                 295                 300

Thr Ile Ser Lys Ala Lys Gly Gln Pro Arg Glu Pro Gln Val Tyr Thr
305                 310                 315                 320

Leu Pro Pro Ser Arg Asp Glu Leu Thr Lys Asn Gln Val Ser Leu Thr
```

```
                   325                 330                 335
Cys Leu Val Lys Gly Phe Tyr Pro Ser Asp Ile Ala Val Glu Trp Glu
            340                 345                 350

Ser Asn Gly Gln Pro Glu Asn Asn Tyr Lys Thr Thr Pro Pro Val Leu
        355                 360                 365

Asp Ser Asp Gly Ser Phe Phe Leu Tyr Ser Lys Leu Thr Val Asp Lys
    370                 375                 380

Ser Arg Trp Gln Gln Gly Asn Val Phe Ser Cys Ser Val Met His Glu
385                 390                 395                 400

Ala Leu His Asn His Tyr Thr Gln Lys Ser Leu Ser Leu Ser Pro Gly
                405                 410                 415

Lys Gly Gly Gly Gly Ser Gly Gly Gly Gly Ser Gly Gly Gly Gly Ser
            420                 425                 430

Ala Met His Val Ala Gln Pro Ala Val Val Leu Ala Ser Ser Arg Gly
        435                 440                 445

Ile Ala Ser Phe Val Cys Glu Tyr Ala Ser Pro Gly Lys Ala Thr Glu
    450                 455                 460

Val Arg Val Thr Val Leu Arg Gln Ala Asp Ser Gln Val Thr Glu Val
465                 470                 475                 480

Cys Ala Ala Thr Tyr Met Met Gly Asn Glu Leu Thr Phe Leu Asp Asp
                485                 490                 495

Ser Ile Cys Thr Gly Thr Ser Ser Gly Asn Gln Val Asn Leu Thr Ile
            500                 505                 510

Gln Gly Leu Arg Ala Met Asp Thr Gly Leu Tyr Ile Cys Lys Val Glu
        515                 520                 525

Leu Met Tyr Pro Pro Pro Tyr Tyr Leu Gly Ile Gly Asn Gly Thr Gln
    530                 535                 540

Ile Tyr Val Ile Asp Pro Glu Pro Cys Pro Asp Ser Asp
545                 550                 555

<210> SEQ ID NO 66
<211> LENGTH: 552
<212> TYPE: PRT
<213> ORGANISM: Homo sapiens

<400> SEQUENCE: 66

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

Gly Gly Gly Gly Ser Gly Gly Gly Gly Ser Gly Gly Gly Gly Ser Thr
        115                 120                 125

His Thr Cys Pro Pro Cys Pro Ala Pro Glu Leu Leu Gly Gly Pro Ser
    130                 135                 140
```

```
Val Phe Leu Phe Pro Pro Lys Pro Lys Asp Thr Leu Met Ile Ser Arg
145                 150                 155                 160

Thr Pro Glu Val Thr Cys Val Val Asp Val Ser His Glu Asp Pro
            165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
            245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
            325                 330                 335

Leu His Asn His Tyr Thr Gln Lys Ser Leu Ser Leu Ser Pro Gly Lys
            340                 345                 350

Gly Gly Gly Gly Ser Gly Gly Gly Gly Ser Gly Gly Gly Gly Ser Gln
        355                 360                 365

Ile Ala Pro Pro Cys Thr Ser Glu Lys His Tyr Glu His Leu Gly Arg
    370                 375                 380

Cys Cys Asn Lys Cys Glu Pro Gly Lys Tyr Met Ser Ser Lys Cys Thr
385                 390                 395                 400

Thr Thr Ser Asp Ser Val Cys Leu Pro Cys Gly Pro Asp Glu Tyr Leu
            405                 410                 415

Asp Ser Trp Asn Glu Glu Asp Lys Cys Leu Leu His Lys Val Cys Asp
            420                 425                 430

Thr Gly Lys Ala Leu Val Ala Val Ala Gly Asn Ser Thr Thr Pro
        435                 440                 445

Arg Arg Cys Ala Cys Thr Ala Gly Tyr His Trp Ser Gln Asp Cys Glu
    450                 455                 460

Cys Cys Arg Arg Asn Thr Glu Cys Ala Pro Gly Leu Gly Ala Gln His
465                 470                 475                 480

Pro Leu Gln Leu Asn Lys Asp Thr Val Cys Lys Pro Cys Leu Ala Gly
            485                 490                 495

Tyr Phe Ser Asp Ala Phe Ser Thr Asp Lys Cys Arg Pro Trp Thr
            500                 505                 510

Asn Cys Thr Phe Leu Gly Lys Arg Val Glu His His Gly Thr Glu Lys
        515                 520                 525

Ser Asp Ala Val Cys Ser Ser Leu Pro Ala Arg Lys Pro Pro Asn
    530                 535                 540

Glu Pro His Val Tyr Leu Pro Gly
545                 550
```

```
<210> SEQ ID NO 67
<211> LENGTH: 552
<212> TYPE: PRT
<213> ORGANISM: Homo sapiens

<400> SEQUENCE: 67

Gln Ile Ala Pro Pro Cys Thr Ser Glu Lys His Tyr Glu His Leu Gly
1               5                   10                  15

Arg Cys Cys Asn Lys Cys Glu Pro Gly Lys Tyr Met Ser Ser Lys Cys
            20                  25                  30

Thr Thr Thr Ser Asp Ser Val Cys Leu Pro Cys Gly Pro Asp Glu Tyr
        35                  40                  45

Leu Asp Ser Trp Asn Glu Glu Asp Lys Cys Leu Leu His Lys Val Cys
    50                  55                  60

Asp Thr Gly Lys Ala Leu Val Ala Val Ala Gly Asn Ser Thr Thr
65                  70                  75                  80

Pro Arg Arg Cys Ala Cys Thr Ala Gly Tyr His Trp Ser Gln Asp Cys
                85                  90                  95

Glu Cys Cys Arg Arg Asn Thr Glu Cys Ala Pro Gly Leu Gly Ala Gln
            100                 105                 110

His Pro Leu Gln Leu Asn Lys Asp Thr Val Cys Lys Pro Cys Leu Ala
        115                 120                 125

Gly Tyr Phe Ser Asp Ala Phe Ser Ser Thr Asp Lys Cys Arg Pro Trp
    130                 135                 140

Thr Asn Cys Thr Phe Leu Gly Lys Arg Val Glu His His Gly Thr Glu
145                 150                 155                 160

Lys Ser Asp Ala Val Cys Ser Ser Ser Leu Pro Ala Arg Lys Pro Pro
                165                 170                 175

Asn Glu Pro His Val Tyr Leu Pro Gly Gly Gly Gly Ser Gly Gly
            180                 185                 190

Gly Gly Ser Gly Gly Gly Gly Ser Thr His Thr Cys Pro Pro Cys Pro
        195                 200                 205

Ala Pro Glu Leu Leu Gly Gly Pro Ser Val Phe Leu Phe Pro Pro Lys
    210                 215                 220

Pro Lys Asp Thr Leu Met Ile Ser Arg Thr Pro Glu Val Thr Cys Val
225                 230                 235                 240

Val Val Asp Val Ser His Glu Asp Pro Glu Val Lys Phe Asn Trp Tyr
                245                 250                 255

Val Asp Gly Val Glu Val His Asn Ala Lys Thr Lys Pro Arg Glu Glu
            260                 265                 270

Gln Tyr Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
    290                 295                 300

Ala Leu Pro Ala Pro Ile Glu Lys Thr Ile Ser Lys Ala Lys Gly Gln
305                 310                 315                 320

Pro Arg Glu Pro Gln Val Tyr Thr Leu Pro Pro Ser Arg Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Phe Leu
    370                 375                 380
```

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
            405                 410                 415

Lys Ser Leu Ser Leu Ser Pro Gly Lys Gly Gly Gly Ser Gly Gly
            420                 425                 430

Gly Gly Ser Gly Gly Gly Ser Ala Leu Asp Thr Asn Tyr Cys Phe
            435                 440                 445

Ser Ser Thr Glu Lys Asn Cys Cys Val Arg Gln Leu Tyr Ile Asp Phe
450                 455                 460

Arg Lys Asp Leu Gly Trp Lys Trp Ile His Glu Pro Lys Gly Tyr His
465                 470                 475                 480

Ala Asn Phe Cys Leu Gly Pro Cys Pro Tyr Ile Trp Ser Leu Asp Thr
            485                 490                 495

Gln Tyr Ser Lys Val Leu Ala Leu Tyr Asn Gln His Asn Pro Gly Ala
            500                 505                 510

Ser Ala Ala Pro Cys Cys Val Pro Gln Ala Leu Glu Pro Leu Pro Ile
            515                 520                 525

Val Tyr Tyr Val Gly Arg Lys Pro Lys Val Glu Gln Leu Ser Asn Met
530                 535                 540

Ile Val Arg Ser Cys Lys Cys Ser
545                 550

<210> SEQ ID NO 68
<211> LENGTH: 729
<212> TYPE: PRT
<213> ORGANISM: Homo sapiens

<400> SEQUENCE: 68

Arg Ile Phe Ala Val Phe Ile Phe Met Thr Tyr Trp His Leu Leu Asn
1               5                   10                  15

Ala Phe Thr Val Thr Val Pro Lys Asp Leu Tyr Val Val Glu Tyr Gly
            20                  25                  30

Ser Asn Met Thr Ile Glu Cys Lys Phe Pro Val Glu Lys Gln Leu Asp
        35                  40                  45

Leu Ala Ala Leu Ile Val Tyr Trp Glu Met Glu Asp Lys Asn Ile Ile
50                  55                  60

Gln Phe Val His Gly Glu Glu Asp Leu Lys Val Gln His Ser Ser Tyr
65                  70                  75                  80

Arg Gln Arg Ala Arg Leu Leu Lys Asp Gln Leu Ser Leu Gly Asn Ala
                85                  90                  95

Ala Leu Gln Ile Thr Asp Val Lys Leu Gln Asp Ala Gly Val Tyr Arg
            100                 105                 110

Cys Met Ile Ser Tyr Gly Gly Ala Asp Tyr Lys Arg Ile Thr Val Lys
        115                 120                 125

Val Asn Ala Pro Tyr Asn Lys Ile Asn Gln Arg Ile Leu Val Val Asp
130                 135                 140

Pro Val Thr Ser Glu His Glu Leu Thr Cys Gln Ala Glu Gly Tyr Pro
145                 150                 155                 160

Lys Ala Glu Val Ile Trp Thr Ser Ser Asp His Gln Val Leu Ser Gly
                165                 170                 175

Lys Thr Thr Thr Thr Asn Ser Lys Arg Glu Glu Lys Leu Phe Asn Val
            180                 185                 190

Thr Ser Thr Leu Arg Ile Asn Thr Thr Asn Glu Ile Phe Tyr Cys
        195                 200                 205

```
Thr Phe Arg Arg Leu Asp Pro Glu Glu Asn His Thr Ala Glu Leu Val
    210                 215                 220
Ile Pro Glu Leu Pro Leu Ala His Pro Pro Asn Glu Arg Thr His Leu
225                 230                 235                 240
Val Ile Leu Gly Ala Ile Leu Leu Cys Leu Gly Val Ala Leu Thr Phe
                245                 250                 255
Ile Phe Arg Leu Arg Lys Gly Arg Met Met Asp Val Lys Lys Cys Gly
            260                 265                 270
Ile Gln Asp Thr Asn Ser Lys Lys Gln Ser Asp Thr His Leu Glu Glu
        275                 280                 285
Thr Gly Gly Gly Ser Gly Gly Gly Ser Gly Gly Gly Ser
290                 295                 300
Thr His Thr Cys Pro Pro Cys Pro Ala Pro Glu Leu Leu Gly Gly Pro
305                 310                 315                 320
Ser Val Phe Leu Phe Pro Pro Lys Pro Lys Asp Thr Leu Met Ile Ser
                325                 330                 335
Arg Thr Pro Glu Val Thr Cys Val Val Val Asp Val Ser His Glu Asp
            340                 345                 350
Pro Glu Val Lys Phe Asn Trp Tyr Val Asp Gly Val Glu Val His Asn
        355                 360                 365
Ala Lys Thr Lys Pro Arg Glu Glu Gln Tyr Asn Ser Thr Tyr Arg Val
    370                 375                 380
Val Ser Val Leu Thr Val Leu His Gln Asp Trp Leu Asn Gly Lys Glu
385                 390                 395                 400
Tyr Lys Cys Lys Val Ser Asn Lys Ala Leu Pro Ala Pro Ile Glu Lys
                405                 410                 415
Thr Ile Ser Lys Ala Lys Gly Gln Pro Arg Glu Pro Gln Val Tyr Thr
            420                 425                 430
Leu Pro Pro Ser Arg Glu Glu Met Thr Lys Asn Gln Val Ser Leu Thr
        435                 440                 445
Cys Leu Val Lys Gly Phe Tyr Pro Ser Asp Ile Ala Val Glu Trp Glu
    450                 455                 460
Ser Asn Gly Gln Pro Glu Asn Asn Tyr Lys Thr Thr Pro Pro Val Leu
465                 470                 475                 480
Asp Ser Asp Gly Ser Phe Phe Leu Tyr Ser Lys Leu Thr Val Asp Lys
                485                 490                 495
Ser Arg Trp Gln Gln Gly Asn Val Phe Ser Cys Ser Val Met His Glu
            500                 505                 510
Ala Leu His Asn His Tyr Thr Gln Lys Ser Leu Ser Leu Ser Pro Gly
        515                 520                 525
Lys Gly Gly Gly Ser Gly Gly Gly Ser Gly Gly Gly Ser
    530                 535                 540
Gln Ile Ala Pro Pro Cys Thr Ser Glu Lys His Tyr Glu His Leu Gly
545                 550                 555                 560
Arg Cys Cys Asn Lys Cys Glu Pro Gly Lys Tyr Met Ser Ser Lys Cys
                565                 570                 575
Thr Thr Thr Ser Asp Ser Val Cys Leu Pro Cys Gly Pro Asp Glu Tyr
            580                 585                 590
Leu Asp Ser Trp Asn Glu Glu Asp Lys Cys Leu Leu His Lys Val Cys
        595                 600                 605
Asp Thr Gly Lys Ala Leu Val Ala Val Ala Gly Asn Ser Thr Thr
    610                 615                 620
```

```
Pro Arg Arg Cys Ala Cys Thr Ala Gly Tyr His Trp Ser Gln Asp Cys
625                 630                 635                 640

Glu Cys Cys Arg Arg Asn Thr Glu Cys Ala Pro Gly Leu Gly Ala Gln
                645                 650                 655

His Pro Leu Gln Leu Asn Lys Asp Thr Val Cys Lys Pro Cys Leu Ala
            660                 665                 670

Gly Tyr Phe Ser Asp Ala Phe Ser Ser Thr Asp Lys Cys Arg Pro Trp
        675                 680                 685

Thr Asn Cys Thr Phe Leu Gly Lys Arg Val Glu His His Gly Thr Glu
            690                 695                 700

Lys Ser Asp Ala Val Cys Ser Ser Ser Leu Pro Ala Arg Lys Pro Pro
705                 710                 715                 720

Asn Glu Pro His Val Tyr Leu Pro Gly
                725

<210> SEQ ID NO 69
<211> LENGTH: 729
<212> TYPE: PRT
<213> ORGANISM: Homo sapiens

<400> SEQUENCE: 69

Gln Ile Ala Pro Pro Cys Thr Ser Glu Lys His Tyr Glu His Leu Gly
1               5                   10                  15

Arg Cys Cys Asn Lys Cys Glu Pro Gly Lys Tyr Met Ser Ser Lys Cys
                20                  25                  30

Thr Thr Thr Ser Asp Ser Val Cys Leu Pro Cys Gly Pro Asp Glu Tyr
            35                  40                  45

Leu Asp Ser Trp Asn Glu Glu Asp Lys Cys Leu Leu His Lys Val Cys
        50                  55                  60

Asp Thr Gly Lys Ala Leu Val Ala Val Ala Gly Asn Ser Thr Thr
65                  70                  75                  80

Pro Arg Arg Cys Ala Cys Thr Ala Gly Tyr His Trp Ser Gln Asp Cys
                85                  90                  95

Glu Cys Cys Arg Arg Asn Thr Glu Cys Ala Pro Gly Leu Gly Ala Gln
                100                 105                 110

His Pro Leu Gln Leu Asn Lys Asp Thr Val Cys Lys Pro Cys Leu Ala
            115                 120                 125

Gly Tyr Phe Ser Asp Ala Phe Ser Ser Thr Asp Lys Cys Arg Pro Trp
        130                 135                 140

Thr Asn Cys Thr Phe Leu Gly Lys Arg Val Glu His His Gly Thr Glu
145                 150                 155                 160

Lys Ser Asp Ala Val Cys Ser Ser Ser Leu Pro Ala Arg Lys Pro Pro
                165                 170                 175

Asn Glu Pro His Val Tyr Leu Pro Gly Gly Gly Gly Ser Gly Gly
            180                 185                 190

Gly Gly Ser Gly Gly Gly Ser Thr His Thr Cys Pro Pro Cys Pro
        195                 200                 205

Ala Pro Glu Leu Leu Gly Gly Pro Ser Val Phe Leu Phe Pro Pro Lys
    210                 215                 220

Pro Lys Asp Thr Leu Met Ile Ser Arg Thr Pro Glu Val Thr Cys Val
225                 230                 235                 240

Val Val Asp Val Ser His Glu Asp Pro Glu Val Lys Phe Asn Trp Tyr
                245                 250                 255

Val Asp Gly Val Glu Val His Asn Ala Lys Thr Lys Pro Arg Glu Glu
                260                 265                 270
```

```
Gln Tyr Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
        290                 295                 300

Ala Leu Pro Ala Pro Ile Glu Lys Thr Ile Ser Lys Ala Lys Gly Gln
305                 310                 315                 320

Pro Arg Glu Pro Gln Val Tyr Thr Leu Pro Pro Ser Arg Glu Glu Met
                325                 330                 335

Thr Lys Asn Gln Val Ser Leu Thr Cys Leu Val Lys Gly Phe Tyr Pro
        340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Phe Leu
        370                 375                 380

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Pro Gly Lys Gly Gly Gly Ser Gly Gly
        420                 425                 430

Gly Gly Ser Gly Gly Gly Gly Ser Arg Ile Phe Ala Val Phe Ile Phe
        435                 440                 445

Met Thr Tyr Trp His Leu Leu Asn Ala Phe Thr Val Thr Val Pro Lys
450                 455                 460

Asp Leu Tyr Val Val Glu Tyr Gly Ser Asn Met Thr Ile Glu Cys Lys
465                 470                 475                 480

Phe Pro Val Glu Lys Gln Leu Asp Leu Ala Ala Leu Ile Val Tyr Trp
                485                 490                 495

Glu Met Glu Asp Lys Asn Ile Ile Gln Phe Val His Gly Glu Glu Asp
                500                 505                 510

Leu Lys Val Gln His Ser Ser Tyr Arg Gln Arg Ala Arg Leu Leu Lys
        515                 520                 525

Asp Gln Leu Ser Leu Gly Asn Ala Ala Leu Gln Ile Thr Asp Val Lys
        530                 535                 540

Leu Gln Asp Ala Gly Val Tyr Arg Cys Met Ile Ser Tyr Gly Gly Ala
545                 550                 555                 560

Asp Tyr Lys Arg Ile Thr Val Lys Val Asn Ala Pro Tyr Asn Lys Ile
                565                 570                 575

Asn Gln Arg Ile Leu Val Val Asp Pro Val Thr Ser Glu His Glu Leu
                580                 585                 590

Thr Cys Gln Ala Glu Gly Tyr Pro Lys Ala Glu Val Ile Trp Thr Ser
        595                 600                 605

Ser Asp His Gln Val Leu Ser Gly Lys Thr Thr Thr Thr Asn Ser Lys
610                 615                 620

Arg Glu Glu Lys Leu Phe Asn Val Thr Ser Thr Leu Arg Ile Asn Thr
625                 630                 635                 640

Thr Thr Asn Glu Ile Phe Tyr Cys Thr Phe Arg Arg Leu Asp Pro Glu
                645                 650                 655

Glu Asn His Thr Ala Glu Leu Val Ile Pro Glu Leu Pro Leu Ala His
                660                 665                 670

Pro Pro Asn Glu Arg Thr His Leu Val Ile Leu Gly Ala Ile Leu Leu
                675                 680                 685
```

```
Cys Leu Gly Val Ala Leu Thr Phe Ile Phe Arg Leu Arg Lys Gly Arg
    690                 695                 700
Met Met Asp Val Lys Lys Cys Gly Ile Gln Asp Thr Asn Ser Lys Lys
705                 710                 715                 720
Gln Ser Asp Thr His Leu Glu Glu Thr
                725

<210> SEQ ID NO 70
<211> LENGTH: 214
<212> TYPE: PRT
<213> ORGANISM: Homo sapiens

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 71
<211> LENGTH: 214
<212> TYPE: PRT
<213> ORGANISM: Homo sapiens

<400> SEQUENCE: 71

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60
```

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 72
<211> LENGTH: 213
<212> TYPE: PRT
<213> ORGANISM: Homo sapiens

<400> SEQUENCE: 72

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 73
<211> LENGTH: 214
<212> TYPE: PRT
<213> ORGANISM: Homo sapiens

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 74
<211> LENGTH: 215
<212> TYPE: PRT
<213> ORGANISM: Homo sapiens

<400> SEQUENCE: 74

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 75
<211> LENGTH: 213
<212> TYPE: PRT
<213> ORGANISM: Homo sapiens

<400> SEQUENCE: 75

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys His Gln Arg Ser Thr Tyr Pro Leu Thr
                85                  90                  95

Phe Gly Gln Gly Thr Lys Val Glu Val Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 76
<211> LENGTH: 210
<212> TYPE: PRT
<213> ORGANISM: Homo sapiens

<400> SEQUENCE: 76

```
Gln Ile Val Ser Thr Gln Ser Pro Ala Ile Met Ser Ala Ser Pro Gly
1               5                   10                  15

Glu Lys Val Thr Met Thr Cys Ser Ala Ser Ser Ser Arg Ser Tyr Met
            20                  25                  30

Gln Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Thr Phe Gly
                85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu
    210

<210> SEQ ID NO 77
<211> LENGTH: 216
<212> TYPE: PRT
<213> ORGANISM: Homo sapiens

<400> SEQUENCE: 77

Ser Tyr Glu Leu Ser Gln Pro Arg Ser Val Ser Val Ser Pro Gly Gln
1               5                   10                  15

Thr Ala Gly Phe Thr Cys Gly Gly Asp Asn Val Gly Arg Lys Ser Val
            20                  25                  30

Gln Trp Tyr Gln Gln Lys Pro Pro Gln Ala Pro Val Leu Val Ile Tyr
        35                  40                  45

Ala Asp Ser Glu Arg Pro Ser Gly Ile Pro Ala Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Ser Thr Ala Asp His
                85                  90                  95

Trp Val Phe Gly Gly Gly Thr Arg Leu Thr Val Leu Gly Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
```

```
                145                 150                 155                 160
Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
                195                 200                 205

Lys Ser Phe Asn Arg Gly Glu Cys
    210                 215
```

<210> SEQ ID NO 78
<211> LENGTH: 214
<212> TYPE: PRT
<213> ORGANISM: Homo sapiens

<400> SEQUENCE: 78

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Leu Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 79
<211> LENGTH: 567
<212> TYPE: PRT
<213> ORGANISM: Homo sapiens

<400> SEQUENCE: 79

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
```

```
                35                  40                  45
Gln Leu Cys Lys Phe Cys Asp Val Arg Phe Ser Thr Cys Asp Asn Gln
 50                  55                  60
Lys Ser Cys Met Ser Asn Cys Ser Ile Thr Ser Ile Cys Glu Lys Pro
 65                  70                  75                  80
Gln Glu Val Cys Val Ala Val Trp Arg Lys Asn Asp Glu Asn Ile Thr
                 85                  90                  95
Leu Glu Thr Val Cys His Asp Pro Lys Leu Pro Tyr His Asp Phe Ile
                100                 105                 110
Leu Glu Asp Ala Ala Ser Pro Lys Cys Ile Met Lys Glu Lys Lys
                115                 120                 125
Pro Gly Glu Thr Phe Phe Met Cys Ser Cys Ser Ser Asp Glu Cys Asn
130                 135                 140
Asp Asn Ile Ile Phe Ser Glu Glu Tyr Asn Thr Ser Asn Pro Asp Leu
145                 150                 155                 160
Leu Leu Val Ile Phe Gln Val Thr Gly Ile Ser Leu Leu Pro Pro Leu
                165                 170                 175
Gly Val Ala Ile Ser Val Ile Ile Phe Tyr Cys Tyr Arg Val Asn
                180                 185                 190
Arg Gln Gln Lys Leu Ser Ser Thr Trp Glu Thr Gly Lys Thr Arg Lys
                195                 200                 205
Leu Met Glu Phe Ser Glu His Cys Ala Ile Ile Leu Glu Asp Asp Arg
210                 215                 220
Ser Asp Ile Ser Ser Thr Cys Ala Asn Asn Ile Asn His Asn Thr Glu
225                 230                 235                 240
Leu Leu Pro Ile Glu Leu Asp Thr Leu Val Gly Lys Gly Arg Phe Ala
                245                 250                 255
Glu Val Tyr Lys Ala Lys Leu Lys Gln Asn Thr Ser Glu Gln Phe Glu
                260                 265                 270
Thr Val Ala Val Lys Ile Phe Pro Tyr Glu Glu Tyr Ala Ser Trp Lys
                275                 280                 285
Thr Glu Lys Asp Ile Phe Ser Asp Ile Asn Leu Lys His Glu Asn Ile
                290                 295                 300
Leu Gln Phe Leu Thr Ala Glu Glu Arg Lys Thr Glu Leu Gly Lys Gln
305                 310                 315                 320
Tyr Trp Leu Ile Thr Ala Phe His Ala Lys Gly Asn Leu Gln Glu Tyr
                325                 330                 335
Leu Thr Arg His Val Ile Ser Trp Glu Asp Leu Arg Lys Leu Gly Ser
                340                 345                 350
Ser Leu Ala Arg Gly Ile Ala His Leu His Ser Asp His Thr Pro Cys
                355                 360                 365
Gly Arg Pro Lys Met Pro Ile Val His Arg Asp Leu Lys Ser Ser Asn
                370                 375                 380
Ile Leu Val Lys Asn Asp Leu Thr Cys Cys Leu Cys Asp Phe Gly Leu
385                 390                 395                 400
Ser Leu Arg Leu Asp Pro Thr Leu Ser Val Asp Asp Leu Ala Asn Ser
                405                 410                 415
Gly Gln Val Gly Thr Ala Arg Tyr Met Ala Pro Glu Val Leu Glu Ser
                420                 425                 430
Arg Met Asn Leu Glu Asn Val Glu Ser Phe Lys Gln Thr Asp Val Tyr
                435                 440                 445
Ser Met Ala Leu Val Leu Trp Glu Met Thr Ser Arg Cys Asn Ala Val
                450                 455                 460
```

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
        515                 520                 525

Leu Thr Ala Gln Cys Val Ala Glu Arg Phe Ser Glu Leu Glu His Leu
    530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 80
<211> LENGTH: 592
<212> TYPE: PRT
<213> ORGANISM: Homo sapiens

<400> SEQUENCE: 80

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
                20                  25                  30

Val Glu Met Glu Ala Gln Lys Asp Glu Ile Ile Cys Pro Ser Cys Asn
            35                  40                  45

Arg Thr Ala His Pro Leu Arg His Ile Asn Asn Asp Met Ile Val Thr
        50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
                100                 105                 110

Trp Arg Lys Asn Asp Glu Asn Ile Thr Leu Glu Thr Val Cys His Asp
            115                 120                 125

Pro Lys Leu Pro Tyr His Asp Phe Ile Leu Glu Asp Ala Ala Ser Pro
        130                 135                 140

Lys Cys Ile Met Lys Glu Lys Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
                180                 185                 190

Thr Gly Ile Ser Leu Leu Pro Pro Leu Gly Val Ala Ile Ser Val Ile
            195                 200                 205

Ile Ile Phe Tyr Cys Tyr Arg Val Asn Arg Gln Gln Lys Leu Ser Ser
        210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp

```
                  260                 265                 270
Thr Leu Val Gly Lys Gly Arg Phe Ala Glu Val Tyr Lys Ala Lys Leu
                275                 280                 285

Lys Gln Asn Thr Ser Glu Gln Phe Glu Thr Val Ala Val Lys Ile Phe
            290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
            340                 345                 350

His Ala Lys Gly Asn Leu Gln Glu Tyr Leu Thr Arg His Val Ile Ser
        355                 360                 365

Trp Glu Asp Leu Arg Lys Leu Gly Ser Ser Leu Ala Arg Gly Ile Ala
    370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
            420                 425                 430

Leu Ser Val Asp Asp Leu Ala Asn Ser Gly Gln Val Gly Thr Ala Arg
        435                 440                 445

Tyr Met Ala Pro Glu Val Leu Glu Ser Arg Met Asn Leu Glu Asn Val
    450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495

Pro Pro Phe Gly Ser Lys Val Arg Glu His Pro Cys Val Glu Ser Met
            500                 505                 510

Lys Asp Asn Val Leu Arg Asp Arg Gly Arg Pro Glu Ile Pro Ser Phe
        515                 520                 525

Trp Leu Asn His Gln Gly Ile Gln Met Val Cys Glu Thr Leu Thr Glu
    530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590

<210> SEQ ID NO 81
<211> LENGTH: 529
<212> TYPE: PRT
<213> ORGANISM: Homo sapiens

<400> SEQUENCE: 81

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45
```

```
Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Phe Tyr Cys Tyr Arg Val Asn
            180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
        275                 280                 285

Thr Glu Lys Asp Ile Phe Ser Asp Ile Asn Leu Lys His Glu Asn Ile
    290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
        355                 360                 365

Gly Arg Pro Lys Met Pro Ile Val His Arg Asp Leu Lys Ser Ser Asn
370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
        435                 440                 445

Ser Met Ala Leu Val Leu Trp Glu Met Thr Ser Arg Cys Asn Ala Val
450                 455                 460

Gly Glu Val Lys Asp Tyr Glu Pro Pro Phe Gly Ser Lys Val Arg Glu
```

```
                 465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
                500                 505                 510

Val Cys Glu Thr Leu Thr Glu Cys Trp Asp His Asp Pro Glu Ala Arg
                515                 520                 525

Leu

<210> SEQ ID NO 82
<211> LENGTH: 554
<212> TYPE: PRT
<213> ORGANISM: Homo sapiens

<400> SEQUENCE: 82

Met Gly Arg Gly Leu Arg Gly Leu Trp Pro Leu His Ile Val Leu
1               5                   10                  15

Trp Thr Arg Ile Ala Ser Thr Ile Pro Pro His Val Gln Lys Ser Asp
                20                  25                  30

Val Glu Met Glu Ala Gln Lys Asp Glu Ile Ile Cys Pro Ser Cys Asn
                35                  40                  45

Arg Thr Ala His Pro Leu Arg His Ile Asn Asn Asp Met Ile Val Thr
        50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
                100                 105                 110

Trp Arg Lys Asn Asp Glu Asn Ile Thr Leu Glu Thr Val Cys His Asp
                115                 120                 125

Pro Lys Leu Pro Tyr His Asp Phe Ile Leu Glu Asp Ala Ala Ser Pro
        130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
                180                 185                 190

Thr Gly Ile Ser Leu Leu Pro Pro Leu Gly Val Ala Ile Ser Val Ile
                195                 200                 205

Ile Ile Phe Tyr Cys Tyr Arg Val Asn Arg Gln Gln Lys Leu Ser Ser
        210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
                260                 265                 270

Thr Leu Val Gly Lys Gly Arg Phe Ala Glu Val Tyr Lys Ala Lys Leu
                275                 280                 285

Lys Gln Asn Thr Ser Glu Gln Phe Glu Thr Val Ala Val Lys Ile Phe
        290                 295                 300

Pro Tyr Glu Glu Tyr Ala Ser Trp Lys Thr Glu Lys Asp Ile Phe Ser
```

```
                305                 310                 315                 320
        Asp Ile Asn Leu Lys His Glu Asn Ile Leu Gln Phe Leu Thr Ala Glu
                        325                 330                 335

Glu Arg Lys Thr Glu Leu Gly Lys Gln Tyr Trp Leu Ile Thr Ala Phe
                        340                 345                 350

His Ala Lys Gly Asn Leu Gln Glu Tyr Leu Thr Arg His Val Ile Ser
                        355                 360                 365

Trp Glu Asp Leu Arg Lys Leu Gly Ser Ser Leu Ala Arg Gly Ile Ala
                370                 375                 380

His Leu His Ser Asp His Thr Pro Cys Gly Arg Pro Lys Met Pro Ile
        385                 390                 395                 400

Val His Arg Asp Leu Lys Ser Ser Asn Ile Leu Val Lys Asn Asp Leu
                        405                 410                 415

Thr Cys Cys Leu Cys Asp Phe Gly Leu Ser Leu Arg Leu Asp Pro Thr
                        420                 425                 430

Leu Ser Val Asp Asp Leu Ala Asn Ser Gly Gln Val Gly Thr Ala Arg
                        435                 440                 445

Tyr Met Ala Pro Glu Val Leu Glu Ser Arg Met Asn Leu Glu Asn Val
                450                 455                 460

Glu Ser Phe Lys Gln Thr Asp Val Tyr Ser Met Ala Leu Val Leu Trp
        465                 470                 475                 480

Glu Met Thr Ser Arg Cys Asn Ala Val Gly Glu Val Lys Asp Tyr Glu
                        485                 490                 495

Pro Pro Phe Gly Ser Lys Val Arg Glu His Pro Cys Val Glu Ser Met
                        500                 505                 510

Lys Asp Asn Val Leu Arg Asp Arg Gly Arg Pro Glu Ile Pro Ser Phe
                        515                 520                 525

Trp Leu Asn His Gln Gly Ile Gln Met Val Cys Glu Thr Leu Thr Glu
                530                 535                 540

Cys Trp Asp His Asp Pro Glu Ala Arg Leu
        545                 550

<210> SEQ ID NO 83
<211> LENGTH: 199
<212> TYPE: PRT
<213> ORGANISM: Homo sapiens

<400> SEQUENCE: 83

Met Gly Arg Gly Leu Leu Arg Gly Leu Trp Pro Leu His Ile Val Leu
        1               5                   10                  15

Trp Thr Arg Ile Ala Ser Thr Ile Pro Pro His Val Gln Lys Ser Val
                        20                  25                  30

Asn Asn Asp Met Ile Val Thr Asp Asn Asn Gly Ala Val Lys Phe Pro
                    35                  40                  45

Gln Leu Cys Lys Phe Cys Asp Val Arg Phe Ser Thr Cys Asp Asn Gln
                50                  55                  60

Lys Ser Cys Met Ser Asn Cys Ser Ile Thr Ser Ile Cys Glu Lys Pro
        65                  70                  75                  80

Gln Glu Val Cys Val Ala Val Trp Arg Lys Asn Asp Glu Asn Ile Thr
                        85                  90                  95

Leu Glu Thr Val Cys His Asp Pro Lys Leu Pro Tyr His Asp Phe Ile
                        100                 105                 110

Leu Glu Asp Ala Ala Ser Pro Lys Cys Ile Met Lys Glu Lys Lys Lys
                        115                 120                 125
```

```
Pro Gly Glu Thr Phe Phe Met Cys Ser Cys Ser Ser Asp Glu Cys Asn
    130                 135                 140
Asp Asn Ile Ile Phe Ser Glu Glu Tyr Asn Thr Ser Asn Pro Asp Leu
145                 150                 155                 160
Leu Leu Val Ile Phe Gln Val Thr Gly Ile Ser Leu Leu Pro Pro Leu
                165                 170                 175
Gly Val Ala Ile Ser Val Ile Ile Phe Tyr Cys Tyr Arg Val Asn
            180                 185                 190
Arg Gln Gln Lys Leu Ser Ser
            195

<210> SEQ ID NO 84
<211> LENGTH: 224
<212> TYPE: PRT
<213> ORGANISM: Homo sapiens

<400> SEQUENCE: 84

Met Gly Arg Gly Leu Leu Arg Gly Leu Trp Pro Leu His Ile Val Leu
1               5                   10                  15
Trp Thr Arg Ile Ala Ser Thr Ile Pro Pro His Val Gln Lys Ser Asp
                20                  25                  30
Val Glu Met Glu Ala Gln Lys Asp Glu Ile Ile Cys Pro Ser Cys Asn
            35                  40                  45
Arg Thr Ala His Pro Leu Arg His Ile Asn Asn Asp Met Ile Val Thr
        50                  55                  60
Asp Asn Asn Gly Ala Val Lys Phe Pro Gln Leu Cys Lys Phe Cys Asp
65                  70                  75                  80
Val Arg Phe Ser Thr Cys Asp Asn Gln Lys Ser Cys Met Ser Asn Cys
                85                  90                  95
Ser Ile Thr Ser Ile Cys Glu Lys Pro Gln Glu Val Cys Val Ala Val
            100                 105                 110
Trp Arg Lys Asn Asp Glu Asn Ile Thr Leu Glu Thr Val Cys His Asp
        115                 120                 125
Pro Lys Leu Pro Tyr His Asp Phe Ile Leu Glu Asp Ala Ala Ser Pro
130                 135                 140
Lys Cys Ile Met Lys Glu Lys Lys Lys Pro Gly Glu Thr Phe Phe Met
145                 150                 155                 160
Cys Ser Cys Ser Ser Asp Glu Cys Asn Asp Asn Ile Ile Phe Ser Glu
                165                 170                 175
Glu Tyr Asn Thr Ser Asn Pro Asp Leu Leu Leu Val Ile Phe Gln Val
            180                 185                 190
Thr Gly Ile Ser Leu Leu Pro Pro Leu Gly Val Ala Ile Ser Val Ile
        195                 200                 205
Ile Ile Phe Tyr Cys Tyr Arg Val Asn Arg Gln Gln Lys Leu Ser Ser
    210                 215                 220

<210> SEQ ID NO 85
<211> LENGTH: 166
<212> TYPE: PRT
<213> ORGANISM: Homo sapiens

<400> SEQUENCE: 85

Met Gly Arg Gly Leu Leu Arg Gly Leu Trp Pro Leu His Ile Val Leu
1               5                   10                  15
Trp Thr Arg Ile Ala Ser Thr Ile Pro Pro His Val Gln Lys Ser Val
                20                  25                  30
```

-continued

Asn Asn Asp Met Ile Val Thr Asp Asn Asn Gly Ala Val Lys Phe Pro
                35                  40                  45

Gln Leu Cys Lys Phe Cys Asp Val Arg Phe Ser Thr Cys Asp Asn Gln
 50                  55                  60

Lys Ser Cys Met Ser Asn Cys Ser Ile Thr Ser Ile Cys Glu Lys Pro
 65                  70                  75                  80

Gln Glu Val Cys Val Ala Val Trp Arg Lys Asn Asp Glu Asn Ile Thr
                 85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
                115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln
                165

<210> SEQ ID NO 86
<211> LENGTH: 191
<212> TYPE: PRT
<213> ORGANISM: Homo sapiens

<400> SEQUENCE: 86

Met Gly Arg Gly Leu Leu Arg Gly Leu Trp Pro Leu His Ile Val Leu
 1               5                  10                  15

Trp Thr Arg Ile Ala Ser Thr Ile Pro Pro His Val Gln Lys Ser Asp
                20                  25                  30

Val Glu Met Glu Ala Gln Lys Asp Glu Ile Ile Cys Pro Ser Cys Asn
                35                  40                  45

Arg Thr Ala His Pro Leu Arg His Ile Asn Asn Asp Met Ile Val Thr
     50                  55                  60

Asp Asn Asn Gly Ala Val Lys Phe Pro Gln Leu Cys Lys Phe Cys Asp
 65                  70                  75                  80

Val Arg Phe Ser Thr Cys Asp Asn Gln Lys Ser Cys Met Ser Asn Cys
                 85                  90                  95

Ser Ile Thr Ser Ile Cys Glu Lys Pro Gln Glu Val Cys Val Ala Val
                100                 105                 110

Trp Arg Lys Asn Asp Glu Asn Ile Thr Leu Glu Thr Val Cys His Asp
            115                 120                 125

Pro Lys Leu Pro Tyr His Asp Phe Ile Leu Glu Asp Ala Ala Ser Pro
    130                 135                 140

Lys Cys Ile Met Lys Glu Lys Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln
                180                 185                 190

<210> SEQ ID NO 87
<211> LENGTH: 137
<212> TYPE: PRT
<213> ORGANISM: Homo sapiens

<400> SEQUENCE: 87

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
                115                 120                 125

Glu Glu Tyr Asn Thr Ser Asn Pro Asp
    130                 135

<210> SEQ ID NO 88
<211> LENGTH: 162
<212> TYPE: PRT
<213> ORGANISM: Homo sapiens

<400> SEQUENCE: 88

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp

<210> SEQ ID NO 89
<211> LENGTH: 112
<212> TYPE: PRT
<213> ORGANISM: Homo sapiens

<400> SEQUENCE: 89

Pro Gln Leu Cys Lys Phe Cys Asp Val Arg Phe Ser Thr Cys Asp Asn
1               5                   10                  15

Gln Lys Ser Cys Met Ser Asn Cys Ser Ile Thr Ser Ile Cys Glu Lys

```
                  20                  25                  30

Pro Gln Glu Val Cys Val Ala Val Trp Arg Lys Asn Asp Glu Asn Ile
            35                  40                  45

Thr Leu Glu Thr Val Cys His Asp Pro Lys Leu Pro Tyr His Asp Phe
 50                  55                  60

Ile Leu Glu Asp Ala Ala Ser Pro Lys Cys Ile Met Lys Glu Lys Lys
 65                  70                  75                  80

Lys Pro Gly Glu Thr Phe Phe Met Cys Ser Cys Ser Ser Asp Glu Cys
                    85                  90                  95

Asn Asp Asn Ile Ile Phe Ser Glu Glu Tyr Asn Thr Ser Asn Pro Asp
                100                 105                 110

<210> SEQ ID NO 90
<211> LENGTH: 507
<212> TYPE: PRT
<213> ORGANISM: Homo sapiens

<400> SEQUENCE: 90

Met Gly Arg Gly Leu Arg Gly Leu Trp Pro Leu His Ile Val Leu
 1               5                  10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
 50                  55                  60

Lys Ser Cys Met Ser Asn Cys Ser Ile Thr Ser Ile Cys Glu Lys Pro
 65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
        130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Phe Tyr Cys Tyr Arg Val Asn
                180                 185                 190

Arg Gln Gln Lys Leu Ser Ser Thr Trp Glu Thr Gly Lys Thr Arg Lys
            195                 200                 205

Leu Met Glu Phe Ser Glu His Cys Ala Ile Ile Leu Glu Asp Asp Arg
        210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Arg Ile Phe Pro Tyr Glu Glu Tyr Ala Ser Trp Lys
        275                 280                 285
```

```
Thr Glu Lys Asp Ile Phe Ser Asp Ile Asn Leu Lys His Glu Asn Ile
290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
        355                 360                 365

Gly Arg Pro Lys Met Pro Ile Val His Arg Asp Leu Lys Ser Ser Asn
370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
        435                 440                 445

Ser Met Ala Leu Val Leu Trp Glu Met Thr Ser Arg Cys Asn Ala Val
    450                 455                 460

Gly Glu Val Lys Asp Tyr Glu Pro Pro Phe Gly Ser Lys Val Arg Glu
465                 470                 475                 480

Leu Glu His Leu Asp Arg Leu Ser Gly Arg Ser Cys Ser Glu Glu Lys
                485                 490                 495

Ile Pro Glu Asp Gly Ser Leu Asn Thr Thr Lys
                500                 505

<210> SEQ ID NO 91
<211> LENGTH: 550
<212> TYPE: PRT
<213> ORGANISM: Homo sapiens

<400> SEQUENCE: 91

Met Gly Arg Gly Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160
```

```
Leu Leu Val Ile Phe Gln Val Thr Gly Ile Ser Leu Pro Pro Leu
                165                 170                 175

Gly Val Ala Ile Ser Val Ile Ile Phe Tyr Cys Tyr Arg Val Asn
            180                 185                 190

Arg Gln Gln Lys Leu Ser Ser Thr Trp Glu Thr Gly Lys Thr Arg Lys
                195                 200                 205

Leu Met Glu Phe Ser Glu His Cys Ala Ile Ile Leu Glu Asp Asp Arg
        210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Gly Gln Phe Glu
            260                 265                 270

Thr Val Ala Val Lys Ile Phe Pro Tyr Glu Glu Tyr Ala Ser Trp Lys
        275                 280                 285

Thr Glu Lys Asp Ile Phe Ser Asp Ile Asn Leu Lys His Glu Asn Ile
    290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
        355                 360                 365

Gly Arg Pro Lys Met Pro Ile Val His Arg Asp Leu Lys Ser Ser Asn
    370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
        435                 440                 445

Ser Met Ala Leu Val Leu Trp Glu Met Thr Ser Arg Cys Asn Ala Val
450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Ala Ser Gly Ile Gln Met Val
                485                 490                 495

Cys Glu Thr Leu Thr Glu Cys Trp Asp His Asp Pro Glu Ala Arg Leu
            500                 505                 510

Thr Ala Gln Cys Val Ala Glu Arg Phe Ser Glu Leu Glu His Leu Asp
        515                 520                 525

Arg Leu Ser Gly Arg Ser Cys Ser Glu Glu Lys Ile Pro Glu Asp Gly
    530                 535                 540

Ser Leu Asn Thr Thr Lys
545                 550

<210> SEQ ID NO 92
<211> LENGTH: 288
```

<212> TYPE: PRT
<213> ORGANISM: Homo sapiens

<400> SEQUENCE: 92

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 93
<211> LENGTH: 150
<212> TYPE: PRT
<213> ORGANISM: Homo sapiens

<400> SEQUENCE: 93

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

```
Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 94
<211> LENGTH: 142
<212> TYPE: PRT
<213> ORGANISM: Homo sapiens

<400> SEQUENCE: 94

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Gln Phe Gln
    130                 135                 140

<210> SEQ ID NO 95
<211> LENGTH: 616
<212> TYPE: PRT
<213> ORGANISM: Homo sapiens

<400> SEQUENCE: 95

Met Ala Pro Arg Ala Arg Arg Arg Pro Leu Phe Ala Leu Leu Leu Leu
1               5                   10                  15

Leu Cys Ala Leu Leu Ala Arg Leu Gln Val Ala Leu Gln Ile Ala Pro
            20                  25                  30

Pro Cys Thr Ser Glu Lys His Tyr Glu His Leu Gly Arg Cys Cys Asn
        35                  40                  45

Lys Cys Glu Pro Gly Lys Tyr Met Ser Ser Lys Cys Thr Thr Thr Ser
    50                  55                  60

Asp Ser Val Cys Leu Pro Cys Gly Pro Asp Glu Tyr Leu Asp Ser Trp
65                  70                  75                  80

Asn Glu Glu Asp Lys Cys Leu Leu His Lys Val Cys Asp Thr Gly Lys
                85                  90                  95
```

```
Ala Leu Val Ala Val Ala Gly Asn Ser Thr Thr Pro Arg Arg Cys
            100                 105                 110

Ala Cys Thr Ala Gly Tyr His Trp Ser Gln Asp Cys Glu Cys Arg
        115                 120                 125

Arg Asn Thr Glu Cys Ala Pro Gly Leu Gly Ala Gln His Pro Leu Gln
    130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
                165                 170                 175

Phe Leu Gly Lys Arg Val Glu His His Gly Thr Glu Lys Ser Asp Ala
            180                 185                 190

Val Cys Ser Ser Ser Leu Pro Ala Arg Lys Pro Pro Asn Glu Pro His
        195                 200                 205

Val Tyr Leu Pro Gly Leu Ile Ile Leu Leu Leu Phe Ala Ser Val Ala
    210                 215                 220

Leu Val Ala Ala Ile Ile Phe Gly Val Cys Tyr Arg Lys Lys Gly Lys
225                 230                 235                 240

Ala Leu Thr Ala Asn Leu Trp His Trp Ile Asn Glu Ala Cys Gly Arg
                245                 250                 255

Leu Ser Gly Asp Lys Glu Ser Ser Gly Asp Ser Cys Val Ser Thr His
            260                 265                 270

Thr Ala Asn Phe Gly Gln Gln Gly Ala Cys Glu Gly Val Leu Leu Leu
        275                 280                 285

Thr Leu Glu Glu Lys Thr Phe Pro Glu Asp Met Cys Tyr Pro Asp Gln
    290                 295                 300

Gly Gly Val Cys Gln Gly Thr Cys Val Gly Gly Pro Tyr Ala Gln
305                 310                 315                 320

Gly Glu Asp Ala Arg Met Leu Ser Leu Val Ser Lys Thr Glu Ile Glu
                325                 330                 335

Glu Asp Ser Phe Arg Gln Met Pro Thr Glu Asp Glu Tyr Met Asp Arg
            340                 345                 350

Pro Ser Gln Pro Thr Asp Gln Leu Leu Phe Leu Thr Glu Pro Gly Ser
        355                 360                 365

Lys Ser Thr Pro Pro Phe Ser Glu Pro Leu Glu Val Gly Glu Asn Asp
    370                 375                 380

Ser Leu Ser Gln Cys Phe Thr Gly Thr Gln Ser Thr Val Gly Ser Glu
385                 390                 395                 400

Ser Cys Asn Cys Thr Glu Pro Leu Cys Arg Thr Asp Trp Thr Pro Met
                405                 410                 415

Ser Ser Glu Asn Tyr Leu Gln Lys Glu Val Asp Ser Gly His Cys Pro
            420                 425                 430

His Trp Ala Ala Ser Pro Ser Pro Asn Trp Ala Asp Val Cys Thr Gly
        435                 440                 445

Cys Arg Asn Pro Pro Gly Glu Asp Cys Glu Pro Leu Val Gly Ser Pro
    450                 455                 460

Lys Arg Gly Pro Leu Pro Gln Cys Ala Tyr Gly Met Gly Leu Pro Pro
465                 470                 475                 480

Glu Glu Glu Ala Ser Arg Thr Glu Ala Arg Asp Gln Pro Glu Asp Gly
                485                 490                 495

Ala Asp Gly Arg Leu Pro Ser Ser Ala Arg Ala Gly Ala Gly Ser Gly
            500                 505                 510

Ser Ser Pro Gly Gly Gln Ser Pro Ala Ser Gly Asn Val Thr Gly Asn
```

```
                515                 520                 525
Ser Asn Ser Thr Phe Ile Ser Ser Gly Gln Val Met Asn Phe Lys Gly
    530                 535                 540

Asp Ile Ile Val Val Tyr Val Ser Gln Thr Ser Gln Glu Gly Ala Ala
545                 550                 555                 560

Ala Ala Ala Glu Pro Met Gly Arg Pro Val Gln Glu Thr Leu Ala
                565                 570                 575

Arg Arg Asp Ser Phe Ala Gly Asn Gly Pro Arg Phe Pro Asp Pro Cys
            580                 585                 590

Gly Gly Pro Glu Gly Leu Arg Glu Pro Glu Lys Ala Ser Arg Pro Val
                595                 600                 605

Gln Glu Gln Gly Gly Ala Lys Ala
    610                 615

<210> SEQ ID NO 96
<211> LENGTH: 185
<212> TYPE: PRT
<213> ORGANISM: Homo sapiens

<400> SEQUENCE: 96

Gln Ile Ala Pro Pro Cys Thr Ser Glu Lys His Tyr Glu His Leu Gly
1               5                   10                  15

Arg Cys Cys Asn Lys Cys Glu Pro Gly Lys Tyr Met Ser Ser Lys Cys
            20                  25                  30

Thr Thr Thr Ser Asp Ser Val Cys Leu Pro Cys Gly Pro Asp Glu Tyr
        35                  40                  45

Leu Asp Ser Trp Asn Glu Glu Asp Lys Cys Leu Leu His Lys Val Cys
    50                  55                  60

Asp Thr Gly Lys Ala Leu Val Ala Val Ala Gly Asn Ser Thr Thr
65                  70                  75                  80

Pro Arg Arg Cys Ala Cys Thr Ala Gly Tyr His Trp Ser Gln Asp Cys
                85                  90                  95

Glu Cys Cys Arg Arg Asn Thr Glu Cys Ala Pro Gly Leu Gly Ala Gln
            100                 105                 110

His Pro Leu Gln Leu Asn Lys Asp Thr Val Cys Lys Pro Cys Leu Ala
        115                 120                 125

Gly Tyr Phe Ser Asp Ala Phe Ser Ser Thr Asp Lys Cys Arg Pro Trp
    130                 135                 140

Thr Asn Cys Thr Phe Leu Gly Lys Arg Val Glu His His Gly Thr Glu
145                 150                 155                 160

Lys Ser Asp Ala Val Cys Ser Ser Ser Leu Pro Ala Arg Lys Pro Pro
                165                 170                 175

Asn Glu Pro His Val Tyr Leu Pro Gly
            180                 185

<210> SEQ ID NO 97
<211> LENGTH: 213
<212> TYPE: PRT
<213> ORGANISM: Homo sapiens

<400> SEQUENCE: 97

Met Ala Pro Arg Ala Arg Arg Arg Pro Leu Phe Ala Leu Leu Leu
1               5                   10                  15

Leu Cys Ala Leu Leu Ala Arg Leu Gln Val Ala Leu Gln Ile Ala Pro
            20                  25                  30

Pro Cys Thr Ser Glu Lys His Tyr Glu His Leu Gly Arg Cys Cys Asn
```

```
                35                  40                  45
Lys Cys Glu Pro Gly Lys Tyr Met Ser Ser Lys Cys Thr Thr Thr Ser
 50                  55                  60

Asp Ser Val Cys Leu Pro Cys Gly Pro Asp Glu Tyr Leu Asp Ser Trp
 65                  70                  75                  80

Asn Glu Glu Asp Lys Cys Leu Leu His Lys Val Cys Asp Thr Gly Lys
                 85                  90                  95

Ala Leu Val Ala Val Ala Gly Asn Ser Thr Thr Pro Arg Arg Cys
                100                 105                 110

Ala Cys Thr Ala Gly Tyr His Trp Ser Gln Asp Cys Glu Cys Cys Arg
                115                 120                 125

Arg Asn Thr Glu Cys Ala Pro Gly Leu Gly Ala Gln His Pro Leu Gln
130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
                165                 170                 175

Phe Leu Gly Lys Arg Val Glu His His Gly Thr Glu Lys Ser Asp Ala
                180                 185                 190

Val Cys Ser Ser Ser Leu Pro Ala Arg Lys Pro Pro Asn Glu Pro His
                195                 200                 205

Val Tyr Leu Pro Gly
                210

<210> SEQ ID NO 98
<211> LENGTH: 401
<212> TYPE: PRT
<213> ORGANISM: Homo sapiens

<400> SEQUENCE: 98

Met Asn Lys Leu Leu Cys Cys Ala Leu Val Phe Leu Asp Ile Ser Ile
 1               5                  10                  15

Lys Trp Thr Thr Gln Glu Thr Phe Pro Pro Lys Tyr Leu His Tyr Asp
                20                  25                  30

Glu Glu Thr Ser His Gln Leu Leu Cys Asp Lys Cys Pro Pro Gly Thr
                35                  40                  45

Tyr Leu Lys Gln His Cys Thr Ala Lys Trp Lys Thr Val Cys Ala Pro
 50                  55                  60

Cys Pro Asp His Tyr Tyr Thr Asp Ser Trp His Thr Ser Asp Glu Cys
 65                  70                  75                  80

Leu Tyr Cys Ser Pro Val Cys Lys Glu Leu Gln Tyr Val Lys Gln Glu
                 85                  90                  95

Cys Asn Arg Thr His Asn Arg Val Cys Glu Cys Lys Glu Gly Arg Tyr
                100                 105                 110

Leu Glu Ile Glu Phe Cys Leu Lys His Arg Ser Cys Pro Pro Gly Phe
                115                 120                 125

Gly Val Val Gln Ala Gly Thr Pro Glu Arg Asn Thr Val Cys Lys Arg
                130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
                180                 185                 190
```

```
Gln Lys Cys Gly Ile Asp Val Thr Leu Cys Glu Glu Ala Phe Phe Arg
            195                 200                 205

Phe Ala Val Pro Thr Lys Phe Thr Pro Asn Trp Leu Ser Val Leu Val
210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
            245                 250                 255

Trp Lys His Gln Asn Lys Ala Gln Asp Ile Val Lys Lys Ile Ile Gln
            260                 265                 270

Asp Ile Asp Leu Cys Glu Asn Ser Val Gln Arg His Ile Gly His Ala
            275                 280                 285

Asn Leu Thr Phe Glu Gln Leu Arg Ser Leu Met Glu Ser Leu Pro Gly
            290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
            325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
            355                 360                 365

Ile Arg Phe Leu His Ser Phe Thr Met Tyr Lys Leu Tyr Gln Lys Leu
            370                 375                 380

Phe Leu Glu Met Ile Gly Asn Gln Val Gln Ser Val Lys Ile Ser Cys
385                 390                 395                 400

Leu

<210> SEQ ID NO 99
<211> LENGTH: 290
<212> TYPE: PRT
<213> ORGANISM: Homo sapiens

<400> SEQUENCE: 99

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
            85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
            130                 135                 140

Asp Pro Val Thr Ser Glu His Glu Leu Thr Cys Gln Ala Glu Gly Tyr
145                 150                 155                 160
```

```
Pro Lys Ala Glu Val Ile Trp Thr Ser Ser Asp His Gln Val Leu Ser
                165                 170                 175
Gly Lys Thr Thr Thr Thr Asn Ser Lys Arg Glu Glu Lys Leu Phe Asn
            180                 185                 190
Val Thr Ser Thr Leu Arg Ile Asn Thr Thr Thr Asn Glu Ile Phe Tyr
        195                 200                 205
Cys Thr Phe Arg Arg Leu Asp Pro Glu Glu Asn His Thr Ala Glu Leu
    210                 215                 220
Val Ile Pro Glu Leu Pro Leu Ala His Pro Asn Glu Arg Thr His
225                 230                 235                 240
Leu Val Ile Leu Gly Ala Ile Leu Leu Cys Leu Gly Val Ala Leu Thr
                245                 250                 255
Phe Ile Phe Arg Leu Arg Lys Gly Arg Met Met Asp Val Lys Lys Cys
                260                 265                 270
Gly Ile Gln Asp Thr Asn Ser Lys Lys Gln Ser Asp Thr His Leu Glu
                275                 280                 285
Glu Thr
    290

<210> SEQ ID NO 100
<211> LENGTH: 209
<212> TYPE: PRT
<213> ORGANISM: Homo sapiens

<400> SEQUENCE: 100

Ala Phe Thr Val Thr Val Pro Lys Asp Leu Tyr Val Val Glu Tyr Gly
1               5                   10                  15
Ser Asn Met Thr Ile Glu Cys Lys Phe Pro Val Glu Lys Gln Leu Asp
            20                  25                  30
Leu Ala Ala Leu Ile Val Tyr Trp Glu Met Glu Asp Lys Asn Ile Ile
        35                  40                  45
Gln Phe Val His Gly Glu Glu Asp Leu Lys Val Gln His Ser Ser Tyr
    50                  55                  60
Arg Gln Arg Ala Arg Leu Leu Lys Asp Gln Leu Ser Leu Gly Asn Ala
65                  70                  75                  80
Ala Leu Gln Ile Thr Asp Val Lys Leu Gln Asp Ala Gly Val Tyr Arg
                85                  90                  95
Cys Met Ile Ser Tyr Gly Gly Ala Asp Tyr Lys Arg Ile Thr Val Lys
                100                 105                 110
Val Asn Ala Pro Tyr Asn Lys Ile Asn Gln Arg Ile Leu Val Val Asp
            115                 120                 125
Pro Val Thr Ser Glu His Glu Leu Thr Cys Gln Ala Glu Gly Tyr Pro
    130                 135                 140
Lys Ala Glu Val Ile Trp Thr Ser Ser Asp His Gln Val Leu Ser Gly
145                 150                 155                 160
Lys Thr Thr Thr Thr Asn Ser Lys Arg Glu Glu Lys Leu Phe Asn Val
                165                 170                 175
Thr Ser Thr Leu Arg Ile Asn Thr Thr Thr Asn Glu Ile Phe Tyr Cys
            180                 185                 190
Thr Phe Arg Arg Leu Asp Pro Glu Glu Asn His Thr Ala Glu Leu Val
        195                 200                 205
Ile

<210> SEQ ID NO 101
<211> LENGTH: 289
```

```
<212> TYPE: PRT
<213> ORGANISM: Homo sapiens

<400> SEQUENCE: 101

Arg Ile Phe Ala Val Phe Ile Phe Met Thr Tyr Trp His Leu Leu Asn
1               5                   10                  15

Ala Phe Thr Val Thr Val Pro Lys Asp Leu Tyr Val Glu Tyr Gly
            20                  25                  30

Ser Asn Met Thr Ile Glu Cys Lys Phe Pro Val Glu Lys Gln Leu Asp
        35                  40                  45

Leu Ala Ala Leu Ile Val Tyr Trp Glu Met Glu Asp Lys Asn Ile Ile
    50                  55                  60

Gln Phe Val His Gly Glu Glu Asp Leu Lys Val Gln His Ser Ser Tyr
65                  70                  75                  80

Arg Gln Arg Ala Arg Leu Leu Lys Asp Gln Leu Ser Leu Gly Asn Ala
                85                  90                  95

Ala Leu Gln Ile Thr Asp Val Lys Leu Gln Asp Ala Gly Val Tyr Arg
            100                 105                 110

Cys Met Ile Ser Tyr Gly Gly Ala Asp Tyr Lys Arg Ile Thr Val Lys
        115                 120                 125

Val Asn Ala Pro Tyr Asn Lys Ile Asn Gln Arg Ile Leu Val Val Asp
    130                 135                 140

Pro Val Thr Ser Glu His Glu Leu Thr Cys Gln Ala Glu Gly Tyr Pro
145                 150                 155                 160

Lys Ala Glu Val Ile Trp Thr Ser Ser Asp His Gln Val Leu Ser Gly
                165                 170                 175

Lys Thr Thr Thr Thr Asn Ser Lys Arg Glu Glu Lys Leu Phe Asn Val
            180                 185                 190

Thr Ser Thr Leu Arg Ile Asn Thr Thr Thr Asn Glu Ile Phe Tyr Cys
        195                 200                 205

Thr Phe Arg Arg Leu Asp Pro Glu Glu Asn His Thr Ala Glu Leu Val
    210                 215                 220

Ile Pro Glu Leu Pro Leu Ala His Pro Pro Asn Glu Arg Thr His Leu
225                 230                 235                 240

Val Ile Leu Gly Ala Ile Leu Leu Cys Leu Gly Val Ala Leu Thr Phe
                245                 250                 255

Ile Phe Arg Leu Arg Lys Gly Arg Met Met Asp Val Lys Lys Cys Gly
            260                 265                 270

Ile Gln Asp Thr Asn Ser Lys Lys Gln Ser Asp Thr His Leu Glu Glu
        275                 280                 285

Thr

<210> SEQ ID NO 102
<211> LENGTH: 390
<212> TYPE: PRT
<213> ORGANISM: Homo sapiens

<400> SEQUENCE: 102

Met Pro Pro Ser Gly Leu Arg Leu Leu Pro Leu Leu Leu Pro Leu Leu
1               5                   10                  15

Arg Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ser Ser Pro Pro Ser
```

```
                50                  55                  60
        Gln Gly Glu Val Pro Pro Val Pro Leu Pro Glu Ala Val Leu Ala Leu
        65                  70                  75                  80

Tyr Asn Ser Thr Arg Asp Arg Val Ala Gly Glu Ser Ala Glu Pro Glu
                        85                  90                  95

Pro Glu Pro Glu Ala Asp Tyr Tyr Ala Lys Glu Val Thr Arg Val Leu
                    100                 105                 110

Met Val Glu Asn Thr Asn Lys Ile Tyr Glu Lys Val Lys Lys Ser Pro
                    115                 120                 125

His Ser Ile Tyr Met Leu Phe Asn Thr Ser Glu Leu Arg Glu Ala Val
                    130                 135                 140

Pro Glu Pro Val Leu Leu Ser Arg Ala Glu Leu Arg Leu Leu Arg Leu
        145                 150                 155                 160

Lys Leu Lys Ala Glu Gln His Val Glu Leu Tyr Gln Lys Tyr Ser Asn
                        165                 170                 175

Asp Ser Trp Arg Tyr Leu Ser Asn Arg Leu Leu Ala Pro Ser Asp Thr
                    180                 185                 190

Pro Glu Trp Leu Ser Phe Asp Val Thr Gly Val Val Arg Gln Trp Leu
                    195                 200                 205

Ser His Gly Gly Glu Val Glu Gly Phe Arg Leu Ser Ala His Cys Ser
                    210                 215                 220

Cys Asp Ser Lys Asp Asn Thr Leu Gln Val Asp Ile Asn Gly Phe Ser
        225                 230                 235                 240

Ser Ser Arg Arg Gly Asp Leu Ala Thr Ile His Gly Met Asn Arg Pro
                        245                 250                 255

Phe Leu Leu Leu Met Ala Thr Pro Leu Glu Arg Ala Gln His Leu His
                    260                 265                 270

Ser Ser Arg Gln Arg Arg Ala Leu Asp Thr Asn Tyr Cys Phe Ser Ser
                    275                 280                 285

Thr Glu Lys Asn Cys Cys Val Arg Gln Leu Tyr Ile Asp Phe Arg Lys
                    290                 295                 300

Asp Leu Gly Trp Lys Trp Ile His Glu Pro Lys Gly Tyr His Ala Asn
        305                 310                 315                 320

Phe Cys Leu Gly Pro Cys Pro Tyr Ile Trp Ser Leu Asp Thr Gln Tyr
                        325                 330                 335

Ser Lys Val Leu Ala Leu Tyr Asn Gln His Asn Pro Gly Ala Ser Ala
                    340                 345                 350

Ala Pro Cys Cys Val Pro Gln Ala Leu Glu Pro Leu Pro Ile Val Tyr
                    355                 360                 365

Tyr Val Gly Arg Lys Pro Lys Val Glu Gln Leu Ser Asn Met Ile Val
                    370                 375                 380

Arg Ser Cys Lys Cys Ser
        385                 390

<210> SEQ ID NO 103
<211> LENGTH: 112
<212> TYPE: PRT
<213> ORGANISM: Homo sapiens

<400> SEQUENCE: 103

Ala Leu Asp Thr Asn Tyr Cys Phe Ser Ser Thr Glu Lys Asn Cys Cys
        1               5                   10                  15

Val Arg Gln Leu Tyr Ile Asp Phe Arg Lys Asp Leu Gly Trp Lys Trp
                        20                  25                  30
```

```
Ile His Glu Pro Lys Gly Tyr His Ala Asn Phe Cys Leu Gly Pro Cys
         35                  40                  45

Pro Tyr Ile Trp Ser Leu Asp Thr Gln Tyr Ser Lys Val Leu Ala Leu
 50                  55                  60

Tyr Asn Gln His Asn Pro Gly Ala Ser Ala Ala Pro Cys Cys Val Pro
 65                  70                  75                  80

Gln Ala Leu Glu Pro Leu Pro Ile Val Tyr Tyr Val Gly Arg Lys Pro
                 85                  90                  95

Lys Val Glu Gln Leu Ser Asn Met Ile Val Arg Ser Cys Lys Cys Ser
            100                 105                 110
```

<210> SEQ ID NO 104
<211> LENGTH: 15
<212> TYPE: PRT
<213> ORGANISM: Artificial Sequence
<220> FEATURE:
<223> OTHER INFORMATION: Synthetic construct

<400> SEQUENCE: 104

```
Gly Gly Gly Gly Ser Gly Gly Gly Ser Gly Gly Gly Gly Ser
 1               5                  10                  15
```

<210> SEQ ID NO 105
<211> LENGTH: 7
<212> TYPE: PRT
<213> ORGANISM: Artificial Sequence
<220> FEATURE:
<223> OTHER INFORMATION: Synthetic construct

<400> SEQUENCE: 105

```
Glu Pro Lys Ser Cys Asp Lys
 1               5
```

<210> SEQ ID NO 106
<211> LENGTH: 7
<212> TYPE: PRT
<213> ORGANISM: Artificial Sequence
<220> FEATURE:
<223> OTHER INFORMATION: Synthetic construct

<400> SEQUENCE: 106

```
Ile Glu Gly Arg Asp Met Asp
 1               5
```

<210> SEQ ID NO 107
<211> LENGTH: 4
<212> TYPE: PRT
<213> ORGANISM: Artificial Sequence
<220> FEATURE:
<223> OTHER INFORMATION: Synthetic construct

<400> SEQUENCE: 107

```
Lys Lys Ala Glu
 1
```

<210> SEQ ID NO 108
<211> LENGTH: 4
<212> TYPE: PRT
<213> ORGANISM: Artificial Sequence
<220> FEATURE:
<223> OTHER INFORMATION: Synthetic construct

<400> SEQUENCE: 108

```
Lys Arg Val Glu
 1
```

```
<210> SEQ ID NO 109
<211> LENGTH: 4
<212> TYPE: PRT
<213> ORGANISM: Artificial Sequence
<220> FEATURE:
<223> OTHER INFORMATION: Synthetic construct

<400> SEQUENCE: 109

Lys Lys Val Glu
1

<210> SEQ ID NO 110
<211> LENGTH: 8
<212> TYPE: PRT
<213> ORGANISM: Artificial Sequence
<220> FEATURE:
<223> OTHER INFORMATION: Synthetic construct

<400> SEQUENCE: 110

Gln Glu Pro Lys Ser Cys Asp Lys
1               5

<210> SEQ ID NO 111
<211> LENGTH: 21
<212> TYPE: DNA
<213> ORGANISM: Artificial Sequence
<220> FEATURE:
<223> OTHER INFORMATION: Primer

<400> SEQUENCE: 111
ctagtgccac ctgggaattc a                                           21

<210> SEQ ID NO 112
<211> LENGTH: 24
<212> TYPE: DNA
<213> ORGANISM: Artificial Sequence
<220> FEATURE:
<223> OTHER INFORMATION: Primer

<400> SEQUENCE: 112
catcattagc tgatctccag ctca                                        24

<210> SEQ ID NO 113
<211> LENGTH: 38
<212> TYPE: DNA
<213> ORGANISM: Artificial Sequence
<220> FEATURE:
<223> OTHER INFORMATION: Synthetic construct

<400> SEQUENCE: 113
catcagtgac agttacttct tcaccttcta cacagaga                         38

<210> SEQ ID NO 114
<211> LENGTH: 1821
<212> TYPE: DNA
<213> ORGANISM: Homo sapiens

<400> SEQUENCE: 114
gagctcgagg tgcagctggt ggaatccggc ggaggactgg tgcagcctgg cggatccctg    60
agactgtctt gcgccgcctc cggcttcaac atcaaggaca cctacatcca ctgggtgcga   120
caggcccctg gcaagggact ggaatgggtg gcccggatct accccaccaa cggctacacc   180
agatacgccg actccgtgaa gggccggttc accatctccc gcgacacctc caagaacacc   240
```

| | |
|---|---|
| gcctacctgc agatgaactc cctgcgggcc gaggacaccg ccgtgtacta ctgctccaga | 300 |
| tggggaggcg acggcttcta cgccatggac tactggggcc agggcaccct ggtgacagtg | 360 |
| tcctctgcct ccaccaaggg ccctctgtg ttccctctgg cccttccag caagtccaca | 420 |
| tctggcggca ccgccgctct gggctgcctg gtgaaagact acttccccga gcccgtgacc | 480 |
| gtgtcctgga actctggcgc cctgacctcc ggcgtgcaca cctttccagc cgtgctgcag | 540 |
| tcctccggcc tgtactccct gtcctccgtg gtgaccgtgc cctccagctc tctgggcacc | 600 |
| cagacctaca tctgcaacgt gaaccacaag ccctccaaca ccaaggtgga caagaaggtg | 660 |
| gaacccaagt cctgcgacaa gacccacacc tgtcccccct gccctgctcc tgaactgctg | 720 |
| ggcggaccct ccgtgttcct gttcccccca agcccaagg acaccctgat gatctcccgg | 780 |
| accccgaag tgacctgcgt ggtggtggac gtgtcccacg aggaccctga agtgaagttc | 840 |
| aattggtatg tggacggcgt ggaagtgcac aacgccaaga ccaagcccag agaggaacag | 900 |
| tacaactcca cctaccgggt ggtgtctgtg ctgaccgtgc tgcaccagga ctggctgaac | 960 |
| ggcaaagagt acaagtgcaa ggtgtccaac aaggccctgc ctgcccccat cgaaaagacc | 1020 |
| atctccaagg ccaagggcca gcctcgcgag cctcaggtgt acacactgcc ccctagccgg | 1080 |
| gaagagatga ccaagaacca ggtgtccctg acctgtctgg tgaaaggctt ctaccctcc | 1140 |
| gatatcgccg tggaatggga gtccaacggc cagcccgaga caactacaa gaccacccc | 1200 |
| cctgtgctgg actccgacgg ctcattcttc ctgtactcca gctgaccgt ggacaagtcc | 1260 |
| cggtggcagc agggcaacgt gttctcctgc tccgtgatgc acgaggccct gcacaaccac | 1320 |
| tacacccaga agtccctgtc cctgagccct ggaaagggcg aggcggctc tggtggtgga | 1380 |
| ggctctggag gcggaggctc taccatccct ccacgtgc agaaatccgt gaacaacgac | 1440 |
| atgatcgtga ccgacaacaa cggcgccgtg aagttccccc agctgtgcaa gttctgcgac | 1500 |
| gtgcggttct ctacctgcga caaccagaaa tcctgcatgt ccaactgctc catcacctcc | 1560 |
| atctgcgaga gccccagga agtgtgcgtg ccgtgtggc ggaagaacga cgagaacatc | 1620 |
| accctggaaa ccgtgtgcca cgaccccaag ctgcctacc acgacttcat cctggaagat | 1680 |
| gccgcctccc ccaagtgcat catgaaggaa aagaagaagc ccggcgagac attcttcatg | 1740 |
| tgcagctgct cctccgacga gtgcaacgac aacatcatct tctccgaaga gtacaacacc | 1800 |
| tccaaccccg actgaggtac c | 1821 |

<210> SEQ ID NO 115
<211> LENGTH: 657
<212> TYPE: DNA
<213> ORGANISM: Homo sapiens

<400> SEQUENCE: 115

| | |
|---|---|
| gagctcgaca tccagatgac ccagtccccc tccagcctgt ccgcctctgt gggcgacaga | 60 |
| gtgaccatca cctgtcgggc ctctcaggac gtgaacaccg ccgtggcctg gtatcagcag | 120 |
| aagcctggca aggcccccaa gctgctgatc tactccgcct ccttcctgta ctccggggtg | 180 |
| ccatcccggt tctccggctc tagatccggc accgacttca ccctgaccat ctccagcctg | 240 |
| cagcccgagg acttcgccac ctactactgc cagcagcact acaccacccc cctgaccttc | 300 |
| ggccagggca ccaaggtgga aatcaagcgg accgtggccg ctccctccgt gttcatcttc | 360 |
| ccacccctccg acgagcagct gaagtctggc accgcctccg tcgtgtgcct gctgaacaac | 420 |
| ttctaccccc gcgaggccaa ggtgcagtgg aaggtggaca acgccctgca gtccggcaac | 480 |
| tcccaggaat ccgtgaccga gcaggactcc aaggacagca cctactccct gtcctccacc | 540 |

```
ctgaccctgt ccaaggccga ctacgagaag cacaaggtgt acgcctgcga agtgacccac    600
cagggcctgt ccagccccgt gaccaagtcc ttcaaccggg gcgagtgctg aggtacc       657
```

<210> SEQ ID NO 116
<211> LENGTH: 1818
<212> TYPE: DNA
<213> ORGANISM: Homo sapiens

<400> SEQUENCE: 116

```
gagctccagg tgcagctgaa gcagtccggc ccaggactgg tgcagccttc ccagtccctg     60
tccatcacct gtaccgtgtc cggcttctcc ctgaccaact acggcgtgca ctgggtccga    120
cagtccccag gcaagggcct ggaatggctg ggagtgattt ggagcggcgg caacaccgac    180
tacaacaccc ccttcacctc ccggctgtcc atcaacaagg acaactccaa gtcccaggtg    240
ttcttcaaga tgaactccct gcagtccaac gacaccgcca tctactactg cgccagagcc    300
ctgacctact atgactacga gttcgcctac tggggacagg gcaccctggt caccgtgtct    360
gccgcctcta ccaagggccc ctccgtgttt cccctggccc cctccagcaa gtccacatct    420
ggcggcaccg ccgctctggg ctgcctggtc aaggactact cccccgagcc cgtgaccgtg    480
tcctggaact ctggcgccct gacctccggc gtgcacacct tccagccgt gctgcagtcc    540 tccggcctgt actccctgtc ctccgtcgtg accgtgccct ccagctctct gggcacccag    600
acctacatct gcaacgtgaa ccacaagccc tccaacacca aggtggacaa gcgggtggaa    660
cccaagtcct gcgacaagac ccacacctgt cccccctgcc ctgcccctga actgctggga    720
ggcccttccg tgttcctgtt cccccccaaag cccaaggaca cctgatgat ctcccggacc    780 cccgaagtga cctgcgtggt ggtggacgtg tcccacgagg accctgaagt gaagttcaat    840
tggtacgtgg acggcgtgga agtgcacaac gccaagacca gcccagaga ggaacagtac    900 aactccacct accgggtggt gtccgtgctg accgtgctgc accaggactg gctgaacggc    960
aaagagtaca gtgcaaggt ctccaacaag gccctgcctg cccccatcga aaagaccatc    1020
tccaaggcca agggccagcc ccgcgagcct caggtgtaca ctctgcctcc cagccgggac    1080
gagctgacca agaaccaggt gtccctgacc tgtctggtca agggcttcta cccctccgat    1140
atcgccgtgg aatgggagtc caacggccag cccgagaaca actacaagac cacccccct    1200 gtgctggact ccgacggctc attcttcctg tactccaagc tgaccgtgga caagtcccgg    1260
tggcagcagg gcaacgtgtt ctcctgctcc gtgatgcacg aggccctgca caaccactac    1320
acccagaagt ccctgtctct gagccccggc aagggcggag cggatctgg tggtggtggc    1380 tctggtggcg gaggctctac catccctcca cacgtgcaga atccgtgaa caacgacatg    1440 atcgtgaccg acaacaacgg cgccgtgaag ttccccagc tgtgcaagtt ctgcgacgtg    1500
cggttctcta cctgcgacaa ccagaaatcc tgcatgtcca actgctccat cacctccatc    1560
tgcgagaagc ccaggaagt gtgcgtcgcc gtctggcgga agaacgacga gaacatcacc    1620
ctggaaaccg tgtgccacga ccccaagctg ccctaccacg acttcatcct ggaagatgcc    1680
gcctccccca gtgcatcat gaaggaaaag aagaagcccg gcgagacttt cttcatgtgc    1740
agctgctcct ccgacgagtg caacgacaac atcatcttct ccgaagagta caacacctcc    1800
aaccccgact gaggtacc                                                  1818
```

<210> SEQ ID NO 117
<211> LENGTH: 657
<212> TYPE: DNA

<213> ORGANISM: Homo sapiens

<400> SEQUENCE: 117

```
gagctcgata tcctgctgac ccagtccccc gtgatcctgt ccgtgtctcc tggcgagcgg      60
gtgtccttct cctgccgggc ctcccagtcc atcggcacca acatccactg gtatcagcag     120
cggaccaacg gctcccctcg gctgctgatt aagtacgcct ccgagtctat ctccggcatc     180
ccctcccggt tctccggctc tggctccggc accgacttca ccctgtccat caactccgtg     240
gaatccgagg atatcgccga ctactactgc cagcagaaca caaactggcc caccaccttc     300
ggcgctggca ccaagctgga actgaagcgg accgtggccg ctccctccgt gttcatcttc     360
ccaccctccg acgagcagct gaagtccggc accgcctccg tcgtgtgcct gctgaacaac     420
ttctacccccc gcgaggccaa ggtgcagtgg aaggtggaca cgccctgca gtccggcaac     480
tcccaggaat ccgtcaccga gcaggactcc aaggacagca cctactccct gtcctccacc     540
ctgaccctgt ccaaggccga ctacgagaag cacaaggtgt acgcctgcga agtgacccac     600
cagggcctgt ccagccccgt gaccaagtcc ttcaaccggg gcgagtgctg aggtacc       657
```

<210> SEQ ID NO 118
<211> LENGTH: 1824
<212> TYPE: DNA
<213> ORGANISM: Homo sapiens

<400> SEQUENCE: 118

```
gagctccagg tgcagctgca gcagcctggc gccgagctgg tcaagcctgg cgcttccgtg      60
aagatgtcct gcaaggcctc cggctacacc ttcaccagct acaacatgca ctgggtcaag     120
cagacccccg gcagaggcct ggaatggatc ggcgccatct accccggcaa cggcgacacc     180
tcctacaacc agaagttcaa gggaaaggcc accctgaccg ccgacaagtc ctcctccacc     240
gcctacatgc agctgtcctc cctgaccctc gaggactccg ccgtgtacta ctgcgcccgg     300
tccacctact acgcggcga ctggtacttc aacgtgtggg gcgctggcac caccgtgacc     360
gtgtctgccg cctctaccaa gggcccctcc gtgtttcccc tggccccctc cagcaagtcc     420
acatctggcg gcaccgccgc tctgggctgc ctggtcaagg actacttccc cgagcccgtg     480
acagtgtcct ggaactctgg cgccctgacc agcggcgtgc acacctttcc agccgtgctg     540
cagtcctctg gcctgtactc cctgtccagc gtcgtgaccg tgccctccag ctctctgggc     600
acccagacct acatctgcaa cgtgaaccac aagccctcca caccaaggt ggacaagaag     660
gccgagccca gtcctgcga caagacccac acctgtcccc cctgccctgc ccctgaactg     720
ctgggaggcc cttctgtgtt cctgttcccc ccaaagccca aggacaccct gatgatctcc     780
cggacccccg aagtgacctg cgtggtggtg gacgtgtccc acgaggaccc tgaagtgaag     840
ttcaattggt acgtggacgg cgtggaagtg cacaacgcca agaccaagcc cagagaggaa     900
cagtacaact ccacctaccg ggtggtgtcc gtgctgaccg tgctgcacca ggactggctg     960
aacggcaaag agtacaagtg caaggtgtcc aacaaggccc tgcctgcccc catcgaaaag    1020
accatctcca aggccaaggg ccagccccgc gagcctcagg tgtacactct gcctcccagc    1080
cgggacgagc tgaccaagaa ccaggtgtcc ctgacctgtc tggtcaaggg cttctacccc    1140
tccgatatcg ccgtggaatg ggagtccaac ggccagcccg agaacaacta caagaccacc    1200
cccctgtgc tggactccga cggctcattc ttcctgtact ccaagctgac cgtggacaag    1260
tccaggtggc agcagggcaa cgtgttctcc tgctccgtga tgcacgaggc cctgcacaac    1320
cactacaccc agaagtccct gtccctgagc cccggaaagg gcggaggcgg atctggtggt    1380
```

| | |
|---|---|
| ggaggatcag gcggcggagg ctctaccatc cccccacacg tgcagaaatc cgtgaacaac | 1440 |
| gacatgatcg tgaccgacaa caacggcgcc gtgaagttcc cccagctgtg caagttctgc | 1500 |
| gacgtgcggt tctctacctg cgacaaccag aaatcctgca tgtccaactg ctccatcacc | 1560 |
| tccatctgcg agaagcccca ggaagtgtgc gtcgccgtct ggcggaagaa cgacgagaac | 1620 |
| atcaccctgg aaaccgtgtg ccacgacccc aagctgccct accacgactt catcctggaa | 1680 |
| gatgccgcct cccccaagtg catcatgaag gaaaagaaga gcccggcga gactttcttc | 1740 |
| atgtgctctt gctcctccga cgagtgcaac gacaacatca tcttctccga gagtacaac | 1800 |
| acctccaacc ccgactgagg tacc | 1824 |

<210> SEQ ID NO 119
<211> LENGTH: 654
<212> TYPE: DNA
<213> ORGANISM: Homo sapiens

<400> SEQUENCE: 119

| | |
|---|---|
| gagctccaga tcgtgctgtc ccagtccccc gccatcctgt ctgctagccc tggcgagaaa | 60 |
| gtgacaatga cctgccgggc ctcctcctcc gtgtcctaca tccactggtt ccagcagaag | 120 |
| cccggctcca gccccaagcc ctggatctac gccacctcca acctggcctc cggcgtgcca | 180 |
| gtgcggttct ctggctccgg ctccggcacc tcctactccc tgaccatctc ccgggtggaa | 240 |
| gccgaggacg ccgccaccta ctactgccag cagtggacct ccaacccccc caccctttggc | 300 |
| ggaggcacca gctggaaaat caagcggacc gtggccgctc cctccgtgtt catcttccca | 360 |
| ccctccgacg agcagctgaa gtccggcacc gcctccgtcg tgtgcctgct gaacaacttc | 420 |
| taccccgcg aggccaaggt gcagtggaag gtggacaacg ccctgcagtc cggcaactcc | 480 |
| caggaatccg tcaccgagca ggactccaag acagcacct acagcctgtc ctccaccctg | 540 |
| accctgtcca aggccgacta cgagaagcac aaggtgtacg cctgcgaagt gacccaccag | 600 |
| ggcctgtcca gccccgtgac caagtccttc aaccggggcg agtgctgagg tacc | 654 |

<210> SEQ ID NO 120
<211> LENGTH: 1830
<212> TYPE: DNA
<213> ORGANISM: Homo sapiens

<400> SEQUENCE: 120

| | |
|---|---|
| gagctcgagg tgcagctggt ggaatccggc ggaggcctgg tccagcctgg cggatccctg | 60 |
| agactgtcct gtgccgcctc cggctacacc ttcaccaact acggcatgaa ctgggtccga | 120 |
| caggcccctg gcaagggcct ggaatgggtc ggatggatca acacctacac cggcgagccc | 180 |
| acctacgccg ccgacttcaa gcggcggttc accttctccc tggacacctc caagtccacc | 240 |
| gcctacctgc agatgaactc cctgcgggcc gaggacaccg ccgtgtacta ctgcgccaag | 300 |
| taccccccact actacggctc ctcccactgg tacttcgacg tgtggggcca gggcaccctg | 360 |
| gtcaccgtgt cctccgcctc taccaagggc ccctccgtgt tccctctggc cccctccagc | 420 |
| aagtccacat ctggcggcac cgccgctctg ggctgcctgg tcaaggacta cttccccgag | 480 |
| cccgtgaccg tgtcctggaa ctctggcgcc ctgacctccg gcgtgcacac ctttccagcc | 540 |
| gtgctgcagt cctccggcct gtactccctg tcctccgtcg tgaccgtgcc ctccagctct | 600 |
| ctgggcaccc agacctacat ctgcaacgtg aaccacaagc cctccaacac caaggtggac | 660 |
| aagaaggtgg aacccaagtc ctgcgacaag acccacacct gtccccctg ccctgcccct | 720 |

```
gaactgctgg gaggccctag cgtgttcctg ttccccccaa agcccaagga caccctgatg      780
atctcccgga cccccgaagt gacctgcgtg gtggtggacg tgtcccacga ggaccctgaa      840
gtgaagttca attggtacgt ggacggcgtg gaagtgcaca acgccaagac caagcccaga      900
gaggaacagt acaactccac ctaccgggtg gtgtccgtgc tgaccgtgct gcaccaggac      960
tggctgaacg gcaaagagta caagtgcaag gtgtccaaca aggccctgcc tgcccccatc     1020
gaaaagacca tctccaaggc caagggccag ccccgcgagc ctcaggtgta cactctgccc     1080
cctagccggg aagagatgac caagaaccag gtgtccctga cctgtctggt caagggcttc     1140 taccctccg atatcgccgt ggaatgggag tccaacggcc agcccgagaa caactacaag      1200
accacccccc ctgtgctgga ctccgacggc tcattcttcc tgtactccaa gctgaccgtg     1260
gacaagtccc ggtggcagca gggcaacgtg ttctcctgct ccgtgatgca cgaggccctg     1320
cacaaccact acacccagaa gtccctgtcc ctgagcccag gcaagggcgg aggcggatct     1380
ggtggtggag atcaggcgg cggaggctct accatccccc cacacgtgca gaaatccgtg      1440
aacaacgaca tgatcgtgac cgacaacaac ggcgccgtga agttccccca gctgtgcaag     1500
ttctgcgacg tgcggttctc tacctgcgac aaccagaaat cctgcatgtc caactgctcc     1560
atcacctcca tctgcgagaa gccccaggaa gtgtgcgtcg ccgtctggcg gaagaacgac     1620
gagaacatca ccctggaaac cgtgtgccac gaccccaagc tgccctacca cgacttcatc     1680
ctggaagatg ccgcctcccc caagtgcatc atgaaggaaa gaagaagcc cggcgagact     1740 ttcttcatgt gcagctgctc ctccgacgag tgcaacgaca acatcatctt ctccgaagag     1800
tacaacacct ccaaccccga ctgaggtacc                                      1830
```

<210> SEQ ID NO 121
<211> LENGTH: 657
<212> TYPE: DNA
<213> ORGANISM: Homo sapiens

<400> SEQUENCE: 121

```
gagctcgata tccagatgac ccagtccccc tccagcctgt ccgcctctgt gggcgacaga       60
gtgaccatca cctgttccgc cagccaggac atctccaact acctgaactg gtatcagcag      120
aagcccggca aggcccctaa ggtgctgatc tacttcacct cctccctgca ctccggcgtg      180
ccctccagat tctccggctc tggctccggc accgacttta ccctgaccat ctccagcctg      240
cagcccgagg acttcgccac ctactactgc cagcagtact ccaccgtgcc ctggaccttc      300
ggccagggca ccaaggtgga aatcaagcgg accgtggccg ctcccctcgt gttcatcttc      360
ccaccctccg acgagcagct gaagtccggc accgcctccg tcgtgtgcct gctgaacaac      420 ttctacccc gcgaggccaa ggtgcagtgg aaggtggaca acgccctgca gtccggcaac      480
tcccaggaat ccgtcaccga gcaggactcc aaggacagca cctactccct gtcctccacc      540
ctgaccctgt ccaaggccga ctacgagaag cacaaggtgt acgcctgcga agtgacccac      600
cagggcctgt ccagccccgt gaccaagtcc ttcaaccggg gcgagtgctg aggtacc         657
```

<210> SEQ ID NO 122
<211> LENGTH: 40
<212> TYPE: PRT
<213> ORGANISM: Artificial Sequence
<220> FEATURE:
<223> OTHER INFORMATION: Synthetic construct

<400> SEQUENCE: 122

Gly Gly Gly Gly Ser Gly Gly Gly Gly Ser Gly Gly Gly Gly Ser Gly

-continued

```
1               5                   10                  15
Gly Gly Gly Ser Gly Gly Gly Gly Ser Gly Gly Gly Gly Ser Gly Gly
                20                  25                  30
Gly Gly Ser Gly Gly Gly Gly Ser
        35              40
```